United States Patent
Wakita et al.

(10) Patent No.: US 9,234,184 B2
(45) Date of Patent: Jan. 12, 2016

(54) NUCLEIC ACID CONSTRUCT COMPRISING NUCLEIC ACID DERIVED FROM GENOME OF HEPATITIS C VIRUS OF GENOTYPE 1B, HEPATITIS C VIRUS GENOME-REPLICATING CELLS TRANSFECTED WITH THE SAME, AND METHOD FOR PRODUCING INFECTIOUS HEPATITIS C VIRUS PARTICLES

(75) Inventors: Takaji Wakita, Tokyo (JP); Tomoko Date, Kanagawa (JP); Yasuhito Tanaka, Aichi (JP); Masashi Mizokami, Chiba (JP)

(73) Assignees: Japan as Represented by Director-General of National Institute of Infectious Diseases, Tokyo (JP); Public University Corporation Nagoya City University, Nagoya-shi (JP); Toray Industries, Inc., Tokyo (JP)

( * ) Notice: Subject to any disclaimer, the term of this patent is extended or adjusted under 35 U.S.C. 154(b) by 117 days.

(21) Appl. No.: 14/009,049

(22) PCT Filed: Mar. 30, 2012

(86) PCT No.: PCT/JP2012/058516
§ 371 (c)(1),
(2), (4) Date: Sep. 30, 2013

(87) PCT Pub. No.: WO2012/133735
PCT Pub. Date: Oct. 4, 2012

(65) Prior Publication Data
US 2014/0302082 A1    Oct. 9, 2014

(30) Foreign Application Priority Data
Mar. 31, 2011  (JP) ................ 2011-080678

(51) Int. Cl.
| | |
|---|---|
| *C12N 7/08* | (2006.01) |
| *C12N 7/00* | (2006.01) |
| *C12N 7/04* | (2006.01) |
| *C12N 15/86* | (2006.01) |
| *C07K 16/10* | (2006.01) |
| *C12Q 1/70* | (2006.01) |
| *C07K 16/08* | (2006.01) |
| *C07K 14/005* | (2006.01) |
| *A61K 39/12* | (2006.01) |
| *A61K 39/00* | (2006.01) |

(52) U.S. Cl.
CPC . *C12N 7/00* (2013.01); *A61K 39/12* (2013.01); *C07K 14/005* (2013.01); *C07K 16/082* (2013.01); *C07K 16/109* (2013.01); *C12N 15/86* (2013.01); *C12Q 1/707* (2013.01); *A61K 39/00* (2013.01); *C12N 2770/24221* (2013.01); *C12N 2770/24222* (2013.01); *C12N 2770/24231* (2013.01); *C12N 2770/24234* (2013.01); *C12N 2770/24243* (2013.01); *C12N 2770/24251* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

2010/0173298 A1  7/2010  Mori et al.
2011/0129868 A1  6/2011  Kato et al.

FOREIGN PATENT DOCUMENTS

| | | |
|---|---|---|
| CA | 2303526 A1 | 10/2000 |
| EP | 2 177 535 A1 | 4/2010 |
| JP | 2001-17187 A | 1/2001 |
| WO | WO 2007/143701 A2 | 12/2007 |
| WO | WO 2008/136470 A1 | 11/2008 |
| WO | WO 2010/026965 A1 | 3/2010 |

OTHER PUBLICATIONS

Date et al. Microbiol Immunol 2012 vol. 56, pp. 308-317.*
Webster, et al., Hepatitis C, The Lancet, vol. 385, Issue 9973, Mar. 21-27, 2015, pp. 1124-1135.*
Blight, K. et al. "Efficient Initiation of HCV RNA Replication in Cell Culture," Science, vol. 290, 2000, pp. 1972-1974.
Choo, Q. et al. "Isolation of a cDNA Clone Derived from a Blood-Borne Non-A, Non-B Viral Hepatitis Genome," Science, vol. 244, 1989, pp. 359-362.
Friebe, P. et al. "Sequences in the 5' Nontranslated Region of Hepatitis C Virus Required for RNA Replication," Journal of Virology, vol. 75, No. 24, 2001, pp. 12047-12057.
Ikeda, M. et al. "Selectable Subgenomic and Genome-Length Dicistronic RNAs Derived from an Infectious Molecular Clone of the HCV-N Strain of Hepatitis C Virus Replicate Efficiently in Cultured Huh7 Cells," Journal of Virology, vol. 76, No. 6, 2002, pp. 2997-3006.
International Search Report issued in PCT/JP2012/058516 mailed Jul. 3, 2012.

(Continued)

*Primary Examiner* — Shanon A Foley
*Assistant Examiner* — Myron Hill
(74) *Attorney, Agent, or Firm* — Birch, Stewart, Kolasch & Birch, LLP

(57) ABSTRACT

A subgenomic replicon RNA (nucleic acid) having an excellent autonomously replicating ability and a fullgenomic replicon RNA (nucleic acid) having an excellent autonomously replicating ability and infectious HCV particle-producing ability, each derived from a novel HCV of genotype 1b, are provided. Particularly, a subgenomic replicon RNA (nucleic acid) and a fullgenomic replicon RNA (nucleic acid), each derived from an HCV genome of the NC1 strain which is a novel HCV genotype 1b isolated from a patient with acute severe hepatitis C, are provided.

19 Claims, 12 Drawing Sheets

(56) References Cited

OTHER PUBLICATIONS

Kato, N. et al. "Establishment of a hepatitis C virus subgenomic replicon derived from human hepatocytes infected in vitro," Biochemical and Biophysical Research Communications, vol. 306, 2003, pp. 756-766.

Kato, T. et al. "Efficient Replication of the Genotype 2a Hepatitis C Virus Subgenomic Replicon," Gastroenterology, vol. 125, 2003, pp. 1808-1817.

Kato, T. et al. "Sequence Analysis of Hepatitis C Virus Isolated From a Fulminant Hepatitis Patient," Journal of Medical Virology, vol. 64, 2001, pp. 334-339.

Lohmann, V. et al. "Replication of Subgenomic Hepatitis C Virus RNAs in a Hepatoma Cell Line," Science, vol. 285, 1999, pp. 110-113.

Mori, S. et al. "A New Type of Hepatitis C Virus in Patients in Thailand," Biochemical and Biophysical Research Communications, vol. 183, No. 1, 1992, pp. 334-342.

Okamoto, H. et al. "Typing hepatitis C virus by polymerase chain reaction with type-specific primers: application to clinical surveys and tracing infectious sources," Journal of General Virology, vol. 73, 1992, pp. 673-679.

Pietschmann, T. et al. "Production of Infectious Genotype 1b Virus Particles in Cell Culture and Impairment by Replication Enhancing Mutations," PLoS Pathogens, 2009, vol. 5: e1000475.

Simmonds, P. et al. "A Proposed System for the Nomenclature of Hepatitis C Viral Genotypes," Hepatology, vol. 19, 1994, pp. 1321-1324.

Wakita, T. et al. "Production of infectious hepatitis C virus in tissue culture from a cloned viral genome," Nature Medicine, vol. 11, No. 7, 2005, pp. 791-796.

Yoshioka, K. et al. "Detection of Hepatitis C Virus by Polymerase Chain Reaction and Response to Interferon-alpha Therapy: Relationship to Genotypes of Hepatitis C Virus," Hepatology, vol. 16, No. 2, 1992, pp. 293-299.

Search Report dated Nov. 18, 2014 for European Application No. 12765083.6.

* cited by examiner

Fig. 7

SEQUENCE LISTING

```
<160> NUMBER OF SEQ ID NOS: 52

<210> SEQ ID NO 1
<211> LENGTH: 9607
<212> TYPE: DNA
<213> ORGANISM: hepatitis C virus

<400> SEQUENCE: 1
gccagccccc tgatgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gattaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcat catgagcaca aatcctaaac     360
ctcaaagaaa aaccacacgt aacaccaacc gccgcccaca ggacgtcaag ttcccgggcg     420
gtggtcagat cgttggtgga gtttacctgt tgccgcgcag gggccccagg ttgggtgtgc     480
gcgcgactag gaagacttcc gagcggtcgc aacctcgtgg aaggcgacaa cctatcccca     540
aggctcgccg gcccgagggc agggcctggg ctcagcccgg gtaccttgg cccctctatg     600 gcaatgaggg tctggggtgg gcaggatggc tcctgtcacc ccgcggatcc cggcctagtt     660
ggggccccac ggaccccgg cgtaggtcgc gtaatttggg taaggtcatc gataccctca     720
catgcggctt cgccgacctc atggggtaca ttccgctcgt cggcgccccc ttaggaggcg     780
ctgccagggc cctggcgcat ggcgtccggg tgctggagga cggcgtgaac tacgcaacag     840
ggaatctgcc cggttgctct ttctctatct tcctcttggc tttgctgtcc tgtctgacca     900
ttccagctgc cgcttatgaa gtgcgcaacg tgtccggggt gtaccatgtc acgaacgact     960
gctccaactc aagtattgtg tatgaggcag cggacatgat catgcacacc cctgggtgcg    1020
tgccctgcgt ccgggagggc aattcctccc gctgctgggt ggcgctcact cccacgctcg    1080
cggccaggaa cagtagcatc cccactacga cgattcgacg ccacgtcgac ttgctcgttg    1140
gggcggccgc tctctgctcc gttgtgtacg tggggatct ctgcgatct gtcttcctcg    1200 tctcccagct gttcacccttc tcacctcgcc agtatgagac ggtacaggac tgcaattgct    1260
cactctatcc cggccacgta tcaggtcacc gcatggcttg ggatatgatg atgaactggt    1320
cgcccacgac agccttggtg gtgtcgcagt tactccggat cccacaagcc atcgtggaca    1380
tggtgtcggg ggcccactgg ggagtcctgg cgggccttgc ctactattcc atggtgggga    1440
actgggccaa ggtcttgatt gtgatgctac tctttgccgg cgttgacggg gacacctaca    1500 cgacagggg ggtagcaagc cgcaccaccg cgggccttgc gtccctcttt gatcagggc    1560
```

```
cgtcccagaa aatccagctc ataaacacca acggcagctg gcacatcaac aggactgccc    1620
taaattgcaa tgactccctc aacactgggt tccttgccgc gctgttctac gtaaacaggt    1680
tcaactcgtc cggctgccca gagcgcatgg ccagctgccg ccccattgat aagttcgctc    1740
aggggtgggg tcccatcacc cacgctgtgc ctcgcgcctc agaccagagg ccttattgct    1800
ggcactacgc gccccaaccg tgcggtattg tacccgcgtc gcaggtgtgt ggtccagtgt    1860
actgcttcac cccgagccct gttgtggtgg ggacgactga tcgctccggc gccccacgt    1920 acacctgggg ggagaatgag acggacgtgc tgatccttaa caacacgcgg ccgccgcacg    1980
gcaactggtt cggctgctca tggatgaata gcaccgggtt caccaagacg tgtgggggcc    2040
ccccgtgcaa catcgggggg gtcggcaata acaccttgac ctgccccacg gattgcttcc    2100
ggaagcaccc cgaggccact tacaccaaat gcggctcggg gccttggttg acacctaggt    2160
gtatggttga ctaccatac aggctttggc attacccctg cactgtcaac tataccatct    2220
tcaaggtcag gatgtatgtg gggggtgtgg agcaccggct caatgccgcg tgcaactgga    2280
cccgagggga gcgttgtgat ctggaggaca gggatagatc agagctcagc ccgctgctac    2340
tgtccacgac agagtggcag atactgcct gttccttcac caccctaccg gctctgtcca    2400
ccggtttaat ccacctccat cagaaacatcg tggacgtaca ataacctgtac ggtgtagggt    2460 cagtggttgt ctctattgtg atcagatggg agtacgtcgt gctgctcttc cttcttctgg    2520
cggacgcgcg cgtctgcgcc tgcttatgga tgatgctgct gatagcccag gctgaggccg    2580
ccttagagaa cctggtggcc ctcaatgcag cgtccgtggc tggagcgcat ggcatcctct    2640
ccttccttgc gttcttctgt gctgcctggt acatcaaagg caagctggtt cctggggcgg    2700
catatgctct ttacagtgtg tggccgctac tcctgctcct gctggcgttg ccgccacggg    2760
catacgccat ggaccgggag atggctgcat cgtgtggagg cgcggtcttc gtaggtctgg    2820
tactcctgac cttgtcacca cactacaaag cactcctcgc caggctcata tggtggttac    2880
aatatcttac caccagggcc gaggcgctcc tgcaagtgtg atccccccc ctcaacgtcc    2940 gggggggccg cgatgccatc atcctcctca cgtgcatggt ccacccagag ctaacttttg    3000
aaatcaccaa aatcttgctc gccatactgg gcccgctcat ggtgctccgg gcaggcctaa    3060
ctagagtgcc gtacttcgtg cgcgctcacg ggctcattcg tgcgtgcatg ctggtgcgga    3120
aagtcgctgg gggccattat gtccagatgg ctctcatgaa gctggccgcg ctgacaggca    3180
cgtacgttta cgaccatctt acccccgctgc gggactgggc ccacgcgggc ctgcgagacc    3240
ttgcggtggc ggttgagccc gttgttttct ctgacacgga gaccaagatt atcacctggg    3300
gggcagacac cgcggcgtgt ggggacatca tcctgggtct acccgtctcc gcccggaggg    3360
ggagggagat acttctagga ccggccgata agtttggaga gcaggggtgg cgactccttg    3420
cacccattac ggcctactcc caacagacgc ggggcgtact tggctgtatc atcactagcc    3480
tcacaggtcg ggacaagaac caggtcgagg ggaggttca ggtggtttcc accgcaacgc    3540
agtccttctt ggcaacctgc gtcaatggcg tgtgttggac cgtctaccat ggcgccggct    3600
caaagaccct agccggcccg aagggaccga tcacccaaat gtacaccaat gttgaccagg    3660
acctcgtcgg ctgcaggcg ccccccgggg cgcgctccat gacaccgtgc acctgcggca    3720
gctcggacct tttttttggtc acgaggcatg ctgatgtcat tccggtgcgc cggcggggtg    3780
acagcagagg agccctactt tcccccaggc ccgtctctta cctgaagggc tcctcgggtg    3840
gtccactgct ttgcccctcg gggcacgttg tgggcatctt ccgggctgcc gtgtgcaccc    3900 gggggggtcgc gaaggcggtg gatttttatac ccgttgagtc catggaaacc accatgcggt    3960
```

```
ctccggtctt cacgcgataat tcatctcccc cggccgtacc gcagacattc caagtggccc    4020
atctgcacgc tcccactggc agcggcaaga gcactaaagt gccggctgca tacgcagccc    4080
aggggtacaa ggtgctcgtc ctgaacccgt ccgttgccgc caccttgagt tttgggggcgt    4140 atatgtccaa ggcatatgga gttgacccta acatcagaac cggggtgagg accatcacta    4200
ctggcgctcc catcacgtac tccacctacg gcaagttcct tgccgacggc ggttgctctg    4260
ggggcgccta tgcatcata atatgtgatg agtgccactc aactgactca actactattt    4320
tgggcattgg cacagtcctg gaccaagcgg agacagctgg agcgcggctc gtcgtgctcg    4380
ccaccgctac gccgccagga tcagtcaccg taccacaccc caacatcgag gaggtggcct    4440
tgtccaatac tggagagatt cccttctatg gcaaagccat cccctcgag accatcaagg    4500 gggggaggca cctcatttc tgccactcca agaagaagtg tgatgagctt gctgcaaagc    4560
tgtcggccct tgggctcaat gctgtagcgt actaccgggg tcttgacgtg tccatcatac    4620
caacaagcgg agacgtcgtt gttgtggcaa cagacgctct aatgacgggc tacaccggtg    4680
attttgactc agtgatcgac tgcaatacat gtgtcaccca gacagtcgac ttcagcttcg    4740
accccacctt cgccattgag acgacgacca tgccccaaga cgcggtgtcg cgctcacagc    4800
ggcgaggcag gactggcagg ggcagaggag gcatatacag gtttgtgact ccaggagaac    4860
ggccctcagg catgttcgat tctgcgatcc tgtgtgaatg ctatgacgcg ggctgtgctt    4920
ggtacgagct cacgcccgcc gagaccacag ttaggttgcg ggcttaccta aatacaccag    4980
ggttgcccgt ctgccaggac catctggagt tttgggaggg cgtcttcaca ggcctcaccc    5040
acatagatgc ccacttcttg tcccagacca agcaggcagg agacaacttc ccctacctgg    5100
tggcatacca agctcagtg tgcgccaggg cccaggctcc acctccatcg tgggatcaaa    5160
tgtggaagtg tctcatacgg ctgaagccta cgctgcacgg gccaacaccc ttgttgtata    5220
ggctaggagc cgtccaaaac gaggtcaccc tcacacatcc cataaccaaa tacatcatga    5280
catgcatgtc ggccgacctg gaggtcgtca ctagcacctg ggtgctagta ggcggggtcc    5340
ttgcagccct ggccgcgtac tgcctgacaa cgggcagcgt ggtcatcgtg gcagggtca    5400 tcttgtccgg aaggccggcc atcattcccg acagggaagt tctctaccgg gagttcgatg    5460
aaatggaaga gtgcgcctcg catctcccct catatgaaca aggcatgcaa ctcgccgagc    5520
aattcaagca gaaggcgctc gggctgctgc aaacagccac caagcaagcg gaggccgctg    5580
ctcccgtggt ggagtccaag tggcgagccc ttgaggcctt ctgggcgaag cacatgtgga    5640
atttcatcag cgggatacag tatctagcag gcttgtcaac tctgcctggg aaccccgcga    5700
tagcatcatt gatggcattc acagcctcca tcaccagccc gctcaccacc aacataccc    5760 ttctgtttaa catcttgggg gggtgggtgg ccgcccaact tgcccccccc ggcgctgctt    5820
cagctttcgt gggcgccggc attgctggcg cggctgttgg cagcataggt cttgggaagg    5880
tgctcgtgga catcctggcg ggttatgggg cagggggtgc aggcgcactc gtggccttta    5940
aggtcatgag cggcgaaatg ccctccaccg aggacctggt caacttactc cctgccatcc    6000
tctctcctgg tgccctggtc gtcggggtcg tgtgcgcagc aatactgcgt cggcatgtgg    6060
gcccagggga gggggctgtg cagtggatga accggctcga tcgttcgct tcgcggggta    6120 accacgtctc ccccacgcac tatgtgcctg agagcgacgc agcagcgcgt gtcacccaga    6180
tcctctccag ccttaccatt actcagctgc taaagaggct ccaccagtgg attaatgaag    6240
attgctccac gccatgctcc ggctcgtggc tcagggatgt ttgggactgg atatgcacgg    6300
```

```
tgttgaccga tttcaaaacc tggctccaat ccaagctcct gccgcggttg ccgggagtcc    6360
ctttcctttc atgtcagcgc gggtacaagg gggtttggcg gggagacggc attatgcaca    6420
ctacctgccc gtgcggagca cagatcagtg acatgtcaa gaacggttcc atgaggatcg     6480
ttgggcctaa gacctgtagc aacacgtggt gcgggacgtt ccccatcaac gcgtacacca    6540
caggcccctg cacaccctcc ccggcgccaa actactccag ggcgttgtgg cgggtggctg    6600
ctgaggagta tgtggaggtt acgcgggtgg gggatttcca ctacgtgacg ggcatgacca    6660
ctgacaactt aaaatgccca tgccaggtcc cggcccctga attctttacg gaagtggatg    6720
gggtgcggct gcacaggtac gctcctgcgt gcaaacctct cctacgggat gaggtcacat    6780
tccaggtcgg gctcaaccaa ttcccggtcg ggtcacagct tccatgtgaa cccgagccgg    6840
atgtgacagt gctcacttcc atgctcaccg accccctcca cattacggca gagacggcta    6900
agcgcaggct ggcccgaggg tccccccccct ctttggccag ctcttcagct agtcagttgt    6960
ctgcggtctc cttgaaggcg gcatgcacca cccgtcataa ccccccagac gccgacctca    7020
tcgaggccaa tctcctgtgg cggcaggaga tgggcgggag catcacccgc gtggagtcag    7080
agagtaaggt ggtaatccta gactcatttg aaccgcttcg agcggaggag gatgagaggg    7140
aagtatccgt gccggcggag attctgcgga aaaccaagaa attccccgcg gcaatgcctg    7200
tatgggcacg cccggactac aacccaccac tcttagagtc ttggagggac ccagactacg    7260
ttcctccggt ggtacacggg tgcccattgc cacctaccaa ggcccctcca ataccccctc    7320
cacggagaaa gaggacggtt attctgacag aatccaccgt gtcctctgcc ctggcggaac    7380
ttgccacaaa gaccttcggc agctccggat cgtcggccgt tgacaacggc acggcgaccg    7440
cccctcctga ccagccctcc attgacggag acgcaggatc agacgttgag tcgtactcct    7500
ccatgccccc ccttgaggga gagccggggg accccgatct cagcgacggg tcttggtcta    7560
ctgtgagcga ggaggctggc gaggacgttg tctgctgctc gatgtcctat acatggacag    7620
gcgccttaat cacaccatgc gccgcagagg agagcaagct gcccatcaac gcgttgagca    7680
attctttgct gcgtcaccac aacatggtct atgccacaac atcccgcagc gcaagccaac    7740
ggcagaagaa ggtcaccttt gacagactgc aagtcctgga cgaccattac cgggacgtgc    7800
tcaaggagat gaaggcgaag gcgtccacag ttaaggctaa acttctatct gtagaagaag    7860
cctgtaggct gacgcccca cattcggcca gatccaaatt tggctatggg caaaggacg     7920 tccggaacct atccagcaag gccgtcaacc acatccactc cgtgtggaag gacttgctgg    7980
aagacactga gacaccaatt gacaccacca tcatggcaaa aaatgaggtc ttttgtgttc    8040
aaccagagaa gggaggccgc aagccagctc gtcttatcgt attcccagac ttgggagttc    8100
gtgtatgcga gaagatggcc ctctacgatg tggtttccac cctccctcag gccgtgatgg    8160
gctcctcata cggattccaa tactctcctg gacagcgggt cgagttcctg gtgaatgcct    8220
ggaagtcaaa gaagaaccct atgggcttcg cgtatgacac ccgctgcttt gactcaacag    8280
tcactgagag tgacatccgt gttgaggagt caatttacca atgttgtgac ttggctcccg    8340
aggccagaca ggtcataagg tcgctcacgg agcggcttta tatcggggc cccctgacta    8400 attcaaaagg gcagaactgc ggttaccgcc ggtgccgcgc cagcggcgtg ctgacgacta    8460
gctgcggcaa caccctcaca tgttacttga aggcttctgc agcctgtcga gctgcaaagc    8520
tccaggactg cacgatgctc gtgtgcggag acgaccttgt cgttatctgt gagagcgcgg    8580
gaacccagga ggacgcggcg agcctacgag tcttcacgga ggctatgact aggtactctg    8640
cccccccggg ggacccgccc caaccggaat acgacttgga gttgataaca tcatgctcct    8700
```

-continued

```
ccaacgtgtc ggtcgcgcac gatgcatccg gcaagcgggt gtactacctg acccgcgacc    8760
ccaccacccc cctcgcacgg gctgcgtggg agacagcaag acacactcca gttaactcct    8820
ggttaggcaa catcatcatg tatgcgccca ccttatgggc aaggatgatt ctgatgaccc    8880
acttcttttc catccttcta gctcaggagc aacttgaaaa agccctagat tgccagatct    8940
acggggccac ttactccatt gaaccacttg acctacctca gatcattcag cgactccacg    9000
gtcttagcgc attttcactc catagttact ctccaggtga gatcaatagg gtggcttcat    9060
gcctcagaaa acttggggta ccgcccttgc gagtctggag acatcgggcc agaagtgtcc    9120
gcgctaagtt actgtcccag ggagggaggg ctgccatttg tggcaagtac ctctttaact    9180
gggctgtaag gaccaagctc aaactcactc caattccggc tgcgtcccag ttggacttgt    9240
ccagctggtt cattgctggt tacagcgggg agagacatata tcacagcctg tctcgtgccc    9300
gaccccgctg gttcatgtgg tgcctactcc tactttctgt aggggtaggc atctacctgc    9360
tccccaatcg atgaacgggg ggctagtcac tccaggccaa taggccattc tgttttttttt   9420
tttttttttt tttttttttt tttttttttt tttttttttt tttttttttt tttttttttc    9480
cttttttcttc ttccttttct tctttctttg gtggctccat cttagcccta gtcacggcta    9540
gctgtgaaag gtccgtgagc cgcatgactg cagagagtgc tgatactggc ctctctgcag    9600
atcatgt                                                              9607

<210> SEQ ID NO 2
<211> LENGTH: 341
<212> TYPE: DNA
<213> ORGANISM: hepatitis C virus

<400> SEQUENCE: 2
gccagccccc tgatggggc gacactccac catagatcac tcccctgtga ggaactactg       60
tcttcacgca gaaagcgtct agccatggcg ttagtatgag tgtcgtgcag cctccaggac      120
cccccctccc gggagagcca tagtggtctg cggaaccggt gagtacaccg gaattgccag      180
gacgaccggg tccttttcttg gattaacccg ctcaatgcct ggagatttgg gcgtgccccc      240
gcgagactgc tagccgagta gtgttgggtc gcgaaaggcc ttgtggtact gcctgatagg      300
gtgcttgcga gtgccccggg aggtctcgta gaccgtgcat c                         341

<210> SEQ ID NO 3
<211> LENGTH: 573
<212> TYPE: DNA
<213> ORGANISM: hepatitis C virus

<400> SEQUENCE: 3
atgagcacaa atcctaaacc tcaaagaaaa accacacgta acaccaaccg ccgcccacag        60
gacgtcaagt tcccgggcgg tggtcagatc gttggtggag tttacctgtt gccgcgcagg      120
ggccccaggt tgggtgtgcg cgcgactagg aagacttccg agcggtcgca acctcgtgga      180
aggcgacaac ctatccccaa ggctcgccgg cccgagggca gggcctgggc tcagcccggg      240
taccccttggc ccctctatgg caatgagggt ctggggtggg caggatggct cctgtcaccc      300
cgcggatccc ggcctagttg gggccccacg gaccccggc gtaggtcgcg taatttgggt      360
aaggtcatcg ataccctcac atgcggcttc gccgacctca tggggtacat tccgctcgtc      420
ggcgcccct taggaggcgc tgccaggcc ctggcgcatg cgtccgggt gctgaggac      480
ggcgtgaact acgcaacagg gaatctgccc ggttgctctt tctctatctt cctcttggct      540
```

```
ttgctgtcct gtctgaccat tccagctgcc gct                                573
```

```
<210> SEQ ID NO 4
<211> LENGTH: 576
<212> TYPE: DNA
<213> ORGANISM: hepatitis C virus

<400> SEQUENCE: 4
tatgaagtgc gcaacgtgtc cggggtgtac catgtcacga acgactgctc caactcaagt     60
attgtgtatg aggcagcgga catgatcatg cacacccctg gtgcgtgcc ctgcgtccgg     120 gagggcaatt cctcccgctg ctgggtggcg ctcactccca cgctcgcggc caggaacagt    180
agcatcccca ctacgacgat tcgacgccac gtcgacttgc tcgttggggc ggccgctctc    240
tgctccgttg tgtacgtggg ggatctctgc ggatctgtct tcctcgtctc ccagctgttc    300
accttctcac ctcgccagta tgagacggta caggactgca attgctcact ctatcccggc    360
cacgtatcag gtcaccgcat ggcttgggat atgatgatga actggtcgcc cacgacagcc    420
ttggtggtgt cgcagttact ccggatccca caagccatcg tggacatggt gtcggggcc    480 cactggggag tcctggcggg ccttgcctac tattccatgg tggggaactg gccaaggtc    540 ttgattgtga tgctactctt tgccggcgtt gacggg                              576
```

```
<210> SEQ ID NO 5
<211> LENGTH: 1089
<212> TYPE: DNA
<213> ORGANISM: hepatitis C virus

<400> SEQUENCE: 5
gacacctaca cgacaggggg ggtagcaagc cgcaccaccg cgggccttgc gtccctcttt     60
gtatcagggc cgtcccagaa aatccagctc ataaacacca cggcagctg cacatcaac     120 aggactgccc taaattgcaa tgactccctc aacactgggt tccttgccgc gctgttctac    180
gtaaacaggt tcaactcgtc cggctgccca gagcgcatgg ccagctgccg ccccattgat    240
aagttcgctc aggggtgggg tcccatcacc cacgctgtgc ctcgcgcctc agaccagagg    300
ccttattgct ggcactacgc gccccaaccg tgcggtattg tacccgcgtc gcaggtgtgt    360
ggtccagtgt actgcttcac cccgagccct gttgtggtgg ggacgactga tcgctccggc    420
gcccccacgt acacctgggg ggagaatgag acggacgtgc tgatccttaa caacacgcgg    480
ccgccgcacg gcaactggtt cggctgctca tggatgaata gcaccgggtt caccaagacg    540
tgtgggggcc cccgtgcaa catcgggggg gtcggcaata acaccttgac ctgccccacg    600
gattgcttcc ggaagcaccc cgaggccact tacaccaaat gcggctcggg gccttggttg    660
acacctaggt gtatggttga ctacccatac aggctttggc attacccctg cactgtcaac    720
tataccatct tcaaggtcag gatgtatgtg gggggtgtgg agcaccggct caatgccgcg    780
tgcaactgga cccagggga gcgttgtgat ctggaggaca gggatagatc agagctcagc    840
ccgctgctac tgtccacgac agagtggcag atactgccct gttccttcac cacccctaccg    900 gctctgtcca ccggtttaat ccacctccat cagaacatcg tggacgtaca atacctgtac    960
ggtgtagggt cagtggttgt ctctattgtg atcagatggg agtacgtcgt gctgctcttc    1020
cttcttctgg cggacgcgcg cgtctgcgcc tgcttatgga tgatgctgct gatagcccag    1080
gctgaggcc                                                            1089
```

```
<210> SEQ ID NO 6
<211> LENGTH: 189
```

<212> TYPE: DNA
<213> ORGANISM: hepatitis C virus

<400> SEQUENCE: 6
gccttagaga acctggtggc cctcaatgca gcgtccgtgg ctggagcgca tggcatcctc 60
tccttccttg cgttcttctg tgctgcctgg tacatcaaag gcaagctggt tcctggggcg 120
gcatatgctc tttacagtgt gtggccgcta ctcctgctcc tgctggcgtt gccgccacgg 180
gcatacgcc 189

<210> SEQ ID NO 7
<211> LENGTH: 651
<212> TYPE: DNA
<213> ORGANISM: hepatitis C virus

<400> SEQUENCE: 7
atggaccggg agatggctgc atcgtgtgga ggcgcggtct tcgtaggtct ggtactcctg 60
accttgtcac cacactacaa agcactcctc gccaggctca tatggtggtt acaatatctt 120
accaccaggg ccgaggcgct cctgcaagtg tggatccccc ccctcaacgt ccgggggggc 180
cgcgatgcca tcatcctcct cacgtgcatg gtccacccag agctaacttt tgaaatcacc 240
aaaatcttgc tcgccatact gggcccgctc atggtgctcc gggcaggcct aactagagtg 300
ccgtacttcg tgcgcgctca cgggctcatt cgtgcgtgca tgctggtgcg gaaagtcgct 360
gggggccatt atgtccagat ggctctcatg aagctggccg cgctgacagg cacgtacgtt 420
tacgaccatc ttaccccgct gcgggactgg gcccacgcgg gcctgcgaga ccttgcggtg 480
gcggttgagc ccgttgtttt ctctgacacg gagaccaaga ttatcacctg gggggcagac 540
accgcggcgt gtggggacat catcctgggt ctacccgtct ccgcccggag ggggagggag 600
atacttctag gaccggccga taagtttgga gagcaggggt ggcgactcct t 651

<210> SEQ ID NO 8
<211> LENGTH: 1893
<212> TYPE: DNA
<213> ORGANISM: hepatitis C virus

<400> SEQUENCE: 8
gcacccatta cggcctactc ccaacagacg cggggcgtac ttggctgtat catcactagc 60
ctcacaggtc gggacaagaa ccaggtcgag ggggaggttc aggtggtttc caccgcaacg 120
cagtccttct tggcaacctg cgtcaatggc gtgtgttgga ccgtctacca tggcgccggc 180
tcaaagaccc tagccggccc gaagggaccg atcacccaaa tgtacaccaa tgttgaccag 240
gacctcgtcg gctggcaggc gccccccggg gcgcgctcca tgacaccgtg cacctgcggc 300
agctcggacc ttttttggt cacgaggcat gctgatgtca ttccggtgcg ccggcggggt 360
gacagcagag gagccctact ttcccccagg cccgtctctt acctgaaggg ctcctcgggt 420
ggtccactgc tttgcccctc ggggcacgtt gtgggcatct tccgggctgc cgtgtgcacc 480
cggggggtcg cgaaggcggt ggattttata cccgttgagt ccatggaaac caccatgcgg 540
tctccggtct tcacggataa ttcatctccc ccggccgtac cgcagacatt ccaagtggcc 600
catctgcacg ctcccactgg cagcggcaag agcactaaag tgccggctgc atacgcagcc 660
caggggtaca aggtgctcgt cctgaacccg tccgttgccg ccaccttgag ttttggggcg 720
tatatgtcca aggcatatgg agttgaccct aacatcagaa ccggggtgag gaccatcact 780
actggcgctc ccatcacgta ctccacctac ggcaagttcc ttgccgacgg cggttgctct 840

```
ggggcgcct atgacatcat aatatgtgat gagtgccact caactgactc aactactatt    900
ttgggcattg gcacagtcct ggaccaagcg gagacagctg gagcgcggct cgtcgtgctc    960
gccaccgcta cgccgccagg atcagtcacc gtaccacacc ccaacatcga ggaggtggcc   1020
ttgtccaata ctggagagat tcccttctat ggcaaagcca tcccctcga gaccatcaag    1080
ggggggaggc acctcatttt ctgccactcc aagaagaagt gtgatgagct tgctgcaaag   1140
ctgtcggccc ttgggctcaa tgctgtagcg tactaccggg gtcttgacgt gtccatcata   1200
ccaacaagcg gagacgtcgt tgttgtggca acagacgctc taatgacggg ctacaccggt   1260
gattttgact cagtgatcga ctgcaataca tgtgtcaccc agacagtcga cttcagcttc   1320
gaccccacct tcgccattga gacgacgacc atgccccaag acgcggtgtc gcgctcacag   1380
cggcgaggca ggactggcag gggcagagga ggcatataca ggtttgtgac tccaggagaa   1440
cggccctcag gcatgttcga ttctgcgatc ctgtgtgaat gctatgacgc gggctgtgct   1500
tggtacgagc tcacgcccgc cgagaccaca gttaggttgc gggcttacct aaatacacca   1560
ggggttgcccg tctgccagga ccatctggag ttttgggagg cgtcttcac aggcctcacc    1620
cacatagatg cccacttctt gtcccagacc aagcaggcag gagacaactt cccctacctg   1680
gtggcatacc aagctacagt gtgcgccagg gcccaggctc cacctccatc gtgggatcaa   1740
atgtggaagt gtctcatacg gctgaagcct acgctgcacg gccaacacc cttgttgtat    1800
aggctaggag ccgtccaaaa cgaggtcacc ctcacacatc ccataaccaa atacatcatg   1860
acatgcatgt cggccgacct ggaggtcgtc act                                1893

<210> SEQ ID NO 9
<211> LENGTH: 162
<212> TYPE: DNA
<213> ORGANISM: hepatitis C virus

<400> SEQUENCE: 9
agcacctggg tgctagtagg cgggtccctt gcagccctgg ccgcgtactg cctgacaacg     60
ggcagcgtgg tcatcgtggg cagggtcatc ttgtccggaa ggccggccat cattcccgac    120
agggaagttc tctaccggga gttcgatgaa atggaagagt gc                       162

<210> SEQ ID NO 10
<211> LENGTH: 783
<212> TYPE: DNA
<213> ORGANISM: hepatitis C virus

<400> SEQUENCE: 10
gcctcgcatc tcccctacat cgaacaaggc atgcaactcg ccgagcaatt caagcagaag     60
gcgctcgggc tgctgcaaac agccaccaag caagcggagg ccgctgctcc cgtggtggag    120
tccaagtggc gagcccttga ggccttctgg gcgaagcaca tgtggaattt catcagcggg    180
atacagtatc tagcaggctt gtcaactctg cctgggaacc ccgcgatagc atcattgatg    240
gcattcacag cctccatcac cagcccgctc accacccaac taccccttct gtttaacatc    300
ttggggggt gggtggccgc ccaacttgcc ccccccggcg ctgcttcagc tttcgtgggc    360
gccggcattg ctggcgcggc tgttggcagc ataggtcttg gaaggtgct cgtggacatc    420
ctggcgggtt atggggcagg ggtggcaggc gcactcgtgg cctttaaggt catgagcggc    480
gaaatgccct ccaccgagga cctggtcaac ttactccctg ccatcctctc tcctggtgcc    540
ctggtcgtcg ggtcgtgtg cgcagcaata ctgcgtcggc atgtgggccc aggggagggg    600
gctgtgcagt ggatgaaccg gctgatagcg ttcgcttcgc ggggtaacca cgtctccccc    660
```

```
acgcactatg tgcctgagag cgacgcagca gcgcgtgtca cccagatcct ctccagcctt    720
accattactc agctgctaaa gaggctccac cagtggatta atgaagattg ctccacgcca    780
tgc                                                                 783
```

<210> SEQ ID NO 11
<211> LENGTH: 1341
<212> TYPE: DNA
<213> ORGANISM: hepatitis C virus

<400> SEQUENCE: 11

```
tccggctcgt ggctcaggga tgtttgggac tggatatgca cggtgttgac cgatttcaaa     60
acctggctcc aatccaagct cctgccgcgg ttgccgggag tccctttcct ttcatgtcag    120
cgcgggtaca aggggtttg gcggggagac ggcattatgc acactacctg cccgtgcgga     180
gcacagatca gtggacatgt caagaacggt tccatgagga tcgttgggcc taagacctgt    240
agcaacacgt ggtgcgggac gttccccatc aacgcgtaca ccacaggccc ctgcacaccc    300
tccccggcgc caaactactc cagggcgttg tggcggtgg ctgctgagga gtatgtggag    360
gttacgcggg tgggggattt ccactacgtg acgggcatga ccactgacaa cttaaaatgc    420
ccatgccagg tcccggcccc tgaattcttt acggaagtgg atggggtgcg gctgcacagg    480
tacgctcctg cgtgcaaacc tctcctacg gatgaggtca cattccaggt cgggctcaac    540
caattcccgg tcgggtcaca gcttccatgt gaacccgagc cggatgtgac agtgctcact    600
tccatgctca ccgaccccctc ccacattacg gcagagacgg ctaagcgcag gctggcccga    660
gggtcccccc cctctttggc cagctcttca gctagtcagt tgtctgcggt ctccttgaag    720
gcggcatgca ccacccgtca taccccccca gacgccgacc tcatcgaggc caatctcctg    780
tggcggcagg agatgggcgg gagcatcacc cgcgtggagt cagagagtaa ggtggtaatc    840
ctagactcat ttgaaccgct tcgagcggag gaggatgaga gggaagtatc cgtgccggcg    900
gagattctgc ggaaaaccaa gaaattcccc gcggcaatgc ctgtatgggc acgcccggac    960
tacaacccac cactcttaga gtcttggagg gacccagact acgttcctcc ggtggtacac   1020
gggtgcccat tgccacctac caaggcccct ccaataccc ctccacggag aaagaggacg   1080
gttattctga cagaatccac cgtgtcctct gccctggcgg aacttgccac aaagaccttc   1140
ggcagctccg gatcgtcggc cgttgacaac ggcacggcga ccgcccctcc tgaccagccc   1200
tccattgacg gagacgcagg atcagacgtt gagtcgtact cctccatgcc ccccccttgag   1260
ggagagccgg ggaccccga tctcagcgac gggtcttggt ctactgtgag cgaggaggct   1320
ggcgaggacg ttgtctgctg c                                            1341
```

<210> SEQ ID NO 12
<211> LENGTH: 1776
<212> TYPE: DNA
<213> ORGANISM: hepatitis C virus

<400> SEQUENCE: 12

```
tcgatgtcct atacatggac aggcgcctta atcacaccat gcgccgcaga ggagagcaag     60
ctgcccatca cgcgttgag caattctttg ctgcgtcacc acaacatggt ctatgccaca    120
acatcccgca gcgcaagcca acggcagaag aagtcaccct ttgacagact gcaagtcctg    180
gacgaccatt accgggacgt gctcaaggag atgaaggcga aggcgtccac agttaaggct    240
aaacttctat ctgtagaaga agcctgtagg ctgacgcccc cacattcggc cagatccaaa    300
```

```
tttggctatg gggcaaagga cgtccggaac ctatccagca aggccgtcaa ccacatccac    360
tccgtgtgga aggacttgct ggaagacact gagacaccaa ttgacaccac catcatggca    420
aaaaatgagg tcttttgtgt tcaaccagag aagggaggcc gcaagccagc tcgtcttatc    480
gtattcccag acttgggagt tcgtgtatgc gagaagatgg ccctctacga tgtggtttcc    540
accctccctc aggccgtgat gggctcctca tacggattcc aatactctcc tggacagcgg    600
gtcgagttcc tggtgaatgc ctggaagtca agaagaacc ctatgggctt cgcgtatgac    660
acccgctgct ttgactcaac agtcactgag agtgacatcc gtgttgagga gtcaatttac    720
caatgttgtg acttggctcc cgaggccaga caggtcataa ggtcgctcac ggagcggctt    780
tatatcgggg gccccctgac taattcaaaa gggcagaact gcggttaccg ccggtgccgc    840
gccagcggcg tgctgacgac tagctgcggc aacacccctca catgttactt gaaggcttct    900
gcagcctgtc gagctgcaaa gctccaggac tgcacgatgc tcgtgtgcgg agacgacctt    960
gtcgttatct gtgagagcgc gggaacccag gaggacgcgg cgagcctacg agtcttcacg   1020
gaggctatga ctaggtactc tgcccccccc ggggacccgc cccaaccgga atacgacttg   1080
gagttgataa catcatgctc ctccaacgtg tcggtcgcgc acgatgcatc cggcaagcgg   1140
gtgtactacc tgacccgcga ccccaccacc cccctcgcac gggctgcgtg ggagacagca   1200
agacacactc cagttaactc ctggttaggc aacatcatca tgtatgcgcc caccttatgg   1260
gcaaggatga ttctgatgac ccacttcttt tccatccttc tagctcagga gcaacttgaa   1320
aaagccctag attgccagat ctacggggcc acttactcca ttgaaccact tgacctacct   1380
cagatcattc agcgactcca cggtcttagc gcatttttcac tccatagtta ctctccaggt   1440
gagatcaata gggtggcttc atgcctcaga aaacttgggg taccgccctt gcgagtctgg   1500
agacatcggg ccagaagtgt ccgcgctaag ttactgtccc agggagggag ggctgccatt   1560
tgtggcaagt acctctttaa ctgggctgta aggaccaagc tcaaactcac tccaattccg   1620
gctgcgtccc agttggactt gtccagctgg ttcattgctg gttacagcgg gggagacata   1680
tatcacagcc tgtctcgtgc ccgaccccgc tggttcatgt ggtgcctact cctactttct   1740
gtaggggtag gcatctacct gctccccaat cgatga                             1776

<210> SEQ ID NO 13
<211> LENGTH: 233
<212> TYPE: DNA
<213> ORGANISM: hepatitis C virus

<400> SEQUENCE: 13 acgggggggct agtcactcca ggccaatagg ccattctgtt ttttttttt tttttttttt     60 tttttttttt tttttttttt tttttttttt tttttttttt tttttccttt tcttcttcc    120 ttttcttctt tctttggtgg ctccatctta gccctagtca cggctagctg tgaaaggtcc    180
gtgagccgca tgactgcaga gagtgctgat actggcctct ctgcagatca tgt           233

<210> SEQ ID NO 14
<211> LENGTH: 3010
<212> TYPE: PRT
<213> ORGANISM: hepatitis C virus

<400> SEQUENCE: 14

Met Ser Thr Asn Pro Lys Pro Gln Arg Lys Thr Thr Arg Asn Thr Asn
1               5                   10                  15

Arg Arg Pro Gln Asp Val Lys Phe Pro Gly Gly Gly Gln Ile Val Gly
                20                  25                  30
```

```
Gly Val Tyr Leu Leu Pro Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
                130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ala Ala Tyr
                180                 185                 190

Glu Val Arg Asn Val Ser Gly Val Tyr His Val Thr Asn Asp Cys Ser
                195                 200                 205

Asn Ser Ser Ile Val Tyr Glu Ala Ala Asp Met Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ser Ser Ile Pro Thr Thr
                245                 250                 255

Thr Ile Arg Arg His Val Asp Leu Leu Val Gly Ala Ala Ala Leu Cys
                260                 265                 270

Ser Val Val Tyr Val Gly Asp Leu Cys Gly Ser Val Phe Leu Val Ser
                275                 280                 285

Gln Leu Phe Thr Phe Ser Pro Arg Gln Tyr Glu Thr Val Gln Asp Cys
                290                 295                 300

Asn Cys Ser Leu Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ser Gly Ala His
                340                 345                 350

Trp Gly Val Leu Ala Gly Leu Ala Tyr Tyr Ser Met Val Gly Asn Trp
                355                 360                 365

Ala Lys Val Leu Ile Val Met Leu Leu Phe Ala Gly Val Asp Gly Asp
                370                 375                 380

Thr Tyr Thr Thr Gly Gly Val Ala Ser Arg Thr Thr Ala Gly Leu Ala
385                 390                 395                 400

Ser Leu Phe Val Ser Gly Pro Ser Gln Lys Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Leu Ala Ala Leu Phe Tyr Val Asn Arg Phe Asn
                435                 440                 445
```

```
Ser Ser Gly Cys Pro Glu Arg Met Ala Ser Cys Arg Pro Ile Asp Lys
    450                 455                 460

Phe Ala Gln Gly Trp Gly Pro Ile Thr His Ala Val Pro Arg Ala Ser
465                 470                 475                 480

Asp Gln Arg Pro Tyr Cys Trp His Tyr Ala Pro Gln Pro Cys Gly Ile
                485                 490                 495

Val Pro Ala Ser Gln Val Cys Gly Pro Val Tyr Cys Phe Thr Pro Ser
                500                 505                 510

Pro Val Val Gly Thr Thr Asp Arg Ser Gly Ala Pro Thr Tyr Thr
        515                 520                 525

Trp Gly Glu Asn Glu Thr Asp Val Leu Ile Leu Asn Asn Thr Arg Pro
530                 535                 540

Pro His Gly Asn Trp Phe Gly Cys Ser Trp Met Asn Ser Thr Gly Phe
545                 550                 555                 560

Thr Lys Thr Cys Gly Pro Pro Cys Asn Ile Gly Gly Val Gly Asn
                565                 570                 575

Asn Thr Leu Thr Cys Pro Thr Asp Cys Phe Arg Lys His Pro Glu Ala
                580                 585                 590

Thr Tyr Thr Lys Cys Gly Ser Gly Pro Trp Leu Thr Pro Arg Cys Met
        595                 600                 605

Val Asp Tyr Pro Tyr Arg Leu Trp His Tyr Pro Cys Thr Val Asn Tyr
    610                 615                 620

Thr Ile Phe Lys Val Arg Met Tyr Val Gly Val Glu His Arg Leu
625                 630                 635                 640

Asn Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Val Val Ser Ile Val Ile Arg Trp Glu Tyr Val Val
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Ala Leu Asn Ala Ala Ser Val Ala Gly Ala His Gly Ile Leu Ser Phe
        755                 760                 765

Leu Ala Phe Phe Cys Ala Ala Trp Tyr Ile Lys Gly Lys Leu Val Pro
    770                 775                 780

Gly Ala Ala Tyr Ala Leu Tyr Ser Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Leu Thr Leu Ser
            820                 825                 830

Pro His Tyr Lys Ala Leu Leu Ala Arg Leu Ile Trp Trp Leu Gln Tyr
        835                 840                 845

Leu Thr Thr Arg Ala Glu Ala Leu Leu Gln Val Trp Ile Pro Pro Leu
    850                 855                 860

Asn Val Arg Gly Gly Arg Asp Ala Ile Ile Leu Leu Thr Cys Met Val
```

-continued

```
865                 870                 875                 880
His Pro Glu Leu Thr Phe Glu Ile Thr Lys Ile Leu Leu Ala Ile Leu
                885                 890                 895
Gly Pro Leu Met Val Leu Arg Ala Gly Leu Thr Arg Val Pro Tyr Phe
                900                 905                 910
Val Arg Ala His Gly Leu Ile Arg Ala Cys Met Leu Val Arg Lys Val
                915                 920                 925
Ala Gly Gly His Tyr Val Gln Met Ala Leu Met Lys Leu Ala Ala Leu
                930                 935                 940
Thr Gly Thr Tyr Val Tyr Asp His Leu Thr Pro Leu Arg Asp Trp Ala
945                 950                 955                 960
His Ala Gly Leu Arg Asp Leu Ala Val Ala Val Glu Pro Val Val Phe
                965                 970                 975
Ser Asp Thr Glu Thr Lys Ile Ile Thr Trp Gly Ala Thr Ala Ala
                980                 985                 990
Cys Gly Asp Ile Ile Leu Gly Leu Pro Val Ser Ala Arg Arg Gly Arg
                995                 1000                1005
Glu Ile Leu Leu Gly Pro Ala Asp Lys Phe Gly Glu Gln Gly Trp
     1010                1015                1020
Arg Leu Leu Ala Pro Ile Thr Ala Tyr Ser Gln Gln Thr Arg Gly
     1025                1030                1035
Val Leu Gly Cys Ile Ile Thr Ser Leu Thr Gly Arg Asp Lys Asn
     1040                1045                1050
Gln Val Glu Gly Glu Val Gln Val Val Ser Thr Ala Thr Gln Ser
     1055                1060                1065
Phe Leu Ala Thr Cys Val Asn Gly Val Cys Trp Thr Val Tyr His
     1070                1075                1080
Gly Ala Gly Ser Lys Thr Leu Ala Gly Pro Lys Gly Pro Ile Thr
     1085                1090                1095
Gln Met Tyr Thr Asn Val Asp Gln Asp Leu Val Gly Trp Gln Ala
     1100                1105                1110
Pro Pro Gly Ala Arg Ser Met Thr Pro Cys Thr Cys Gly Ser Ser
     1115                1120                1125
Asp Leu Phe Leu Val Thr Arg His Ala Asp Val Ile Pro Val Arg
     1130                1135                1140
Arg Arg Gly Asp Ser Arg Gly Ala Leu Leu Ser Pro Arg Pro Val
     1145                1150                1155
Ser Tyr Leu Lys Gly Ser Ser Gly Gly Pro Leu Leu Cys Pro Ser
     1160                1165                1170
Gly His Val Val Gly Ile Phe Arg Ala Ala Val Cys Thr Arg Gly
     1175                1180                1185
Val Ala Lys Ala Val Asp Phe Ile Pro Val Glu Ser Met Glu Thr
     1190                1195                1200
Thr Met Arg Ser Pro Val Phe Thr Asp Asn Ser Ser Pro Pro Ala
     1205                1210                1215
Val Pro Gln Thr Phe Gln Val Ala His Leu His Ala Pro Thr Gly
     1220                1225                1230
Ser Gly Lys Ser Thr Lys Val Pro Ala Ala Tyr Ala Ala Gln Gly
     1235                1240                1245
Tyr Lys Val Leu Val Leu Asn Pro Ser Val Ala Ala Thr Leu Ser
     1250                1255                1260
Phe Gly Ala Tyr Met Ser Lys Ala Tyr Gly Val Asp Pro Asn Ile
     1265                1270                1275
```

-continued

```
Arg Thr Gly Val Arg Thr Ile Thr Thr Gly Ala Pro Ile Thr Tyr
    1280            1285            1290

Ser Thr Tyr Gly Lys Phe Leu Ala Asp Gly Gly Cys Ser Gly Gly
    1295            1300            1305

Ala Tyr Asp Ile Ile Ile Cys Asp Glu Cys His Ser Thr Asp Ser
    1310            1315            1320

Thr Thr Ile Leu Gly Ile Gly Thr Val Leu Asp Gln Ala Glu Thr
    1325            1330            1335

Ala Gly Ala Arg Leu Val Val Leu Ala Thr Ala Thr Pro Pro Gly
    1340            1345            1350

Ser Val Thr Val Pro His Pro Asn Ile Glu Glu Val Ala Leu Ser
    1355            1360            1365

Asn Thr Gly Glu Ile Pro Phe Tyr Gly Lys Ala Ile Pro Leu Glu
    1370            1375            1380

Thr Ile Lys Gly Gly Arg His Leu Ile Phe Cys His Ser Lys Lys
    1385            1390            1395

Lys Cys Asp Glu Leu Ala Ala Lys Leu Ser Ala Leu Gly Leu Asn
    1400            1405            1410

Ala Val Ala Tyr Tyr Arg Gly Leu Asp Val Ser Ile Ile Pro Thr
    1415            1420            1425

Ser Gly Asp Val Val Val Ala Thr Asp Ala Leu Met Thr Gly
    1430            1435            1440

Tyr Thr Gly Asp Phe Asp Ser Val Ile Asp Cys Asn Thr Cys Val
    1445            1450            1455

Thr Gln Thr Val Asp Phe Ser Phe Asp Pro Thr Phe Ala Ile Glu
    1460            1465            1470

Thr Thr Thr Met Pro Gln Asp Ala Val Ser Arg Ser Gln Arg Arg
    1475            1480            1485

Gly Arg Thr Gly Arg Gly Arg Gly Gly Ile Tyr Arg Phe Val Thr
    1490            1495            1500

Pro Gly Glu Arg Pro Ser Gly Met Phe Asp Ser Ala Ile Leu Cys
    1505            1510            1515

Glu Cys Tyr Asp Ala Gly Cys Ala Trp Tyr Glu Leu Thr Pro Ala
    1520            1525            1530

Glu Thr Thr Val Arg Leu Arg Ala Tyr Leu Asn Thr Pro Gly Leu
    1535            1540            1545

Pro Val Cys Gln Asp His Leu Glu Phe Trp Glu Gly Val Phe Thr
    1550            1555            1560

Gly Leu Thr His Ile Asp Ala His Phe Leu Ser Gln Thr Lys Gln
    1565            1570            1575

Ala Gly Asp Asn Phe Pro Tyr Leu Val Ala Tyr Gln Ala Thr Val
    1580            1585            1590

Cys Ala Arg Ala Gln Ala Pro Pro Pro Ser Trp Asp Gln Met Trp
    1595            1600            1605

Lys Cys Leu Ile Arg Leu Lys Pro Thr Leu His Gly Pro Thr Pro
    1610            1615            1620

Leu Leu Tyr Arg Leu Gly Ala Val Gln Asn Glu Val Thr Leu Thr
    1625            1630            1635

His Pro Ile Thr Lys Tyr Ile Met Thr Cys Met Ser Ala Asp Leu
    1640            1645            1650

Glu Val Val Thr Ser Thr Trp Val Leu Val Gly Gly Val Leu Ala
    1655            1660            1665
```

-continued

```
Ala Leu Ala Ala Tyr Cys Leu Thr Thr Gly Ser Val Val Ile Val
    1670            1675                1680

Gly Arg Val Ile Leu Ser Gly Arg Pro Ala Ile Ile Pro Asp Arg
    1685            1690                1695

Glu Val Leu Tyr Arg Glu Phe Asp Glu Met Glu Cys Ala Ser
    1700            1705                1710

His Leu Pro Tyr Ile Glu Gln Gly Met Gln Leu Ala Glu Gln Phe
    1715            1720                1725

Lys Gln Lys Ala Leu Gly Leu Leu Gln Thr Ala Thr Lys Gln Ala
    1730            1735                1740

Glu Ala Ala Ala Pro Val Val Glu Ser Lys Trp Arg Ala Leu Glu
    1745            1750                1755

Ala Phe Trp Ala Lys His Met Trp Asn Phe Ile Ser Gly Ile Gln
    1760            1765                1770

Tyr Leu Ala Gly Leu Ser Thr Leu Pro Gly Asn Pro Ala Ile Ala
    1775            1780                1785

Ser Leu Met Ala Phe Thr Ala Ser Ile Thr Ser Pro Leu Thr Thr
    1790            1795                1800

Gln His Thr Leu Leu Phe Asn Ile Leu Gly Gly Trp Val Ala Ala
    1805            1810                1815

Gln Leu Ala Pro Pro Gly Ala Ala Ser Ala Phe Val Gly Ala Gly
    1820            1825                1830

Ile Ala Gly Ala Ala Val Gly Ser Ile Gly Leu Gly Lys Val Leu
    1835            1840                1845

Val Asp Ile Leu Ala Gly Tyr Gly Ala Gly Val Ala Gly Ala Leu
    1850            1855                1860

Val Ala Phe Lys Val Met Ser Gly Glu Met Pro Ser Thr Glu Asp
    1865            1870                1875

Leu Val Asn Leu Leu Pro Ala Ile Leu Ser Pro Gly Ala Leu Val
    1880            1885                1890

Val Gly Val Val Cys Ala Ala Ile Leu Arg Arg His Val Gly Pro
    1895            1900                1905

Gly Glu Gly Ala Val Gln Trp Met Asn Arg Leu Ile Ala Phe Ala
    1910            1915                1920

Ser Arg Gly Asn His Val Ser Pro Thr His Tyr Val Pro Glu Ser
    1925            1930                1935

Asp Ala Ala Ala Arg Val Thr Gln Ile Leu Ser Ser Leu Thr Ile
    1940            1945                1950

Thr Gln Leu Leu Lys Arg Leu His Gln Trp Ile Asn Glu Asp Cys
    1955            1960                1965

Ser Thr Pro Cys Ser Gly Ser Trp Leu Arg Asp Val Trp Asp Trp
    1970            1975                1980

Ile Cys Thr Val Leu Thr Asp Phe Lys Thr Trp Leu Gln Ser Lys
    1985            1990                1995

Leu Leu Pro Arg Leu Pro Gly Val Pro Phe Leu Ser Cys Gln Arg
    2000            2005                2010

Gly Tyr Lys Gly Val Trp Arg Gly Asp Gly Ile Met His Thr Thr
    2015            2020                2025

Cys Pro Cys Gly Ala Gln Ile Ser Gly His Val Lys Asn Gly Ser
    2030            2035                2040

Met Arg Ile Val Gly Pro Lys Thr Cys Ser Asn Thr Trp Cys Gly
    2045            2050                2055

Thr Phe Pro Ile Asn Ala Tyr Thr Thr Gly Pro Cys Thr Pro Ser
```

```
                    2060                2065                2070
Pro Ala  Pro Asn Tyr Ser Arg  Ala Leu Trp Arg Val  Ala Ala Glu
        2075                2080                2085

Glu Tyr  Val Glu Val Thr Arg  Val Gly Asp Phe His  Tyr Val Thr
        2090                2095                2100

Gly Met  Thr Thr Asp Asn Leu  Lys Cys Pro Cys Gln  Val Pro Ala
        2105                2110                2115

Pro Glu  Phe Phe Thr Glu Val  Asp Gly Val Arg Leu  His Arg Tyr
        2120                2125                2130

Ala Pro  Ala Cys Lys Pro Leu  Leu Arg Asp Glu Val  Thr Phe Gln
        2135                2140                2145

Val Gly  Leu Asn Gln Phe Pro  Val Gly Ser Gln Leu  Pro Cys Glu
        2150                2155                2160

Pro Glu  Pro Asp Val Thr Val  Leu Thr Ser Met Leu  Thr Asp Pro
        2165                2170                2175

Ser His  Ile Thr Ala Glu Thr  Ala Lys Arg Arg Leu  Ala Arg Gly
        2180                2185                2190

Ser Pro  Pro Ser Leu Ala Ser  Ser Ser Ala Ser Gln  Leu Ser Ala
        2195                2200                2205

Val Ser  Leu Lys Ala Ala Cys  Thr Thr Arg His Asn  Pro Pro Asp
        2210                2215                2220

Ala Asp  Leu Ile Glu Ala Asn  Leu Leu Trp Arg Gln  Glu Met Gly
        2225                2230                2235

Gly Ser  Ile Thr Arg Val Glu  Ser Glu Ser Lys Val  Val Ile Leu
        2240                2245                2250

Asp Ser  Phe Glu Pro Leu Arg  Ala Glu Glu Asp Glu  Arg Glu Val
        2255                2260                2265

Ser Val  Pro Ala Glu Ile Leu  Arg Lys Thr Lys Lys  Phe Pro Ala
        2270                2275                2280

Ala Met  Pro Val Trp Ala Arg  Pro Asp Tyr Asn Pro  Pro Leu Leu
        2285                2290                2295

Glu Ser  Trp Arg Asp Pro Asp  Tyr Val Pro Pro Val  Val His Gly
        2300                2305                2310

Cys Pro  Leu Pro Pro Thr Lys  Ala Pro Pro Ile Pro  Pro Pro Arg
        2315                2320                2325

Arg Lys  Arg Thr Val Ile Leu  Thr Glu Ser Thr Val  Ser Ser Ala
        2330                2335                2340

Leu Ala  Glu Leu Ala Thr Lys  Thr Phe Gly Ser Ser  Gly Ser Ser
        2345                2350                2355

Ala Val  Asp Asn Gly Thr Ala  Thr Ala Pro Pro Asp  Gln Pro Ser
        2360                2365                2370

Ile Asp  Gly Asp Ala Gly Ser  Asp Val Glu Ser Tyr  Ser Ser Met
        2375                2380                2385

Pro Pro  Leu Glu Gly Glu Pro  Gly Asp Pro Asp Leu  Ser Asp Gly
        2390                2395                2400

Ser Trp  Ser Thr Val Ser Glu  Glu Ala Gly Glu Asp  Val Val Cys
        2405                2410                2415

Cys Ser  Met Ser Tyr Thr Trp  Thr Gly Ala Leu Ile  Thr Pro Cys
        2420                2425                2430

Ala Ala  Glu Glu Ser Lys Leu  Pro Ile Asn Ala Leu  Ser Asn Ser
        2435                2440                2445

Leu Leu  Arg His His Asn Met  Val Tyr Ala Thr Thr  Ser Arg Ser
        2450                2455                2460
```

-continued

```
Ala Ser Gln Arg Gln Lys Lys Val Thr Phe Asp Arg Leu Gln Val
2465                2470                2475

Leu Asp Asp His Tyr Arg Asp Val Leu Lys Glu Met Lys Ala Lys
2480                2485                2490

Ala Ser Thr Val Lys Ala Lys Leu Leu Ser Val Glu Glu Ala Cys
2495                2500                2505

Arg Leu Thr Pro Pro His Ser Ala Arg Ser Lys Phe Gly Tyr Gly
2510                2515                2520

Ala Lys Asp Val Arg Asn Leu Ser Ser Lys Ala Val Asn His Ile
2525                2530                2535

His Ser Val Trp Lys Asp Leu Leu Glu Asp Thr Glu Thr Pro Ile
2540                2545                2550

Asp Thr Thr Ile Met Ala Lys Asn Glu Val Phe Cys Val Gln Pro
2555                2560                2565

Glu Lys Gly Gly Arg Lys Pro Ala Arg Leu Ile Val Phe Pro Asp
2570                2575                2580

Leu Gly Val Arg Val Cys Glu Lys Met Ala Leu Tyr Asp Val Val
2585                2590                2595

Ser Thr Leu Pro Gln Ala Val Met Gly Ser Ser Tyr Gly Phe Gln
2600                2605                2610

Tyr Ser Pro Gly Gln Arg Val Glu Phe Leu Val Asn Ala Trp Lys
2615                2620                2625

Ser Lys Lys Asn Pro Met Gly Phe Ala Tyr Asp Thr Arg Cys Phe
2630                2635                2640

Asp Ser Thr Val Thr Glu Ser Asp Ile Arg Val Glu Glu Ser Ile
2645                2650                2655

Tyr Gln Cys Cys Asp Leu Ala Pro Glu Ala Arg Gln Val Ile Arg
2660                2665                2670

Ser Leu Thr Glu Arg Leu Tyr Ile Gly Gly Pro Leu Thr Asn Ser
2675                2680                2685

Lys Gly Gln Asn Cys Gly Tyr Arg Arg Cys Arg Ala Ser Gly Val
2690                2695                2700

Leu Thr Thr Ser Cys Gly Asn Thr Leu Thr Cys Tyr Leu Lys Ala
2705                2710                2715

Ser Ala Ala Cys Arg Ala Ala Lys Leu Gln Asp Cys Thr Met Leu
2720                2725                2730

Val Cys Gly Asp Asp Leu Val Val Ile Cys Glu Ser Ala Gly Thr
2735                2740                2745

Gln Glu Asp Ala Ala Ser Leu Arg Val Phe Thr Glu Ala Met Thr
2750                2755                2760

Arg Tyr Ser Ala Pro Pro Gly Asp Pro Pro Gln Pro Glu Tyr Asp
2765                2770                2775

Leu Glu Leu Ile Thr Ser Cys Ser Ser Asn Val Ser Val Ala His
2780                2785                2790

Asp Ala Ser Gly Lys Arg Val Tyr Tyr Leu Thr Arg Asp Pro Thr
2795                2800                2805

Thr Pro Leu Ala Arg Ala Ala Trp Glu Thr Ala Arg His Thr Pro
2810                2815                2820

Val Asn Ser Trp Leu Gly Asn Ile Ile Met Tyr Ala Pro Thr Leu
2825                2830                2835

Trp Ala Arg Met Ile Leu Met Thr His Phe Phe Ser Ile Leu Leu
2840                2845                2850
```

```
Ala Gln Glu Gln Leu Glu Lys Ala Leu Asp Cys Gln Ile Tyr Gly
    2855                2860                2865

Ala Thr Tyr Ser Ile Glu Pro Leu Asp Leu Pro Gln Ile Ile Gln
    2870                2875                2880

Arg Leu His Gly Leu Ser Ala Phe Ser Leu His Ser Tyr Ser Pro
    2885                2890                2895

Gly Glu Ile Asn Arg Val Ala Ser Cys Leu Arg Lys Leu Gly Val
    2900                2905                2910

Pro Pro Leu Arg Val Trp Arg His Arg Ala Arg Ser Val Arg Ala
    2915                2920                2925

Lys Leu Leu Ser Gln Gly Gly Arg Ala Ala Ile Cys Gly Lys Tyr
    2930                2935                2940

Leu Phe Asn Trp Ala Val Arg Thr Lys Leu Lys Leu Thr Pro Ile
    2945                2950                2955

Pro Ala Ala Ser Gln Leu Asp Leu Ser Ser Trp Phe Ile Ala Gly
    2960                2965                2970

Tyr Ser Gly Gly Asp Ile Tyr His Ser Leu Ser Arg Ala Arg Pro
    2975                2980                2985

Arg Trp Phe Met Trp Cys Leu Leu Leu Leu Ser Val Gly Val Gly
    2990                2995                3000

Ile Tyr Leu Leu Pro Asn Arg
    3005                3010

<210> SEQ ID NO 15
<211> LENGTH: 1984
<212> TYPE: PRT
<213> ORGANISM: hepatitis C virus

<400> SEQUENCE: 15

Ala Pro Ile Thr Ala Tyr Ser Gln Gln Thr Arg Gly Val Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr Leu
    50                  55                  60

Ala Gly Pro Lys Gly Pro Ile Thr Gln Met Tyr Thr Asn Val Asp Gln
65                  70                  75                  80

Asp Leu Val Gly Trp Gln Ala Pro Pro Gly Ala Arg Ser Met Thr Pro
                85                  90                  95

Cys Thr Cys Gly Ser Ser Asp Leu Phe Leu Val Thr Arg His Ala Asp
            100                 105                 110

Val Ile Pro Val Arg Arg Arg Gly Asp Ser Arg Gly Ala Leu Leu Ser
        115                 120                 125

Pro Arg Pro Val Ser Tyr Leu Lys Gly Ser Ser Gly Gly Pro Leu Leu
    130                 135                 140

Cys Pro Ser Gly His Val Gly Ile Phe Arg Ala Ala Val Cys Thr
145                 150                 155                 160

Arg Gly Val Ala Lys Ala Val Asp Phe Ile Pro Val Glu Ser Met Glu
                165                 170                 175

Thr Thr Met Arg Ser Pro Val Phe Thr Asp Asn Ser Ser Pro Pro Ala
            180                 185                 190

Val Pro Gln Thr Phe Gln Val Ala His Leu His Ala Pro Thr Gly Ser
        195                 200                 205
```

-continued

```
Gly Lys Ser Thr Lys Val Pro Ala Ala Tyr Ala Ala Gln Gly Tyr Lys
    210                 215                 220
Val Leu Val Leu Asn Pro Ser Val Ala Thr Leu Ser Phe Gly Ala
225                 230                 235                 240
Tyr Met Ser Lys Ala Tyr Gly Val Asp Pro Asn Ile Arg Thr Gly Val
                    245                 250                 255
Arg Thr Ile Thr Thr Gly Ala Pro Ile Thr Tyr Ser Thr Tyr Gly Lys
                260                 265                 270
Phe Leu Ala Asp Gly Gly Cys Ser Gly Ala Tyr Asp Ile Ile Ile
                275                 280                 285
Cys Asp Glu Cys His Ser Thr Asp Ser Thr Thr Ile Leu Gly Ile Gly
290                 295                 300
Thr Val Leu Asp Gln Ala Glu Thr Ala Gly Ala Arg Leu Val Val Leu
305                 310                 315                 320
Ala Thr Ala Thr Pro Pro Gly Ser Val Thr Val Pro His Pro Asn Ile
                325                 330                 335
Glu Glu Val Ala Leu Ser Asn Thr Gly Glu Ile Pro Phe Tyr Gly Lys
                340                 345                 350
Ala Ile Pro Leu Glu Thr Ile Lys Gly Gly Arg His Leu Ile Phe Cys
            355                 360                 365
His Ser Lys Lys Lys Cys Asp Glu Leu Ala Ala Lys Leu Ser Ala Leu
    370                 375                 380
Gly Leu Asn Ala Val Ala Tyr Tyr Arg Gly Leu Asp Val Ser Ile Ile
385                 390                 395                 400
Pro Thr Ser Gly Asp Val Val Val Ala Thr Asp Ala Leu Met Thr
                405                 410                 415
Gly Tyr Thr Gly Asp Phe Asp Ser Val Ile Asp Cys Asn Thr Cys Val
                420                 425                 430
Thr Gln Thr Val Asp Phe Ser Phe Asp Pro Thr Phe Ala Ile Glu Thr
            435                 440                 445
Thr Thr Met Pro Gln Asp Ala Val Ser Arg Ser Gln Arg Arg Gly Arg
    450                 455                 460
Thr Gly Arg Gly Arg Gly Ile Tyr Arg Phe Val Thr Pro Gly Glu
465                 470                 475                 480
Arg Pro Ser Gly Met Phe Asp Ser Ala Ile Leu Cys Glu Cys Tyr Asp
                485                 490                 495
Ala Gly Cys Ala Trp Tyr Glu Leu Thr Pro Ala Glu Thr Thr Val Arg
                500                 505                 510
Leu Arg Ala Tyr Leu Asn Thr Pro Gly Leu Pro Val Cys Gln Asp His
            515                 520                 525
Leu Glu Phe Trp Glu Gly Val Phe Thr Gly Leu Thr His Ile Asp Ala
    530                 535                 540
His Phe Leu Ser Gln Thr Lys Gln Ala Gly Asp Asn Phe Pro Tyr Leu
545                 550                 555                 560
Val Ala Tyr Gln Ala Thr Val Cys Ala Arg Ala Gln Ala Pro Pro Pro
                565                 570                 575
Ser Trp Asp Gln Met Trp Lys Cys Leu Ile Arg Leu Lys Pro Thr Leu
                580                 585                 590
His Gly Pro Thr Pro Leu Leu Tyr Arg Leu Gly Ala Val Gln Asn Glu
            595                 600                 605
Val Thr Leu Thr His Pro Ile Thr Lys Tyr Ile Met Thr Cys Met Ser
    610                 615                 620
```

-continued

```
Ala Asp Leu Glu Val Val Thr Ser Thr Trp Val Leu Val Gly Gly Val
625                 630                 635                 640

Leu Ala Ala Leu Ala Ala Tyr Cys Leu Thr Thr Gly Ser Val Val Ile
            645                 650                 655

Val Gly Arg Val Ile Leu Ser Gly Arg Pro Ala Ile Ile Pro Asp Arg
        660                 665                 670

Glu Val Leu Tyr Arg Glu Phe Asp Glu Met Glu Glu Cys Ala Ser His
    675                 680                 685

Leu Pro Tyr Ile Glu Gln Gly Met Gln Leu Ala Glu Gln Phe Lys Gln
690                 695                 700

Lys Ala Leu Gly Leu Leu Gln Thr Ala Thr Lys Gln Ala Glu Ala Ala
705                 710                 715                 720

Ala Pro Val Val Glu Ser Lys Trp Arg Ala Leu Glu Ala Phe Trp Ala
                725                 730                 735

Lys His Met Trp Asn Phe Ile Ser Gly Ile Gln Tyr Leu Ala Gly Leu
            740                 745                 750

Ser Thr Leu Pro Gly Asn Pro Ala Ile Ala Ser Leu Met Ala Phe Thr
        755                 760                 765

Ala Ser Ile Thr Ser Pro Leu Thr Thr Gln His Thr Leu Leu Phe Asn
770                 775                 780

Ile Leu Gly Gly Trp Val Ala Ala Gln Leu Ala Pro Pro Gly Ala Ala
785                 790                 795                 800

Ser Ala Phe Val Gly Ala Gly Ile Ala Gly Ala Ala Val Gly Ser Ile
                805                 810                 815

Gly Leu Gly Lys Val Leu Val Asp Ile Leu Ala Gly Tyr Gly Ala Gly
            820                 825                 830

Val Ala Gly Ala Leu Val Ala Phe Lys Val Met Ser Gly Glu Met Pro
        835                 840                 845

Ser Thr Glu Asp Leu Val Asn Leu Leu Pro Ala Ile Leu Ser Pro Gly
850                 855                 860

Ala Leu Val Val Gly Val Val Cys Ala Ala Ile Leu Arg Arg His Val
865                 870                 875                 880

Gly Pro Gly Glu Gly Ala Val Gln Trp Met Asn Arg Leu Ile Ala Phe
                885                 890                 895

Ala Ser Arg Gly Asn His Val Ser Pro Thr His Tyr Val Pro Glu Ser
            900                 905                 910

Asp Ala Ala Ala Arg Val Thr Gln Ile Leu Ser Ser Leu Thr Ile Thr
        915                 920                 925

Gln Leu Leu Lys Arg Leu His Gln Trp Ile Asn Glu Asp Cys Ser Thr
930                 935                 940

Pro Cys Ser Gly Ser Trp Leu Arg Asp Val Trp Asp Trp Ile Cys Thr
945                 950                 955                 960

Val Leu Thr Asp Phe Lys Thr Trp Leu Gln Ser Lys Leu Leu Pro Arg
                965                 970                 975

Leu Pro Gly Val Pro Phe Leu Ser Cys Gln Arg Gly Tyr Lys Gly Val
            980                 985                 990

Trp Arg Gly Asp Gly Ile Met His Thr Thr Cys Pro Cys Gly Ala Gln
        995                 1000                1005

Ile Ser Gly His Val Lys Asn Gly Ser Met Arg Ile Val Gly Pro
        1010                1015                1020

Lys Thr Cys Ser Asn Thr Trp Cys Gly Thr Phe Pro Ile Asn Ala
        1025                1030                1035

Tyr Thr Thr Gly Pro Cys Thr Pro Ser Pro Ala Pro Asn Tyr Ser
```

```
              1040                1045                1050
 Arg  Ala  Leu  Trp  Arg  Val  Ala  Ala  Glu  Glu  Tyr  Val  Glu  Val  Thr
              1055                1060                1065
 Arg  Val  Gly  Asp  Phe  His  Tyr  Val  Thr  Gly  Met  Thr  Thr  Asp  Asn
              1070                1075                1080
 Leu  Lys  Cys  Pro  Cys  Gln  Val  Pro  Ala  Pro  Glu  Phe  Phe  Thr  Glu
              1085                1090                1095
 Val  Asp  Gly  Val  Arg  Leu  His  Arg  Tyr  Ala  Pro  Ala  Cys  Lys  Pro
              1100                1105                1110
 Leu  Leu  Arg  Asp  Glu  Val  Thr  Phe  Gln  Val  Gly  Leu  Asn  Gln  Phe
              1115                1120                1125
 Pro  Val  Gly  Ser  Gln  Leu  Pro  Cys  Glu  Pro  Glu  Pro  Asp  Val  Thr
              1130                1135                1140
 Val  Leu  Thr  Ser  Met  Leu  Thr  Asp  Pro  Ser  His  Ile  Thr  Ala  Glu
              1145                1150                1155
 Thr  Ala  Lys  Arg  Arg  Leu  Ala  Arg  Gly  Ser  Pro  Pro  Ser  Leu  Ala
              1160                1165                1170
 Ser  Ser  Ser  Ala  Ser  Gln  Leu  Ser  Ala  Val  Ser  Leu  Lys  Ala  Ala
              1175                1180                1185
 Cys  Thr  Thr  Arg  His  Asn  Pro  Pro  Asp  Ala  Asp  Leu  Ile  Glu  Ala
              1190                1195                1200
 Asn  Leu  Leu  Trp  Arg  Gln  Glu  Met  Gly  Gly  Ser  Ile  Thr  Arg  Val
              1205                1210                1215
 Glu  Ser  Glu  Ser  Lys  Val  Val  Ile  Leu  Asp  Ser  Phe  Glu  Pro  Leu
              1220                1225                1230
 Arg  Ala  Glu  Glu  Asp  Glu  Arg  Glu  Val  Ser  Val  Pro  Ala  Glu  Ile
              1235                1240                1245
 Leu  Arg  Lys  Thr  Lys  Lys  Phe  Pro  Ala  Ala  Met  Pro  Val  Trp  Ala
              1250                1255                1260
 Arg  Pro  Asp  Tyr  Asn  Pro  Pro  Leu  Leu  Glu  Ser  Trp  Arg  Asp  Pro
              1265                1270                1275
 Asp  Tyr  Val  Pro  Pro  Val  Val  His  Gly  Cys  Pro  Leu  Pro  Pro  Thr
              1280                1285                1290
 Lys  Ala  Pro  Pro  Ile  Pro  Pro  Arg  Arg  Lys  Arg  Thr  Val  Ile
              1295                1300                1305
 Leu  Thr  Glu  Ser  Thr  Val  Ser  Ser  Ala  Leu  Ala  Glu  Leu  Ala  Thr
              1310                1315                1320
 Lys  Thr  Phe  Gly  Ser  Ser  Gly  Ser  Ser  Ala  Val  Asp  Asn  Gly  Thr
              1325                1330                1335
 Ala  Thr  Ala  Pro  Pro  Asp  Gln  Pro  Ser  Ile  Asp  Gly  Asp  Ala  Gly
              1340                1345                1350
 Ser  Asp  Val  Glu  Ser  Tyr  Ser  Ser  Met  Pro  Pro  Leu  Glu  Gly  Glu
              1355                1360                1365
 Pro  Gly  Asp  Pro  Asp  Leu  Ser  Asp  Gly  Ser  Trp  Ser  Thr  Val  Ser
              1370                1375                1380
 Glu  Glu  Ala  Gly  Glu  Asp  Val  Val  Cys  Cys  Ser  Met  Ser  Tyr  Thr
              1385                1390                1395
 Trp  Thr  Gly  Ala  Leu  Ile  Thr  Pro  Cys  Ala  Ala  Glu  Glu  Ser  Lys
              1400                1405                1410
 Leu  Pro  Ile  Asn  Ala  Leu  Ser  Asn  Ser  Leu  Leu  Arg  His  His  Asn
              1415                1420                1425
 Met  Val  Tyr  Ala  Thr  Thr  Ser  Arg  Ser  Ala  Ser  Gln  Arg  Gln  Lys
              1430                1435                1440
```

```
Lys Val Thr Phe Asp Arg Leu Gln Val Leu Asp Asp His Tyr Arg
1445                 1450                1455

Asp Val Leu Lys Glu Met Lys Ala Lys Ala Ser Thr Val Lys Ala
1460                 1465                1470

Lys Leu Leu Ser Val Glu Glu Ala Cys Arg Leu Thr Pro Pro His
1475                 1480                1485

Ser Ala Arg Ser Lys Phe Gly Tyr Gly Ala Lys Asp Val Arg Asn
1490                 1495                1500

Leu Ser Ser Lys Ala Val Asn His Ile His Ser Val Trp Lys Asp
1505                 1510                1515

Leu Leu Glu Asp Thr Glu Thr Pro Ile Asp Thr Thr Ile Met Ala
1520                 1525                1530

Lys Asn Glu Val Phe Cys Val Gln Pro Glu Lys Gly Gly Arg Lys
1535                 1540                1545

Pro Ala Arg Leu Ile Val Phe Pro Asp Leu Gly Val Arg Val Cys
1550                 1555                1560

Glu Lys Met Ala Leu Tyr Asp Val Val Ser Thr Leu Pro Gln Ala
1565                 1570                1575

Val Met Gly Ser Ser Tyr Gly Phe Gln Tyr Ser Pro Gly Gln Arg
1580                 1585                1590

Val Glu Phe Leu Val Asn Ala Trp Lys Ser Lys Lys Asn Pro Met
1595                 1600                1605

Gly Phe Ala Tyr Asp Thr Arg Cys Phe Asp Ser Thr Val Thr Glu
1610                 1615                1620

Ser Asp Ile Arg Val Glu Glu Ser Ile Tyr Gln Cys Cys Asp Leu
1625                 1630                1635

Ala Pro Glu Ala Arg Gln Val Ile Arg Ser Leu Thr Glu Arg Leu
1640                 1645                1650

Tyr Ile Gly Gly Pro Leu Thr Asn Ser Lys Gly Gln Asn Cys Gly
1655                 1660                1665

Tyr Arg Arg Cys Arg Ala Ser Gly Val Leu Thr Thr Ser Cys Gly
1670                 1675                1680

Asn Thr Leu Thr Cys Tyr Leu Lys Ala Ser Ala Ala Cys Arg Ala
1685                 1690                1695

Ala Lys Leu Gln Asp Cys Thr Met Leu Val Cys Gly Asp Asp Leu
1700                 1705                1710

Val Val Ile Cys Glu Ser Ala Gly Thr Gln Glu Asp Ala Ala Ser
1715                 1720                1725

Leu Arg Val Phe Thr Glu Ala Met Thr Arg Tyr Ser Ala Pro Pro
1730                 1735                1740

Gly Asp Pro Pro Gln Pro Glu Tyr Asp Leu Glu Leu Ile Thr Ser
1745                 1750                1755

Cys Ser Ser Asn Val Ser Val Ala His Asp Ala Ser Gly Lys Arg
1760                 1765                1770

Val Tyr Tyr Leu Thr Arg Asp Pro Thr Thr Pro Leu Ala Arg Ala
1775                 1780                1785

Ala Trp Glu Thr Ala Arg His Thr Pro Val Asn Ser Trp Leu Gly
1790                 1795                1800

Asn Ile Ile Met Tyr Ala Pro Thr Leu Trp Ala Arg Met Ile Leu
1805                 1810                1815

Met Thr His Phe Phe Ser Ile Leu Leu Ala Gln Glu Gln Leu Glu
1820                 1825                1830
```

| | | | | | | | | | | |
|---|---|---|---|---|---|---|---|---|---|---|
| Lys | Ala | Leu | Asp | Cys | Gln | Ile | Tyr | Gly | Ala | Thr | Tyr | Ser | Ile | Glu |
| | 1835 | | | | 1840 | | | | 1845 | |

Pro Leu Asp Leu Pro Gln Ile Ile Gln Arg Leu His Gly Leu Ser
    1850                1855                1860

Ala Phe Ser Leu His Ser Tyr Ser Pro Gly Glu Ile Asn Arg Val
    1865                1870                1875

Ala Ser Cys Leu Arg Lys Leu Gly Val Pro Leu Arg Val Trp
    1880                1885                1890

Arg His Arg Ala Arg Ser Val Arg Ala Lys Leu Leu Ser Gln Gly
    1895                1900                1905

Gly Arg Ala Ala Ile Cys Gly Lys Tyr Leu Phe Asn Trp Ala Val
    1910                1915                1920

Arg Thr Lys Leu Lys Leu Thr Pro Ile Pro Ala Ala Ser Gln Leu
    1925                1930                1935

Asp Leu Ser Ser Trp Phe Ile Ala Gly Tyr Ser Gly Gly Asp Ile
    1940                1945                1950

Tyr His Ser Leu Ser Arg Ala Arg Pro Arg Trp Phe Met Trp Cys
    1955                1960                1965

Leu Leu Leu Leu Ser Val Gly Val Gly Ile Tyr Leu Leu Pro Asn
    1970                1975                1980

Arg

<210> SEQ ID NO 16
<211> LENGTH: 7993
<212> TYPE: DNA
<213> ORGANISM: hepatitis C virus

<400> SEQUENCE: 16

```
gccagccccc tgatggggc gacactccac catagatcac tcccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag     180
gacgaccggg tcctttcttg gattaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta ccgtgcat catgagcaca atcctaaac      360
ctcaaagaaa aaccacacgt aacaccaacc gccgcccaat gattgaacaa gatggattgc     420
acgcaggttc tccggccgtt tgggtggaga ggctattcgg ctatgactgg gcacaacaga     480
caaccggctg ctctgatgcc gccgtgttcc ggctgtcagc gcgggggcga ccggttcttt     540
ttgtcaagac cgacctgtcc ggtgccctga atgaactgca ggacgaggca gcgcggctat     600
cgtggctggc cacgacgggc gttccttgcg cagctgtgct cgacgttgtc actgaagcgg     660
gaagggactg gctgctattg ggcgaagtgc cggggcagga tcctgtgtca tctcaccttg     720
ctcctgccga aaagtgtcc atcatggctg atgcaatacg cggctgcat acgcttgatc     780
cggctacctg cccattcgac caccaagcga aacatcgcat cgagcgagca cgtactcgga     840
tggaagccgg tcttgtcgat caggatgatc tggacgaaga gcatcagggg ctcgcgccag     900
ccgaactgtt cgccaggctc aaggcgcgca tgcccgacgg cgaggatctc gtcgtgaccc     960
atggcgatgc ctgcttgccg aatgtcatgg tggaaaatgg ccgcttttct ggattcatcg    1020
actgtggccg ctgggtgtg gcggaccgct atcaggacat agcgttggct acccgtgata    1080
ttgctgaaga gcttggcggc gaatgggctg accgcttcct cgtgctttac ggtatcgccg    1140
ctcccgattc gaagcgcatc gccttctatc gccttcttga cgagttcttc tgagtttaaa    1200
```

```
cagcccacaa cggtttccct ctagcgggat caattccgcc cccccccta acgttactgg    1260
ccgaagccgc ttggaataag gccggtgtgc gtttgtctat atgttatttt ccaccatatt    1320
gccgtctttt ggcaatgtga gggcccggaa acctggccct gtcttcttga cgagcattcc    1380
taggggtctt tcccctctcg ccaaaggaat gcaaggtctg ttggatgtcg tgaaggaagc    1440
agttcctctg gaagcttctt gaagacaaac aacgtctgta gcgaccctt gcaggcagcg     1500
gaaccccca cctggcgaca ggtgcctctg cggccaaaag ccacgtgtat aagatacacc     1560
tgcaaaggcg gtacaacccc agtgccacgt tgtgagttgg atagttgtgg aaagagtcaa    1620
atggctctcc tcaagcgtat tcaacaaggg gctgaaggat gcccagaagg taccccattg    1680
tatgggatct gatctggggc ctcggtgcac atgctctaca tgtgtttagt cgaggttaaa    1740
aaaacgtcta ggcccccga accacgggga cgtggttttc ctttgaaaaa cacgataata    1800
ccatggcacc cattacggcc tactcccaac agacgcgggg cgtacttggc tgtatcatca    1860
ctagcctcac aggtcgggac aagaaccagg tcgagggga ggttcaggtg gtttccaccg     1920
caacgcagtc cttcttggca acctgcgtca atggcgtgtg ttggaccgtc taccatggcg    1980
ccggctcaaa gaccctagcc ggcccgaagg gaccgatcac ccaaatgtac accaatgttg    2040
accaggacct cgtcggctgg caggcgcccc ccggggcgcg ctccatgaca ccgtgcacct    2100
gcggcagctc ggacctttt ttggtcacga ggcatgctga tgtcattccg gtgcgccggc     2160
ggggtgacag cagaggagcc ctactttccc ccaggcccgt ctcttacctg aagggctcct    2220
cggtggtcc actgctttgc ccctcggggc acgttgtggg catcttccgg gctgccgtgt     2280
gcacccgggg ggtcgcgaag gcggtggatt ttatacccgt tgagtccatg gaaaccacca    2340
tgcggtctcc ggtcttcacg gataattcat ctccccccgg cgtaccgcag acattccaag    2400
tggcccatct gcacgctccc actggcagcg gcaagagcac taaagtgccg gctgcatacg    2460
cagcccaggg gtacaaggtg ctcgtcctga accgtccgt tgccgccacc ttgagttttg     2520
gggcgtatat gtccaaggca tatggagttg accctaacat cagaaccggg gtgaggacca    2580
tcactactgg cgctcccatc acgtactcca cctacggcaa gttccttgcc gacggcggtt    2640
gctctggggg cgcctatgac atcataatat gtgatgagtg ccactcaact gactcaacta    2700
ctattttggg cattggcaca gtcctggacc aagcggagac agctggagcg cggctcgtcg    2760
tgctcgccac cgctacgccg ccaggatcag tcaccgtacc acaccccaac atcgaggagg    2820
tggccttgtc caatactgga gagattccct tctatggcaa agccatcccc ctcgagacca    2880
tcaagggggg gaggcacctc attttctgcc actccaagaa gaagtgtgat gagcttgctg    2940
caaagctgtc ggcccttggg ctcaatgctg tagcgtacta ccggggtctt gacgtgtcca    3000
tcataccaac aagcggagac gtcgttgttg tggcaacaga cgctctaatg acgggctaca    3060
ccggtgattt tgactcagtg atcgactgca atacatgtgt cacccagaca gtcgacttca    3120
gcttcgaccc caccttcgcc attgagacga cgaccatgcc caagacgcg gtgtcgcgct     3180
cacagcggcg aggcaggact ggcagggca gaggaggcat atacaggttt gtgactccag      3240
gagaacggcc ctcaggcatg ttcgattctg cgatcctgtg tgaatgctat gacgcgggct    3300
gtgcttggta cgagctcacg cccgccgaga ccacagttag gttgcgggct tacctaaata    3360
caccagggtt gccgtctgc caggaccatc tggagttttg ggaggcgtc ttcacaggcc      3420
tcacccacat agatgcccac ttcttgtccc agaccaagca ggcaggagac aacttcccct    3480
acctggtggc ataccaagct acagtgtgcg ccagggccca ggctccacct ccatcgtggg    3540
```

```
atcaaatgtg gaagtgtctc atacggctga agcctacgct gcacgggcca acacccttgt   3600
tgtataggct aggagccgtc caaaacgagg tcaccctcac acatcccata accaaataca   3660
tcatgacatg catgtcggcc gacctggagg tcgtcactag cacctgggtg ctagtaggcg   3720
gggtccttgc agccctggcc gcgtactgcc tgacaacggg cagcgtggtc atcgtgggca   3780
gggtcatctt gtccggaagg ccggccatca ttcccgacag ggaagttctc taccgggagt   3840
tcgatgaaat ggaagagtgc gcctcgcatc tcccctacat cgaacaaggc atgcaactcg   3900
ccgagcaatt caagcagaag gcgctcgggc tgctgcaaac agccaccaag caagcggagg   3960
ccgctgctcc cgtggtggag tccaagtggc gagcccttga ggccttctgg gcgaagcaca   4020
tgtggaattt catcagcggg atacagtatc tagcaggctt gtcaactctg cctgggaacc   4080
ccgcgatagc atcattgatg gcattcacag cctccatcac cagcccgctc accacccaac   4140
ataccctcct gtttaacatc ttgggggggt gggtggccgc ccaacttgcc ccccccggcg   4200
ctgcttcagc tttcgtgggc gccggcattg ctggcgcggc tgttggcagc ataggtcttg   4260
ggaaggtgct cgtggacatc ctggcgggtt atggggcagg ggtggcaggc gcactcgtgg   4320
cctttaaggt catgagcggc gaaatgcct ccaccgagga cctggtcaac ttactccctg   4380
ccatcctctc tcctggtgcc ctggtcgtcg gggtcgtgtg cgcagcaata ctgcgtcggc   4440
atgtgggccc aggggagggg gctgtgcagt ggatgaaccg gctgatagcg ttcgcttcgc   4500
ggggtaacca cgtctccccc acgcactatg tgcctgagag cgacgcagca gcgcgtgtca   4560
cccagatcct ctccagcctt accattactc agctgctaaa gaggctccac cagtggatta   4620
atgaagattg ctccacgcca tgctccggct cgtggctcag ggatgtttgg gactggatat   4680
gcacggtgtt gaccgatttc aaaacctggc tccaatccaa gctcctgccg cggttgccgg   4740
gagtcccttt cctttcatgt cagcgcgggt acaagggggt ttggcgggga gacggcatta   4800
tgcacactac ctgcccgtgc ggagcacaga tcagtggaca tgtcaagaac ggttccatga   4860
ggatcgttgg gcctaagacc tgtagcaaca cgtggtgcgg gacgttcccc atcaacgcgt   4920
acaccacagg cccctgcaca ccctcccgg cgccaaacta ctccagggcg ttgtggcggg   4980
tggctgctga ggagtatgtg gaggttacgc gggtggggga tttccactac gtgacgggca   5040
tgaccactga caacttaaaa tgcccatgcc aggtcccggc cctgaattc tttacggaag   5100
tggatgggt gcggctgcac aggtacgctc ctgcgtgcaa acctctccta cgggatgagg   5160
tcacattcca ggtcgggctc aaccaattcc cggtcgggtc acagcttcca tgtgaacccg   5220
agccggatgt gacagtgctc acttccatgc tcaccgaccc ctcccacatt acggcagaga   5280
cggctaagcg caggctggcc cgagggtccc ccccctcttt ggccagctct tcagctagtc   5340
agttgtctgc ggtctccttg aaggcggcat gcaccacccg tcataacccc ccagacgccg   5400
acctcatcga ggccaatctc ctgtggcggc aggagatggg cgggagcatc acccgcgtgg   5460
agtcagagag taaggtggta atcctagact catttgaacc gcttcgagcg gaggaggatg   5520
agagggaagt atccgtgccg gcggagattc tgcgaaaaac caagaaattc cccgcggcaa   5580
tgcctgtatg ggcacgcccg gactacaacc caccactctt agagtcttgg agggacccag   5640
actacgttcc tccggtggta cacgggtgcc cattgccacc taccaaggcc ctccaatac   5700
cccctccacg gagaaagagg acggttattc tgacagaatc caccgtgtcc tctgccctgg   5760
cggaacttgc cacaaagacc ttcggcagct ccggatcgtc ggccgttgac aacggcacgg   5820
cgaccgcccc tcctgaccag ccctccattg acgagacgc aggatcagac gttgagtcgt   5880
actcctccat gccccccctt gagggagagc cggggaccc cgatctcagc gacgggtctt   5940
```

```
ggtctactgt gagcgaggag gctggcgagg acgttgtctg ctgctcgatg tcctatacat    6000
ggacaggcgc cttaatcaca ccatgcgccg cagaggagag caagctgccc atcaacgcgt    6060
tgagcaattc tttgctgcgt caccacaaca tggtctatgc cacaacatcc cgcagcgcaa    6120
gccaacggca gaagaaggtc acctttgaca gactgcaagt cctggacgac cattaccggg    6180
acgtgctcaa ggagatgaag gcgaaggcgt ccacagttaa ggctaaactt ctatctgtag    6240
aagaagcctg taggctgacg cccccacatt cggccagatc caaatttggc tatggggcaa    6300
aggacgtccg gaacctatcc agcaaggccg tcaaccacat ccactccgtg tggaaggact    6360
tgctggaaga cactgagaca ccaattgaca ccaccatcat ggcaaaaaat gaggtctttt    6420
gtgttcaacc agagaaggga ggccgcaagc cagctcgtct tatcgtattc ccagacttgg    6480
gagttcgtgt atgcgagaag atggccctct acgatgtggt ttccaccctc cctcaggccg    6540
tgatgggctc ctcatacgga ttccaatact ctcctggaca gcgggtcgag ttcctggtga    6600
atgcctggaa gtcaaagaag aaccctatgg gcttcgcgta tgacacccgc tgctttgact    6660
caacagtcac tgagagtgac atccgtgttg aggagtcaat ttaccaatgt tgtgacttgg    6720
ctcccgaggc cagacaggtc ataaggtcgc tcacggagcg gctttatatc gggggccccc    6780
tgactaattc aaaagggcag aactgcggtt accgccggtg ccgcgccagc ggcgtgctga    6840
cgactagctg cggcaacacc ctcacatgtt acttgaaggc ttctgcagcc tgtcgagctg    6900
caaagctcca ggactgcacg atgctcgtgt gcggagacga ccttgtcgtt atctgtgaga    6960
gcgcgggaac ccaggaggac gcggcgagcc tacgagtctt cacggaggct atgactaggt    7020
actctgcccc cccggggac ccgccccaac cggaatacga cttggagttg ataacatcat    7080
gctcctccaa cgtgtcggtc gcgcacgatg catccggcaa gcgggtgtac tacctgaccc    7140 gcgacccac accccctc gcacgggctg cgtgggagac agcaagacac actccagtta    7200
actcctggtt aggcaacatc atcatgtatg cgcccacctt atgggcaagg atgattctga    7260
tgacccactt cttttccatc cttctagctc aggagcaact tgaaaagcc ctagattgcc    7320 agatctacgg ggccacttac tccattgaac cacttgacct acctcagatc attcagcgac    7380
tccacggtct tagcgcatt tcactccata gttactctcc aggtgagatc aatagggtgg    7440
cttcatgcct cagaaaactt ggggtaccgc ccttgcgagt ctggagacat cgggccagaa    7500
gtgtccgcgc taagttactg tcccagggag ggagggctgc catttgtggc aagtacctct    7560
ttaactgggc tgtaaggacc aagctcaaac tcactccaat tccggctgcg tcccagttgg    7620
acttgtccag ctggttcatt gctggttaca gcggggagga catatatcac agcctgtctc    7680
gtgcccgacc ccgctggttc atgtggtgcc tactcctact ttctgtaggg gtaggcatct    7740
acctgctccc caatcgatga acggggggct agtcactcca ggccaatagg ccattctgtt    7800 ttttttttt ttttttttt ttttttttt ttttttttt ttttttttt ttttttttt          7860 tttttccttt tcttcttcc ttttcttctt tctttggtgg ctccatctta gcccttagtca    7920 cggctagctg tgaaaggtcc gtgagccgca tgactgcaga gagtgctgat actggcctct    7980
ctgcagatca tgt                                                       7993
```

<210> SEQ ID NO 17
<211> LENGTH: 7993
<212> TYPE: DNA
<213> ORGANISM: Artificial
<220> FEATURE:
<223> OTHER INFORMATION: synthetic

<400> SEQUENCE: 17

```
gccagccccc tgatgggggc gacactccac catagatcac tccctgtga ggaactactg      60
tcttcacgca gaaagcgtct agccatggcg ttagtatgag tgtcgtgcag cctccaggac    120
ccccctccc gggagagcca tagtggtctg cggaaccggt gagtacaccg gaattgccag     180
gacgaccggg tcctttcttg gattaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcat catgagcaca atcctaaac     360
ctcaaagaaa aaccacacgt aacaccaacc gccgcccaat gattgaacaa gatggattgc    420
acgcaggttc tccggccgtt tgggtggaga ggctattcgg ctatgactgg gcacaacaga    480
caaccggctg ctctgatgcc gccgtgttcc ggctgtcagc gcggggggcga ccggttcttt   540
ttgtcaagac cgacctgtcc ggtgccctga atgaactgca ggacgaggca gcgcggctat    600
cgtggctggc cacgacgggc gttccttgcg cagctgtgct cgacgttgtc actgaagcgg    660
gaagggactg gctgctattg ggcgaagtgc cggggcagga tctcctgtca tctcaccttg    720
ctcctgccga gaaagtgtcc atcatggctg atgcaatacg gcggctgcat acgcttgatc    780
cggctacctg cccattcgac caccaagcga aacatcgcat cgagcgagca cgtactcgga    840
tggaagccgg tcttgtcgat caggatgatc tggacgaaga gcatcagggg ctcgcgccag    900
ccgaactgtt cgccaggctc aaggcgcgca tgcccgacgg cgaggatctc gtcgtgaccc    960
atggcgatgc ctgcttgccg aatgtcatgg tggaaaatgg ccgcttttct ggattcatcg   1020
actgtggccg gctgggtgtg gcggaccgct atcaggacat agcgttggct acccgtgata   1080
ttgctgaaga gcttggcggc gaatgggctg accgcttcct cgtgctttac ggtatcgccg   1140
ctcccgattc gaagcgcatc gccttctatc gccttcttga cgagttcttc tgagtttaaa   1200
cagcccacaa cggtttccct ctagcgggat caattccgcc cccccccta acgttactgg   1260
ccgaagccgc ttggaataag gccggtgtgc gtttgtctat atgttatttt ccaccatatt   1320
gccgtcttt  ggcaatgtga gggcccggaa acctggccct gtcttcttga cgagcattcc   1380
tagggtgtct tcccctctcg ccaaaggaat gcaaggtctg ttggatgtcg tgaaggaagc   1440
agttcctctg gaagcttctt gaagacaaac aacgtctgta gcgaccctt  gcaggcagcg   1500
gaacccccca cctggcgaca ggtgcctctg cggccaaaag ccacgtgtat aagatacacc   1560
tgcaaaggcg gtacaacccc agtgccacgt tgtgagttgg atagttgtgg aaagagtcaa   1620
atggctctcc tcaagcgtat tcaacaaggg gctgaaggat gcccagaagg taccccattg   1680
tatgggatct gatctggggc ctcggtgcac atgctctaca tgtgtttagt cgaggttaaa   1740
aaaacgtcta ggccccccga accacgggga cgtggttttc ctttgaaaaa cacgataata   1800
ccatggcacc cattacggcc tactcccaac agacgcgggg cgtacttggc tgtatcatca   1860
ctagcctcac aggtcgggac aagaaccagg tcgaggggga ggttcaggtg gtttccaccg   1920
caacgcagtc cttcttggca acctgcgtca atggcgtgtg ttggaccgtc taccatggcg   1980
ccggctcaaa gaccctagcc ggcccgaagg gaccgatcac ccaaatgtac accaatgttg   2040
accaggacct cgtcggctgg caggcgcccc cggggcgcg  ctccatgaca ccgtgcacct   2100
gcggcagctc ggacctttt  ttggtcacga ggcatgctga tgtcattccg gtgcgccggc   2160
ggggtgacag cagaggagcc ctactttccc ccaggcccgt ctcttacctg aagggctcct   2220
cgggtggtcc actgctttgc ccctcggggc acgttgtggg catcttccgg gctgccgtgt   2280
gcacccgggg ggtcgcgaag gcggtggatt ttataccgt tgagtccatg gaaaccacca   2340
```

```
tgcggtctcc ggtcttcacg gataattcat ctcccccggc cgtaccgcag acattccaag    2400
tggcccatct gcacgctccc actggcagcg gcaagagcac taaagtgccg gctgcatacg    2460
cagcccaggg gtacaaggtg ctcgtcctga acccgtccgt tgccgccacc ttgagttttg    2520
gggcgtatat gtccaaggca tatggagttg accctaacat cagaaccggg gtgaggacca    2580
tcactactgg cgctcccatc acgtactcca cctacggcaa gttccttgcc gacggcggtt    2640
gctctggggg cgcctatgac atcataatat gtgatgagtg ccactcaact gactcaacta    2700
ctattttggg cattggcaca gtcctggacc aagcggagac agctggagcg cggctcgtcg    2760
tgctcgccac cgctacgccg ccaggatcag tcaccgtacc acaccccaac atcgaggagg    2820
tggccttgtc caatactgga gagattccct tctatggcaa agccatcccc ctcgagacca    2880
tcaagggggg gaggcacctc atttctgcc actccaagaa gaagtgtgat gagcttgctg    2940
caaagctgtc ggcccttggg ctcaatgctg tagcgtacta ccggggtctt gacgtgtcca    3000
tcataccaac aagcggagac gtcgttgttg tggcaacaga cgctctaatg acgggctaca    3060
ccggtgattt tgactcagtg atcgactgca atacatgtgt cacccagaca gtcgacttca    3120
gcttcgaccc caccttcgcc attgagacga cgaccatgcc ccaagacgcg gtgtcgcgct    3180
cacagcggcg aggcaggact ggcaggggca gaggaggcat atacaggttt gtgactccag    3240
gagaacggcc ctcaggcatg ttcgattctg cgatcctgtg tgaatgctat gacgcgggct    3300
gtgcttggta cgagctcacg cccgccgaga ccacagttag gttgcgggct tacctaaata    3360
caccagggtt gccccgtctgc caggaccatc tggagttttg ggagggcgtc ttcacaggcc    3420
tcacccacat agatgcccac ttcttgtccc agaccaagca ggcaggagac aacttcccct    3480
acctggtggc ataccaagct acagtgtgcg ccagggccca ggctccacct ccatcgtggg    3540
atcaaatgtg gaagtgtctc atacggctga agcctacgct gcacgggcca acacccttgt    3600
tgtataggct aggagccgtc caaaacgagg tcaccctcac acatcccata accaaataca    3660
tcatgacatg catgtcggcc gacctggagg tcgtcactag cacctgggtg ctagtaggcg    3720
gggtccttgc agccctggcc gcgtactgcc tgacaacggg cagcgtggtc atcgtgggca    3780
gggtcatctt gtccggaagg ccggccatca ttcccgacag ggaagttctc taccgggagt    3840
tcgatgaaat ggaagagtgc gcctcgcatc tcccctacat cgaacaaggc atgcaactcg    3900
ccgagcaatt caagcagaag gcgctcgggc tgctgcaaac agccaccaag caagcggagg    3960
ccgctgctcc cgtggtggag tccaagtggc gagcccttga ggccttctgg gcgaagcaca    4020
tgtggaattt catcagcggg atacagtatc tagcaggctt gtcaactctg cctgggaacc    4080
ccgcgatagc atcattgatg gcattcacag cctccatcac cagcccgctc accacccaac    4140 ataccttct gttaacatc ttggggggt gggtggccgc caacttgcc ccccccggcg    4200 ctgcttcagc tttcgtgggc gccggcattg ctggcgcggc tgttggcagc ataggtcttg    4260
ggaaggtgct cgtggacatc ctggcgggtt atggggcagg ggtggcaggc gcactcgtgg    4320
cctttaaggt catgagcggc gaaatgcct ccaccgagga cctggtcaac ttactccctg    4380
ccatcctctc tcctggtgcc ctggtcgtcg ggtcgtgtg cgcagcaata ctgcgtcggc    4440
atgtgggccc aggggagggg gctgtgcagt ggatgaaccg gctgatagcg ttcgcttcgc    4500
ggggtaacca cgtctccccc acgcactatg tgcctgagag cgacgcagca gcgcgtgtca    4560
cccagatcct ctccagcctt accattactc agctgctaaa gaggctccac cagtggatta    4620
atgaagattg ctccacgcca tgctccggct cgtggctcag ggatgtttgg gactggatat    4680
```

-continued

```
gcacggtgtt gaccgatttc aaaacctggc tccaatccaa gctcctgccg cggttgccgg      4740
gagtcccttt cctttcatgt cagcgcgggt acaaggggt ttggcgggga gacggcatta      4800
tgcacactac ctgcccgtgc ggagcacaga tcagtggaca tgtcaagaac ggttccatga      4860
ggatcgttgg gcctaagacc tgtagcaaca cgtggtgcgg gacgttcccc atcaacgcgt      4920
acaccacagg ccctgcaca ccctccccgg cgccaaacta ctccagggcg ttgtggcggg      4980
tggctgctga ggagtatgtg gaggttacgc gggtgggga tttccactac gtgacgggca      5040
tgaccactga caacttaaaa tgcccatgcc aggtcccggc cctgaattc tttacggaag      5100 tggatggggt gcggctgcac aggtacgctc ctgcgtgcaa acctctccta cgggatgagg      5160
tcacattcca ggtcgggctc aaccaattcc cggtcgggtc acagcttcca tgtgaacccg      5220
agccggatgt gacagtgctc acttccatgc tcaccgaccc ctcccacatt acggcagaga      5280
cggctaagcg caggctggcc cgagggtccc ccccctattt ggccagctct tcagctagtc      5340
agttgtctgc ggtctccttg aaggcggcat gcaccacccg tcataacccc ccagacgccg      5400
acctcatcga ggccaatctc ctgtggcggc aggagatggg cggagcatc accccgcgtgg      5460 agtcagagag taaggtggta atcctagact catttgaacc gcttcgagcg gaggaggatg      5520
agagggaagt atccgtgccg gcggagattc tgcggaaaaac caagaaattc cccgcggcaa      5580
tgcctgtatg ggcacgcccg gactacaacc caccactctt agagtcttgg agggacccag      5640
actacgttcc tccggtggta cacgggtgcc cattgccacc taccaaggcc cctccaatac      5700
cccctccacg gagaaagagg acggttattc tgacagaatc caccgtgtcc tctgccctgg      5760
cggaacttgc cacaaagacc ttcggcagct ccggatcgtc ggccgttgac aacggcacgg      5820
cgaccgcccc tcctgaccag ccctccattg acggagacgc aggatcagac gttgagtcgt      5880
actcctccat gccccccctt gagggagagc cgggggaccc cgatctcagc gacgggtctt      5940
ggtctactgt gagcgaggag gctggcgagg acgttgtctg ctgctcgatg tcctatacat      6000
ggacaggcgc cttaatcaca ccatgcgccg cagaggagag caagctgccc atcaacgcgt      6060
tgagcaattc tttgctgcgt caccacaaca tggtctatgc cacaacatcc cgcagcgcaa      6120
gccaacggca gaagaaggtc acctttgaca gactgcaagt cctggacgac cattaccggg      6180
acgtgctcaa ggagatgaag gcgaaggcgt ccacagttaa ggctaaactt ctatctgtag      6240
aagaagcctg taggctgacg cccccacatt cggccagatc caaatttggc tatgggcaa      6300 aggacgtccg gaacctatcc agcaaggccg tcaaccacat ccactccgtg tggaaggact      6360
tgctggaaga cactgagaca ccaattgaca ccaccatcat ggcaaaaaat gaggtctttt      6420
gtgttcaacc agagaaggga ggccgcaagc cagctcgtct tatcgtattc ccagacttgg      6480
gagttcgtgt atgcgagaag atggcccctct acgatgtggt ttccaccctc cctcaggccg      6540
tgatgggctc ctcatacgga ttccaatact ctcctggaca gcgggtcgag ttcctggtga      6600
atgcctggaa gtcaaagaag aaccctatgg gcttcgcgta tgacacccgc tgctttgact      6660
caacagtcac tgagagtgac atccgtgttg aggagtcaat ttaccaatgt gtgacttgg      6720 ctcccgaggc cagacaggtc ataaggtcgc tcacggagcg gctttatatc gggggcccc      6780 tgactaattc aaaagggcag aactgcggtt accgccggtg ccgcgccagc ggcgtgctga      6840
cgactagctg cggcaacacc ctcacatgtt acttgaaggc ttctgcagcc tgtcgagctg      6900
caaagctcca ggactgcacg atgctcgtgt gcggagacga ccttgtcgtt atctgtgaga      6960
gcgcgggaac ccaggaggac gcggcagcc tacgagtctt cacgcgaggct atgactaggt      7020 actctgcccc cccgggggac ccgccccaac cggaatacga cttggagttg ataacatcat      7080
```

```
gctcctccaa cgtgtcggtc gcgcacgatg catccggcaa gcgggtgtac tacctgaccc    7140
gcgaccccac cacccccctc gcacgggctg cgtgggagag agcaagacac actccagtta    7200
actcctggtt aggcaacatc atcatgtatg cgcccacctt atgggcaagg atgattctga    7260
tgacccactt cttttccatc cttctagctc aggagcaact tgaaaaagcc ctagattgcc    7320
agatctacgg ggccacttac tccattgaac cacttgacct acctcagatc attcagcgac    7380
tccacggtct tagcgcattt tcactccata gttactctcc aggtgagatc aatagggtgg    7440
cttcatgcct cagaaaactt ggggtaccgc ccttgcgagt ctggagacat cgggccagaa    7500
gtgtccgcgc taagttactg tcccagggag ggagggctgc catttgtggc aagtacctct    7560
ttaactgggc tgtaaggacc aagctcaaac tcactccaat tccggctgcg tcccagttgg    7620
acttgtccag ctggttcatt gctggttaca gcggggggaga catatatcac agcctgtctc    7680
gtgcccgacc ccgctggttc atgtggtgcc tactcctact ttctgtaggg gtaggcatct    7740
acctgctccc caatcgatga acgggggggct agtcactcca ggccaatagg ccattctgtt    7800
tttttttttt tttttttttt tttttttttt tttttttttt tttttttttt tttttttttt    7860
tttttccttt ttcttcttcc ttttcttctt tctttggtgg ctccatctta gccctagtca    7920
cggctagctg tgaaaggtcc gtgagccgca tgactgcaga gagtgctgat actggcctct    7980
ctgcagatca tgt                                                        7993

<210> SEQ ID NO 18
<211> LENGTH: 7993
<212> TYPE: DNA
<213> ORGANISM: Artificial
<220> FEATURE:
<223> OTHER INFORMATION: synthetic

<400> SEQUENCE: 18
gccagccccc tgatggggggc gacactccac catagatcac tccctgtga ggaactactg      60
tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gattaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcat catgagcaca aatcctaaac     360
ctcaaagaaa aaccacacgt aacaccaacc gccgcccaat gattgaacaa gatggattgc     420
acgcaggttc tccggccgtt tgggtggaga ggctattcgg ctatgactgg gcacaacaga     480
caaccggctg ctctgatgcc gccgtgttcc ggctgtcagc gcggggggcga ccggttctttt    540
ttgtcaagac cgacctgtcc ggtgccctga atgaactgca ggacgaggca gcgcggctat     600
cgtggctggc cacgacgggc gttccttgcg cagctgtgct cgacgttgtc actgaagcgg     660
gaagggactg gctgctattg ggcgaagtgc cggggcagga tctcctgtca tctcaccttg     720
ctcctgccga gaaagtgtcc atcatggctg atgcaatacg gcggctgcat acgcttgatc     780
cggctacctg cccattcgac caccaagcga aacatcgcat cgagcgagca cgtactcgga     840
tggaagccgt cttgtcgat caggatgatc tggacgaaga gcatcagggg ctcgcgccag     900
ccgaactgtt cgccaggctc aaggcgcgca tgcccgacgg cgaggatctc gtcgtgaccc     960
atggcgatgc ctgcttgccg aatgtcatgg tggaaaatgg ccgcttttct ggattcatcg    1020
actgtggccg gctgggtgtg gcggaccgct atcaggacat agcgttggct acccgtgata    1080
```

```
ttgctgaaga gcttggcggc gaatgggctg accgcttcct cgtgctttac ggtatcgccg   1140
ctcccgattc gaagcgcatc gccttctatc gccttcttga cgagttcttc tgagtttaaa   1200
cagcccacaa cggtttccct ctagcgggat caattccgcc ccccccccta acgttactgg   1260
ccgaagccgc ttggaataag gccggtgtgc gtttgtctat atgttatttt ccaccatatt   1320
gccgtctttt ggcaatgtga gggcccggaa acctggccct gtcttcttga cgagcattcc   1380
tagggggtctt tcccctctcg ccaaaggaat gcaaggtctg ttggatgtcg tgaaggaagc   1440
agttcctctg gaagcttctt gaagacaaac aacgtctgta gcgaccctttt gcaggcagcg   1500
gaaccccca cctggcgaca ggtgcctctg cggccaaaag ccacgtgtat aagatacacc   1560
tgcaaaggcg gtacaacccc agtgccacgt tgtgagttgg atagttgtgg aaagagtcaa   1620
atggctctcc tcaagcgtat tcaacaaggg gctgaaggat gcccagaagg tacccccattg  1680
tatgggatct gatctggggc ctcggtgcac atgctctaca tgtgtttagt cgaggttaaa   1740
aaaacgtcta ggccccccga accacgggga cgtggttttc ctttgaaaaa cacgataata   1800
ccatggcacc cattacggcc tactcccaac agacgcgggg cgtacttggc tgtatcatca   1860
ctagcctcac aggtcgggac aagaaccagg tcgaggggga ggttcaggtg gtttccaccg   1920
caacgcagtc cttcttggca acctgcgtca atggcgtgtg ttggaccgtc taccatggcg   1980
ccggctcaaa gaccctagcc ggcccgaagg gaccgatcac ccaaatgtac accaatgttg   2040
accaggacct cgtcggctgg caggcgcccc cggggcgcg ctccatgaca ccgtgcacct    2100
gcggcagctc ggaccttttt ttggtcacga ggcatgctga tgtcattccg gtgcgccggc   2160
ggggtgacag cagaggagcc ctactttccc ccaggcccgt ctcttacctg aagggctcct   2220
cgggtggtcc actgctttgc ccctcggggc acgttgtggg catcttccgg gctgccgtgt   2280
gcacccgggg ggtcgcgaag gcggtggatt ttatacccgt tgagtccatg gaaaccacca   2340
tgcggtctcc ggtcttcacg gataattcat ctcccccggc cgtaccgcag acattccaag   2400
tggcccatct gcacgctccc actggcagcg gcaagagcac taaagtgccg gctgcatacg   2460
cagcccaggg gtacaaggtg ctcgtcctga accgtccgt tgccgccacc ttgagttttg    2520
gggcgtatat gtccaaggca tatggagttg accctaacat cagaaccggg gtgaggacca   2580
tcactactgg cgctcccatc acgtactcca cctacggcaa gttccttgcc gacggcggtt   2640
gctctggggg cgcctatgac atcataatat gtgatgagtg ccactcaact gactcaacta   2700
ctattttggg cattggcaca gtcctggacc aagcggagac agctggagcg cggctcgtcg   2760
tgctcgccac cgctacgccg ccaggatcag tcaccgtacc acaccccaac atcgaggagg   2820
tggccttgtc caatactgga gagattccct tctatggcaa agccatcccc ctcgagacca   2880
tcaagggggg gaggcacctc attttctgcc actccaagaa gaagtgtgat gagcttgctg   2940
caaagctgtc ggcccttggg ctcaatgctg tagcgtacta ccggggtctt gacgtgtcca   3000
tcataccaac aagcggagac gtcgttgttg tggcaacaga cgctctaatg acgggctaca   3060
ccggtgattt tgactcagtg atcgactgca atacatgtgt cacccagaca gtcgacttca   3120
gcttcgaccc caccttcgcc attgagacga cgaccatgcc ccaagacgcg gtgtcgcgct   3180
cacagcggcg aggcaggact ggcaggggca gaggaggcat atacaggttt gtgactccag   3240
gagaacggcc ctcaggcatg ttcgattctg cgatcctgtg tgaatgctat gacgcgggct   3300
gtgcttggta cgagctcacg cccgccgaga ccacagttag gttgcgggct tacctaaata   3360
caccaggggtt gccccgtctgc caggaccatc tggagttttg ggagggcgtc ttcacaggcc   3420
tcacccacat agatgcccac ttcttgtccc agaccaagca ggcaggagac aacttcccct   3480
```

-continued

```
acctggtggc ataccaagct acagtgtgcg ccagggccca ggctccacct ccatcgtggg    3540
atcaaatgtg gaagtgtctc atacggctga agcctacgct gcacgggcca acacccttgt    3600
tgtataggct aggagccgtc caaaacgagg tcaccctcac acatcccata accaaataca    3660
tcatgacatg catgtcggcc gacctggagg tcgtcactag cacctgggtg ctagtaggcg    3720
gggtccttgc agccctggcc gcgtactgcc tgacaacggg cagcgtggtc atcgtgggca    3780
gggtcatctt gtccggaagg ccggccatca ttcccgacag gaagttctc taccgggagt     3840 tcgatgaaat ggaagagtgc gcctcgcatc tcccctacat cgaacaaggc atgcaactcg    3900
ccgagcaatt caagcagaag gcgctcgggc tgctgcaaac agccaccaag caagcggagg    3960
ccgctgctcc cgtggtggag tccaagtggc gagcccttga ggccttctgg gcgaagcaca    4020 tgtgaattt catcagcggg atacagtatc tagcaggctt gtcaactctg cctgggaacc     4080
ccgcgatagc atcattgatg gcattcacag cctccatcac cagcccgctc accacccaac    4140
atacccttct gtttaacatc ttgggggggt gggtggccgc ccaacttgcc cccccggcg     4200 ctgcttcagc tttcgtgggc gccggcattg ctggcgcggc tgttggcagc ataggtcttg    4260
ggaaggtgct cgtggacatc ctggcgggtt atggggcagg ggtggcaggc gcactcgtgg    4320
cctttaaggt catgagcggc gaaatgccct ccaccgagga cctggtcaac ttactccctg    4380
ccatcctctc tcctggtgcc ctggtcgtcg gggtcgtgtg cgcagcaata ctgcgtcggc    4440
atgtgggccc aggggagggg gctgtgcagt ggatgaaccg gctgatagcg ttcgcttcgc    4500
ggggtaacca cgtctccccc acgcactatg tgcctgagag cgacgcagca gcgcgtgtca    4560
cccagatcct ctccagcctt accattactc agctgctaaa gaggctccac cagtggatta    4620
atgaagattg ctccacgcca tgctccggct cgtggctcag ggatgtttgg gactggatat    4680
gcacggtgtt gaccgatttc aaaacctggc tccaatccaa gctcctgccg cggttgccgg    4740
gagtcccttt cctttcatgt cagcgcgggt acaaggggt ttggcgggga gacggcatta    4800
tgcacactac ctgcccgtgc ggagcacaga tcagtggaca tgtcaagaac ggttccatga    4860
ggatcgttgg gcctaagacc tgtagcaaca cgtggtgcgg gacgttcccc atcaacgcgt    4920
acaccacagg ccctgcaca ccctccccgg cgccaaacta ctccagggcg ttgtggcggg     4980
tggctgctga ggagtatgtg gaggttacgc gggtggggga tttccactac gtgacgggca    5040
tgaccactga caacttaaaa tgcccatgcc aggtccggc ccctgaattc tttacggaag     5100
tggatggggt gcggctgcac aggtacgctc ctgcgtgcaa acctctccta cgggatgagg    5160
tcacattcca ggtcgggctc aaccaattcc cggtcgggtc acagcttcca tgtgaacccg    5220
agccggatgt gacagtgctc acttccatgc tcaccgaccc ctcccacatt acggcagaga    5280
cggctaagcg caggctggcc cgagggtccc cccctctttt ggccagctct tcagctggtc    5340
agttgtctgc ggtctccttg aaggcggcat gcaccacccg tcataacccc ccagacgccg    5400
acctcatcga ggccaatctc ctgtggcggc aggagatggg cggagcatc acccgcgtgg     5460 agtcagagag taaggtggta atcctagact catttgaacc gcttcgagcg gaggaggatg    5520
agagggaagt atccgtgccg gcggagattc tgcggaaaac caagaaattc ccgcgcgcaa    5580
tgcctgtatg ggcacgcccg gactacaacc caccactctt agagtcttgg agggacccag    5640
actacgttcc tccggtggta cacgggtgcc cattgccacc taccaaggcc cctccaatac    5700
cccctccacg gagaaagagg acggttattc tgacagaatc caccgtgtcc tctgccctgg    5760
cggaacttgc cacaaagacc ttcggcagct ccggatcgtc ggccgttgac aacggcacgg    5820
```

```
cgaccgcccc tcctgaccag ccctccattg acggagacgc aggatcagac gttgagtcgt    5880
actcctccat gcccccccctt gagggagagc cggggggaccc cgatctcagc gacgggtctt  5940
ggtctactgt gagcgaggag gctggcgagg acgttgtctg ctgctcgatg tcctatacat    6000
ggacaggcgc cttaatcaca ccatgcgccg cagaggagag caagctgccc atcaacgcgt    6060
tgagcaattc tttgctgcgt caccacaaca tggtctatgc cacaacatcc cgcagcgcaa    6120
gccaacggca gaagaaggtc acctttgaca gactgcaagt cctggacgac cattaccggg    6180
acgtgctcaa ggagatgaag gcgaaggcgt ccacagttaa ggctaaactt ctatctgtag    6240
aagaagcctg taggctgacg cccccacatt cggccagatc caaatttggc tatggggcaa    6300
aggacgtccg gaacctatcc agcaaggccg tcaaccacat ccactccgtg tggaaggact    6360
tgctggaaga cactgagaca ccaattgaca ccaccatcat ggcaaaaaat gaggtctttt    6420
gtgttcaacc agagaaggga ggccgcaagc cagctcgtct tatcgtattc ccagacttgg    6480
gagttcgtgt atgcgagaag atggccctct acgatgtggt ttccaccctc cctcaggccg    6540
tgatgggctc ctcatacgga ttccaatact ctcctggaca gcgggtcgag ttcctggtga    6600
atgcctggaa gtcaaagaag aaccctatgg gcttcgcgta tgacacccgc tgctttgact    6660
caacagtcac tgagagtgac atccgtgttg aggagtcaat ttaccaatgt tgtgacttgg    6720
ctcccgaggc cagacaggtc ataaggtcgc tcacggagcg gctttatatc ggggggcccc    6780
tgactaattc aaaagggcag aactgcggtt accgccggtg ccgcgccagc ggcgtgctga    6840
cgactagctg cggcaacacc ctcacatgtt acttgaaggc ttctgcagcc tgtcgagctg    6900
caaagctcca ggactgcacg atgctcgtgt gcggagacga ccttgtcgtt atctgtgaga    6960
gcgcgggaac ccaggaggac gcggcgagcc tacgagtctt cacggaggct atgactaggt    7020
actctgcccc cccccgggga ccgccccaac cggaatacga cttggagttg ataacatcat    7080
gctcctccaa cgtgtcggtc gcgcacgatg catccggcaa gcgggtgtac tacctgaccc    7140
gcgaccccac cacccccctc gcacgggctg cgtgggagac agcaagacac actccagtta    7200
actcctggtt aggcaacatc atcatgtatg cgcccacctt atgggcaagg atgattctga    7260
tgacccactt cttttccatc cttctagctc aggagcaact tgaaaaagcc ctagattgcc    7320
agatctacgg ggccacttac tccattgaac cacttgacct acctcagatc attcagcgac    7380
tccacggtct tagcgcattt tcactccata gttactctcc aggtgagatc aatagggtgg    7440
cttcatgcct cagaaaactt ggggtaccgc ccttgcgagt ctggagacat cgggccagaa    7500
gtgtccgcgc taagttactg tcccaggag ggagggctgc catttgtggc aagtacctct     7560
ttaactgggc tgtaaggacc aagctcaaac tcactccaat tccggctgcg tcccagttgg    7620
acttgtccag ctggttcatt gctggttaca gcgggggaga catatatcac agcctgtctc    7680
gtgcccgacc ccgctggttc atgtggtgcc tactcctact ttctgtaggg gtaggcatct    7740
acctgctccc caatcgatga acggggggct agtcactcca ggccaatagg ccattctgtt    7800
tttttttttt tttttttttt tttttttttt tttttttttt tttttttttt tttttttttt    7860
tttttccttt ttcttcttcc ttttcttctt tctttggtgg ctccatctta gccctagtca    7920
cggctagctg tgaaaggtcc gtgagccgca tgactgcaga gagtgctgat actggcctct    7980
ctgcagatca tgt                                                       7993

<210> SEQ ID NO 19
<211> LENGTH: 9607
<212> TYPE: DNA
<213> ORGANISM: Artificial
```

<220> FEATURE:
<223> OTHER INFORMATION: synthetic

<400> SEQUENCE: 19

| | | | | | |
|---|---|---|---|---|---|
| gccagccccc | tgatggggc | gacactccac | catagatcac | tcccctgtga | ggaactactg | 60 |
| tcttcacgca | gaaagcgtct | agccatggcg | ttagtatgag | tgtcgtgcag | cctccaggac | 120 |
| ccccctccc | gggagagcca | tagtggtctg | cggaaccggt | gagtacaccg | gaattgccag | 180 |
| gacgaccggg | tcctttcttg | gattaacccg | ctcaatgcct | ggagatttgg | gcgtgccccc | 240 |
| gcgagactgc | tagccgagta | gtgttgggtc | gcgaaaggcc | ttgtggtact | gcctgatagg | 300 |
| gtgcttgcga | gtgccccggg | aggtctcgta | gaccgtgcat | catgagcaca | aatcctaaac | 360 |
| ctcaaagaaa | aaccacacgt | aacaccaacc | gccgcccaca | ggacgtcaag | ttcccgggcg | 420 |
| gtggtcagat | cgttggtgga | gtttacctgt | tgccgcgcag | gggccccagg | ttgggtgtgc | 480 |
| gcgcgactag | gaagacttcc | gagcggtcgc | aacctcgtgg | aaggcgacaa | cctatcccca | 540 |
| aggctcgccg | gcccgaggc | agggcctggg | ctcagcccgg | gtaccettgg | cccctctatg | 600 |
| gcaatgaggg | tctggggtgg | gcaggatggc | tcctgtcacc | ccgcggatcc | cggcctagtt | 660 |
| ggggccccac | ggaccccgg | cgtaggtcgc | gtaatttggg | taaggtcatc | gatacccta | 720 |
| catgcggctt | cgccgacctc | atggggtaca | ttccgctcgt | cggcgccccc | ttaggaggcg | 780 |
| ctgccagggc | cctggcgcat | ggcgtccggg | tgctggagga | cggcgtgaac | tacgcaacag | 840 |
| ggaatctgcc | cggttgctct | ttctctatct | tcctcttggc | tttgctgtcc | tgtctgacca | 900 |
| ttccagctgc | cgcttatgaa | gtgcgcaacg | tgtccgggt | gtaccatgtc | acgaacgact | 960 |
| gctccaactc | aagtattgtg | tatgaggcag | cggacatgat | catgcacacc | cctgggtgcg | 1020 |
| tgccctgcgt | ccgggaggc | aattcctccc | gctgctgggt | ggcgctcact | cccacgctcg | 1080 |
| cggccaggaa | cagtagcatc | cccactacga | cgattcgacg | ccacgtcgac | ttgctcgttg | 1140 |
| gggcggccgc | tctctgctcc | gttgtgtacg | tgggggatct | ctgcggatct | gtcttcctcg | 1200 |
| tctcccagct | gttcaccttc | tcacctcgcc | agtatgagac | ggtacaggac | tgcaattgct | 1260 |
| cactctatcc | cggccacgta | tcaggtcacc | gcatggcttg | ggatatgatg | atgaactggt | 1320 |
| cgcccacgac | agccttggtg | gtgtcgcagt | tactccggat | cccacaagcc | atcgtggaca | 1380 |
| tggtgtcggg | ggcccactgg | ggagtcctgg | cgggccttgc | ctactattcc | atggtgggga | 1440 |
| actgggccaa | ggtcttgatt | gtgatgctac | tctttgccgg | cgttgacggg | gacacctaca | 1500 |
| cgacagggg | ggtagcaagc | cgcaccaccg | cgggccttgc | gtccctcttt | gtatcagggc | 1560 |
| cgtcccagaa | aatccagctc | ataaacacca | acggcagctg | gcacatcaac | aggactgccc | 1620 |
| taaattgcaa | tgactccctc | aacactgggt | tccttgccgc | gctgttctac | gtaaacaggt | 1680 |
| tcaactcgtc | cggctgccca | gagcgcatgg | ccagctgccg | ccccattgat | aagttcgctc | 1740 |
| aggggtgggg | tcccatcacc | cacgctgtgc | ctcgcgcctc | agaccagagg | ccttattgct | 1800 |
| ggcactacgc | gccccaaccg | tgcggtattg | tacccgcgtc | gcaggtgtgt | ggtccagtgt | 1860 |
| actgcttcac | cccgagccct | gttgtggtgg | ggacgactga | tcgctccggc | gccccacgt | 1920 |
| acacctgggg | ggagaatgag | acggacgtgc | tgatccttaa | caacacgcgg | ccgccgcacg | 1980 |
| gcaactggtt | cggctgctca | tggatgaata | gcaccgggtt | caccaagacg | tgtggggcc | 2040 |
| ccccgtgcaa | catcggggg | gtcggcaata | acaccttgac | ctgccccacg | gattgcttcc | 2100 |
| ggaagcaccc | cgaggccact | tacaccaaat | gcggctcggg | gccttggttg | acacctaggt | 2160 |
| gtatggttga | ctaccatac | aggctttggc | attaccctg | cactgtcaac | tataccatct | 2220 |

```
tcaaggtcag gatgtatgtg gggggtgtgg agcaccggct caatgccgcg tgcaactgga    2280
cccgagggga gcgttgtgat ctggaggaca gggatagatc agagctcagc ccgctgctac    2340
tgtccacgac agagtggcag atactgccct gttccttcac caccctaccg gctctgtcca    2400
ccggtttaat ccacctccat cagaacatcg tggacgtaca atacctgtac ggtgtagggt    2460
cagtggttgt ctctattgtg atcagatggg agtacgtcgt gctgctcttc cttcttctgg    2520
cggacgcgcg cgtctgcgcc tgcttatgga tgatgctgct gatagcccag gctgaggccg    2580
ccttagagaa cctggtggcc ctcaatgcag cgtccgtggc tggagcgcat ggcatcctct    2640
ccttccttgc gttcttctgt gctgcctggt acatcaaagg caagctggtt cctggggcgg    2700
catatgctct ttacagtgtg tggccgctac tcctgctcct gctggcgttg ccgccacggg    2760
catacgccat ggaccgggag atggctgcat cgtgtggagg cgcggtcttc gtaggtctgg    2820
tactcctgac cttgtcacca cactacaaag cactcctcgc caggctcata tggtggttac    2880
aatatcttac caccagggcc gaggcgctcc tgcaagtgtg atcccccccc ctcaacgtcc    2940
gggggggccg cgatgccatc atcctcctca cgtgcatggt ccacccagag ctaactttig    3000 aaatcaccaa aatcttgctc gccatactgg gcccgctcat ggtgctccgg gcaggcctaa    3060
ctagagtgcc gtacttcgtg cgcgctcacg ggctcattcg tgcgtgcatg ctggtgcgga    3120
aagtcgctgg gggccattat gtccagatgg ctctcatgaa gctggccgcg ctgacaggca    3180
cgtacgttta cgaccatctt accccgctgc gggactgggc ccacgcgggc ctgcgagacc    3240
ttgcggtggc ggttgagccc gttgttttct ctgacacgga gaccaagatt atcacctggg    3300
gggcagacac cgcggcgtgt ggggacatca tcctgggtct acccgtctcc gcccggaggg    3360
ggagggagat acttctagga ccggccgata agtttggaga gcaggggtgg cgactccttg    3420
cacccattac ggcctactcc caacagacgc ggggcgtact tggctgtatc atcactagcc    3480
tcacaggtcg ggacaagaac caggtcgagg gggaggttca ggtggtttcc accgcaacgc    3540
agtccttctt ggcaacctgc gtcaatgcg tgtgttggac cgtctaccat ggcgccggct    3600
caaagaccct agccggcccg aagggaccga tcacccaaat gtacaccaat gttgaccagg    3660
acctcgtcgg ctggcaggcg ccccccgggg cgcgctccat gacaccgtgc acctgcggca    3720
gctcggacct ttttttggtc acgaggcatg ctgatgtcat tccggtgcgc cggcggggtg    3780
acagcagagg agccctactt tcccccaggc ccgtctctta cctgaagggc tcctcgggtg    3840
gtccactgct ttgcccctcg gggcacgttg tgggcatctt ccgggctgcc gtgtgcaccc    3900
ggggggtcgc gaaggcggtg gattttatac ccgttgagtc catggaaacc accatgcggt    3960
ctccggtctt cacggataat tcatctcccc cggccgtacc gcagacattc caagtggccc    4020
atctgcacgc tcccactggc agcggcaaga gcactaaagt gccggctgca tacgcagccc    4080
aggggtacaa ggtgctcgtc ctgaacccgt ccgttgccgc caccttgagt tttgggcgt     4140 atatgtccaa ggcatatgga gttgacccta acatcagaac cggggtgagg accatcacta    4200
ctggcgctcc catcacgtac tccacctacg gcaagttcct tgccgacggc ggttgctctg    4260
ggggcgccta tgacatcata atatgtgatg agtgccactc aactgactca actactattt    4320
tgggcattgg cacagtcctg gaccaagcgg agacagctgg agcgcggctc gtcgtgctcg    4380
ccaccgctac gccgccagga tcagtcaccg taccacaccc caacatcgag gaggtggcct    4440
tgtccaatac tggagagatt cccttctatg gcaaagccat ccccctcgag accatcaagg    4500
gggggaggca cctcattttc tgccactcca agaagaagtg tgatgagctt gctgcaaagc    4560
tgtcggccct tgggctcaat gctgtagcgt actaccgggg tcttgacgtg tccatcatac    4620
```

```
caacaagcgg agacgtcgtt gttgtggcaa cagacgctct aatgacgggc tacaccggtg    4680
attttgactc agtgatcgac tgcaatacat gtgtcaccca gacagtcgac ttcagcttcg    4740
accccacctt cgccattgag acgacgacca tgccccaaga cgcggtgtcg cgctcacagc    4800
ggcgaggcag gactggcagg ggcagaggag gcatatacag gtttgtgact ccaggagaac    4860
ggccctcagg catgttcgat tctgcgatcc tgtgtgaatg ctatgacgcg ggctgtgctt    4920
ggtacgagct cacgcccgcc gagaccacag ttaggttgcg ggcttaccta aatacaccag    4980
ggttgcccgt ctgccaggac catctggagt tttgggaggg cgtcttcaca ggcctcaccc    5040
acatagatgc ccacttcttg tcccagacca agcaggcagg agacaacttc ccctacctgg    5100
tggcatacca agctacagtg tgcgccaggg cccaggctcc acctccatcg tgggatcaaa    5160
tgtggaagtg tctcatacgg ctgaagccta cgctgcacgg gccaacaccc ttgttgtata    5220
ggctaggagc cgtccaaaac gaggtcaccc tcacacatcc cataaccaaa tacatcatga    5280
catgcatgtc ggccgacctg gaggtcgtca ctagcacctg ggtgctagta ggcggggtcc    5340
ttgcagccct ggccgcgtac tgcctgacaa cgggcagcgt ggtcatcgtg gcagggtca    5400 tcttgtccgg aaggccggcc atcattcccg acagggaagt tctctaccgg gagttcgatg    5460
aaatggaaga gtgcgcctcg catctccccct acatcgaaca aggcatgcaa ctcgccgagc    5520
aattcaagca gaaggcgctc gggctgctgc aaacagccac caagcaagcg gaggccgctg    5580
ctcccgtggt ggagtccaag tggcgagccc ttgaggcctt ctgggcgaag cacatgtgga    5640
atttcatcag cgggatacag tatctagcag gcttgtcaac tctgcctggg aaccccgcga    5700
tagcatcatt gatggcattc acagcctcca tcaccagccc gctcaccacc aacataccc    5760 ttctgtttaa catcttgggg gggtgggtgg ccgcccaact tgccccccc ggcgctgctt    5820 cagctttcgt gggcgccggc attgctggcg cggctgttgg cagcataggt cttgggaagg    5880
tgctcgtgga catcctggcg ggttatgggg caggggtggc aggcgcactc gtggccttta    5940
aggtcatgag cggcgaaatg ccctccaccg aggacctggt caacttactc cctgccatcc    6000
tctctcctgg tgccctggtc gtcggggtcg tgtgcgcagc aatactgcgt cggcatgtgg    6060
gcccagggga gggggctgtg cagtggatga accggctgat agcgttcgct tcgcggggta    6120
accacgtctc ccccacgcac tatgtgcctg agagcgacgc agcagcgcgt gtcacccaga    6180
tcctctccag ccttaccatt actcagctgc taaagaggct ccaccagtgg attaatgaag    6240
attgctccac gccatgctcc ggctcgtggc tcagggatgt ttgggactgg atatgcacgg    6300
tgttgaccga tttcaaaacc tggctccaat ccaagctcct gccgcggttg ccgggagtcc    6360
ctttcctttc atgtcagcgc gggtacaagg gggtttggcg gggagacggc attatgcaca    6420
ctacctgccc gtgcggagca cagatcagtg gacatgtcaa gaacggttcc atgaggatcg    6480
ttgggcctaa gacctgtagc aacacgtggt gcgggacgtt ccccatcaac gcgtacacca    6540
caggcccctg cacaccctcc ccggcgccaa actactccag ggcgttgtgg cgggtggctg    6600
ctgaggagta tgtggaggtt acgcgggtgg gggatttcca ctacgtgacg ggcatgacca    6660
ctgacaactt aaaatgccca tgccaggtcc cggcccctga attctttacg gaagtggatg    6720
gggtgcggct gcacaggtac gctcctgcgt gcaaacctct cctacgggat gaggtcacat    6780
tccaggtcgg gctcaaccaa ttccggtcg ggtcacagct tccatgtgaa cccgagccgg    6840
atgtgacagt gctcacttcc atgctcaccg acccctccca cattacggca gagacggcta    6900
agcgcaggct ggcccgaggg tccccccct atttggccag ctcttcagct agtcagttgt    6960
```

```
ctgcggtctc cttgaaggcg gcatgcacca cccgtcataa ccccccagac gccgacctca    7020
tcgaggccaa tctcctgtgg cggcaggaga tgggcgggag catcacccgc gtggagtcag    7080
agagtaaggt ggtaatccta gactcatttg aaccgcttcg agcggaggag gatgagaggg    7140
aagtatccgt gccggcggag attctgcgga aaaccaagaa attccccgcg gcaatgcctg    7200
tatgggcacg cccggactac aacccaccac tcttagagtc ttggagggac ccagactacg    7260
ttcctccggt ggtacacggg tgcccattgc cacctaccaa ggcccctcca ataccccctc    7320
cacggagaaa gaggacggtt attctgacag aatccaccgt gtcctctgcc ctggcggaac    7380
ttgccacaaa gaccttcggc agctccggat cgtcggccgt tgacaacggc acggcgaccg    7440
cccctcctga ccagccctcc attgacggag acgcaggatc agacgttgag tcgtactcct    7500
ccatgccccc ccttgaggga gagccggggg accccgatct cagcgacggg tcttggtcta    7560
ctgtgagcga ggaggctggc gaggacgttg tctgctgctc gatgtcctat acatggacag    7620
gcgccttaat cacaccatgc gccgcagagg agagcaagct gcccatcaac gcgttgagca    7680
attctttgct gcgtcaccac aacatggtct atgcacacaa atcccgcagc gcaagccaac    7740
ggcagaagaa ggtcaccttt gacagactgc aagtcctgga cgaccattac cgggacgtgc    7800
tcaaggagat gaaggcgaag gcgtccacag ttaaggctaa acttctatct gtagaagaag    7860
cctgtaggct gacgccccca cattcggcca gatccaaatt tggctatggg gcaaaggacg    7920
tccggaacct atccagcaag gccgtcaacc acatccactc cgtgtggaag gacttgctgg    7980
aagacactga gacaccaatt gacaccacca tcatggcaaa aaatgaggtc ttttgtgttc    8040
aaccagagaa gggaggccgc aagccagctc gtcttatcgt attcccagac ttgggagttc    8100
gtgtatgcga gaagatggcc ctctacgatg tggtttccac cctccctcag gccgtgatgg    8160
gctcctcata cggattccaa tactctcctg gacagcgggt cgagttcctg gtgaatgcct    8220
ggaagtcaaa gaagaaccct atgggcttcg cgtatgacac ccgctgcttt gactcaacag    8280
tcactgagag tgacatccgt gttgaggagt caatttacca atgttgtgac ttggctcccg    8340
aggccagaca ggtcataagg tcgctcacgg agcggcttta tatcggggc cccctgacta    8400 attcaaaagg gcagaactgc ggttaccgcc ggtgccgcgc cagcggcgtg ctgacgacta    8460
gctgcggcaa caccctcaca tgttacttga aggcttctgc agcctgtcga gctgcaaagc    8520
tccaggactg cacgatgctc gtgtgcggag acgaccttgt cgttatctgt gagagcgcgg    8580
gaacccagga ggacgcggcg agcctacgag tcttcacgga ggctatgact aggtactctg    8640
ccccccccgg ggaccccgcc caaccggaat acgacttgga gttgataaca tcatgctcct    8700
ccaacgtgtc ggtcgcgcac gatgcatccg gcaagcgggt gtactacctg acccgcgacc    8760
ccaccacccc cctcgcacgg gctgcgtggg agacagcaag acacactcca gttaactcct    8820
ggttaggcaa catcatcatg tatgcgccca ccttatgggc aaggatgatt ctgatgaccc    8880 acttctttc catccttcta gctcaggagc aacttgaaaa agcccttagat tgccagatct    8940 acggggccac ttactccatt gaaccacttg acctacctca gatcattcag cgactccacg    9000
gtcttagcgc atttttcactc catagttact ctccaggtga gatcaatagg gtggcttcat    9060
gcctcagaaa acttggggta ccgcccttgc gagtctggag acatcgggcc agaagtgtcc    9120
gcgctaagtt actgtcccag ggagggaggg ctgccatttg tggcaagtac ctctttaact    9180
gggctgtaag gaccaagctc aaactcactc caattccggc tgcgtcccag ttggacttgt    9240
ccagctggtt cattgctggt tacagcgggg gagacatata tcacagcctg tctcgtgccc    9300
gaccccgctg gttcatgtgg tgcctactcc tactttctgt aggggtaggc atctacctgc    9360
```

```
tccccaatcg atgaacgggg ggctagtcac tccaggccaa taggccattc tgttttttttt    9420 tttttttttt tttttttttt tttttttttt tttttttttt tttttttttt ttttttttttc    9480 cttttcttc ttccttttct tctttctttg gtggctccat cttagcccta gtcacggcta     9540
gctgtgaaag gtccgtgagc cgcatgactg cagagagtgc tgatactggc ctctctgcag    9600
atcatgt                                                              9607
```

<210> SEQ ID NO 20
<211> LENGTH: 9607
<212> TYPE: DNA
<213> ORGANISM: Artificial
<220> FEATURE:
<223> OTHER INFORMATION: synthetic

<400> SEQUENCE: 20

```
gccagccccc tgatgggggc gacactccac catagatcac tccctgtga ggaactactg      60 tcttcacgca gaaagcgtct agccatggcg ttagtatgag tgtcgtgcag cctccaggac    120
cccccctccc gggagagcca tagtggtctg cggaaccggt gagtacaccg gaattgccag    180
gacgaccggg tcctttcttg gattaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcat catgagcaca atcctaaac     360 ctcaaagaaa aaccacacgt aacaccaacc gccgcccaca ggacgtcaag ttcccgggcg    420
gtggtcagat cgttggtgga gtttacctgt tgccgcgcag gggccccagg ttgggtgtgc    480
gcgcgactag gaagacttcc gagcggtcgc aacctcgtgg aaggcgacaa cctatcccca    540
aggctcgccg gcccgagggc agggcctggg ctcagcccgg gtaccttgg ccctctatg     600 gcaatgaggg tctgggtgg gcaggatggc tcctgtcacc ccgcggatcc cggcctagtt    660
gggcccccac ggaccccgg cgtaggtcgc gtaatttggg taaggtcatc gatacccctca   720 catgcggctt cgccgacctc atggggtaca ttccgctcgt cggcgcccc ttaggaggcg    780 ctgccagggc cctggcgcat ggcgtccggg tgctggagga cggcgtgaac tacgcaacag    840
ggaatctgcc cggttgctct ttctctatct tcctcttggc tttgctgtcc tgtctgacca    900
ttccagctgc cgcttatgaa gtgcgcaacg tgtccggggt gtaccatgtc acgaacgact    960
gctccaactc aagtattgtg tatgaggcag cggacatgat catgcacacc ctgggtgcg    1020 tgccctgcgt ccgggagggc aattcctccc gctgctgggt ggcgctcact cccacgctcg    1080 cggcaggaa cagtagcatc cccactacga cgattcgacg ccacgtcgac ttgctcgttg    1140
gggcggccgc tctctgctcc gttgtgtacg tgggggatct ctgcggatct gtcttcctcg    1200
tctcccagct gttcaccttc tcacctcgcc agtatgagac ggtacaggac tgcaattgct    1260
cactctatcc cggccacgta tcaggtcacc gcatggcttg ggatatgatg atgaactggt    1320
cgcccacgac agccttggtg gtgtcgcagt tactccggat cccacaagcc atcgtggaca    1380
tggtgtcggg ggcccactgg ggagtcctgg cgggccttgc ctactattcc atggtgggga    1440
actgggccaa ggtcttgatt gtgatgctac tctttgccgg cgttgacggg gacacctaca    1500 cgacagggg ggtagcaagc cgcaccaccg cgggccttgc gtccctcttt gtatcagggc    1560
cgtcccagaa aatccagctc ataaacacca acggcagctg gcacatcaac aggactgccc    1620
taaattgcaa tgactccctc aacactgggt tccttgccgc gctgttctac gtaaacaggt    1680
tcaactcgtc cggctgccca gagcgcatgg ccagctgccg ccccattgat aagttcgctc    1740
```

-continued

```
aggggtgggg tcccatcacc cacgctgtgc ctcgcgcctc agaccagagg ccttattgct    1800
ggcactacgc gccccaaccg tgcggtattg tacccgcgtc gcaggtgtgt ggtccagtgt    1860
actgcttcac cccgagccct gttgtggtgg ggacgactga tcgctccggc gcccccacgt    1920
acacctgggg ggagaatgag acggacgtgc tgatccttaa caacgcgg  ccgccgcacg    1980 gcaactggtt cggctgctca tggatgaata gcaccgggtt caccaagacg tgtgggggcc    2040
ccccgtgcaa catcggggg  gtcggcaata acaccttgac ctgccccacg gattgcttcc    2100
ggaagcaccc cgaggccact acaccaaat  gcggctcggg gccttggttg acacctaggt    2160
gtatggttga ctaccatac  aggctttggc attaccctg  cactgtcaac tataccatct    2220
tcaaggtcag gatgtatgtg gggggtgtgg agcaccggct caatgccgcg tgcaactgga    2280
cccgagggga gcgttgtgat ctggaggaca gggatagatc agagctcagc ccgctgctac    2340
tgtccacgac agagtggcag atactgccct gttccttcac caccctaccg gctctgtcca    2400
ccggtttaat ccacctccat cagaacatcg tggacgtaca atacctgtac ggtgtagggt    2460
cagtggttgt ctctattgtg atcagatggg agtacgtcgt gctgctcttc cttcttctgg    2520
cggacgcgcg cgtctgcgcc tgcttatgga tgatgctgct gatagcccag gctgaggccg    2580
ccttagagaa cctggtggcc ctcaatgcag cgtccgtggc tggagcgcat ggcatcctct    2640
ccttccttgc gttcttctgt gctgcctggt acatcaaagg caagctggtt cctggggcgg    2700
catatgctct ttacagtgtg tggccgctac tcctgctcct gctggcgttg ccgccacggg    2760
catacgccat ggaccgggag atggctgcat cgtgtggagg cgcggtcttc gtaggtctgg    2820
tactcctgac cttgtcacca cactacaaag cactcctcgc caggctcata tggtggttac    2880
aatatcttac caccagggcc gaggcgctcc tgcaagtgtg gatccccccc ctcaacgtcc    2940 ggggggggccg cgatgccatc atcctcctca cgtgcatggt ccaccagag ctaacttttg    3000 aaatcaccaa aatcttgctc gccatactgg gcccgctcat ggtgctccgg gcaggcctaa    3060
ctagagtgcc gtacttcgtg cgcgctcacg ggctcattcg tgcgtgcatg ctggtgcgga    3120
aagtcgctgg gggccattat gtccagatgg ctctcatgaa gctggccgcg ctgacaggca    3180
cgtacgttta cgaccatctt accccgctgc gggactgggc ccacgcgggc ctgcgagacc    3240
ttgcggtggc ggttgagccc gttgtttttct ctgacacgga gaccaagatt atcacctggg    3300
gggcagacac cgcggcgtgt gggggacatca tcctgggtct acccgtctcc gcccggaggg    3360
ggagggagat acttctagga ccggccgata agtttggaga gcaggggtgg cgactccttg    3420
cacccattac ggcctactcc caacagacgc ggggcgtact tggctgtatc atcactagcc    3480
tcacaggtcg ggacaagaac caggtcgagg gggaggttca ggtggtttcc accgcaacgc    3540
agtccttctt ggcaacctgc gtcaatgcg  tgtgttggac cgtctaccat ggcgccggct    3600
caaagaccct agccggcccg aagggaccga tcacccaaat gtacaccaat gttgaccagg    3660
acctcgtcgg ctggcaggcg cccccggggg cgcgctccat gacaccgtgc acctgcggca    3720
gctcggacct ttttttggtc acgaggcatg ctgatgtcat tccggtgcgc cggcggggtg    3780
acagcagagg agccctactt tcccccaggc ccgtctctta cctgaagggc cctcgggtg     3840 gtccactgct ttgcccctcg gggcacgttg tgggcatctt ccgggctgcc gtgtgcaccc    3900 gggggggtcgc gaaggcggtg gattttatac ccgttgagtc catggaaacc accatgcggt    3960
ctccggtctt cacggataat tcatctcccc cggccgtacc gcagacattc caagtggccc    4020
atctgcacgc tccactggc  agcggcaaga gcactaaagt gccggctgca tacgcagccc    4080
aggggtacaa ggtgctcgtc ctgaacccgt ccgttgccgc caccttgagt tttggggcgt    4140
```

```
atatgtccaa ggcatatgga gttgaccota acatcagaac cggggtgagg accatcacta    4200
ctggcgctcc catcacgtac tccacctacg gcaagttcct tgccgacggc ggttgctctg    4260
ggggcgccta tgacatcata atatgtgatg agtgccactc aactgactca actactattt    4320
tgggcattgg cacagtcctg gaccaagcgg agacagctgg agcgcggctc gtcgtgctcg    4380
ccaccgctac gccgccagga tcagtcaccg taccacaccc caacatcgag gaggtggcct    4440
tgtccaatac tggagagatt cccttctatg caaagccat ccccctcgag accatcaagg     4500
gggggaggca cctcattttc tgccactcca agaagaagtg tgatgagctt gctgcaaagc    4560
tgtcggccct tgggctcaat gctgtagcgt actaccgggg tcttgacgtg tccatcatac    4620
caacaagcgg agacgtcgtt gttgtggcaa cagacgctct aatgacgggc tacaccggtg    4680
attttgactc agtgatcgac tgcaatacat gtgtcaccca gacagtcgac ttcagcttcg    4740
accccacctt cgccattgag acgacgacca tgccccaaga cgcggtgtcg cgctcacagc    4800
ggcgaggcag gactggcagg ggcagaggag gcatatacag gtttgtgact ccaggagaac    4860
ggccctcagg catgttcgat tctgcgatcc tgtgtgaatg ctatgacgcg ggctgtgctt    4920
ggtacgagct cacgcccgcc gagaccacag ttaggttgcg ggcttaccta aatacaccag    4980
ggttgcccgt ctgccaggac catctggagt tttgggaggg cgtcttcaca ggcctcaccc    5040
acatagatgc ccacttcttg tcccagacca agcaggcagg agacaacttc ccctacctgg    5100
tggcatacca agctacagtg tgcgccaggg cccaggctcc acctccatcg tgggatcaaa    5160
tgtggaagtg tctcatacgg ctgaagccta cgctgcacgg gccaacaccc ttgttgtata    5220
ggctaggagc cgtccaaaac gaggtcaccc tcacacatcc cataaccaaa tacatcatga    5280
catgcatgtc ggccgacctg gaggtcgtca ctagcacctg ggtgctagta ggcgggtcc     5340
ttgcagccct ggccgcgtac tgcctgacaa cgggcagcgt ggtcatcgtg gcagggtca    5400
tcttgtccgg aaggccggcc atcattcccg acagggaagt tctctaccgg gagttcgatg    5460
aaatggaaga gtgcgcctcg catctcccct acatcgaaca aggcatgcaa ctcgccgagc    5520
aattcaagca gaaggcgctc gggctgctgc aaacagccac caagcaagcg gaggccgctg    5580
ctcccgtggt ggagtccaag tggcgagccc ttgaggcctt ctgggcgaag cacatgtgga    5640
atttcatcag cgggatacag tatctagcag gcttgtcaac tctgcctggg aaccccgcga    5700
tagcatcatt gatggcattc acagcctcca tcaccagccc gctcaccacc caacataccc    5760
ttctgtttaa catcttgggg gggtgggtgg ccgcccaact tgcccccccc ggcgctgctt    5820
cagctttcgt gggcgccggc attgctggcg cggctgttgg cagcataggt cttgggaagg    5880
tgctcgtgga catcctggcg ggttatgggg caggggtggc aggcgcactc gtggcctta    5940
aggtcatgag cggcgaaatg ccctccaccg aggacctggt caacttactc cctgccatcc    6000
tctctcctgg tgccctggtc gtcggggtcg tgtgcgcagc aatactgcgt cggcatgtgg    6060
gcccagggga gggggctgtg cagtggatga accggctgat agcgttcgct tcgcggggta    6120
accacgtctc ccccacgcac tatgtgcctg agagcgacgc agcagcgcgt gtcacccaga    6180
tcctctccag ccttaccatt actcagctgc taaagaggct ccaccagtgg attaatgaag    6240
attgctccac gccatgctcc ggctcgtggc tcagggatgt ttgggactgg atatgcacgg    6300
tgttgaccga tttcaaaacc tggctccaat ccaagctcct gccgcggttg ccgggagtcc    6360
ctttcctttc atgtcagcgc gggtacaagg ggtttggcg gggagacggc attatgcaca    6420
ctacctgccc gtgcggagca cagatcagtg gacatgtcaa gaacggttcc atgaggatcg    6480
```

```
ttgggcctaa gacctgtagc aacacgtggt gcgggacgtt ccccatcaac gcgtacacca    6540
caggcccctg cacaccctcc ccggcgccaa actactccag ggcgttgtgg cgggtggctg    6600
ctgaggagta tgtggaggtt acgcgggtgg gggatttcca ctacgtgacg ggcatgacca    6660
ctgacaactt aaaatgccca tgccaggtcc cggcccctga attctttacg gaagtggatg    6720
gggtgcggct gcacaggtac gctcctgcgt gcaaacctct cctacgggat gaggtcacat    6780
tccaggtcgg gctcaaccaa ttcccggtcg ggtcacagct tccatgtgaa cccgagccgg    6840
atgtgacagt gctcacttcc atgctcaccg acccctccca cattacggca gagacggcta    6900
agcgcaggct ggcccgaggg tcccccccct ctttggccag ctcttcagct ggtcagttgt    6960
ctgcggtctc cttgaaggcg gcatgcacca cccgtcataa ccccccagac gccgacctca    7020
tcgaggccaa tctcctgtgg cggcaggaga tgggcgggag catcacccgc gtggagtcag    7080
agagtaaggt ggtaatccta gactcatttg aaccgcttcg agcggaggag gatgagaggg    7140
aagtatccgt gccggcggag attctgcgga aaccaagaa attccccgcg gcaatgcctg     7200
tatgggcacg cccggactac aacccaccac tcttagagtc ttggagggac ccagactacg    7260
ttcctccggt ggtacacggg tgcccattgc cacctaccaa ggcccctcca ataccccctc    7320
cacggagaaa gaggacggtt attctgacag aatccaccgt gtcctctgcc ctggcggaac    7380
ttgccacaaa gaccttcggc agctccggat cgtcggccgt tgacaacggc acggcgaccg    7440
cccctcctga ccagccctcc attgacgagg acgcaggatc agacgttgag tcgtactcct    7500
ccatgccccc ccttgaggga gagccggggg accccgatct cagcgacggg tcttggtcta    7560
ctgtgagcga ggaggctggc gaggacgttg tctgctgctc gatgtcctat acatggacag    7620
gcgccttaat cacaccatgc gccgcagagg agagcaagct gcccatcaac gcgttgagca    7680
attctttgct gcgtcaccac aacatggtct atgccacaac atcccgcagc gcaagccaac    7740
ggcagaagaa ggtcacccttt gacagactgc aagtcctgga cgaccattac cgggacgtgc    7800
tcaaggagat gaaggcgaag gcgtccacag ttaaggctaa acttctatct gtagaagaag    7860
cctgtaggct gacgccccca cattcggcca gatccaaatt tggctatggg gcaaaggacg    7920
tccggaacct atccagcaag gccgtcaacc acatccactc cgtgtggaag gacttgctgg    7980
aagacactga gacaccaatt gacaccacca tcatggcaaa aaatgaggtc ttttgtgttc    8040
aaccagagaa gggaggccgc aagccagctc gtcttatcgt attcccagac ttgggagttc    8100
gtgtatgcga gaagatggcc ctctacgatg tggttccac cctccctcag gccgtgatgg    8160
gctcctcata cggattccaa tactctcctg gacagcgggt cgagttcctg gtgaatgcct    8220
ggaagtcaaa gaagaaccct atgggcttcg cgtatgacac ccgctgcttt gactcaacag    8280
tcactgagag tgacatccgt gttgaggagt caatttacca atgttgtgac ttggctcccg    8340
aggccagaca ggtcataagg tcgctcacgg agcggcttta tatcgggggc cccctgacta    8400
attcaaaagg gcagaactgc ggttaccgcc ggtgccgcgc cagcggcgtg ctgacgacta    8460
gctgcggcaa caccctcaca tgttacttga aggcttctgc agcctgtcga gctgcaaagc    8520
tccaggactg cacgatgctc gtgtgcggag acgaccttgt cgttatctgt gagagcgcgg    8580
gaacccagga ggacgcggcg agcctacgag tcttcacgga ggctatgact aggtactctg    8640
cccccccccgg ggacccgccc caaccggaat acgacttgga gttgataaca tcatgctcct    8700
ccaacgtgtc ggtcgcgcac gatgcatccg gcaagcgggt gtactacctg acccgcgacc    8760
ccaccacccc cctcgcacgg gctgcgtggg agacagcaag acacactcca gttaactcct    8820
ggttaggcaa catcatcatg tatgcgccca cccttatgggc aaggatgatt ctgatgaccc    8880
```

```
acttcttttc catccttcta gctcaggagc aacttgaaaa agccctagat tgccagatct    8940
acggggccac ttactccatt gaaccacttg acctacctca gatcattcag cgactccacg    9000
gtcttagcgc attttcactc catagttact ctccaggtga gatcaatagg gtggcttcat    9060
gcctcagaaa acttggggta ccgcccttgc gagtctggag acatcgggcc agaagtgtcc    9120
gcgctaagtt actgtcccag ggagggaggg ctgccatttg tggcaagtac ctctttaact    9180
gggctgtaag gaccaagctc aaactcactc caattccggc tgcgtcccag ttggacttgt    9240
ccagctggtt cattgctggt tacagcgggg gagacatata tcacagcctg tctcgtgccc    9300
gaccccgctg gttcatgtgg tgcctactcc tactttctgt aggggtaggc atctacctgc    9360
tccccaatcg atgaacgggg ggctagtcac tccaggccaa taggccattc tgttttttttt    9420
ttttttttttt tttttttttt tttttttttt tttttttttt tttttttttt ttttttttttc    9480
cttttcttc ttccttttct tctttctttg gtggctccat cttagcccta gtcacggcta    9540
gctgtgaaag gtccgtgagc cgcatgactg cagagagtgc tgatactggc ctctctgcag    9600
atcatgt                                                               9607
```

<210> SEQ ID NO 21
<211> LENGTH: 9607
<212> TYPE: DNA
<213> ORGANISM: Artificial
<220> FEATURE:
<223> OTHER INFORMATION: synthetic

<400> SEQUENCE: 21

```
gccagccccc tgatggggc gacactccac catagatcac tccctgtga ggaactactg      60
tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gattaacccg ctcaatgcct ggagatttgg gcgtgccccc     240
gcgagactgc tagccgagta tgttgggtc gcgaaaggcc ttgtggtact gcctgatagg     300
gtgcttgcga gtgccccggg aggtctcgta gaccgtgcat catgagcaca aatcctaaac     360
ctcaaagaaa aaccacacgt aacaccaacc gccgcccaca ggacgtcaag ttcccgggcg     420
gtggtcagat cgttggtgga gtttacctgt tgccgcgcag ggggccccagg ttgggtgtgc    480
gcgcgactag gaagacttcc gagcggtcgc aacctcgtgg aaggcgacaa cctatcccca     540
aggctcgccg gcccgagggc agggcctggg ctcagcccgg gtaccctttgg cccctctatg    600
gcaatgaggg tctgggggtgg gcaggatggc tcctgtcacc ccgcggatcc cggcctagtt     660
ggggccccac ggaccccgg cgtaggtcgc gtaattttgg taaggtcatc gataccctca     720
catgcggctt cgccgacctc atggggtaca ttccgctcgt cggcgccccc ttaggaggcg     780
ctgccagggc cctggcgcat ggcgtccggg tgctggagga cggcgtgaac tacgcaacag    840
ggaatctgcc cggttgctct ttctctatct tcctcttggc tttgctgtcc tgtctgacca     900
ttccagctgc cgcttatgaa gtgcgcaacg tgtccggggt gtaccatgtc acgaacgact    960
gctccaactc aagtattgtg tatgaggcag cggacatgat catgcacacc cctgggtgcg    1020
tgccctgcgt ccgggagggc aattcctccc gctgctgggt ggcgctcact cccacgctcg    1080
cggccaggaa cagtagcatc cccactacga cgattcgacg ccacgtcgac ttgctcgttg    1140
gggcggccgc tctctgctcc gttgtgtacg tggggggatct ctgcgggatct gtcttcctcg   1200
tctcccagct gttcacccttc tcacctcgcc agtatgagac ggtacaggac tgcaattgct   1260
```

```
cactctatcc cggccacgta tcaggtcacc gcatggcttg ggatatgatg atgaactggt    1320
cgcccacgac agccttggtg gtgtcgcagt tactccggat cccacaagcc atcgtggaca    1380
tggtgtcggg ggcccactgg ggagtcctgg cgggccttgc ctactattcc atggtgggga    1440
actgggccaa ggtcttgatt gtgatgctac tctttgccgg cgttgacggg gacacctaca    1500
cgacaggggg ggtagcaagc cgcaccaccg cgggccttgc gtccctcttt gtatcagggc    1560
cgtcccagaa aatccagctc ataaacacca acggcagctg gcacatcaac aggactgccc    1620
taaattgcaa tgactccctc aacactgggt tccttgccgc gctgttctac gtaaacaggt    1680
tcaactcgtc cggctgccca gagcgcatgg ccagctgccg ccccattgat aagttcgctc    1740
aggggtgggg tcccatcacc cacgctgtgc ctcgcgcctc agaccagagg ccttattgct    1800
ggcactacgc gccccaaccg tgcggtattg tacccgcgtc gcaggtgtgt ggtccagtgt    1860
actgcttcac cccgagccct gttgtggtgg ggacgactga tcgctccggc gccccacgt    1920
acacctgggg ggagaatgag acggacgtgc tgatccttaa caacacgcgg ccgccgcacg    1980
gcaactggtt cggctgctca tggatgaata gcaccggggtt caccaagacg tgtggggcc    2040
ccccgtgcaa catcgggggg gtcggcaata cacccttgac ctgccccacg gattgcttcc    2100
ggaagcaccc cgaggccact tacaccaaat gcggctcggg gccttggttg acacctaggt    2160
gtatggttga ctaccatac aggctttggc attacccctg cactgtcaac tataccatct    2220
tcaaggtcag gatgtatgtg gggggtgtgg agcaccggct caatgccgcg tgcaactgga    2280
cccgagggga gcgttgtgat ctggaggaca gggatagatc agagctcagc ccgctgctac    2340
tgtccacgac agagtggcag atactgccct gttccttcac cacccctaccg gctctgtcca    2400
ccggtttaat ccacctccat cagaacatcg tggacgtaca atacctgtac ggtgtagggt    2460
cagtggttgt ctctattgtg atcagatggg agtacgtcgt gctgctcttc cttcttctgg    2520
cggacgcgcg cgtctgcgcc tgcttatgga tgatgctgct gatagcccag gctgaggccg    2580
ccttagagaa cctggtggcc ctcaatgcag cgtccgtggc tggagcgcat ggcatcctct    2640
ccttccttgc gttcttctgt gctgcctggt acatcaaagg caagctggtt cctggggcgg    2700
catatgctct ttacagtgtg tggccgctac tcctgctcct gctggcgttg ccgccacggg    2760
catacgccat ggaccgggag atggctgcat cgtgtggagg cgcggtcttc gtaggtctgg    2820
tactcctgac cttgtcacca cactacaaag cactcctcgc caggctcata tggtggttac    2880
aatatcttac caccagggcc gaggcgctcc tgcaagtgtg gatccccccc ctcaacgtcc    2940
ggggggggccg cgatgccatc atcctcctca cgtgcatggt ccaccagag ctaacttttg    3000
aaatcaccaa aatcttgctc gccatactgg gcccgctcat ggtgctccgg gcaggcctaa    3060
ctagagtgcc gtacttcgtg cgcgctcacg ggctcattcg tgcgtgcatg ctggtgcgga    3120
aagtcgctgg gggccattat gtccagatgg ctctcatgaa gctggccgcg ctgacaggca    3180
cgtacgttta cgaccatctt accccgctgc gggactgggc ccacgcgggc ctgcgagacc    3240
ttgcggtggc ggttgagccc gttgtttttct ctgacacgga gaccaagatt atcacctggg    3300
gggcagacac cgcggcgtgt ggggacatca tcctgggtct acccgtctcc gcccggaggg    3360
ggagggagat acttctagga ccggccgata agtttggaga gcaggggtgg cgactccttg    3420
cacccattac ggcctactcc caacagacgc ggggcgtact tggctgtatc atcactagcc    3480
tcacaggtcg ggacaagaac caggtcgagg gggaggttca ggtggtttcc accgcaacgc    3540
agtccttctt ggcaacctgc gtcaatggcg tgtgttggac cgtctaccat ggcgccggct    3600
caaagacccct agccggcccg aagggaccga tcacccaaat gtacaccaat gttgaccagg    3660
```

```
acctcgtcgg ctggcaggcg ccccccgggg cgcgctccat gacaccgtgc acctgcggca    3720
gctcggacct ttttttggtc acgaggcatg ctgatgtcat tccggtgcgc cggcggggtg    3780
acagcagagg agccctactt tcccccaggc ccgtctctta cctgaagggc tcctcgggtg    3840
gtccactgct ttgcccctcg gggcacgttg tgggcatctt ccgggctgcc gtgtgcaccc    3900 gggggtcgc gaaggcggtg gattttatac ccgttgagtc catgggaacc accatgcggt    3960
ctccggtctt cacggataat tcatctcccc cggccgtacc gcagacattc caagtggccc    4020
atctgcacgc tcccactggc agcggcaaga gcactaaagt gccggctgca tacgcagccc    4080
aggggtacaa ggtgctcgtc ctgaacccgt ccgttgccgc caccttgagt tttgggcgt    4140 atatgtccaa ggcatatgga gttgacccta acatcagaac cggggtgagg accatcacta    4200
ctggcgctcc catcacgtac tccacctacg gcaagttcct tgccgacggc ggttgctctg    4260
ggggcgccta tgacatcata atatgtgatg agtgccactc aactgactca actactattt    4320
tgggcattgg cacagtcctg gaccaagcgg agacagctgg agcgcggctc gtcgtgctcg    4380
ccaccgctac gccgccagga tcagtcaccg taccacaccc caacatcgag gaggtggcct    4440
tgtccaatac tggagagatt cccttctatg gcaaagccat ccccctcgag accatcaagg    4500
gggggaggca cctcattttc tgccactcca agaagaagtg tgatgagctt gctgcaaagc    4560
tgtcggccct tgggctcaat gctgtagcgt actaccgggg tcttgacgtg tccatcatac    4620
caacaagcgg agacgtcgtt gttgtggcaa cagacgctct aatgacgggc tacaccggtg    4680
attttgactc agtgatcgac tgcaatacat gtgtcaccca gacagtcgac ttcagcttcg    4740
accccacctt cgccattgag acgacgacca tgccccaaga cgcggtgtcg cgctcacagc    4800
ggcgaggcag gactggcagg ggcagaggag gcatatacag gtttgtgact ccaggagaac    4860
ggccctcagg catgttcgat tctgcgatcc tgtgtgaatg ctatgacgcg ggctgtgctt    4920
ggtacgagct cacgcccgcc gagaccacag ttaggttgcg ggcttaccta aatacaccag    4980
ggttgcccgt ctgccaggac catctggagt tttgggaggg cgtcttcaca ggcctcaccc    5040
acatagatgc ccacttcttg tcccagacca agcaggcagg agacaacttc ccctacctgg    5100
tggcatacca agctacagtg tgcgccaggg cccaggctcc acctccatcg tgggatcaaa    5160
tgtggaagtg tctcatacgg ctgaagccta cgctgcacgg gccaacaccc ttgttgtata    5220
ggctaggagc cgtccaaaac gaggtcaccc tcacacatcc cataaccaaa tacatcatga    5280
catgcatgtc ggccgacctg gaggtcgtca ctagcacctg ggtgctagta ggcggggtcc    5340
ttgcagccct ggccgcgtac tgcctgacaa cgggcagcgt ggtcatcgtg gcagggtca    5400 tcttgtccgg aaggccggcc atcattcccg acagggaagt tctctaccgg gagttcgatg    5460
aaatggaaga gtgcgcctcg catctcccct acatcgaaca aggcatgcaa ctcgccgagc    5520
aattcaagca gaaggcgctc gggctgctgc aaacagccac caagcaagcg gaggccgctg    5580
ctcccgtggt ggagtccaag tggcagcccc ttgaggcctt ctgggcgaag cacatgtgga    5640
atttcatcag cgggatacag tatctagcag gcttgtcaac tctgcctggg aaccccgcga    5700
tagcatcatt gatggcattc acagcctcca tcaccagccc gctcaccacc caacataccc    5760 ttctgttta catcttgggg gggtgggtgg ccgcccaact tgcccccccc ggcgctgctt    5820
cagctttcgt gggcgccggc attgctggcg cggctgttgg cagcataggt cttgggaagg    5880
tgctcgtgga catcctggcg ggttatgggg caggggtggc aggcgcactc gtggccttta    5940
aggtcatgag cggcgaaatg ccctccaccg aggacctggt caacttactc cctgccatcc    6000
```

```
tctctcctgg tgccctggtc gtcggggtcg tgtgcgcagc aatactgcgt cggcatgtgg    6060
gcccagggga gggggctgtg cagtggatga accggctgat agcgttcgct tcgcggggta    6120
accacgtctc ccccacgcac tatgtgcctg agagcgacgc agcagcgcgt gtcacccaga    6180
tcctctccag ccttaccatt actcagctgc taaagaggct ccaccagtgg attaatgaag    6240
attgctccac gccatgctcc ggctcgtggc tcagggatgt ttgggactgg atatgcacgg    6300
tgttgaccga tttcaaaacc tggctccaat ccaagctcct gccgcggttg ccgggagtcc    6360
cttttccttt c atgtcagcgc gggtacaagg gggtttggcg gggagacggc attatgcaca   6420
ctacctgccc gtgcggagca cagatcagtg gacatgtcaa gaacggttcc atgaggatcg    6480
ttgggcctaa gacctgtagc aacacgtggt gcgggacgtt ccccatcaac gcgtacacca    6540
caggcccctg cacaccctcc ccggcgccaa actactccag ggcgttgtgg cgggtggctg    6600
ctgaggagta tgtggaggtt acgcgggtgg gggatttcca ctacgtgacg ggcatgacca    6660
ctgcaaactt aaaatgccca tgccaggtcc cggcccctga attctttacg gaagtggatg    6720
gggtgcggct gcacaggtac gctcctgcgt gcaaacctct cctacgggat gaggtcacat    6780
tccaggtcgg gctcaaccaa ttcccggtcg ggtcacagct tccatgtgaa cccgagccgg    6840
atgtgacagt gctcacttcc atgctcaccg acccctccca cattacggca gagacggcta    6900
agcgcaggct ggcccgaggg tccccccccct atttggccag ctcttcagct agtcagttgt    6960
ctgcggtctc cttgaaggcg gcatgcacca cccgtcataa ccccccagac gccgacctca    7020
tcgaggccaa tctcctgtgg cggcaggaga tgggcgggag catcacccgc gtggagtcag    7080
agagtaaggt ggtaatccta gactcatttg aaccgcttcg agcggaggag gatgagaggg    7140
aagtatccgt gccggcggag attctgcgga aaccaagaa attccccgcg gcaatgcctg    7200
tatgggcacg cccggactac aacccaccac tcttagagtc ttggagggac ccagactacg    7260
ttcctccggt ggtacacggg tgcccattgc cacctaccaa ggcccctcca ataccccctc    7320
cacgagaaa gaggacggtt attctgacag aatccaccgt gtcctctgcc ctggcggaac    7380
ttgccacaaa gaccttcggc agctccggat cgtcggccgt tgacaacggc acggcgaccg    7440
cccctcctga ccagccctcc attgacgag acgcaggatc agacgttgag tcgtactcct    7500
ccatgccccc ccttgaggga gagccggggg accccgatct cagcgacggg tcttggtcta    7560
ctgtgagcga ggaggctggc gaggacgttg tctgctgctc gatgtcctat acatggacag    7620
gcgccttaat cacaccatgc gccgcagagg agagcaagct gcccatcaac gcgttgagca    7680
attctttgct gcgtcaccac aacatggtct atgccacaac atcccgcagc gcaagccaac    7740
ggcagaagaa ggtcaccttt gacagactgc aagtcctgga cgaccattac cgggacgtgc    7800
tcaaggagat gaaggcgaag gcgtccacag ttaaggctaa acttctatct gtagaagaag    7860
cctgtaggct gacgcccca cattcggcca gatccaaatt tggctatggg gcaaaggacg    7920
tccgaacct atccagcaag gccgtcaacc acatccactc cgtgtggaag gacttgctgg    7980
aagacactga gacaccaatt gacaccacca tcatggcaaa aaatgaggtc ttttgtgttc    8040
aaccagagaa gggaggccgc aagccagctc gtcttatcgt attcccagac ttgggagttc    8100
gtgtatgcga gaagatggcc ctctacgatg tggtttccac cctccctcag gccgatgatg    8160
gctcctcata cggattccaa tactctcctg gacagcgggt cgagttcctg gtgaatgcct    8220
ggaagtcaaa gaagaaccct atgggcttcg cgtatgacac ccgctgcttt gactcaacag    8280
tcactgagag tgacatccgt gttgaggagt caatttacca atgttgtgac ttggctcccg    8340
aggccagaca ggtcataagg tcgctcacgg agcggcttta tatcgggggc cccctgacta    8400
```

| | |
|---|---|
| attcaaaagg gcagaactgc ggttaccgcc ggtgccgcgc cagcggcgtg ctgacgacta | 8460 |
| gctgcggcaa caccctcaca tgttacttga aggcttctgc agcctgtcga gctgcaaagc | 8520 |
| tccaggactg cacgatgctc gtgtgcggag acgaccttgt cgttatctgt gagagcgcgg | 8580 |
| gaacccagga ggacgcggcg agcctacgag tcttcacgga ggctatgact aggtactctg | 8640 |
| ccccccccgg ggacccgccc caaccggaat acgacttgga gttgataaca tcatgctcct | 8700 |
| ccaacgtgtc ggtcgcgcac gatgcatccg gcaagcgggt gtactacctg acccgcgacc | 8760 |
| ccaccacccc cctcgcacgg gctgcgtggg agacagcaag acacactcca gttaactcct | 8820 |
| ggttaggcaa catcatcatg tatgcgccca cctatgggc aaggatgatt ctgatgaccc | 8880 |
| acttcttttc catccttcta gctcaggagc aacttgaaaa agccctagat tgccagatct | 8940 |
| acggggccac ttactccatt gaaccacttg acctacctca gatcattcag cgactccacg | 9000 |
| gtcttagcgc attttcactc catagttact ctccaggtga gatcaatagg gtggcttcat | 9060 |
| gcctcagaaa acttgggta ccgcccttgc gagtctggag acatcgggcc agaagtgtcc | 9120 |
| gcgctaagtt actgtcccag ggagggaggg ctgccatttg tggcaagtac ctcttttaact | 9180 |
| gggctgtaag gaccaagctc aaactcactc caattccggc tgcgtcccag ttggacttgt | 9240 |
| ccagctggtt cattgctggt tacagcgggg gagacatata tcacagcctg tctcgtgccc | 9300 |
| gaccccgctg gttcatgtgg tgcctactcc tactttctgt aggggtaggc atctacctgc | 9360 |
| tccccaatcg atgaacgggg ggctagtcac tccaggccaa taggccattc tgtttttttt | 9420 |
| tttttttttt tttttttttt tttttttttt tttttttttt tttttttttt tttttttttc | 9480 |
| cttttcttc ttccttttct tctttctttg gtggctccat cttagccta gtcacggcta | 9540 |
| gctgtgaaag gtccgtgagc cgcatgactg cagagagtgc tgatactggc ctctctgcag | 9600 |
| atcatgt | 9607 |

<210> SEQ ID NO 22
<211> LENGTH: 9607
<212> TYPE: DNA
<213> ORGANISM: Artificial
<220> FEATURE:
<223> OTHER INFORMATION: synthetic

<400> SEQUENCE: 22

| | |
|---|---|
| gccagccccc tgatgggggc gacactccac catagatcac tcccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gattaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta ccgtgcat catgagcaca atcctaaac | 360 |
| ctcaaagaaa aaccacacgt aacaccaacc gccgcccaca ggacgtcaag ttcccgggcg | 420 |
| gtggtcagat cgttggtgga gtttacctgt tgccgcgcag gggcccagg ttgggtgtgc | 480 |
| gcgcgactag gaagacttcc gagcggtcgc aacctcgtgg aaggcgacaa cctatcccca | 540 |
| aggctcgccg gcccgagggc agggcctggg ctcagcccgg gtacccttgg cccctctatg | 600 |
| gcaatgaggg tctggggtgg gcaggatggc tcctgtcacc ccgcggatcc cggcctagtt | 660 |
| ggggccccac ggaccccgg cgtaggtcgc gtaatttggg taaggtcatc gatacccctca | 720 |
| catgcggctt cgccgacctc atgggtaca ttccgctcgt cggcgccccc ttaggaggcg | 780 |

```
ctgccagggc cctggcgcat ggcgtccggg tgctggagga cggcgtgaac tacgcaacag      840
ggaatctgcc cggttgctct ttctctatct tcctcttggc tttgctgtcc tgtctgacca      900
ttccagctgc cgcttatgaa gtgcgcaacg tgtccgggt gtaccatgtc acgaacgact       960
gctccaactc aagtattgtg tatgaggcag cggacatgat catgcacacc cctgggtgcg     1020
tgccctgcgt ccgggagggc aattcctccc gctgctgggt ggcgctcact cccacgctcg     1080
cggccaggaa cagtagcatc cccactacga cgattcgacg ccacgtcgac ttgctcgttg     1140
gggcggccgc tctctgctcc gttgtgtacg tgggggatct ctgcggatct gtcttcctcg     1200
tctcccagct gttcaccttc tcacctcgcc agtatgagac ggtacaggac tgcaattgct     1260
cactctatcc cggccacgta tcaggtcacc gcatggcttg ggatatgatg atgaactggt     1320
cgcccacgac agccttggtg gtgtcgcagt tactccggat cccacaagcc atcgtggaca     1380
tggtgtcggg ggcccactgg ggagtcctgg cgggccttgc ctactattcc atggtgggga     1440
actgggccaa ggtcttgatt gtgatgctac tctttgccgg cgttgacggg gacacctaca     1500 cgacagggg ggtagcaagc cgcaccaccg cgggccttgc gtccctcttt gtatcagggc      1560
cgtcccagaa aatccagctc ataaacacca acggcagctg gcacatcaac aggactgccc     1620
taaattgcaa tgactccctc aacactgggt tccttgccgc gctgttctac gtaaacaggt     1680
tcaactcgtc cggctgccca gagcgcatgg ccagctgccg ccccattgat aagttcgctc     1740
aggggtgggg tccatcacc cacgctgtgc ctcgcgcctc agaccagagg ccttattgct      1800
ggcactacgc gccccaaccg tgcggtattg tacccgcgtc gcaggtgtgt ggtccagtgt     1860
actgcttcac cccgagccct gttgtggtgg ggacgactga tcgctccggc gcccccacgt     1920
acacctgggg ggagaatgag acggacgtgc tgatccttaa caacacgcgg ccgccgcacg     1980
gcaactggtt cggctgctca tggatgaata gcaccgggtt caccaagacg tgtgggggcc     2040
ccccgtgcaa catcgggggg gtcggcaata acaccttgac ctgccccacg gattgcttcc     2100
ggaagcaccc cgaggccact tacaccaaat gcggctcggg ccttggttg acacctaggt      2160 gtatggttga ctaccatac aggctttggc attaccctg cactgtcaac tataccatct       2220
tcaaggtcag gatgtatgtg ggggtgtgg agcaccggct caatgccgcg tgcaactgga     2280
cccgagggga gcgttgtgat ctggaggaca gggatagatc agagctcagc ccgctgctac     2340
tgtccacgac agagtggcag atactgcccct gttccttcac cacccataccg gctctgtcca     2400 ccggtttaat ccacctccat cagaacatcg tggacgtaca atacctgtac ggtgtagggt     2460
cagtggttgt ctctattgtg atcagatggg agtacgtcgt gctgctcttc cttcttctgg     2520
cggacgcgcg cgtctgcgcc tgcttatgga tgatgctgct gatagcccag gctgaggccg     2580
ccttagagaa cctggtggcc ctcaatgcag cgtccgtggc tggagcgcat ggcatcctct     2640
ccttccttgc gttcttctgt gctgcctggt acatcaaagg caagctggtt cctgggccgg     2700
catatgctct ttacagtgtg tggccgctac tcctgctcct gctggcgttg ccgcacgggg     2760
catacgccat ggaccgggag atggctgcat cgtgtggagg cgcggtcttc gtaggtctgg     2820
tactcctgac cttgtcacca cactacaaag cactcctcgc caggctcata tggtggttac     2880
aatatcttac caccagggcc gaggcgctcc tgcaagtgtg atccccccc ctcaacgtcc      2940 gggggggccg cgatgccatc atcctcctca cgtgcatggt ccacccagag ctaactttg     3000 aaatcaccaa aatcttgctc gccatactgg gcccgctcat ggtgctccgg gcaggcctaa     3060
ctagagtgcc gtacttcgtg cgcgctcacg ggctcattcg tgcgtgcatg ctggtgcgga     3120
aagtcgctgg gggccattat gtccagatgg ctctcatgaa gctggccgcg ctgacaggca     3180
```

```
cgtacgttta cgaccatctt accccgctgc gggactgggc ccacgcgggc ctgcgagacc    3240
ttgcggtggc ggttgagccc gttgtttct ctgacacgga gaccaagatt atcacctggg    3300
gggcagacac cgcggcgtgt ggggacatca tcctgggtct acccgtctcc gcccggaggg    3360
ggagggagat acttctagga ccggccgata agtttggaga gcaggggtgg cgactccttg    3420
cacccattac ggcctactcc aacagacgc ggggcgtact tggctgtatc atcactagcc    3480
tcacaggtcg ggacaagaac caggtcgagg gggaggttca ggtggtttcc accgcaacgc    3540
agtccttctt ggcaacctgc gtcaatggcg tgtgttggac cgtctaccat ggcgccggct    3600
caaagaccct agccggcccg aagggaccga tcacccaaat gtacaccaat gttgaccagg    3660
acctcgtcgg ctggcaggcg ccccccgggg cgcgctccat gacaccgtgc acctgcggca    3720
gctcggacct tttttggtc acgaggcatg ctgatgtcat tccggtgcgc cggcggggtg    3780
acagcagagg agccctactt tcccccaggc ccgtctctta cctgaagggc tcctcgggtg    3840
gtccactgct ttgcccctcg gggcacgttg tgggcatctt ccgggctgcc gtgtgcaccc    3900 gggggggtcgc gaaggcggtg gattttatac ccgttgagtc catgggaacc accatgcggt    3960
ctccggtctt cacggataat tcatctcccc cggccgtacc gcagacattc caagtggccc    4020
atctgcacgc tcccactggc agcggcaaga gcactaaagt gccggctgca tacgcagccc    4080 agggtacaa ggtgctcgtc ctgaacccgt ccgttgccgc caccttgagt tttgggcgt    4140 atatgtccaa ggcatatgga gttgaccta acatcagaac cggggtgagg accatcacta    4200
ctggcgctcc catcacgtac tccacctacg gcaagttcct tgccgacggc ggttgctctg    4260
ggggcgccta tgacatcata atatgtgatg agtgccactc aactgactca actactattt    4320
tgggcattgg cacagtcctg gaccaagcgg agacagctgg agcgcggctc gtcgtgctcg    4380
ccaccgctac gccgccagga tcagtcaccg taccacaccc caacatcgag gaggtggcct    4440
tgtccaatac tggagagatt cccttctatg gcaaagccat ccccctcgag accatcaagg    4500
gggggaggca cctcattttc tgccactcca agaagaagtg tgatgagctt gctgcaaagc    4560
tgtcggccct tgggctcaat gctgtagcgt actaccgggg tcttgacgtg tccatcatac    4620
caacaagcgg agacgtcgtt gttgtggcaa cagacgctct aatgacgggc tacaccggtg    4680
attttgactc agtgatcgac tgcaatacat gtgtcaccca gacagtcgac ttcagcttcg    4740
accccacctt cgccattgag acgacgacca tgccccaaga cgcggtgtcg cgctcacagc    4800
ggcgaggcag gactggcagg ggcagaggag gcatatacag gtttgtgact ccaggagaac    4860
ggccctcagg catgttcgat tctgcgatcc tgtgtgaatg ctatgacgcg ggctgtgctt    4920
ggtacgagct cacgcccgcc gagaccacag ttaggttgcg ggcttaccta aatacaccag    4980 ggttgccgt ctgccaggac catctggagt tttgggaggg cgtcttcaca ggcctcaccc    5040
acatagatgc ccacttcttg tcccagacca agcaggcagg agacaacttc ccctacctgg    5100
tggcatacca agctacagtg tgcgccaggg cccaggctcc acctccatcg tgggatcaaa    5160
tgtggaagtg tctcatacgg ctgaagccta cgctgcacgg gccaacaccc ttgttgtata    5220
ggctaggagc cgtccaaaac gaggtcaccc tcacacatcc cataaccaaa tacatcatga    5280
catgcatgtc ggccgacctg gaggtcgtca ctagcacctg ggtgctagta ggcggggtcc    5340
ttgcagccct ggccgcgtac tgcctgacaa cgggcagcgt ggtcatcgtg gcagggtca    5400 tcttgtccgg aaggccggcc atcattcccg acagggaagt tctctaccgg gagttcgatg    5460
aaatggaaga gtgcgcctcg catctcccct acatcgaaca aggcatgcaa ctcgccgagc    5520
```

```
aattcaagca gaaggcgctc gggctgctgc aaacagccac caagcaagcg gaggccgctg   5580
ctcccgtggt ggagtccaag tggcgagccc ttgaggcctt ctgggcgaag cacatgtgga   5640
atttcatcag cgggatacag tatctagcag gcttgtcaac tctgcctggg aaccccgcga   5700
tagcatcatt gatggcattc acagcctcca tcaccagccc gctcaccacc caacataccc   5760
ttctgtttaa catcttgggg gggtgggtgg ccgcccaact tgcccccccc ggcgctgctt   5820
cagctttcgt gggcgccggc attgctggcg cggctgttgg cagcataggt cttgggaagg   5880
tgctcgtgga catcctggcg ggttatgggg caggggtggc aggcgcactc gtggcccttta   5940 aggtcatgag cggcgaaatg ccctccaccg aggacctggt caacttactc cctgccatcc   6000
tctctcctgg tgccctggtc gtcggggtcg tgtgcgcagc aatactgcgt cggcatgtgg   6060
gcccagggga gggggctgtg cagtggatga accggctgat agcgttcgct tcgcggggta   6120
accacgtctc ccccacgcac tatgtgcctg agagcgacgc agcagcgcgt gtcacccaga   6180
tcctctccag ccttaccatt actcagctgc taaagaggct ccaccagtgg attaatgaag   6240
attgctccac gccatgctcc ggctcgtggc tcagggatgt ttgggactgg atatgcacgg   6300
tgttgaccga tttcaaaacc tggctccaat ccaagctcct gccgcggttg ccgggagtcc   6360
cttttccttt catgtcagcg cgggtacaag gggtttggcg gggagacggc attatgcaca   6420
ctacctgccc gtgcggagca cagatcagtg acatgtcaa gaacggttcc atgaggatcg   6480
ttgggcctaa gacctgtagc aacacgtggt gcggacgtt ccccatcaac gcgtacacca   6540
caggcccctg cacaccctcc ccggcgccaa actactccag ggcgttgtgg cgggtggctg   6600
ctgaggagta tgtggaggtt acgcgggtgg gggatttcca ctacgtgacg gcatgacca   6660 ctgacaactt aaaatgccca tgccaggtcc cggcccctga attctttacg aagtggatg   6720 gggtgcggct gcacaggtac gctcctgcgt gcaaacctct cctacgggat gaggtcacat   6780
tccaggtcgg gctcaaccaa ttcccggtcg ggtcacagct tccatgtgaa cccgagccgg   6840
atgtgacagt gctcacttcc atgctcaccg acccctccca cattacggca gagacggcta   6900
agcgcaggct ggcccgaggg tccccccccct ctttggccag ctcttcagct ggtcagttgt   6960
ctgcggtctc cttgaaggcg gcatgcacca cccgtcataa ccccccagac gccgacctca   7020
tcgaggccaa tctcctgtgg cggcaggaga tgggcgggag catcacccgc gtggagtcag   7080
agagtaaggt ggtaatccta gactcatttg aaccgcttcg agcggaggag gatgagaggg   7140
aagtatccgt gccggcggag attctgcgga aaaccaagaa attccccgcg gcaatgcctg   7200
tatgggcacg cccggactac aacccaccac tcttagagtc ttggagggac ccagactacg   7260
ttcctccggt ggtacacggg tgcccattgc cacctaccaa ggccccctcca ataccccctc   7320 cacggagaaa gaggacggtt attctgacag aatccaccgt gtcctctgcc ctggcggaac   7380
ttgccacaaa gaccttcggc agctccggat cgtcggccgt tgacaacggc acggcgaccg   7440
cccctcctga ccagccctcc attgacgag acgcaggatc agacgttgag tcgtactcct   7500
ccatgccccc ccttgaggga gagccggggg acccgatct cagcgacggg tcttggtcta   7560
ctgtgagcga ggaggctggc gaggacgttg tctgctgctc gatgtcctat acatggacag   7620
gcgccttaat cacaccatgc gccgcagagg agagcaagct gcccatcaac gcgttgagca   7680
attctttgct gcgtcaccac aacatggtct atgccacaac atcccgcagc gcaagccaac   7740
ggcagaagaa ggtcaccttt gacagactgc aagtcctgga cgaccattac cgggacgtgc   7800
tcaaggagat gaaggcgaag gcgtccacag ttaaggctaa acttctatct gtagaagaag   7860
cctgtaggct gacgccccca cattcggcca gatccaaatt tggctatggg gcaaaggacg   7920
```

```
tccggaacct atccagcaag gccgtcaacc acatccactc cgtgtggaag gacttgctgg     7980
aagacactga gacaccaatt gacaccacca tcatggcaaa aaatgaggtc ttttgtgttc     8040
aaccagagaa gggaggccgc aagccagctc gtcttatcgt attcccagac ttgggagttc     8100
gtgtatgcga gaagatggcc ctctacgatg tggtttccac cctccctcag gccgtgatgg     8160
gctcctcata cggattccaa tactctcctg gacagcgggt cgagttcctg gtgaatgcct     8220
ggaagtcaaa gaagaaccct atgggcttcg cgtatgacac ccgctgcttt gactcaacag     8280
tcactgagag tgacatccgt gttgaggagt caatttacca atgttgtgac ttggctcccg     8340
aggccagaca ggtcataagg tcgctcacgg agcggcttta tcgggggc cccctgacta     8400 attcaaaagg gcagaactgc ggttaccgcc ggtgccgcgc cagcggcgtg ctgacgacta     8460
gctgcggcaa caccctcaca tgttacttga aggcttctgc agcctgtcga gctgcaaagc     8520
tccaggactg cacgatgctc gtgtgcggag acgaccttgt cgttatctgt gagagcgcgg     8580
gaacccagga ggacgcggcg agcctacgag tcttcacgga ggctatgact aggtactctg     8640 cccccccgg ggacccgccc caaccggaat acgacttgga gttgataaca tcatgctcct     8700
ccaacgtgtc ggtcgcgcac gatgcatccg gcaagcgggt gtactacctg acccgcgacc     8760
ccaccacccc cctcgcacgg gctgcgtggg agacagcaag acacactcca gttaactcct     8820
ggttaggcaa catcatcatg tatgcgccca cctatgggc aaggatgatt ctgatgaccc     8880
acttcttttc catccttcta gctcaggagc aacttgaaaa agccctagat tgccagatct     8940
acggggccac ttactccatt gaaccacttg acctacctca gatcattcag cgactccacg     9000
gtcttagcgc attttcactc catagttact ctccaggtga gatcaatagg gtggcttcat     9060
gcctcagaaa acttggggta ccgcccttgc gagtctggag acatcgggcc agaagtgtcc     9120
gcgctaagtt actgtcccag ggagggaggg ctgccatttg tggcaagtac ctctttaact     9180
gggctgtaag gaccaagctc aaactcactc caattccggc tgcgtcccag ttggacttgt     9240
ccagctggtt cattgctggt tacagcgggg gagacatata tcacagcctg tctcgtgccc     9300
gaccccgctg gttcatgtgg tgcctactcc tactttctgt aggggtaggc atctacctgc     9360
tccccaatcg atgaacgggg ggctagtcac tccaggccaa taggcattc tgttttttt     9420 tttttttttt tttttttttt tttttttttt tttttttttt tttttttttt ttttttttc     9480 cttttcttc ttccttttct tctttctttg gtggctccat cttagccta gtcacggcta     9540 gctgtgaaag gtccgtgagc cgcatgactg cagagagtgc tgatactggc ctctctgcag     9600
atcatgt                                                              9607
```

`<210>` SEQ ID NO 23
`<211>` LENGTH: 3010
`<212>` TYPE: PRT
`<213>` ORGANISM: Artificial
`<220>` FEATURE:
`<223>` OTHER INFORMATION: synthetic

`<400>` SEQUENCE: 23

```
Met Ser Thr Asn Pro Lys Pro Gln Arg Lys Thr Thr Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
```

```
                50                  55                  60

Ile Pro Lys Ala Arg Arg Pro Glu Gly Arg Ala Trp Ala Gln Pro Gly
 65                  70                  75                  80

Tyr Pro Trp Pro Leu Tyr Gly Asn Glu Gly Leu Gly Trp Ala Gly Trp
                     85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ala Ala Tyr
                180                 185                 190

Glu Val Arg Asn Val Ser Gly Val Tyr His Val Thr Asn Asp Cys Ser
                195                 200                 205

Asn Ser Ser Ile Val Tyr Glu Ala Ala Asp Met Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ser Ser Ile Pro Thr Thr
                245                 250                 255

Thr Ile Arg Arg His Val Asp Leu Leu Val Gly Ala Ala Ala Leu Cys
                260                 265                 270

Ser Val Val Tyr Val Gly Asp Leu Cys Gly Ser Val Phe Leu Val Ser
                275                 280                 285

Gln Leu Phe Thr Phe Ser Pro Arg Gln Tyr Glu Thr Val Gln Asp Cys
290                 295                 300

Asn Cys Ser Leu Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ser Gly Ala His
                340                 345                 350

Trp Gly Val Leu Ala Gly Leu Ala Tyr Tyr Ser Met Val Gly Asn Trp
                355                 360                 365

Ala Lys Val Leu Ile Val Met Leu Leu Phe Ala Gly Val Asp Gly Asp
370                 375                 380

Thr Tyr Thr Thr Gly Gly Val Ala Ser Arg Thr Thr Ala Gly Leu Ala
385                 390                 395                 400

Ser Leu Phe Val Ser Gly Pro Ser Gln Lys Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Leu Ala Ala Leu Phe Tyr Val Asn Arg Phe Asn
                435                 440                 445

Ser Ser Gly Cys Pro Glu Arg Met Ala Ser Cys Arg Pro Ile Asp Lys
                450                 455                 460

Phe Ala Gln Gly Trp Gly Pro Ile Thr His Ala Val Pro Arg Ala Ser
465                 470                 475                 480
```

```
Asp Gln Arg Pro Tyr Cys Trp His Tyr Ala Pro Gln Pro Cys Gly Ile
                485                 490                 495
Val Pro Ala Ser Gln Val Cys Gly Pro Val Tyr Cys Phe Thr Pro Ser
            500                 505                 510
Pro Val Val Gly Thr Thr Asp Arg Ser Gly Ala Pro Thr Tyr Thr
        515                 520                 525
Trp Gly Glu Asn Glu Thr Asp Val Leu Ile Leu Asn Asn Thr Arg Pro
    530                 535                 540
Pro His Gly Asn Trp Phe Gly Cys Ser Trp Met Asn Ser Thr Gly Phe
545                 550                 555                 560
Thr Lys Thr Cys Gly Gly Pro Pro Cys Asn Ile Gly Gly Val Gly Asn
                565                 570                 575
Asn Thr Leu Thr Cys Pro Thr Asp Cys Phe Arg Lys His Pro Glu Ala
            580                 585                 590
Thr Tyr Thr Lys Cys Gly Ser Gly Pro Trp Leu Thr Pro Arg Cys Met
        595                 600                 605
Val Asp Tyr Pro Tyr Arg Leu Trp His Tyr Pro Cys Thr Val Asn Tyr
    610                 615                 620
Thr Ile Phe Lys Val Arg Met Tyr Val Gly Gly Val Glu His Arg Leu
625                 630                 635                 640
Asn Ala Ala Cys Asn Trp Thr Arg Gly Glu Arg Cys Asp Leu Glu Asp
                645                 650                 655
Arg Asp Arg Ser Glu Leu Ser Pro Leu Leu Leu Ser Thr Thr Glu Trp
            660                 665                 670
Gln Ile Leu Pro Cys Ser Phe Thr Thr Leu Pro Ala Leu Ser Thr Gly
        675                 680                 685
Leu Ile His Leu His Gln Asn Ile Val Asp Val Gln Tyr Leu Tyr Gly
    690                 695                 700
Val Gly Ser Val Val Ser Ile Val Arg Trp Glu Tyr Val Val
705                 710                 715                 720
Leu Leu Phe Leu Leu Leu Ala Asp Ala Arg Val Cys Ala Cys Leu Trp
                725                 730                 735
Met Met Leu Leu Ile Ala Gln Ala Glu Ala Ala Leu Glu Asn Leu Val
            740                 745                 750
Ala Leu Asn Ala Ala Ser Val Ala Gly Ala His Gly Ile Leu Ser Phe
        755                 760                 765
Leu Ala Phe Phe Cys Ala Ala Trp Tyr Ile Lys Gly Lys Leu Val Pro
    770                 775                 780
Gly Ala Ala Tyr Ala Leu Tyr Ser Val Trp Pro Leu Leu Leu Leu Leu
785                 790                 795                 800
Leu Ala Leu Pro Pro Arg Ala Tyr Ala Met Asp Arg Glu Met Ala Ala
                805                 810                 815
Ser Cys Gly Gly Ala Val Phe Val Gly Leu Val Leu Leu Thr Leu Ser
            820                 825                 830
Pro His Tyr Lys Ala Leu Leu Ala Arg Leu Ile Trp Trp Leu Gln Tyr
        835                 840                 845
Leu Thr Thr Arg Ala Glu Ala Leu Leu Gln Val Trp Ile Pro Pro Leu
    850                 855                 860
Asn Val Arg Gly Gly Arg Asp Ala Ile Ile Leu Leu Thr Cys Met Val
865                 870                 875                 880
His Pro Glu Leu Thr Phe Glu Ile Thr Lys Ile Leu Leu Ala Ile Leu
                885                 890                 895
```

```
Gly Pro Leu Met Val Leu Arg Ala Gly Leu Thr Arg Val Pro Tyr Phe
            900                 905                 910

Val Arg Ala His Gly Leu Ile Arg Ala Cys Met Leu Val Arg Lys Val
        915                 920                 925

Ala Gly Gly His Tyr Val Gln Met Ala Leu Met Lys Leu Ala Ala Leu
    930                 935                 940

Thr Gly Thr Tyr Val Tyr Asp His Leu Thr Pro Leu Arg Asp Trp Ala
945                 950                 955                 960

His Ala Gly Leu Arg Asp Leu Ala Val Ala Val Glu Pro Val Val Phe
                965                 970                 975

Ser Asp Thr Glu Thr Lys Ile Ile Thr Trp Gly Ala Asp Thr Ala Ala
            980                 985                 990

Cys Gly Asp Ile Ile Leu Gly Leu Pro Val Ser Ala Arg Arg Gly Arg
        995                 1000                1005

Glu Ile Leu Leu Gly Pro Ala Asp Lys Phe Gly Glu Gln Gly Trp
    1010                1015                1020

Arg Leu Leu Ala Pro Ile Thr Ala Tyr Ser Gln Gln Thr Arg Gly
    1025                1030                1035

Val Leu Gly Cys Ile Ile Thr Ser Leu Thr Gly Arg Asp Lys Asn
    1040                1045                1050

Gln Val Glu Gly Glu Val Gln Val Val Ser Thr Ala Thr Gln Ser
    1055                1060                1065

Phe Leu Ala Thr Cys Val Asn Gly Val Cys Trp Thr Val Tyr His
    1070                1075                1080

Gly Ala Gly Ser Lys Thr Leu Ala Gly Pro Lys Gly Pro Ile Thr
    1085                1090                1095

Gln Met Tyr Thr Asn Val Asp Gln Asp Leu Val Gly Trp Gln Ala
    1100                1105                1110

Pro Pro Gly Ala Arg Ser Met Thr Pro Cys Thr Cys Gly Ser Ser
    1115                1120                1125

Asp Leu Phe Leu Val Thr Arg His Ala Asp Val Ile Pro Val Arg
    1130                1135                1140

Arg Arg Gly Asp Ser Arg Gly Ala Leu Leu Ser Pro Arg Pro Val
    1145                1150                1155

Ser Tyr Leu Lys Gly Ser Ser Gly Gly Pro Leu Leu Cys Pro Ser
    1160                1165                1170

Gly His Val Val Gly Ile Phe Arg Ala Ala Val Cys Thr Arg Gly
    1175                1180                1185

Val Ala Lys Ala Val Asp Phe Ile Pro Val Glu Ser Met Glu Thr
    1190                1195                1200

Thr Met Arg Ser Pro Val Phe Thr Asp Asn Ser Ser Pro Pro Ala
    1205                1210                1215

Val Pro Gln Thr Phe Gln Val Ala His Leu His Ala Pro Thr Gly
    1220                1225                1230

Ser Gly Lys Ser Thr Lys Val Pro Ala Ala Tyr Ala Ala Gln Gly
    1235                1240                1245

Tyr Lys Val Leu Val Leu Asn Pro Ser Val Ala Ala Thr Leu Ser
    1250                1255                1260

Phe Gly Ala Tyr Met Ser Lys Ala Tyr Gly Val Asp Pro Asn Ile
    1265                1270                1275

Arg Thr Gly Val Arg Thr Ile Thr Thr Gly Ala Pro Ile Thr Tyr
    1280                1285                1290

Ser Thr Tyr Gly Lys Phe Leu Ala Asp Gly Gly Cys Ser Gly Gly
```

-continued

```
          1295                1300                1305
Ala Tyr Asp Ile Ile Ile Cys Asp Glu Cys His Ser Thr Asp Ser
    1310                1315                1320
Thr Thr Ile Leu Gly Ile Gly Thr Val Leu Asp Gln Ala Glu Thr
    1325                1330                1335
Ala Gly Ala Arg Leu Val Val Leu Ala Thr Ala Thr Pro Pro Gly
    1340                1345                1350
Ser Val Thr Val Pro His Pro Asn Ile Glu Glu Val Ala Leu Ser
    1355                1360                1365
Asn Thr Gly Glu Ile Pro Phe Tyr Gly Lys Ala Ile Pro Leu Glu
    1370                1375                1380
Thr Ile Lys Gly Gly Arg His Leu Ile Phe Cys His Ser Lys Lys
    1385                1390                1395
Lys Cys Asp Glu Leu Ala Ala Lys Leu Ser Ala Leu Gly Leu Asn
    1400                1405                1410
Ala Val Ala Tyr Tyr Arg Gly Leu Asp Val Ser Ile Ile Pro Thr
    1415                1420                1425
Ser Gly Asp Val Val Val Val Ala Thr Asp Ala Leu Met Thr Gly
    1430                1435                1440
Tyr Thr Gly Asp Phe Asp Ser Val Ile Asp Cys Asn Thr Cys Val
    1445                1450                1455
Thr Gln Thr Val Asp Phe Ser Phe Asp Pro Thr Phe Ala Ile Glu
    1460                1465                1470
Thr Thr Thr Met Pro Gln Asp Ala Val Ser Arg Ser Gln Arg Arg
    1475                1480                1485
Gly Arg Thr Gly Arg Gly Arg Gly Gly Ile Tyr Arg Phe Val Thr
    1490                1495                1500
Pro Gly Glu Arg Pro Ser Gly Met Phe Asp Ser Ala Ile Leu Cys
    1505                1510                1515
Glu Cys Tyr Asp Ala Gly Cys Ala Trp Tyr Glu Leu Thr Pro Ala
    1520                1525                1530
Glu Thr Thr Val Arg Leu Arg Ala Tyr Leu Asn Thr Pro Gly Leu
    1535                1540                1545
Pro Val Cys Gln Asp His Leu Glu Phe Trp Glu Gly Val Phe Thr
    1550                1555                1560
Gly Leu Thr His Ile Asp Ala His Phe Leu Ser Gln Thr Lys Gln
    1565                1570                1575
Ala Gly Asp Asn Phe Pro Tyr Leu Val Ala Tyr Gln Ala Thr Val
    1580                1585                1590
Cys Ala Arg Ala Gln Ala Pro Pro Pro Ser Trp Asp Gln Met Trp
    1595                1600                1605
Lys Cys Leu Ile Arg Leu Lys Pro Thr Leu His Gly Pro Thr Pro
    1610                1615                1620
Leu Leu Tyr Arg Leu Gly Ala Val Gln Asn Glu Val Thr Leu Thr
    1625                1630                1635
His Pro Ile Thr Lys Tyr Ile Met Thr Cys Met Ser Ala Asp Leu
    1640                1645                1650
Glu Val Val Thr Ser Thr Trp Val Leu Val Gly Gly Val Leu Ala
    1655                1660                1665
Ala Leu Ala Ala Tyr Cys Leu Thr Thr Gly Ser Val Val Ile Val
    1670                1675                1680
Gly Arg Val Ile Leu Ser Gly Arg Pro Ala Ile Ile Pro Asp Arg
    1685                1690                1695
```

-continued

Glu Val Leu Tyr Arg Glu Phe Asp Glu Met Glu Glu Cys Ala Ser
1700                    1705                1710

His Leu Pro Tyr Ile Glu Gln Gly Met Gln Leu Ala Glu Gln Phe
1715                    1720                1725

Lys Gln Lys Ala Leu Gly Leu Leu Gln Thr Ala Thr Lys Gln Ala
1730                    1735                1740

Glu Ala Ala Ala Pro Val Val Glu Ser Lys Trp Arg Ala Leu Glu
1745                    1750                1755

Ala Phe Trp Ala Lys His Met Trp Asn Phe Ile Ser Gly Ile Gln
1760                    1765                1770

Tyr Leu Ala Gly Leu Ser Thr Leu Pro Gly Asn Pro Ala Ile Ala
1775                    1780                1785

Ser Leu Met Ala Phe Thr Ala Ser Ile Thr Ser Pro Leu Thr Thr
1790                    1795                1800

Gln His Thr Leu Leu Phe Asn Ile Leu Gly Gly Trp Val Ala Ala
1805                    1810                1815

Gln Leu Ala Pro Pro Gly Ala Ala Ser Ala Phe Val Gly Ala Gly
1820                    1825                1830

Ile Ala Gly Ala Ala Val Gly Ser Ile Gly Leu Gly Lys Val Leu
1835                    1840                1845

Val Asp Ile Leu Ala Gly Tyr Gly Ala Gly Val Ala Gly Ala Leu
1850                    1855                1860

Val Ala Phe Lys Val Met Ser Gly Glu Met Pro Ser Thr Glu Asp
1865                    1870                1875

Leu Val Asn Leu Leu Pro Ala Ile Leu Ser Pro Gly Ala Leu Val
1880                    1885                1890

Val Gly Val Val Cys Ala Ala Ile Leu Arg Arg His Val Gly Pro
1895                    1900                1905

Gly Glu Gly Ala Val Gln Trp Met Asn Arg Leu Ile Ala Phe Ala
1910                    1915                1920

Ser Arg Gly Asn His Val Ser Pro Thr His Tyr Val Pro Glu Ser
1925                    1930                1935

Asp Ala Ala Ala Arg Val Thr Gln Ile Leu Ser Ser Leu Thr Ile
1940                    1945                1950

Thr Gln Leu Leu Lys Arg Leu His Gln Trp Ile Asn Glu Asp Cys
1955                    1960                1965

Ser Thr Pro Cys Ser Gly Ser Trp Leu Arg Asp Val Trp Asp Trp
1970                    1975                1980

Ile Cys Thr Val Leu Thr Asp Phe Lys Thr Trp Leu Gln Ser Lys
1985                    1990                1995

Leu Leu Pro Arg Leu Pro Gly Val Pro Phe Leu Ser Cys Gln Arg
2000                    2005                2010

Gly Tyr Lys Gly Val Trp Arg Gly Asp Gly Ile Met His Thr Thr
2015                    2020                2025

Cys Pro Cys Gly Ala Gln Ile Ser Gly His Val Lys Asn Gly Ser
2030                    2035                2040

Met Arg Ile Val Gly Pro Lys Thr Cys Ser Asn Thr Trp Cys Gly
2045                    2050                2055

Thr Phe Pro Ile Asn Ala Tyr Thr Thr Gly Pro Cys Thr Pro Ser
2060                    2065                2070

Pro Ala Pro Asn Tyr Ser Arg Ala Leu Trp Arg Val Ala Ala Glu
2075                    2080                2085

```
Glu Tyr Val Glu Val Thr Arg Val Gly Asp Phe His Tyr Val Thr
2090                2095                2100

Gly Met Thr Thr Asp Asn Leu Lys Cys Pro Cys Gln Val Pro Ala
2105                2110                2115

Pro Glu Phe Phe Thr Glu Val Asp Gly Val Arg Leu His Arg Tyr
2120                2125                2130

Ala Pro Ala Cys Lys Pro Leu Leu Arg Asp Glu Val Thr Phe Gln
2135                2140                2145

Val Gly Leu Asn Gln Phe Pro Val Gly Ser Gln Leu Pro Cys Glu
2150                2155                2160

Pro Glu Pro Asp Val Thr Val Leu Thr Ser Met Leu Thr Asp Pro
2165                2170                2175

Ser His Ile Thr Ala Glu Thr Ala Lys Arg Arg Leu Ala Arg Gly
2180                2185                2190

Ser Pro Pro Tyr Leu Ala Ser Ser Ala Ser Gln Leu Ser Ala
2195                2200                2205

Val Ser Leu Lys Ala Ala Cys Thr Thr Arg His Asn Pro Pro Asp
2210                2215                2220

Ala Asp Leu Ile Glu Ala Asn Leu Leu Trp Arg Gln Glu Met Gly
2225                2230                2235

Gly Ser Ile Thr Arg Val Glu Ser Glu Ser Lys Val Val Ile Leu
2240                2245                2250

Asp Ser Phe Glu Pro Leu Arg Ala Glu Glu Asp Glu Arg Glu Val
2255                2260                2265

Ser Val Pro Ala Glu Ile Leu Arg Lys Thr Lys Lys Phe Pro Ala
2270                2275                2280

Ala Met Pro Val Trp Ala Arg Pro Asp Tyr Asn Pro Pro Leu Leu
2285                2290                2295

Glu Ser Trp Arg Asp Pro Asp Tyr Val Pro Pro Val Val His Gly
2300                2305                2310

Cys Pro Leu Pro Pro Thr Lys Ala Pro Pro Ile Pro Pro Pro Arg
2315                2320                2325

Arg Lys Arg Thr Val Ile Leu Thr Glu Ser Thr Val Ser Ser Ala
2330                2335                2340

Leu Ala Glu Leu Ala Thr Lys Thr Phe Gly Ser Ser Gly Ser Ser
2345                2350                2355

Ala Val Asp Asn Gly Thr Ala Thr Ala Pro Pro Asp Gln Pro Ser
2360                2365                2370

Ile Asp Gly Asp Ala Gly Ser Asp Val Glu Ser Tyr Ser Ser Met
2375                2380                2385

Pro Pro Leu Glu Gly Glu Pro Gly Asp Pro Asp Leu Ser Asp Gly
2390                2395                2400

Ser Trp Ser Thr Val Ser Glu Glu Ala Gly Glu Asp Val Val Cys
2405                2410                2415

Cys Ser Met Ser Tyr Thr Trp Thr Gly Ala Leu Ile Thr Pro Cys
2420                2425                2430

Ala Ala Glu Glu Ser Lys Leu Pro Ile Asn Ala Leu Ser Asn Ser
2435                2440                2445

Leu Leu Arg His His Asn Met Val Tyr Ala Thr Thr Ser Arg Ser
2450                2455                2460

Ala Ser Gln Arg Gln Lys Lys Val Thr Phe Asp Arg Leu Gln Val
2465                2470                2475

Leu Asp Asp His Tyr Arg Asp Val Leu Lys Glu Met Lys Ala Lys
```

-continued

```
                2480                2485                2490
Ala Ser Thr Val Lys Ala Lys Leu Leu Ser Val Glu Glu Ala Cys
    2495                2500                2505

Arg Leu Thr Pro Pro His Ser Ala Arg Ser Lys Phe Gly Tyr Gly
    2510                2515                2520

Ala Lys Asp Val Arg Asn Leu Ser Ser Lys Ala Val Asn His Ile
    2525                2530                2535

His Ser Val Trp Lys Asp Leu Leu Glu Asp Thr Glu Thr Pro Ile
    2540                2545                2550

Asp Thr Thr Ile Met Ala Lys Asn Glu Val Phe Cys Val Gln Pro
    2555                2560                2565

Glu Lys Gly Gly Arg Lys Pro Ala Arg Leu Ile Val Phe Pro Asp
    2570                2575                2580

Leu Gly Val Arg Val Cys Glu Lys Met Ala Leu Tyr Asp Val Val
    2585                2590                2595

Ser Thr Leu Pro Gln Ala Val Met Gly Ser Ser Tyr Gly Phe Gln
    2600                2605                2610

Tyr Ser Pro Gly Gln Arg Val Glu Phe Leu Val Asn Ala Trp Lys
    2615                2620                2625

Ser Lys Lys Asn Pro Met Gly Phe Ala Tyr Asp Thr Arg Cys Phe
    2630                2635                2640

Asp Ser Thr Val Thr Glu Ser Asp Ile Arg Val Glu Glu Ser Ile
    2645                2650                2655

Tyr Gln Cys Cys Asp Leu Ala Pro Glu Ala Arg Gln Val Ile Arg
    2660                2665                2670

Ser Leu Thr Glu Arg Leu Tyr Ile Gly Gly Pro Leu Thr Asn Ser
    2675                2680                2685

Lys Gly Gln Asn Cys Gly Tyr Arg Arg Cys Arg Ala Ser Gly Val
    2690                2695                2700

Leu Thr Thr Ser Cys Gly Asn Thr Leu Thr Cys Tyr Leu Lys Ala
    2705                2710                2715

Ser Ala Ala Cys Arg Ala Ala Lys Leu Gln Asp Cys Thr Met Leu
    2720                2725                2730

Val Cys Gly Asp Asp Leu Val Val Ile Cys Glu Ser Ala Gly Thr
    2735                2740                2745

Gln Glu Asp Ala Ala Ser Leu Arg Val Phe Thr Glu Ala Met Thr
    2750                2755                2760

Arg Tyr Ser Ala Pro Pro Gly Asp Pro Pro Gln Pro Glu Tyr Asp
    2765                2770                2775

Leu Glu Leu Ile Thr Ser Cys Ser Ser Asn Val Ser Val Ala His
    2780                2785                2790

Asp Ala Ser Gly Lys Arg Val Tyr Tyr Leu Thr Arg Asp Pro Thr
    2795                2800                2805

Thr Pro Leu Ala Arg Ala Ala Trp Glu Thr Ala Arg His Thr Pro
    2810                2815                2820

Val Asn Ser Trp Leu Gly Asn Ile Ile Met Tyr Ala Pro Thr Leu
    2825                2830                2835

Trp Ala Arg Met Ile Leu Met Thr His Phe Phe Ser Ile Leu Leu
    2840                2845                2850

Ala Gln Glu Gln Leu Glu Lys Ala Leu Asp Cys Gln Ile Tyr Gly
    2855                2860                2865

Ala Thr Tyr Ser Ile Glu Pro Leu Asp Leu Pro Gln Ile Ile Gln
    2870                2875                2880
```

-continued

```
Arg Leu His Gly Leu Ser Ala Phe Ser Leu His Ser Tyr Ser Pro
    2885                2890                2895

Gly Glu Ile Asn Arg Val Ala Ser Cys Leu Arg Lys Leu Gly Val
    2900                2905                2910

Pro Pro Leu Arg Val Trp Arg His Arg Ala Arg Ser Val Arg Ala
    2915                2920                2925

Lys Leu Leu Ser Gln Gly Gly Arg Ala Ala Ile Cys Gly Lys Tyr
    2930                2935                2940

Leu Phe Asn Trp Ala Val Arg Thr Lys Leu Lys Leu Thr Pro Ile
    2945                2950                2955

Pro Ala Ala Ser Gln Leu Asp Leu Ser Ser Trp Phe Ile Ala Gly
    2960                2965                2970

Tyr Ser Gly Gly Asp Ile Tyr His Ser Leu Ser Arg Ala Arg Pro
    2975                2980                2985

Arg Trp Phe Met Trp Cys Leu Leu Leu Ser Val Gly Val Gly
    2990                2995                3000

Ile Tyr Leu Leu Pro Asn Arg
    3005                3010

<210> SEQ ID NO 24
<211> LENGTH: 3010
<212> TYPE: PRT
<213> ORGANISM: Artificial
<220> FEATURE:
<223> OTHER INFORMATION: synthetic

<400> SEQUENCE: 24

Met Ser Thr Asn Pro Lys Pro Gln Arg Lys Thr Thr Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ala Ala Tyr
            180                 185                 190

Glu Val Arg Asn Val Ser Gly Val Tyr His Val Thr Asn Asp Cys Ser
        195                 200                 205

Asn Ser Ser Ile Val Tyr Glu Ala Ala Asp Met Ile Met His Thr Pro
    210                 215                 220
```

```
Gly Cys Val Pro Cys Val Arg Glu Gly Asn Ser Ser Arg Cys Trp Val
225                 230                 235                 240

Ala Leu Thr Pro Thr Leu Ala Ala Arg Asn Ser Ser Ile Pro Thr Thr
            245                 250                 255

Thr Ile Arg Arg His Val Asp Leu Leu Val Gly Ala Ala Ala Leu Cys
        260                 265                 270

Ser Val Val Tyr Val Gly Asp Leu Cys Gly Ser Val Phe Leu Val Ser
    275                 280                 285

Gln Leu Phe Thr Phe Ser Pro Arg Gln Tyr Glu Thr Val Gln Asp Cys
290                 295                 300

Asn Cys Ser Leu Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ser Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Asp
370                 375                 380

Thr Tyr Thr Thr Gly Gly Val Ala Ser Arg Thr Thr Ala Gly Leu Ala
385                 390                 395                 400

Ser Leu Phe Val Ser Gly Pro Ser Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Val Asn Arg Phe Asn
        435                 440                 445

Ser Ser Gly Cys Pro Glu Arg Met Ala Ser Cys Arg Pro Ile Asp Lys
    450                 455                 460

Phe Ala Gln Gly Trp Gly Pro Ile Thr His Ala Val Pro Arg Ala Ser
465                 470                 475                 480

Asp Gln Arg Pro Tyr Cys Trp His Tyr Ala Pro Gln Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Ser Gly Ala Pro Thr Tyr Thr
        515                 520                 525

Trp Gly Glu Asn Glu Thr Asp Val Leu Ile Leu Asn Asn Thr Arg Pro
    530                 535                 540

Pro His Gly Asn Trp Phe Gly Cys Ser Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Met
        595                 600                 605

Val Asp Tyr Pro Tyr Arg Leu Trp His Tyr Pro Cys Thr Val Asn Tyr
    610                 615                 620

Thr Ile Phe Lys Val Arg Met Tyr Val Gly Gly Val Glu His Arg Leu
625                 630                 635                 640
```

-continued

Asn Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Glu Trp
        660                 665                 670

Gln Ile Leu Pro Cys Ser Phe Thr Thr Leu Pro Ala Leu Ser Thr Gly
    675                 680                 685

Leu Ile His Leu His Gln Asn Ile Val Asp Val Gln Tyr Leu Tyr Gly
690                 695                 700

Val Gly Ser Val Val Ser Ile Val Ile Arg Trp Glu Tyr Val Val
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Ala Leu Asn Ala Ala Ser Val Ala Gly Ala His Gly Ile Leu Ser Phe
        755                 760                 765

Leu Ala Phe Phe Cys Ala Ala Trp Tyr Ile Lys Gly Lys Leu Val Pro
    770                 775                 780

Gly Ala Ala Tyr Ala Leu Tyr Ser Val Trp Pro Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Thr Leu Ser
            820                 825                 830

Pro His Tyr Lys Ala Leu Leu Ala Arg Leu Ile Trp Trp Leu Gln Tyr
        835                 840                 845

Leu Thr Thr Arg Ala Glu Ala Leu Leu Gln Val Trp Ile Pro Pro Leu
    850                 855                 860

Asn Val Arg Gly Gly Arg Asp Ala Ile Ile Leu Leu Thr Cys Met Val
865                 870                 875                 880

His Pro Glu Leu Thr Phe Glu Ile Thr Lys Ile Leu Leu Ala Ile Leu
                885                 890                 895

Gly Pro Leu Met Val Leu Arg Ala Gly Leu Thr Arg Val Pro Tyr Phe
            900                 905                 910

Val Arg Ala His Gly Leu Ile Arg Ala Cys Met Leu Val Arg Lys Val
        915                 920                 925

Ala Gly Gly His Tyr Val Gln Met Ala Leu Met Lys Leu Ala Ala Leu
    930                 935                 940

Thr Gly Thr Tyr Val Tyr Asp His Leu Thr Pro Leu Arg Asp Trp Ala
945                 950                 955                 960

His Ala Gly Leu Arg Asp Leu Ala Val Ala Val Glu Pro Val Phe
                965                 970                 975

Ser Asp Thr Glu Thr Lys Ile Ile Thr Trp Gly Ala Asp Thr Ala Ala
            980                 985                 990

Cys Gly Asp Ile Ile Leu Gly Leu Pro Val Ser Ala Arg Arg Gly Arg
        995                 1000                1005

Glu Ile Leu Leu Gly Pro Ala Asp Lys Phe Gly Glu Gln Gly Trp
    1010                1015                1020

Arg Leu Leu Ala Pro Ile Thr Ala Tyr Ser Gln Gln Thr Arg Gly
    1025                1030                1035

Val Leu Gly Cys Ile Ile Thr Ser Leu Thr Gly Arg Asp Lys Asn
    1040                1045                1050

Gln Val Glu Gly Glu Val Gln Val Val Ser Thr Ala Thr Gln Ser

```
            1055                1060                1065
Phe Leu Ala Thr Cys Val Asn Gly Val Cys Trp Thr Val Tyr His
    1070                1075                1080
Gly Ala Gly Ser Lys Thr Leu Ala Gly Pro Lys Gly Pro Ile Thr
    1085                1090                1095
Gln Met Tyr Thr Asn Val Asp Gln Asp Leu Val Gly Trp Gln Ala
    1100                1105                1110
Pro Pro Gly Ala Arg Ser Met Thr Pro Cys Thr Cys Gly Ser Ser
    1115                1120                1125
Asp Leu Phe Leu Val Thr Arg His Ala Asp Val Ile Pro Val Arg
    1130                1135                1140
Arg Arg Gly Asp Ser Arg Gly Ala Leu Leu Ser Pro Arg Pro Val
    1145                1150                1155
Ser Tyr Leu Lys Gly Ser Ser Gly Gly Pro Leu Leu Cys Pro Ser
    1160                1165                1170
Gly His Val Val Gly Ile Phe Arg Ala Ala Val Cys Thr Arg Gly
    1175                1180                1185
Val Ala Lys Ala Val Asp Phe Ile Pro Val Glu Ser Met Glu Thr
    1190                1195                1200
Thr Met Arg Ser Pro Val Phe Thr Asp Asn Ser Ser Pro Pro Ala
    1205                1210                1215
Val Pro Gln Thr Phe Gln Val Ala His Leu His Ala Pro Thr Gly
    1220                1225                1230
Ser Gly Lys Ser Thr Lys Val Pro Ala Ala Tyr Ala Ala Gln Gly
    1235                1240                1245
Tyr Lys Val Leu Val Leu Asn Pro Ser Val Ala Ala Thr Leu Ser
    1250                1255                1260
Phe Gly Ala Tyr Met Ser Lys Ala Tyr Gly Val Asp Pro Asn Ile
    1265                1270                1275
Arg Thr Gly Val Arg Thr Ile Thr Thr Gly Ala Pro Ile Thr Tyr
    1280                1285                1290
Ser Thr Tyr Gly Lys Phe Leu Ala Asp Gly Gly Cys Ser Gly Gly
    1295                1300                1305
Ala Tyr Asp Ile Ile Ile Cys Asp Glu Cys His Ser Thr Asp Ser
    1310                1315                1320
Thr Thr Ile Leu Gly Ile Gly Thr Val Leu Asp Gln Ala Glu Thr
    1325                1330                1335
Ala Gly Ala Arg Leu Val Val Leu Ala Thr Ala Thr Pro Pro Gly
    1340                1345                1350
Ser Val Thr Val Pro His Pro Asn Ile Glu Glu Val Ala Leu Ser
    1355                1360                1365
Asn Thr Gly Glu Ile Pro Phe Tyr Gly Lys Ala Ile Pro Leu Glu
    1370                1375                1380
Thr Ile Lys Gly Gly Arg His Leu Ile Phe Cys His Ser Lys Lys
    1385                1390                1395
Lys Cys Asp Glu Leu Ala Ala Lys Leu Ser Ala Leu Gly Leu Asn
    1400                1405                1410
Ala Val Ala Tyr Tyr Arg Gly Leu Asp Val Ser Ile Ile Pro Thr
    1415                1420                1425
Ser Gly Asp Val Val Val Val Ala Thr Asp Ala Leu Met Thr Gly
    1430                1435                1440
Tyr Thr Gly Asp Phe Asp Ser Val Ile Asp Cys Asn Thr Cys Val
    1445                1450                1455
```

-continued

```
Thr Gln Thr Val Asp Phe Ser Phe Asp Pro Thr Phe Ala Ile Glu
    1460                1465                1470
Thr Thr Thr Met Pro Gln Asp Ala Val Ser Arg Ser Gln Arg Arg
    1475                1480                1485
Gly Arg Thr Gly Arg Gly Arg Gly Gly Ile Tyr Arg Phe Val Thr
    1490                1495                1500
Pro Gly Glu Arg Pro Ser Gly Met Phe Asp Ser Ala Ile Leu Cys
    1505                1510                1515
Glu Cys Tyr Asp Ala Gly Cys Ala Trp Tyr Glu Leu Thr Pro Ala
    1520                1525                1530
Glu Thr Thr Val Arg Leu Arg Ala Tyr Leu Asn Thr Pro Gly Leu
    1535                1540                1545
Pro Val Cys Gln Asp His Leu Glu Phe Trp Glu Gly Val Phe Thr
    1550                1555                1560
Gly Leu Thr His Ile Asp Ala His Phe Leu Ser Gln Thr Lys Gln
    1565                1570                1575
Ala Gly Asp Asn Phe Pro Tyr Leu Val Ala Tyr Gln Ala Thr Val
    1580                1585                1590
Cys Ala Arg Ala Gln Ala Pro Pro Pro Ser Trp Asp Gln Met Trp
    1595                1600                1605
Lys Cys Leu Ile Arg Leu Lys Pro Thr Leu His Gly Pro Thr Pro
    1610                1615                1620
Leu Leu Tyr Arg Leu Gly Ala Val Gln Asn Glu Val Thr Leu Thr
    1625                1630                1635
His Pro Ile Thr Lys Tyr Ile Met Thr Cys Met Ser Ala Asp Leu
    1640                1645                1650
Glu Val Val Thr Ser Thr Trp Val Leu Val Gly Gly Val Leu Ala
    1655                1660                1665
Ala Leu Ala Ala Tyr Cys Leu Thr Thr Gly Ser Val Val Ile Val
    1670                1675                1680
Gly Arg Val Ile Leu Ser Gly Arg Pro Ala Ile Ile Pro Asp Arg
    1685                1690                1695
Glu Val Leu Tyr Arg Glu Phe Asp Glu Met Glu Glu Cys Ala Ser
    1700                1705                1710
His Leu Pro Tyr Ile Glu Gln Gly Met Gln Leu Ala Glu Gln Phe
    1715                1720                1725
Lys Gln Lys Ala Leu Gly Leu Leu Gln Thr Ala Thr Lys Gln Ala
    1730                1735                1740
Glu Ala Ala Ala Pro Val Val Glu Ser Lys Trp Arg Ala Leu Glu
    1745                1750                1755
Ala Phe Trp Ala Lys His Met Trp Asn Phe Ile Ser Gly Ile Gln
    1760                1765                1770
Tyr Leu Ala Gly Leu Ser Thr Leu Pro Gly Asn Pro Ala Ile Ala
    1775                1780                1785
Ser Leu Met Ala Phe Thr Ala Ser Ile Thr Ser Pro Leu Thr Thr
    1790                1795                1800
Gln His Thr Leu Leu Phe Asn Ile Leu Gly Gly Trp Val Ala Ala
    1805                1810                1815
Gln Leu Ala Pro Pro Gly Ala Ala Ser Ala Phe Val Gly Ala Gly
    1820                1825                1830
Ile Ala Gly Ala Ala Val Gly Ser Ile Gly Leu Gly Lys Val Leu
    1835                1840                1845
```

-continued

Val Asp Ile Leu Ala Gly Tyr Gly Ala Gly Val Ala Gly Ala Leu
        1850                1855                1860

Val Ala Phe Lys Val Met Ser Gly Glu Met Pro Ser Thr Glu Asp
        1865                1870                1875

Leu Val Asn Leu Leu Pro Ala Ile Leu Ser Pro Gly Ala Leu Val
        1880                1885                1890

Val Gly Val Val Cys Ala Ala Ile Leu Arg Arg His Val Gly Pro
        1895                1900                1905

Gly Glu Gly Ala Val Gln Trp Met Asn Arg Leu Ile Ala Phe Ala
        1910                1915                1920

Ser Arg Gly Asn His Val Ser Pro Thr His Tyr Val Pro Glu Ser
        1925                1930                1935

Asp Ala Ala Ala Arg Val Thr Gln Ile Leu Ser Ser Leu Thr Ile
        1940                1945                1950

Thr Gln Leu Leu Lys Arg Leu His Gln Trp Ile Asn Glu Asp Cys
        1955                1960                1965

Ser Thr Pro Cys Ser Gly Ser Trp Leu Arg Asp Val Trp Asp Trp
        1970                1975                1980

Ile Cys Thr Val Leu Thr Asp Phe Lys Thr Trp Leu Gln Ser Lys
        1985                1990                1995

Leu Leu Pro Arg Leu Pro Gly Val Pro Phe Leu Ser Cys Gln Arg
        2000                2005                2010

Gly Tyr Lys Gly Val Trp Arg Gly Asp Gly Ile Met His Thr Thr
        2015                2020                2025

Cys Pro Cys Gly Ala Gln Ile Ser Gly His Val Lys Asn Gly Ser
        2030                2035                2040

Met Arg Ile Val Gly Pro Lys Thr Cys Ser Asn Thr Trp Cys Gly
        2045                2050                2055

Thr Phe Pro Ile Asn Ala Tyr Thr Thr Gly Pro Cys Thr Pro Ser
        2060                2065                2070

Pro Ala Pro Asn Tyr Ser Arg Ala Leu Trp Arg Val Ala Ala Glu
        2075                2080                2085

Glu Tyr Val Glu Val Thr Arg Val Gly Asp Phe His Tyr Val Thr
        2090                2095                2100

Gly Met Thr Thr Asp Asn Leu Lys Cys Pro Cys Gln Val Pro Ala
        2105                2110                2115

Pro Glu Phe Phe Thr Glu Val Asp Gly Val Arg Leu His Arg Tyr
        2120                2125                2130

Ala Pro Ala Cys Lys Pro Leu Leu Arg Asp Glu Val Thr Phe Gln
        2135                2140                2145

Val Gly Leu Asn Gln Phe Pro Val Gly Ser Gln Leu Pro Cys Glu
        2150                2155                2160

Pro Glu Pro Asp Val Thr Val Leu Thr Ser Met Leu Thr Asp Pro
        2165                2170                2175

Ser His Ile Thr Ala Glu Thr Ala Lys Arg Arg Leu Ala Arg Gly
        2180                2185                2190

Ser Pro Pro Ser Leu Ala Ser Ser Ser Ala Gly Gln Leu Ser Ala
        2195                2200                2205

Val Ser Leu Lys Ala Ala Cys Thr Thr Arg His Asn Pro Pro Asp
        2210                2215                2220

Ala Asp Leu Ile Glu Ala Asn Leu Leu Trp Arg Gln Glu Met Gly
        2225                2230                2235

Gly Ser Ile Thr Arg Val Glu Ser Glu Ser Lys Val Val Ile Leu

```
                2240                2245                2250
Asp Ser Phe Glu Pro Leu Arg Ala Glu Asp Glu Arg Glu Val
    2255                2260                2265
Ser Val Pro Ala Glu Ile Leu Arg Lys Thr Lys Lys Phe Pro Ala
    2270                2275                2280
Ala Met Pro Val Trp Ala Arg Pro Asp Tyr Asn Pro Pro Leu Leu
    2285                2290                2295
Glu Ser Trp Arg Asp Pro Asp Tyr Val Pro Pro Val Val His Gly
    2300                2305                2310
Cys Pro Leu Pro Pro Thr Lys Ala Pro Pro Ile Pro Pro Pro Arg
    2315                2320                2325
Arg Lys Arg Thr Val Ile Leu Thr Glu Ser Thr Val Ser Ser Ala
    2330                2335                2340
Leu Ala Glu Leu Ala Thr Lys Thr Phe Gly Ser Ser Gly Ser Ser
    2345                2350                2355
Ala Val Asp Asn Gly Thr Ala Thr Ala Pro Pro Asp Gln Pro Ser
    2360                2365                2370
Ile Asp Gly Asp Ala Gly Ser Asp Val Glu Ser Tyr Ser Ser Met
    2375                2380                2385
Pro Pro Leu Glu Gly Glu Pro Gly Asp Pro Asp Leu Ser Asp Gly
    2390                2395                2400
Ser Trp Ser Thr Val Ser Glu Glu Ala Gly Glu Asp Val Val Cys
    2405                2410                2415
Cys Ser Met Ser Tyr Thr Trp Thr Gly Ala Leu Ile Thr Pro Cys
    2420                2425                2430
Ala Ala Glu Glu Ser Lys Leu Pro Ile Asn Ala Leu Ser Asn Ser
    2435                2440                2445
Leu Leu Arg His His Asn Met Val Tyr Ala Thr Thr Ser Arg Ser
    2450                2455                2460
Ala Ser Gln Arg Gln Lys Lys Val Thr Phe Asp Arg Leu Gln Val
    2465                2470                2475
Leu Asp Asp His Tyr Arg Asp Val Leu Lys Glu Met Lys Ala Lys
    2480                2485                2490
Ala Ser Thr Val Lys Ala Lys Leu Leu Ser Val Glu Glu Ala Cys
    2495                2500                2505
Arg Leu Thr Pro Pro His Ser Ala Arg Ser Lys Phe Gly Tyr Gly
    2510                2515                2520
Ala Lys Asp Val Arg Asn Leu Ser Ser Lys Ala Val Asn His Ile
    2525                2530                2535
His Ser Val Trp Lys Asp Leu Leu Glu Asp Thr Glu Thr Pro Ile
    2540                2545                2550
Asp Thr Thr Ile Met Ala Lys Asn Glu Val Phe Cys Val Gln Pro
    2555                2560                2565
Glu Lys Gly Gly Arg Lys Pro Ala Arg Leu Ile Val Phe Pro Asp
    2570                2575                2580
Leu Gly Val Arg Val Cys Glu Lys Met Ala Leu Tyr Asp Val Val
    2585                2590                2595
Ser Thr Leu Pro Gln Ala Val Met Gly Ser Ser Tyr Gly Phe Gln
    2600                2605                2610
Tyr Ser Pro Gly Gln Arg Val Glu Phe Leu Val Asn Ala Trp Lys
    2615                2620                2625
Ser Lys Lys Asn Pro Met Gly Phe Ala Tyr Asp Thr Arg Cys Phe
    2630                2635                2640
```

```
Asp Ser Thr Val Thr Glu Ser Asp Ile Arg Val Glu Glu Ser Ile
        2645                2650                2655

Tyr Gln Cys Cys Asp Leu Ala Pro Glu Ala Arg Gln Val Ile Arg
        2660                2665                2670

Ser Leu Thr Glu Arg Leu Tyr Ile Gly Gly Pro Leu Thr Asn Ser
        2675                2680                2685

Lys Gly Gln Asn Cys Gly Tyr Arg Arg Cys Arg Ala Ser Gly Val
        2690                2695                2700

Leu Thr Thr Ser Cys Gly Asn Thr Leu Thr Cys Tyr Leu Lys Ala
        2705                2710                2715

Ser Ala Ala Cys Arg Ala Ala Lys Leu Gln Asp Cys Thr Met Leu
        2720                2725                2730

Val Cys Gly Asp Asp Leu Val Val Ile Cys Glu Ser Ala Gly Thr
        2735                2740                2745

Gln Glu Asp Ala Ala Ser Leu Arg Val Phe Thr Glu Ala Met Thr
        2750                2755                2760

Arg Tyr Ser Ala Pro Pro Gly Asp Pro Gln Pro Glu Tyr Asp
        2765                2770                2775

Leu Glu Leu Ile Thr Ser Cys Ser Ser Asn Val Ser Val Ala His
        2780                2785                2790

Asp Ala Ser Gly Lys Arg Val Tyr Tyr Leu Thr Arg Asp Pro Thr
        2795                2800                2805

Thr Pro Leu Ala Arg Ala Ala Trp Glu Thr Ala Arg His Thr Pro
        2810                2815                2820

Val Asn Ser Trp Leu Gly Asn Ile Ile Met Tyr Ala Pro Thr Leu
        2825                2830                2835

Trp Ala Arg Met Ile Leu Met Thr His Phe Phe Ser Ile Leu Leu
        2840                2845                2850

Ala Gln Glu Gln Leu Glu Lys Ala Leu Asp Cys Gln Ile Tyr Gly
        2855                2860                2865

Ala Thr Tyr Ser Ile Glu Pro Leu Asp Leu Pro Gln Ile Ile Gln
        2870                2875                2880

Arg Leu His Gly Leu Ser Ala Phe Ser Leu His Ser Tyr Ser Pro
        2885                2890                2895

Gly Glu Ile Asn Arg Val Ala Ser Cys Leu Arg Lys Leu Gly Val
        2900                2905                2910

Pro Pro Leu Arg Val Trp Arg His Arg Ala Arg Ser Val Arg Ala
        2915                2920                2925

Lys Leu Leu Ser Gln Gly Gly Arg Ala Ala Ile Cys Gly Lys Tyr
        2930                2935                2940

Leu Phe Asn Trp Ala Val Arg Thr Lys Leu Lys Leu Thr Pro Ile
        2945                2950                2955

Pro Ala Ala Ser Gln Leu Asp Leu Ser Ser Trp Phe Ile Ala Gly
        2960                2965                2970

Tyr Ser Gly Gly Asp Ile Tyr His Ser Leu Ser Arg Ala Arg Pro
        2975                2980                2985

Arg Trp Phe Met Trp Cys Leu Leu Leu Leu Ser Val Gly Val Gly
        2990                2995                3000

Ile Tyr Leu Leu Pro Asn Arg
        3005                3010

<210> SEQ ID NO 25
<211> LENGTH: 3010
```

```
<212> TYPE: PRT
<213> ORGANISM: Artificial
<220> FEATURE:
<223> OTHER INFORMATION: synthetic

<400> SEQUENCE: 25
```

| | | | | | | | | | | | | | | | |
|---|---|---|---|---|---|---|---|---|---|---|---|---|---|---|---|
| Met | Ser | Thr | Asn | Pro | Lys | Pro | Gln | Arg | Lys | Thr | Thr | Arg | Asn | Thr | Asn |
| 1 | | | | 5 | | | | | 10 | | | | | 15 | |
| Arg | Arg | Pro | Gln | Asp | Val | Lys | Phe | Pro | Gly | Gly | Gln | Ile | Val | Gly | |
| | | 20 | | | | 25 | | | | | 30 | | | | |
| Gly | Val | Tyr | Leu | Leu | Pro | Arg | Arg | Gly | Pro | Arg | Leu | Gly | Val | Arg | Ala |
| | | 35 | | | | | 40 | | | | | 45 | | | |
| Thr | Arg | Lys | Thr | Ser | Glu | Arg | Ser | Gln | Pro | Arg | Gly | Arg | Arg | Gln | Pro |
| | 50 | | | | | 55 | | | | | 60 | | | | |
| Ile | Pro | Lys | Ala | Arg | Arg | Pro | Glu | Gly | Arg | Ala | Trp | Ala | Gln | Pro | Gly |
| 65 | | | | 70 | | | | | 75 | | | | | | 80 |
| Tyr | Pro | Trp | Pro | Leu | Tyr | Gly | Asn | Glu | Gly | Leu | Gly | Trp | Ala | Gly | Trp |
| | | | | 85 | | | | 90 | | | | | 95 | | |
| Leu | Leu | Ser | Pro | Arg | Gly | Ser | Arg | Pro | Ser | Trp | Gly | Pro | Thr | Asp | Pro |
| | | | | 100 | | | | | 105 | | | | | 110 | |
| Arg | Arg | Arg | Ser | Arg | Asn | Leu | Gly | Lys | Val | Ile | Asp | Thr | Leu | Thr | Cys |
| | | 115 | | | | | 120 | | | | | 125 | | | |
| Gly | Phe | Ala | Asp | Leu | Met | Gly | Tyr | Ile | Pro | Leu | Val | Gly | Ala | Pro | Leu |
| | 130 | | | | | 135 | | | | | 140 | | | | |
| Gly | Gly | Ala | Ala | Arg | Ala | Leu | Ala | His | Gly | Val | Arg | Val | Leu | Glu | Asp |
| 145 | | | | 150 | | | | | 155 | | | | | | 160 |
| Gly | Val | Asn | Tyr | Ala | Thr | Gly | Asn | Leu | Pro | Gly | Cys | Ser | Phe | Ser | Ile |
| | | | | 165 | | | | 170 | | | | | 175 | | |
| Phe | Leu | Leu | Ala | Leu | Leu | Ser | Cys | Leu | Thr | Ile | Pro | Ala | Ala | Ala | Tyr |
| | | | | 180 | | | | 185 | | | | | 190 | | |
| Glu | Val | Arg | Asn | Val | Ser | Gly | Val | Tyr | His | Val | Thr | Asn | Asp | Cys | Ser |
| | | 195 | | | | | 200 | | | | | 205 | | | |
| Asn | Ser | Ser | Ile | Val | Tyr | Glu | Ala | Ala | Asp | Met | Ile | Met | His | Thr | Pro |
| | 210 | | | | | 215 | | | | | 220 | | | | |
| Gly | Cys | Val | Pro | Cys | Val | Arg | Glu | Gly | Asn | Ser | Ser | Arg | Cys | Trp | Val |
| 225 | | | | 230 | | | | | 235 | | | | | | 240 |
| Ala | Leu | Thr | Pro | Thr | Leu | Ala | Ala | Arg | Asn | Ser | Ser | Ile | Pro | Thr | Thr |
| | | | | 245 | | | | 250 | | | | | 255 | | |
| Thr | Ile | Arg | Arg | His | Val | Asp | Leu | Leu | Val | Gly | Ala | Ala | Ala | Leu | Cys |
| | | | 260 | | | | | 265 | | | | | 270 | | |
| Ser | Val | Val | Tyr | Val | Gly | Asp | Leu | Cys | Gly | Ser | Val | Phe | Leu | Val | Ser |
| | | 275 | | | | | 280 | | | | | 285 | | | |
| Gln | Leu | Phe | Thr | Phe | Ser | Pro | Arg | Gln | Tyr | Glu | Thr | Val | Gln | Asp | Cys |
| | 290 | | | | | 295 | | | | | 300 | | | | |
| Asn | Cys | Ser | Leu | Tyr | Pro | Gly | His | Val | Ser | Gly | His | Arg | Met | Ala | Trp |
| 305 | | | | | 310 | | | | | 315 | | | | | 320 |
| Asp | Met | Met | Met | Asn | Trp | Ser | Pro | Thr | Thr | Ala | Leu | Val | Val | Ser | Gln |
| | | | | 325 | | | | | 330 | | | | | 335 | |
| Leu | Leu | Arg | Ile | Pro | Gln | Ala | Ile | Val | Asp | Met | Val | Ser | Gly | Ala | His |
| | | | 340 | | | | | 345 | | | | | 350 | | |
| Trp | Gly | Val | Leu | Ala | Gly | Leu | Ala | Tyr | Tyr | Ser | Met | Val | Gly | Asn | Trp |
| | | 355 | | | | | 360 | | | | | 365 | | | |
| Ala | Lys | Val | Leu | Ile | Val | Met | Leu | Leu | Phe | Ala | Gly | Val | Asp | Gly | Asp |
| | 370 | | | | | 375 | | | | | 380 | | | | |

```
Thr Tyr Thr Thr Gly Gly Val Ala Ser Arg Thr Ala Gly Leu Ala
385                 390                 395                 400

Ser Leu Phe Val Ser Gly Pro Ser Gln Lys Ile Gln Leu Ile Asn Thr
            405                 410                 415

Asn Gly Ser Trp His Ile Asn Arg Thr Ala Leu Asn Cys Asn Asp Ser
        420                 425                 430

Leu Asn Thr Gly Phe Leu Ala Ala Leu Phe Tyr Val Asn Arg Phe Asn
        435                 440                 445

Ser Ser Gly Cys Pro Glu Arg Met Ala Ser Cys Arg Pro Ile Asp Lys
    450                 455                 460

Phe Ala Gln Gly Trp Gly Pro Ile Thr His Ala Val Pro Arg Ala Ser
465                 470                 475                 480

Asp Gln Arg Pro Tyr Cys Trp His Tyr Ala Pro Gln Pro Cys Gly Ile
            485                 490                 495

Val Pro Ala Ser Gln Val Cys Gly Pro Val Tyr Cys Phe Thr Pro Ser
                500                 505                 510

Pro Val Val Val Gly Thr Thr Asp Arg Ser Gly Ala Pro Thr Tyr Thr
            515                 520                 525

Trp Gly Glu Asn Glu Thr Asp Val Leu Ile Leu Asn Asn Thr Arg Pro
530                 535                 540

Pro His Gly Asn Trp Phe Gly Cys Ser Trp Met Asn Ser Thr Gly Phe
545                 550                 555                 560

Thr Lys Thr Cys Gly Pro Pro Cys Asn Ile Gly Gly Val Gly Asn
            565                 570                 575

Asn Thr Leu Thr Cys Pro Thr Asp Cys Phe Arg Lys His Pro Glu Ala
        580                 585                 590

Thr Tyr Thr Lys Cys Gly Ser Gly Pro Trp Leu Thr Pro Arg Cys Met
        595                 600                 605

Val Asp Tyr Pro Tyr Arg Leu Trp His Tyr Pro Cys Thr Val Asn Tyr
    610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Glu Trp
                660                 665                 670

Gln Ile Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Val Val Ser Ile Val Arg Trp Glu Tyr Val Val
705                 710                 715                 720

Leu Leu Phe Leu Leu Leu Ala Asp Ala Arg Val Cys Ala Cys Leu Trp
            725                 730                 735

Met Met Leu Leu Ile Ala Gln Ala Glu Ala Leu Glu Asn Leu Val
            740                 745                 750

Ala Leu Asn Ala Ala Ser Val Ala Gly Ala His Gly Ile Leu Ser Phe
        755                 760                 765

Leu Ala Phe Phe Cys Ala Ala Trp Tyr Ile Lys Gly Lys Leu Val Pro
        770                 775                 780

Gly Ala Ala Tyr Ala Leu Tyr Ser Val Trp Pro Leu Leu Leu Leu Leu
785                 790                 795                 800

Leu Ala Leu Pro Pro Arg Ala Tyr Ala Met Asp Arg Glu Met Ala Ala
```

```
            805                 810                 815
Ser Cys Gly Gly Ala Phe Val Gly Leu Val Leu Thr Leu Ser
                820                 825                 830

Pro His Tyr Lys Ala Leu Leu Ala Arg Leu Ile Trp Trp Leu Gln Tyr
                835                 840                 845

Leu Thr Thr Arg Ala Glu Ala Leu Leu Gln Val Trp Ile Pro Pro Leu
    850                 855                 860

Asn Val Arg Gly Gly Arg Asp Ala Ile Ile Leu Leu Thr Cys Met Val
865                 870                 875                 880

His Pro Glu Leu Thr Phe Glu Ile Thr Lys Ile Leu Leu Ala Ile Leu
                885                 890                 895

Gly Pro Leu Met Val Leu Arg Ala Gly Leu Thr Arg Val Pro Tyr Phe
                900                 905                 910

Val Arg Ala His Gly Leu Ile Arg Ala Cys Met Leu Val Arg Lys Val
                915                 920                 925

Ala Gly Gly His Tyr Val Gln Met Ala Leu Met Lys Leu Ala Ala Leu
            930                 935                 940

Thr Gly Thr Tyr Val Tyr Asp His Leu Thr Pro Leu Arg Asp Trp Ala
945                 950                 955                 960

His Ala Gly Leu Arg Asp Leu Ala Val Ala Val Glu Pro Val Val Phe
                965                 970                 975

Ser Asp Thr Glu Thr Lys Ile Ile Thr Trp Gly Ala Asp Thr Ala Ala
            980                 985                 990

Cys Gly Asp Ile Ile Leu Gly Leu Pro Val Ser Ala Arg Arg Gly Arg
                995                1000                1005

Glu Ile Leu Leu Gly Pro Ala Asp Lys Phe Gly Glu Gln Gly Trp
            1010                1015                1020

Arg Leu Leu Ala Pro Ile Thr Ala Tyr Ser Gln Gln Thr Arg Gly
            1025                1030                1035

Val Leu Gly Cys Ile Ile Thr Ser Leu Thr Gly Arg Asp Lys Asn
            1040                1045                1050

Gln Val Glu Gly Glu Val Gln Val Val Ser Thr Ala Thr Gln Ser
            1055                1060                1065

Phe Leu Ala Thr Cys Val Asn Gly Val Cys Trp Thr Val Tyr His
            1070                1075                1080

Gly Ala Gly Ser Lys Thr Leu Ala Gly Pro Lys Gly Pro Ile Thr
            1085                1090                1095

Gln Met Tyr Thr Asn Val Asp Gln Asp Leu Val Gly Trp Gln Ala
            1100                1105                1110

Pro Pro Gly Ala Arg Ser Met Thr Pro Cys Thr Cys Gly Ser Ser
            1115                1120                1125

Asp Leu Phe Leu Val Thr Arg His Ala Asp Val Ile Pro Val Arg
            1130                1135                1140

Arg Arg Gly Asp Ser Arg Gly Ala Leu Leu Ser Pro Arg Pro Val
            1145                1150                1155

Ser Tyr Leu Lys Gly Ser Ser Gly Gly Pro Leu Leu Cys Pro Ser
            1160                1165                1170

Gly His Val Val Gly Ile Phe Arg Ala Ala Val Cys Thr Arg Gly
            1175                1180                1185

Val Ala Lys Ala Val Asp Phe Ile Pro Val Glu Ser Met Gly Thr
            1190                1195                1200

Thr Met Arg Ser Pro Val Phe Thr Asp Asn Ser Ser Pro Pro Ala
            1205                1210                1215
```

-continued

Val Pro Gln Thr Phe Gln Val Ala His Leu His Ala Pro Thr Gly
1220                1225                1230

Ser Gly Lys Ser Thr Lys Val Pro Ala Ala Tyr Ala Ala Gln Gly
1235                1240                1245

Tyr Lys Val Leu Val Leu Asn Pro Ser Val Ala Ala Thr Leu Ser
1250                1255                1260

Phe Gly Ala Tyr Met Ser Lys Ala Tyr Gly Val Asp Pro Asn Ile
1265                1270                1275

Arg Thr Gly Val Arg Thr Ile Thr Thr Gly Ala Pro Ile Thr Tyr
1280                1285                1290

Ser Thr Tyr Gly Lys Phe Leu Ala Asp Gly Gly Cys Ser Gly Gly
1295                1300                1305

Ala Tyr Asp Ile Ile Ile Cys Asp Glu Cys His Ser Thr Asp Ser
1310                1315                1320

Thr Thr Ile Leu Gly Ile Gly Thr Val Leu Asp Gln Ala Glu Thr
1325                1330                1335

Ala Gly Ala Arg Leu Val Val Leu Ala Thr Ala Thr Pro Pro Gly
1340                1345                1350

Ser Val Thr Val Pro His Pro Asn Ile Glu Glu Val Ala Leu Ser
1355                1360                1365

Asn Thr Gly Glu Ile Pro Phe Tyr Gly Lys Ala Ile Pro Leu Glu
1370                1375                1380

Thr Ile Lys Gly Gly Arg His Leu Ile Phe Cys His Ser Lys Lys
1385                1390                1395

Lys Cys Asp Glu Leu Ala Ala Lys Leu Ser Ala Leu Gly Leu Asn
1400                1405                1410

Ala Val Ala Tyr Tyr Arg Gly Leu Asp Val Ser Ile Ile Pro Thr
1415                1420                1425

Ser Gly Asp Val Val Val Ala Thr Asp Ala Leu Met Thr Gly
1430                1435                1440

Tyr Thr Gly Asp Phe Asp Ser Val Ile Asp Cys Asn Thr Cys Val
1445                1450                1455

Thr Gln Thr Val Asp Phe Ser Phe Asp Pro Thr Phe Ala Ile Glu
1460                1465                1470

Thr Thr Thr Met Pro Gln Asp Ala Val Ser Arg Ser Gln Arg Arg
1475                1480                1485

Gly Arg Thr Gly Arg Gly Arg Gly Gly Ile Tyr Arg Phe Val Thr
1490                1495                1500

Pro Gly Glu Arg Pro Ser Gly Met Phe Asp Ser Ala Ile Leu Cys
1505                1510                1515

Glu Cys Tyr Asp Ala Gly Cys Ala Trp Tyr Glu Leu Thr Pro Ala
1520                1525                1530

Glu Thr Thr Val Arg Leu Arg Ala Tyr Leu Asn Thr Pro Gly Leu
1535                1540                1545

Pro Val Cys Gln Asp His Leu Glu Phe Trp Glu Gly Val Phe Thr
1550                1555                1560

Gly Leu Thr His Ile Asp Ala His Phe Leu Ser Gln Thr Lys Gln
1565                1570                1575

Ala Gly Asp Asn Phe Pro Tyr Leu Val Ala Tyr Gln Ala Thr Val
1580                1585                1590

Cys Ala Arg Ala Gln Ala Pro Pro Pro Ser Trp Asp Gln Met Trp
1595                1600                1605

```
Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Leu Thr
1625                1630                1635

His Pro Ile Thr Lys Tyr Ile Met Thr Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Thr Thr Gly Ser Val Val Ile Val
1670                1675                1680

Gly Arg Val Ile Leu Ser Gly Arg Pro Ala Ile Ile Pro Asp Arg
1685                1690                1695

Glu Val Leu Tyr Arg Glu Phe Asp Glu Met Glu Cys Ala Ser
1700                1705                1710

His Leu Pro Tyr Ile Glu Gln Gly Met Gln Leu Ala Glu Gln Phe
1715                1720                1725

Lys Gln Lys Ala Leu Gly Leu Leu Gln Thr Ala Thr Lys Gln Ala
1730                1735                1740

Glu Ala Ala Ala Pro Val Val Glu Ser Lys Trp Arg Ala Leu Glu
1745                1750                1755

Ala Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ser Ile Thr Ser Pro Leu Thr Thr
1790                1795                1800

Gln His Thr Leu Leu Phe Asn Ile Leu Gly Gly Trp Val Ala Ala
1805                1810                1815

Gln Leu Ala Pro Pro Gly Ala Ala Ser Ala Phe Val Gly Ala Gly
1820                1825                1830

Ile Ala Gly Ala Ala Val Gly Ser Ile Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Val Met Ser Gly Glu Met Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Ala Arg Val Thr Gln Ile Leu Ser Ser Leu Thr Ile
1940                1945                1950

Thr Gln Leu Leu Lys Arg Leu His Gln Trp Ile Asn Glu Asp Cys
1955                1960                1965

Ser Thr Pro Cys Ser Gly Ser Trp Leu Arg Asp Val Trp Asp Trp
1970                1975                1980

Ile Cys Thr Val Leu Thr Asp Phe Lys Thr Trp Leu Gln Ser Lys
1985                1990                1995

Leu Leu Pro Arg Leu Pro Gly Val Pro Phe Leu Ser Cys Gln Arg
```

```
                    2000                    2005                     2010
Gly Tyr Lys Gly Val Trp Arg Gly Asp Gly Ile Met His Thr Thr
    2015                    2020                     2025
Cys Pro Cys Gly Ala Gln Ile Ser Gly His Val Lys Asn Gly Ser
    2030                    2035                     2040
Met Arg Ile Val Gly Pro Lys Thr Cys Ser Asn Thr Trp Cys Gly
    2045                    2050                     2055
Thr Phe Pro Ile Asn Ala Tyr Thr Thr Gly Pro Cys Thr Pro Ser
    2060                    2065                     2070
Pro Ala Pro Asn Tyr Ser Arg Ala Leu Trp Arg Val Ala Ala Glu
    2075                    2080                     2085
Glu Tyr Val Glu Val Thr Arg Val Gly Asp Phe His Tyr Val Thr
    2090                    2095                     2100
Gly Met Thr Thr Asp Asn Leu Lys Cys Pro Cys Gln Val Pro Ala
    2105                    2110                     2115
Pro Glu Phe Phe Thr Glu Val Asp Gly Val Arg Leu His Arg Tyr
    2120                    2125                     2130
Ala Pro Ala Cys Lys Pro Leu Leu Arg Asp Glu Val Thr Phe Gln
    2135                    2140                     2145
Val Gly Leu Asn Gln Phe Pro Val Gly Ser Gln Leu Pro Cys Glu
    2150                    2155                     2160
Pro Glu Pro Asp Val Thr Val Leu Thr Ser Met Leu Thr Asp Pro
    2165                    2170                     2175
Ser His Ile Thr Ala Glu Thr Ala Lys Arg Arg Leu Ala Arg Gly
    2180                    2185                     2190
Ser Pro Pro Tyr Leu Ala Ser Ser Ser Ala Ser Gln Leu Ser Ala
    2195                    2200                     2205
Val Ser Leu Lys Ala Ala Cys Thr Thr Arg His Asn Pro Pro Asp
    2210                    2215                     2220
Ala Asp Leu Ile Glu Ala Asn Leu Leu Trp Arg Gln Glu Met Gly
    2225                    2230                     2235
Gly Ser Ile Thr Arg Val Glu Ser Glu Ser Lys Val Val Ile Leu
    2240                    2245                     2250
Asp Ser Phe Glu Pro Leu Arg Ala Glu Glu Asp Glu Arg Glu Val
    2255                    2260                     2265
Ser Val Pro Ala Glu Ile Leu Arg Lys Thr Lys Lys Phe Pro Ala
    2270                    2275                     2280
Ala Met Pro Val Trp Ala Arg Pro Asp Tyr Asn Pro Pro Leu Leu
    2285                    2290                     2295
Glu Ser Trp Arg Asp Pro Asp Tyr Val Pro Pro Val Val His Gly
    2300                    2305                     2310
Cys Pro Leu Pro Pro Thr Lys Ala Pro Pro Ile Pro Pro Pro Arg
    2315                    2320                     2325
Arg Lys Arg Thr Val Ile Leu Thr Glu Ser Thr Val Ser Ser Ala
    2330                    2335                     2340
Leu Ala Glu Leu Ala Thr Lys Thr Phe Gly Ser Ser Gly Ser Ser
    2345                    2350                     2355
Ala Val Asp Asn Gly Thr Ala Thr Ala Pro Pro Asp Gln Pro Ser
    2360                    2365                     2370
Ile Asp Gly Asp Ala Gly Ser Asp Val Glu Ser Tyr Ser Ser Met
    2375                    2380                     2385
Pro Pro Leu Glu Gly Glu Pro Gly Asp Pro Asp Leu Ser Asp Gly
    2390                    2395                     2400
```

-continued

```
Ser Trp Ser Thr Val Ser Glu Glu Ala Gly Glu Asp Val Val Cys
    2405            2410            2415

Cys Ser Met Ser Tyr Thr Trp Thr Gly Ala Leu Ile Thr Pro Cys
    2420            2425            2430

Ala Ala Glu Glu Ser Lys Leu Pro Ile Asn Ala Leu Ser Asn Ser
    2435            2440            2445

Leu Leu Arg His His Asn Met Val Tyr Ala Thr Thr Ser Arg Ser
    2450            2455            2460

Ala Ser Gln Arg Gln Lys Lys Val Thr Phe Asp Arg Leu Gln Val
    2465            2470            2475

Leu Asp Asp His Tyr Arg Asp Val Leu Lys Glu Met Lys Ala Lys
    2480            2485            2490

Ala Ser Thr Val Lys Ala Lys Leu Leu Ser Val Glu Glu Ala Cys
    2495            2500            2505

Arg Leu Thr Pro Pro His Ser Ala Arg Ser Lys Phe Gly Tyr Gly
    2510            2515            2520

Ala Lys Asp Val Arg Asn Leu Ser Ser Lys Ala Val Asn His Ile
    2525            2530            2535

His Ser Val Trp Lys Asp Leu Leu Glu Asp Thr Glu Thr Pro Ile
    2540            2545            2550

Asp Thr Thr Ile Met Ala Lys Asn Glu Val Phe Cys Val Gln Pro
    2555            2560            2565

Glu Lys Gly Gly Arg Lys Pro Ala Arg Leu Ile Val Phe Pro Asp
    2570            2575            2580

Leu Gly Val Arg Val Cys Glu Lys Met Ala Leu Tyr Asp Val Val
    2585            2590            2595

Ser Thr Leu Pro Gln Ala Val Met Gly Ser Ser Tyr Gly Phe Gln
    2600            2605            2610

Tyr Ser Pro Gly Gln Arg Val Glu Phe Leu Val Asn Ala Trp Lys
    2615            2620            2625

Ser Lys Lys Asn Pro Met Gly Phe Ala Tyr Asp Thr Arg Cys Phe
    2630            2635            2640

Asp Ser Thr Val Thr Glu Ser Asp Ile Arg Val Glu Glu Ser Ile
    2645            2650            2655

Tyr Gln Cys Cys Asp Leu Ala Pro Glu Ala Arg Gln Val Ile Arg
    2660            2665            2670

Ser Leu Thr Glu Arg Leu Tyr Ile Gly Gly Pro Leu Thr Asn Ser
    2675            2680            2685

Lys Gly Gln Asn Cys Gly Tyr Arg Arg Cys Arg Ala Ser Gly Val
    2690            2695            2700

Leu Thr Thr Ser Cys Gly Asn Thr Leu Thr Cys Tyr Leu Lys Ala
    2705            2710            2715

Ser Ala Ala Cys Arg Ala Ala Lys Leu Gln Asp Cys Thr Met Leu
    2720            2725            2730

Val Cys Gly Asp Asp Leu Val Val Ile Cys Glu Ser Ala Gly Thr
    2735            2740            2745

Gln Glu Asp Ala Ala Ser Leu Arg Val Phe Thr Glu Ala Met Thr
    2750            2755            2760

Arg Tyr Ser Ala Pro Pro Gly Asp Pro Pro Gln Pro Glu Tyr Asp
    2765            2770            2775

Leu Glu Leu Ile Thr Ser Cys Ser Ser Asn Val Ser Val Ala His
    2780            2785            2790
```

-continued

```
Asp Ala Ser Gly Lys Arg Val Tyr Tyr Leu Thr Arg Asp Pro Thr
    2795                2800                2805

Thr Pro Leu Ala Arg Ala Ala Trp Glu Thr Ala Arg His Thr Pro
    2810                2815                2820

Val Asn Ser Trp Leu Gly Asn Ile Ile Met Tyr Ala Pro Thr Leu
    2825                2830                2835

Trp Ala Arg Met Ile Leu Met Thr His Phe Phe Ser Ile Leu Leu
    2840                2845                2850

Ala Gln Glu Gln Leu Glu Lys Ala Leu Asp Cys Gln Ile Tyr Gly
    2855                2860                2865

Ala Thr Tyr Ser Ile Glu Pro Leu Asp Leu Pro Gln Ile Ile Gln
    2870                2875                2880

Arg Leu His Gly Leu Ser Ala Phe Ser Leu His Ser Tyr Ser Pro
    2885                2890                2895

Gly Glu Ile Asn Arg Val Ala Ser Cys Leu Arg Lys Leu Gly Val
    2900                2905                2910

Pro Pro Leu Arg Val Trp Arg His Arg Ala Arg Ser Val Arg Ala
    2915                2920                2925

Lys Leu Leu Ser Gln Gly Gly Arg Ala Ala Ile Cys Gly Lys Tyr
    2930                2935                2940

Leu Phe Asn Trp Ala Val Arg Thr Lys Leu Lys Leu Thr Pro Ile
    2945                2950                2955

Pro Ala Ala Ser Gln Leu Asp Leu Ser Ser Trp Phe Ile Ala Gly
    2960                2965                2970

Tyr Ser Gly Gly Asp Ile Tyr His Ser Leu Ser Arg Ala Arg Pro
    2975                2980                2985

Arg Trp Phe Met Trp Cys Leu Leu Leu Ser Val Gly Val Gly
    2990                2995                3000

Ile Tyr Leu Leu Pro Asn Arg
    3005                3010

<210> SEQ ID NO 26
<211> LENGTH: 3010
<212> TYPE: PRT
<213> ORGANISM: Artificial
<220> FEATURE:
<223> OTHER INFORMATION: synthetic

<400> SEQUENCE: 26

Met Ser Thr Asn Pro Lys Pro Gln Arg Lys Thr Thr Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125
```

```
Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ala Ala Tyr
                180                 185                 190

Glu Val Arg Asn Val Ser Gly Tyr His Val Thr Asn Asp Cys Ser
                195                 200                 205

Asn Ser Ser Ile Val Tyr Glu Ala Ala Asp Met Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ser Ser Ile Pro Thr Thr
                245                 250                 255

Thr Ile Arg Arg His Val Asp Leu Leu Val Gly Ala Ala Ala Leu Cys
                260                 265                 270

Ser Val Val Tyr Val Gly Asp Leu Cys Gly Ser Val Phe Leu Val Ser
                275                 280                 285

Gln Leu Phe Thr Phe Ser Pro Arg Gln Tyr Glu Thr Val Gln Asp Cys
290                 295                 300

Asn Cys Ser Leu Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ser Gly Ala His
                340                 345                 350

Trp Gly Val Leu Ala Gly Leu Ala Tyr Tyr Ser Met Val Gly Asn Trp
                355                 360                 365

Ala Lys Val Leu Ile Val Met Leu Leu Phe Ala Gly Val Asp Gly Asp
370                 375                 380

Thr Tyr Thr Thr Gly Gly Val Ala Ser Arg Thr Thr Ala Gly Leu Ala
385                 390                 395                 400

Ser Leu Phe Val Ser Gly Pro Ser Gln Lys Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Leu Ala Ala Leu Phe Tyr Val Asn Arg Phe Asn
                435                 440                 445

Ser Ser Gly Cys Pro Glu Arg Met Ala Ser Cys Arg Pro Ile Asp Lys
450                 455                 460

Phe Ala Gln Gly Trp Gly Pro Ile Thr His Ala Val Pro Arg Ala Ser
465                 470                 475                 480

Asp Gln Arg Pro Tyr Cys Trp His Tyr Ala Pro Gln Pro Cys Gly Ile
                485                 490                 495

Val Pro Ala Ser Gln Val Cys Gly Pro Val Tyr Cys Phe Thr Pro Ser
                500                 505                 510

Pro Val Val Gly Thr Thr Asp Arg Ser Gly Ala Pro Thr Tyr Thr
                515                 520                 525

Trp Gly Glu Asn Glu Thr Asp Val Leu Ile Leu Asn Asn Thr Arg Pro
530                 535                 540

Pro His Gly Asn Trp Phe Gly Cys Ser Trp Met Asn Ser Thr Gly Phe
```

```
            545                 550                 555                 560
        Thr Lys Thr Cys Gly Gly Pro Pro Cys Asn Ile Gly Val Gly Asn
                        565                 570                 575

Asn Thr Leu Thr Cys Pro Thr Asp Cys Phe Arg Lys His Pro Glu Ala
                        580                 585                 590

Thr Tyr Thr Lys Cys Gly Ser Gly Pro Trp Leu Thr Pro Arg Cys Met
                        595                 600                 605

Val Asp Tyr Pro Tyr Arg Leu Trp His Tyr Pro Cys Thr Val Asn Tyr
        610                 615                 620

Thr Ile Phe Lys Val Arg Met Tyr Val Gly Val Glu His Arg Leu
        625                 630                 635                 640

Asn Ala Ala Cys Asn Trp Thr Arg Gly Glu Arg Cys Asp Leu Glu Asp
                        645                 650                 655

Arg Asp Arg Ser Glu Leu Ser Pro Leu Leu Ser Thr Glu Trp
                        660                 665                 670

Gln Ile Leu Pro Cys Ser Phe Thr Thr Leu Pro Ala Leu Ser Thr Gly
                        675                 680                 685

Leu Ile His Leu His Gln Asn Ile Val Asp Val Gln Tyr Leu Tyr Gly
                        690                 695                 700

Val Gly Ser Val Val Ser Ile Val Ile Arg Trp Glu Tyr Val Val
        705                 710                 715                 720

Leu Leu Phe Leu Leu Leu Ala Asp Ala Arg Val Cys Ala Cys Leu Trp
                        725                 730                 735

Met Met Leu Leu Ile Ala Gln Ala Glu Ala Ala Leu Glu Asn Leu Val
                        740                 745                 750

Ala Leu Asn Ala Ala Ser Val Ala Gly Ala His Gly Ile Leu Ser Phe
                        755                 760                 765

Leu Ala Phe Phe Cys Ala Ala Trp Tyr Ile Lys Gly Lys Leu Val Pro
                        770                 775                 780

Gly Ala Ala Tyr Ala Leu Tyr Ser Val Trp Pro Leu Leu Leu Leu
        785                 790                 795                 800

Leu Ala Leu Pro Pro Arg Ala Tyr Ala Met Asp Arg Glu Met Ala Ala
                        805                 810                 815

Ser Cys Gly Gly Ala Val Phe Val Gly Leu Val Leu Thr Leu Ser
                        820                 825                 830

Pro His Tyr Lys Ala Leu Leu Ala Arg Leu Ile Trp Trp Leu Gln Tyr
                        835                 840                 845

Leu Thr Thr Arg Ala Glu Ala Leu Leu Gln Val Trp Ile Pro Pro Leu
        850                 855                 860

Asn Val Arg Gly Gly Arg Asp Ala Ile Ile Leu Leu Thr Cys Met Val
        865                 870                 875                 880

His Pro Glu Leu Thr Phe Glu Ile Thr Lys Ile Leu Leu Ala Ile Leu
                        885                 890                 895

Gly Pro Leu Met Val Leu Arg Ala Gly Leu Thr Arg Val Pro Tyr Phe
                        900                 905                 910

Val Arg Ala His Gly Leu Ile Arg Ala Cys Met Leu Val Arg Lys Val
                        915                 920                 925

Ala Gly Gly His Tyr Val Gln Met Ala Leu Met Lys Leu Ala Ala Leu
                        930                 935                 940

Thr Gly Thr Tyr Val Tyr Asp His Leu Thr Pro Leu Arg Asp Trp Ala
        945                 950                 955                 960

His Ala Gly Leu Arg Asp Leu Ala Val Ala Val Glu Pro Val Val Phe
                        965                 970                 975
```

-continued

```
Ser Asp Thr Glu Thr Lys Ile Ile Thr Trp Gly Ala Asp Thr Ala Ala
            980                 985                 990

Cys Gly Asp Ile Ile Leu Gly Leu Pro Val Ser Ala Arg Arg Gly Arg
        995                1000                1005

Glu Ile Leu Leu Gly Pro Ala Asp Lys Phe Gly Glu Gln Gly Trp
        1010                1015                1020

Arg Leu Leu Ala Pro Ile Thr Ala Tyr Ser Gln Gln Thr Arg Gly
        1025                1030                1035

Val Leu Gly Cys Ile Ile Thr Ser Leu Thr Gly Arg Asp Lys Asn
        1040                1045                1050

Gln Val Glu Gly Glu Val Gln Val Val Ser Thr Ala Thr Gln Ser
        1055                1060                1065

Phe Leu Ala Thr Cys Val Asn Gly Val Cys Trp Thr Val Tyr His
        1070                1075                1080

Gly Ala Gly Ser Lys Thr Leu Ala Gly Pro Lys Gly Pro Ile Thr
        1085                1090                1095

Gln Met Tyr Thr Asn Val Asp Gln Asp Leu Val Gly Trp Gln Ala
        1100                1105                1110

Pro Pro Gly Ala Arg Ser Met Thr Pro Cys Thr Cys Gly Ser Ser
        1115                1120                1125

Asp Leu Phe Leu Val Thr Arg His Ala Asp Val Ile Pro Val Arg
        1130                1135                1140

Arg Arg Gly Asp Ser Arg Gly Ala Leu Leu Ser Pro Arg Pro Val
        1145                1150                1155

Ser Tyr Leu Lys Gly Ser Ser Gly Gly Pro Leu Leu Cys Pro Ser
        1160                1165                1170

Gly His Val Val Gly Ile Phe Arg Ala Ala Val Cys Thr Arg Gly
        1175                1180                1185

Val Ala Lys Ala Val Asp Phe Ile Pro Val Glu Ser Met Gly Thr
        1190                1195                1200

Thr Met Arg Ser Pro Val Phe Thr Asp Asn Ser Ser Pro Pro Ala
        1205                1210                1215

Val Pro Gln Thr Phe Gln Val Ala His Leu His Ala Pro Thr Gly
        1220                1225                1230

Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Ser
        1250                1255                1260

Phe Gly Ala Tyr Met Ser Lys Ala Tyr Gly Val Asp Pro Asn Ile
        1265                1270                1275

Arg Thr Gly Val Arg Thr Ile Thr Thr Gly Ala Pro Ile Thr Tyr
        1280                1285                1290

Ser Thr Tyr Gly Lys Phe Leu Ala Asp Gly Gly Cys Ser Gly Gly
        1295                1300                1305

Ala Tyr Asp Ile Ile Ile Cys Asp Glu Cys His Ser Thr Asp Ser
        1310                1315                1320

Thr Thr Ile Leu Gly Ile Gly Thr Val Leu Asp Gln Ala Glu Thr
        1325                1330                1335

Ala Gly Ala Arg Leu Val Val Leu Ala Thr Ala Thr Pro Pro Gly
        1340                1345                1350

Ser Val Thr Val Pro His Pro Asn Ile Glu Glu Val Ala Leu Ser
        1355                1360                1365
```

-continued

```
Asn Thr Gly Glu Ile Pro Phe Tyr Gly Lys Ala Ile Pro Leu Glu
    1370                1375                1380

Thr Ile Lys Gly Gly Arg His Leu Ile Phe Cys His Ser Lys Lys
    1385                1390                1395

Lys Cys Asp Glu Leu Ala Ala Lys Leu Ser Ala Leu Gly Leu Asn
    1400                1405                1410

Ala Val Ala Tyr Tyr Arg Gly Leu Asp Val Ser Ile Ile Pro Thr
    1415                1420                1425

Ser Gly Asp Val Val Val Ala Thr Asp Ala Leu Met Thr Gly
    1430                1435                1440

Tyr Thr Gly Asp Phe Asp Ser Val Ile Asp Cys Asn Thr Cys Val
    1445                1450                1455

Thr Gln Thr Val Asp Phe Ser Phe Asp Pro Thr Phe Ala Ile Glu
    1460                1465                1470

Thr Thr Thr Met Pro Gln Asp Ala Val Ser Arg Ser Gln Arg Arg
    1475                1480                1485

Gly Arg Thr Gly Arg Gly Arg Gly Gly Ile Tyr Arg Phe Val Thr
    1490                1495                1500

Pro Gly Glu Arg Pro Ser Gly Met Phe Asp Ser Ala Ile Leu Cys
    1505                1510                1515

Glu Cys Tyr Asp Ala Gly Cys Ala Trp Tyr Glu Leu Thr Pro Ala
    1520                1525                1530

Glu Thr Thr Val Arg Leu Arg Ala Tyr Leu Asn Thr Pro Gly Leu
    1535                1540                1545

Pro Val Cys Gln Asp His Leu Glu Phe Trp Glu Gly Val Phe Thr
    1550                1555                1560

Gly Leu Thr His Ile Asp Ala His Phe Leu Ser Gln Thr Lys Gln
    1565                1570                1575

Ala Gly Asp Asn Phe Pro Tyr Leu Val Ala Tyr Gln Ala Thr Val
    1580                1585                1590

Cys Ala Arg Ala Gln Ala Pro Pro Ser Trp Asp Gln Met Trp
    1595                1600                1605

Lys Cys Leu Ile Arg Leu Lys Pro Thr Leu His Gly Pro Thr Pro
    1610                1615                1620

Leu Leu Tyr Arg Leu Gly Ala Val Gln Asn Glu Val Thr Leu Thr
    1625                1630                1635

His Pro Ile Thr Lys Tyr Ile Met Thr Cys Met Ser Ala Asp Leu
    1640                1645                1650

Glu Val Val Thr Ser Thr Trp Val Leu Val Gly Gly Val Leu Ala
    1655                1660                1665

Ala Leu Ala Ala Tyr Cys Leu Thr Thr Gly Ser Val Val Ile Val
    1670                1675                1680

Gly Arg Val Ile Leu Ser Gly Arg Pro Ala Ile Ile Pro Asp Arg
    1685                1690                1695

Glu Val Leu Tyr Arg Glu Phe Asp Glu Met Glu Glu Cys Ala Ser
    1700                1705                1710

His Leu Pro Tyr Ile Glu Gln Gly Met Gln Leu Ala Glu Gln Phe
    1715                1720                1725

Lys Gln Lys Ala Leu Gly Leu Leu Gln Thr Ala Thr Lys Gln Ala
    1730                1735                1740

Glu Ala Ala Ala Pro Val Val Glu Ser Lys Trp Arg Ala Leu Glu
    1745                1750                1755

Ala Phe Trp Ala Lys His Met Trp Asn Phe Ile Ser Gly Ile Gln
```

-continued

```
            1760                1765                1770
Tyr Leu Ala Gly Leu Ser Thr Leu Pro Gly Asn Pro Ala Ile Ala
    1775                1780                1785
Ser Leu Met Ala Phe Thr Ala Ser Ile Thr Ser Pro Leu Thr Thr
    1790                1795                1800
Gln His Thr Leu Leu Phe Asn Ile Leu Gly Gly Trp Val Ala Ala
    1805                1810                1815
Gln Leu Ala Pro Pro Gly Ala Ala Ser Ala Phe Val Gly Ala Gly
    1820                1825                1830
Ile Ala Gly Ala Ala Val Gly Ser Ile Gly Leu Gly Lys Val Leu
    1835                1840                1845
Val Asp Ile Leu Ala Gly Tyr Gly Ala Gly Val Ala Gly Ala Leu
    1850                1855                1860
Val Ala Phe Lys Val Met Ser Gly Glu Met Pro Ser Thr Glu Asp
    1865                1870                1875
Leu Val Asn Leu Leu Pro Ala Ile Leu Ser Pro Gly Ala Leu Val
    1880                1885                1890
Val Gly Val Val Cys Ala Ala Ile Leu Arg Arg His Val Gly Pro
    1895                1900                1905
Gly Glu Gly Ala Val Gln Trp Met Asn Arg Leu Ile Ala Phe Ala
    1910                1915                1920
Ser Arg Gly Asn His Val Ser Pro Thr His Tyr Val Pro Glu Ser
    1925                1930                1935
Asp Ala Ala Arg Val Thr Gln Ile Leu Ser Ser Leu Thr Ile
    1940                1945                1950
Thr Gln Leu Leu Lys Arg Leu His Gln Trp Ile Asn Glu Asp Cys
    1955                1960                1965
Ser Thr Pro Cys Ser Gly Ser Trp Leu Arg Asp Val Trp Asp Trp
    1970                1975                1980
Ile Cys Thr Val Leu Thr Asp Phe Lys Thr Trp Leu Gln Ser Lys
    1985                1990                1995
Leu Leu Pro Arg Leu Pro Gly Val Pro Phe Leu Ser Cys Gln Arg
    2000                2005                2010
Gly Tyr Lys Gly Val Trp Arg Gly Asp Gly Ile Met His Thr Thr
    2015                2020                2025
Cys Pro Cys Gly Ala Gln Ile Ser Gly His Val Lys Asn Gly Ser
    2030                2035                2040
Met Arg Ile Val Gly Pro Lys Thr Cys Ser Asn Thr Trp Cys Gly
    2045                2050                2055
Thr Phe Pro Ile Asn Ala Tyr Thr Thr Gly Pro Cys Thr Pro Ser
    2060                2065                2070
Pro Ala Pro Asn Tyr Ser Arg Ala Leu Trp Arg Val Ala Ala Glu
    2075                2080                2085
Glu Tyr Val Glu Val Thr Arg Val Gly Asp Phe His Tyr Val Thr
    2090                2095                2100
Gly Met Thr Thr Asp Asn Leu Lys Cys Pro Cys Gln Val Pro Ala
    2105                2110                2115
Pro Glu Phe Phe Thr Glu Val Asp Gly Val Arg Leu His Arg Tyr
    2120                2125                2130
Ala Pro Ala Cys Lys Pro Leu Leu Arg Asp Glu Val Thr Phe Gln
    2135                2140                2145
Val Gly Leu Asn Gln Phe Pro Val Gly Ser Gln Leu Pro Cys Glu
    2150                2155                2160
```

```
Pro Glu Pro Asp Val Thr Val Leu Thr Ser Met Leu Thr Asp Pro
    2165            2170                2175
Ser His Ile Thr Ala Glu Thr Ala Lys Arg Arg Leu Ala Arg Gly
    2180            2185                2190
Ser Pro Pro Ser Leu Ala Ser Ser Ser Ala Gly Gln Leu Ser Ala
    2195            2200                2205
Val Ser Leu Lys Ala Ala Cys Thr Thr Arg His Asn Pro Pro Asp
    2210            2215                2220
Ala Asp Leu Ile Glu Ala Asn Leu Leu Trp Arg Gln Glu Met Gly
    2225            2230                2235
Gly Ser Ile Thr Arg Val Glu Ser Glu Ser Lys Val Val Ile Leu
    2240            2245                2250
Asp Ser Phe Glu Pro Leu Arg Ala Glu Glu Asp Glu Arg Glu Val
    2255            2260                2265
Ser Val Pro Ala Glu Ile Leu Arg Lys Thr Lys Lys Phe Pro Ala
    2270            2275                2280
Ala Met Pro Val Trp Ala Arg Pro Asp Tyr Asn Pro Pro Leu Leu
    2285            2290                2295
Glu Ser Trp Arg Asp Pro Asp Tyr Val Pro Pro Val Val His Gly
    2300            2305                2310
Cys Pro Leu Pro Pro Thr Lys Ala Pro Pro Ile Pro Pro Pro Arg
    2315            2320                2325
Arg Lys Arg Thr Val Ile Leu Thr Glu Ser Thr Val Ser Ser Ala
    2330            2335                2340
Leu Ala Glu Leu Ala Thr Lys Thr Phe Gly Ser Ser Gly Ser Ser
    2345            2350                2355
Ala Val Asp Asn Gly Thr Ala Thr Ala Pro Pro Asp Gln Pro Ser
    2360            2365                2370
Ile Asp Gly Asp Ala Gly Ser Asp Val Glu Ser Tyr Ser Ser Met
    2375            2380                2385
Pro Pro Leu Glu Gly Glu Pro Gly Asp Pro Asp Leu Ser Asp Gly
    2390            2395                2400
Ser Trp Ser Thr Val Ser Glu Glu Ala Gly Glu Asp Val Val Cys
    2405            2410                2415
Cys Ser Met Ser Tyr Thr Trp Thr Gly Ala Leu Ile Thr Pro Cys
    2420            2425                2430
Ala Ala Glu Glu Ser Lys Leu Pro Ile Asn Ala Leu Ser Asn Ser
    2435            2440                2445
Leu Leu Arg His His Asn Met Val Tyr Ala Thr Thr Ser Arg Ser
    2450            2455                2460
Ala Ser Gln Arg Gln Lys Lys Val Thr Phe Asp Arg Leu Gln Val
    2465            2470                2475
Leu Asp Asp His Tyr Arg Asp Val Leu Lys Glu Met Lys Ala Lys
    2480            2485                2490
Ala Ser Thr Val Lys Ala Lys Leu Leu Ser Val Glu Glu Ala Cys
    2495            2500                2505
Arg Leu Thr Pro Pro His Ser Ala Arg Ser Lys Phe Gly Tyr Gly
    2510            2515                2520
Ala Lys Asp Val Arg Asn Leu Ser Ser Lys Ala Val Asn His Ile
    2525            2530                2535
His Ser Val Trp Lys Asp Leu Leu Glu Asp Thr Glu Thr Pro Ile
    2540            2545                2550
```

-continued

```
Asp Thr Thr Ile Met Ala Lys Asn Glu Val Phe Cys Val Gln Pro
2555                2560                2565

Glu Lys Gly Gly Arg Lys Pro Ala Arg Leu Ile Val Phe Pro Asp
2570                2575                2580

Leu Gly Val Arg Val Cys Glu Lys Met Ala Leu Tyr Asp Val Val
2585                2590                2595

Ser Thr Leu Pro Gln Ala Val Met Gly Ser Ser Tyr Gly Phe Gln
2600                2605                2610

Tyr Ser Pro Gly Gln Arg Val Glu Phe Leu Val Asn Ala Trp Lys
2615                2620                2625

Ser Lys Lys Asn Pro Met Gly Phe Ala Tyr Asp Thr Arg Cys Phe
2630                2635                2640

Asp Ser Thr Val Thr Glu Ser Asp Ile Arg Val Glu Glu Ser Ile
2645                2650                2655

Tyr Gln Cys Cys Asp Leu Ala Pro Glu Ala Arg Gln Val Ile Arg
2660                2665                2670

Ser Leu Thr Glu Arg Leu Tyr Ile Gly Gly Pro Leu Thr Asn Ser
2675                2680                2685

Lys Gly Gln Asn Cys Gly Tyr Arg Arg Cys Arg Ala Ser Gly Val
2690                2695                2700

Leu Thr Thr Ser Cys Gly Asn Thr Leu Thr Cys Tyr Leu Lys Ala
2705                2710                2715

Ser Ala Ala Cys Arg Ala Ala Lys Leu Gln Asp Cys Thr Met Leu
2720                2725                2730

Val Cys Gly Asp Asp Leu Val Val Ile Cys Glu Ser Ala Gly Thr
2735                2740                2745

Gln Glu Asp Ala Ala Ser Leu Arg Val Phe Thr Glu Ala Met Thr
2750                2755                2760

Arg Tyr Ser Ala Pro Pro Gly Asp Pro Pro Gln Pro Glu Tyr Asp
2765                2770                2775

Leu Glu Leu Ile Thr Ser Cys Ser Ser Asn Val Ser Val Ala His
2780                2785                2790

Asp Ala Ser Gly Lys Arg Val Tyr Tyr Leu Thr Arg Asp Pro Thr
2795                2800                2805

Thr Pro Leu Ala Arg Ala Ala Trp Glu Thr Ala Arg His Thr Pro
2810                2815                2820

Val Asn Ser Trp Leu Gly Asn Ile Ile Met Tyr Ala Pro Thr Leu
2825                2830                2835

Trp Ala Arg Met Ile Leu Met Thr His Phe Phe Ser Ile Leu Leu
2840                2845                2850

Ala Gln Glu Gln Leu Glu Lys Ala Leu Asp Cys Gln Ile Tyr Gly
2855                2860                2865

Ala Thr Tyr Ser Ile Glu Pro Leu Asp Leu Pro Gln Ile Ile Gln
2870                2875                2880

Arg Leu His Gly Leu Ser Ala Phe Ser Leu His Ser Tyr Ser Pro
2885                2890                2895

Gly Glu Ile Asn Arg Val Ala Ser Cys Leu Arg Lys Leu Gly Val
2900                2905                2910

Pro Pro Leu Arg Val Trp Arg His Arg Ala Arg Ser Val Arg Ala
2915                2920                2925

Lys Leu Leu Ser Gln Gly Gly Arg Ala Ala Ile Cys Gly Lys Tyr
2930                2935                2940

Leu Phe Asn Trp Ala Val Arg Thr Lys Leu Lys Leu Thr Pro Ile
```

-continued

```
                      2945                2950                2955

Pro Ala  Ala Ser Gln Leu Asp  Leu Ser Ser Trp Phe  Ile Ala Gly
         2960                2965               2970

Tyr Ser  Gly Gly Asp Ile Tyr  His Ser Leu Ser Arg  Ala Arg Pro
    2975                2980               2985

Arg Trp  Phe Met Trp Cys Leu  Leu Leu Leu Ser Val  Gly Val Gly
    2990                2995               3000

Ile Tyr  Leu Leu Pro Asn Arg
    3005                3010

<210> SEQ ID NO 27
<211> LENGTH: 18
<212> TYPE: DNA
<213> ORGANISM: Artificial
<220> FEATURE:
<223> OTHER INFORMATION: primer

<400> SEQUENCE: 27
taatacgact cactatag                                                  18

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
gcggctcacg gacctttcac                                                20

<210> SEQ ID NO 29
<211> LENGTH: 24
<212> TYPE: DNA
<213> ORGANISM: Artificial
<220> FEATURE:
<223> OTHER INFORMATION: primer

<400> SEQUENCE: 29
tacgcgggtg ggggatttcc acta                                           24

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
gctggccaaa tagggggggg accctcgggc                                     30

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
tcccccccct atttggccag ctcttcagct                                     30

<210> SEQ ID NO 32
<211> LENGTH: 20
<212> TYPE: DNA
<213> ORGANISM: Artificial
```

<220> FEATURE:
<223> OTHER INFORMATION: primer

<400> SEQUENCE: 32
acgataagac gagctggctt                                                    20

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
gacaactgac cagctgaaga gctggccaaa                                         30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
ctcttcagct ggtcagttgt ctgcggtctc                                         30

<210> SEQ ID NO 35
<211> LENGTH: 28
<212> TYPE: DNA
<213> ORGANISM: Artificial
<220> FEATURE:
<223> OTHER INFORMATION: primer

<400> SEQUENCE: 35
gggttcacat cgaagctgtg acccgacc                                           28

<210> SEQ ID NO 36
<211> LENGTH: 30
<212> TYPE: DNA
<213> ORGANISM: Artificial
<220> FEATURE:
<223> OTHER INFORMATION: primer

<400> SEQUENCE: 36
tcacagcttc gatgtgaacc cgagccggat                                         30

<210> SEQ ID NO 37
<211> LENGTH: 30
<212> TYPE: DNA
<213> ORGANISM: Artificial
<220> FEATURE:
<223> OTHER INFORMATION: primer

<400> SEQUENCE: 37
gggggaccct agggccagcc tgcgcttagc                                         30

<210> SEQ ID NO 38
<211> LENGTH: 29
<212> TYPE: DNA
<213> ORGANISM: Artificial
<220> FEATURE:
<223> OTHER INFORMATION: primer

<400> SEQUENCE: 38
aggctggccc tagggtcccc ccctctttt                                          29

```
<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
gggggaccct tgggccagcc tgcgcttagc                                    30

<210> SEQ ID NO 40
<211> LENGTH: 29
<212> TYPE: DNA
<213> ORGANISM: Artificial
<220> FEATURE:
<223> OTHER INFORMATION: primer

<400> SEQUENCE: 40
aggctggccc aagggtcccc ccctctttt                                     29

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
gtcggtcgcg cacgatgcat                                               20

<210> SEQ ID NO 42
<211> LENGTH: 29
<212> TYPE: DNA
<213> ORGANISM: Artificial
<220> FEATURE:
<223> OTHER INFORMATION: primer

<400> SEQUENCE: 42
ttcaatggag caagtggccc cgtagatct                                     29

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
ggggccactt gctccattga accacttgac                                    30

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
tgtgttggac cgtctaccat                                               20

<210> SEQ ID NO 45
<211> LENGTH: 30
<212> TYPE: DNA
<213> ORGANISM: Artificial
<220> FEATURE:
<223> OTHER INFORMATION: primer
```

<400> SEQUENCE: 45
gcatggtggt tcccatggac tcaacgggta          30

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
gtccatggga accaccatgc ggtctccggt          30

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
cggtagtacg ctacagcatt          20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
gccgacctgg aggtcgtcac          20

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
gaaccgttcc tgacatgtcc actgatctgt          30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
ggacatgtca ggaacggttc catgaggatc          30

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
gacctggaat gtgacctcat          20

```
<210> SEQ ID NO 52
<211> LENGTH: 7993
<212> TYPE: DNA
<213> ORGANISM: Artificial
<220> FEATURE:
<223> OTHER INFORMATION: synthetic

<400> SEQUENCE: 52
gccagccccc tgatggggc gacactccac catagatcac tccctgtga ggaactactg      60 tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gattaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcat catgagcaca aatcctaaac     360
ctcaaagaaa aaccacacgt aacaccaacc gccgcccaat gattgaacaa gatggattgc     420
acgcaggttc tccggccgtt tgggtggaga ggctattcgg ctatgactgg gcacaacaga     480
caaccggctg ctctgatgcc gccgtgttcc ggctgtcagc gcggggcga ccggttcttt      540 ttgtcaagac cgacctgtcc ggtgccctga atgaactgca ggacgaggca gcgcggctat     600
cgtggctggc cacgacgggc gttccttgcg cagctgtgct cgacgttgtc actgaagcgg     660
gaagggactg gctgctattg ggcgaagtgc cggggcagga tctcctgtca tctcaccttg     720
ctcctgccga gaaagtgtcc atcatggctg atgcaatacg cggctgcat acgcttgatc      780 cggctacctg cccattcgac caccaagcga aacatcgcat cgagcgagca cgtactcgga     840
tggaagccgg tcttgtcgat caggatgatc tggacgaaga gcatcagggg ctcgcgccag     900
ccgaactgtt cgccaggctc aaggcgcgca tgcccgacgg cgaggatctc gtcgtgaccc     960
atggcgatgc ctgcttgccg aatgtcatgg tggaaaatgg ccgcttttct ggattcatcg    1020
actgtggccg gctgggtgtg gcggaccgct atcaggacat agcgttggct acccgtgata    1080
ttgctgaaga gcttggcggc gaatgggctg accgcttcct cgtgctttac ggtatcgccg    1140
ctcccgattc gaagcgcatc gccttctatc gccttcttga cgagttcttc tgagtttaaa    1200
cagcccacaa cggtttccct ctagcgggat caattccgcc cccccccta acgttactgg    1260 ccgaagccgc ttggaataag gccggtgtgc gtttgtctat atgttatttt ccaccatatt    1320
gccgtctttt ggcaatgtga gggcccggaa acctggccct gtcttcttga cgagcattcc    1380 tagggggtctt tcccctctcg ccaaaggaat gcaaggtctg ttggatgtcg tgaaggaagc    1440
agttcctctg gaagcttctt gaagacaaac aacgtctgta gcgacccttt gcaggcagcg    1500 gaaccccca cctggcgaca ggtgcctctg cggccaaaag ccacgtgtat aagatacacc    1560
tgcaaaggcg gtacaacccc agtgccacgt tgtgagttgg atagttgtgg aaagagtcaa    1620
atggctctcc tcaagcgtat tcaacaaggg gctgaaggat gcccagaagg tacccattg     1680 tatgggatct gatctgggc ctcggtgcac atgctctaca tgtgtttagt cgaggttaaa    1740
aaaacgtcta ggccccccga accacgggga cgtggttttc ctttgaaaaa cacgataata    1800
ccatggcacc cattacggcc tactcccaac agacgcgggg cgtacttggc tgtatcatca    1860
ctagcctcac aggtcgggac aagaaccagg tcgaggggga ggttcaggtg gtttccaccg    1920
caacgcagtc cttcttggca acctgcgtca atgcgtgtgt ttggaccgtc taccatggcg    1980
ccggctcaaa gaccctagcc ggcccgaagg gaccgatcac ccaaatgtac accaatgttg    2040
accaggacct cgtcggctgg caggcgcccc ccggggcgcg ctccatgaca ccgtgcacct    2100
```

```
gcggcagctc ggaccttttt ttggtcacga ggcatgctga tgtcattccg gtgcgccggc    2160 gggggtgacag cagaggagcc ctactttccc ccaggcccgt ctcttacctg aagggctcct    2220
cgggtggtcc actgctttgc ccctcggggc acgttgtggg catcttccgg gctgccgtgt    2280
gcacccgggg ggtcgcgaag gcggtggatt ttatacccgt tgagtccatg gaaaccacca    2340
tgcggtctcc ggtcttcacg gataattcat ctcccccggc cgtaccgcag acattccaag    2400
tggcccatct gcacgctccc actggcagcg gcaagagcac taaagtgccg gctgcatacg    2460
cagcccaggg gtacaaggtg ctcgtcctga acccgtccgt tgccgccacc ttgagttttg    2520
gggcgtatat gtccaaggca tatggagttg accctaacat cagaaccggg gtgaggacca    2580
tcactactgg cgctcccatc acgtactcca cctacggcaa gttccttgcc gacggcggtt    2640
gctctggggg cgcctatgac atcataatat gtgatgagtg ccactcaact gactcaacta    2700
ctattttggg cattggcaca gtcctggacc aagcggagac agctggagcg cggctcgtcg    2760
tgctcgccac cgctacgccg ccaggatcag tcaccgtacc acaccccaac atcgaggagg    2820
tggccttgtc caatactgga gagattccct tctatggcaa agccatcccc ctcgagacca    2880
tcaagggggg gaggcacctc attttctgcc actccaagaa gaagtgtgat gagcttgctg    2940
caaagctgtc ggcccttggg ctcaatgctg tagcgtacta ccggggtctt gacgtgtcca    3000
tcataccaac aagcggagac gtcgttgttg tggcaacaga cgctctaatg acgggctaca    3060
ccggtgattt tgactcagtg atcgactgca atacatgtgt cacccagaca gtcgacttca    3120
gcttcgaccc caccttcgcc attgagacga cgaccatgcc ccaagacgcg gtgtcgcgct    3180
cacagcggcg aggcaggact ggcaggggca gaggaggcat atacaggttt gtgactccag    3240
gagaacggcc ctcaggcatg ttcgattctg cgatcctgtg tgaatgctat gacgcgggct    3300
gtgcttggta cgagctcacg cccgccgaga ccacagttag gttgcgggct tacctaaata    3360
caccagggtt gcccgtctgc caggaccatc tggagttttg ggagggcgtc ttcacaggcc    3420
tcacccacat agatgcccac ttcttgtccc agaccaagca ggcaggagac aacttcccct    3480
acctggtggc ataccaagct acagtgtgcg ccagggccca ggctccacct ccatcgtggg    3540
atcaaatgtg gaagtgtctc atacggctga agcctacgct gcacgggcca acacccttgt    3600
tgtataggct aggagccgtc caaaacgagg tcaccctcac acatcccata accaaataca    3660
tcatgacatg catgtcggcc gacctggagg tcgtcactag cacctgggtg ctagtaggcg    3720
gggtccttgc agccctggcc gcgtactgcc tgacaacggg cagcgtggtc atcgtgggca    3780
gggtcatctt gtccggaagg ccggccatca ttcccgacag ggaagttctc taccgggagt    3840
tcgatgaaat ggaagagtgc gcctcgcatc tccccctacat cgaacaaggc atgcaactcg    3900
ccgagcaatt caagcagaag gcgctcgggc tgctgcaaac agccaccaag caagcggagg    3960
ccgctgctcc cgtggtggag tccaagtggc gagcccttga ggccttctgg gcgaagcaca    4020
tgtggaattt catcagcggg atacagtatc tagcaggctt gtcaactctg cctgggaacc    4080
ccgcgatagc atcattgatg gcattcacag cctccatcac cagcccgctc accacccaac    4140
atacccttct gtttaacatc ttgggggggt gggtggccgc ccaacttgcc cccccggcg    4200 ctgcttcagt tttcgtgggc gccggcattg ctggcgcggc tgttggcagc ataggtcttg    4260
ggaaggtgct cgtggacatc ctggcgggtt atggggcagg ggtggcaggc gcactcgtgg    4320
cctttaaggt catgagcggc gaaatgcccc ccaccgagga cctggtcaac ttactccctg    4380
ccatcctctc tcctggtgcc ctggtcgtcg ggtcgtgtg cgcagcaata ctgcgtcggc    4440
atgtgggccc agggggaggg gctgtgcagt ggatgaaccg gctgatagcg ttcgcttcgc    4500
```

| | |
|---|---|
| ggggtaacca cgtctccccc acgcactatg tgcctgagag cgacgcagca gcgcgtgtca | 4560 |
| cccagatcct ctccagcctt accattactc agctgctaaa gaggctccac cagtggatta | 4620 |
| atgaagattg ctccacgcca tgctccggct cgtggctcag ggatgtttgg gactggatat | 4680 |
| gcacggtgtt gaccgatttc aaaacctggc tccaatccaa gctcctgccg cggttgccgg | 4740 |
| gagtcccttt cctttcatgt cagcgcgggt acaagggggt ttggcgggga gacggcatta | 4800 |
| tgcacactac ctgcccgtgc ggagcacaga tcagtggaca tgtcaagaac ggttccatga | 4860 |
| ggatcgttgg gcctaagacc tgtagcaaca cgtggtgcgg gacgttcccc atcaacgcgt | 4920 |
| acaccacagg cccctgcaca ccctccccgg cgccaaacta ctccagggcg ttgtggcggg | 4980 |
| tggctgctga ggagtatgtg gaggttacgc gggtggggga tttccactac gtgacgggca | 5040 |
| tgaccactga caacttaaaa tgcccatgcc aggtcccggc ccctgaattc tttacggaag | 5100 |
| tggatggggt gcggctgcac aggtacgctc ctgcgtgcaa acctctccta cgggatgagg | 5160 |
| tcacattcca ggtcgggctc aaccaattcc cggtcgggtc acagcttcga tgtgaacccg | 5220 |
| agccggatgt gacagtgctc acttccatgc tcaccgaccc ctcccacatt acggcagaga | 5280 |
| cggctaagcg caggctggcc cgagggtccc cccctctttt ggccagctct tcagctagtc | 5340 |
| agttgtctgc ggtctccttg aaggcggcat gcaccacccg tcataacccc ccagacgccg | 5400 |
| acctcatcga ggccaatctc ctgtggcggc aggagatggg cgggagcatc acccgcgtgg | 5460 |
| agtcagagag taaggtggta atcctagact catttgaacc gcttcgagcg gaggaggatg | 5520 |
| agagggaagt atccgtgccg gcggagattc tgcggaaaac caagaaattc cccgcggcaa | 5580 |
| tgcctgtatg ggcacgcccg gactacaacc caccactctt agagtcttgg agggacccag | 5640 |
| actacgttcc tccggtggta cacgggtgcc cattgccacc taccaaggcc cctccaatac | 5700 |
| cccctccacg gagaaagagg acggttattc tgacagaatc caccgtgtcc tctgccctgg | 5760 |
| cggaacttgc cacaaagacc ttcggcagct ccggatcgtc ggccgttgac aacggcacgg | 5820 |
| cgaccgcccc tcctgaccag ccctccattg acgagacgc aggatcagac gttgagtcgt | 5880 |
| actcctccat gccccccctt gagggagagc cggggggaccc cgatctcagc gacgggtctt | 5940 |
| ggtctactgt gagcgaggag gctggcgagg acgttgtctg ctgctcgatg tcctatacat | 6000 |
| ggacaggcgc cttaatcaca ccatgcgccg cagaggagag caagctgccc atcaacgcgt | 6060 |
| tgagcaattc tttgctgcgt caccacaaca tggtctatgc cacaacatcc cgcagcgcaa | 6120 |
| gccaacggca gaagaaggtc acctttgaca gactgcaagt cctggacgac cattaccggg | 6180 |
| acgtgctcaa ggagatgaag gcgaaggcgt ccacagttaa ggctaaactt ctatctgtag | 6240 |
| aagaagcctg taggctgacg cccccacatt cggccagatc caaatttggc tatgggcaa | 6300 |
| aggacgtccg gaacctatcc agcaaggccg tcaaccacat ccactccgtg tggaaggact | 6360 |
| tgctggaaga cactgagaca ccaattgaca ccaccatcat ggcaaaaaat gaggtctttt | 6420 |
| gtgttcaacc agagaaggga ggccgcaagc cagctcgtct tatcgtattc ccagacttgg | 6480 |
| gagttcgtgt atgcgagaag atggcccctct acgatgtggt ttccaccctc cctcaggccg | 6540 |
| tgatgggctc ctcatacgga ttccaatact ctcctggaca gcgggtcgag ttcctggtga | 6600 |
| atgcctggaa gtcaaagaag aaccctatgg gcttcgcgta tgacacccgc tgctttgact | 6660 |
| caacagtcac tgagagtgac atccgtgttg aggagtcaat ttaccaatgt gtgacttgg | 6720 |
| ctcccgaggc cagacaggtc ataaggtcgc tcacggagcg gctttatatc ggggccccc | 6780 |
| tgactaattc aaaagggcag aactgcggtt accgccggtg ccgcgccagc ggcgtgctga | 6840 |
| cgactagctg cggcaacacc ctcacatgtt acttgaaggc ttctgcagcc tgtcgagctg | 6900 |

```
caaagctcca ggactgcacg atgctcgtgt gcggagacga ccttgtcgtt atctgtgaga    6960
gcgcgggaac ccaggaggac gcggcgagcc tacgagtctt cacggaggct atgactaggt    7020
actctgcccc ccccggggac ccgccccaac cggaatacga cttggagttg ataacatcat    7080
gctcctccaa cgtgtcggtc gcgcacgatg catccggcaa gcgggtgtac tacctgaccc    7140 gcgacccac cacccccctc gcacgggctg cgtgggagac agcaagacac actccagtta    7200
actcctggtt aggcaacatc atcatgtatg cgcccacctt atgggcaagg atgattctga    7260
tgacccactt cttttccatc cttctagctc aggagcaact tgaaaaagcc ctagattgcc    7320
agatctacgg ggccacttac tccattgaac cacttgacct acctcagatc attcagcgac    7380
tccacggtct tagcgcattt tcactccata gttactctcc aggtgagatc aatagggtgg    7440
cttcatgcct cagaaaactt ggggtaccgc ccttgcgagt ctggagacat cgggccagaa    7500
gtgtccgcgc taagttactg tcccagggag ggagggctgc catttgtggc aagtacctct    7560
ttaactgggc tgtaaggacc aagctcaaac tcactccaat tccggctgcg tcccagttgg    7620
acttgtccag ctggttcatt gctggttaca gcggggggaga catatatcac agcctgtctc    7680
gtgcccgacc ccgctggttc atgtggtgcc tactcctact ttctgtaggg gtaggcatct    7740
acctgctccc caatcgatga acggggggct agtcactcca ggccaatagg ccattctgtt    7800
tttttttttt tttttttttt tttttttttt tttttttttt tttttttttt tttttttttt    7860
tttttccttt ttcttcttcc ttttcttctt tctttggtgg ctccatctta gccctagtca    7920
cggctagctg tgaaaggtcc gtgagccgca tgactgcaga gagtgctgat actggcctct    7980
ctgcagatca tgt                                                       7993
```

NUCLEIC ACID CONSTRUCT COMPRISING NUCLEIC ACID DERIVED FROM GENOME OF HEPATITIS C VIRUS OF GENOTYPE 1B, HEPATITIS C VIRUS GENOME-REPLICATING CELLS TRANSFECTED WITH THE SAME, AND METHOD FOR PRODUCING INFECTIOUS HEPATITIS C VIRUS PARTICLES

TECHNICAL FIELD

The present invention relates to a nucleic acid construct containing a hepatitis C virus genome of genotype 1b, hepatitis C virus genome-replicating cells transfected with the nucleic acid construct, and a method of producing infectious hepatitis C virus particles.

BACKGROUND ART

In basic research for hepatitis C virus (hereinafter, also referred to as HCV) and development of anti-HCV drugs, an experimental system that can efficiently amplify HCV is essential. Specifically, a system for amplifying HCV in cultured cells and a system for evaluating the propagation of HCV in cultured cells are necessary, and it is thought that construction of these systems can dramatically advance the above-mentioned research.

HCV is a virus belonging to the flavivirus family of which genome is a single-stranded (+) sense RNA and is known to cause hepatitis C. Recently, it has been revealed that the HCV is classified into many types depending on genotypes or serotypes. According to phylogenetic analysis by Simmonds et al. using nucleotide sequences of HCV strains, it has been found that HCV genotypes are classified into six types, and each type is further classified into several subtypes (Non Patent Literature 1). At present, the full-length genome nucleotide sequences of a plurality of HCV genotypes have also been determined (Non Patent Literatures 2 to 5).

Until recently, infection of cultured cells with HCV and replication of the HCV genome in cultured cells have been impossible. Accordingly, studies on mechanisms of HCV replication and infection have required in vivo experiments using chimpanzees as an experimental animal. However, subgenomic replicon RNAs have been produced from a Con1 strain (GenBank Accession No. AJ238799), an HCV-N strain (GenBank Accession No. AF139594), and an HCV-O strain (GenBank Accession No. AB191333) belonging to the HCV of genotype 1b, and the H77c strain (GenBank Accession No. AF011751), which is the HCV of genotype 1a, and, thereby, studies on HCV replication mechanism can be performed by in vitro experiments using cultured cells (Patent Literature 1 and Non Patent Literatures 6 to 9). Herein, HCV subgenomic replicon RNA means an RNA comprising a part of an HCV genome, which does not have an ability to produce infectious HCV particles, but can autonomously replicate the RNA derived from the HCV genome in cultured cells transfected with it.

In addition, subgenomic replicon RNAs, and fullgenomic replicon RNAs producing infectious HCV particles in in vitro have been produced from a JFH-1 strain, which is an HCV strain of genotype 2a. and, thereby, studies on HCV infection mechanism can also be performed by in vitro experiments using cultured cells (Non Patent Literatures 10 and 11). Herein, the fullgenomic replicon RNA of HCV means an RNA comprising a full-length HCV genome, i.e., an RNA comprising a 5' UTR, structural genes, non-structural genes, and a 3'UTR. and can autonomously replicate the RNA derived from the HCV genome in cultured cells transfected with it.

Pietschmann et al. have investigated production of infectious HCV particles using HCV fullgenomic replicon RNAs of a Con1 strain of genotype 1b and of a mutant having replication enhancing mutation. The replication level of the viral genome is, however, significantly low, and the current situation is therefore that detection of the HCV particles of genotype 1b requires addition of a casein kinase 1 inhibitor enhancing replication of the replicon RNA of HCV to a cell culture system or an infection experiment by an in vivo system using an animal (Non Patent Literature 12). This means that, at present, only RNAs derived from the JFH-1 strain of genotype 2a can produce infectious HCV particles in an in vitro system using cultured cells and that only HCV JFH-1 strain or fullgenomic replicon derived from the JFH-1 strain can produce a large amount of HCV particles in an in vitro system for obtaining an HCV vaccine raw material.

Incidentally, current main therapy for hepatitis C is monotherapy with interferon-α or interferon-β and combined therapy with interferon-α and ribavirin, a purine nucleoside derivative. The therapeutic effect of such therapy, however, is recognized in only about 60% of the total subjects, and it is known that even in patients to whom the therapy was effective, hepatitis C recurs in more than the half thereof by stopping the therapy. The therapeutic effect of interferon is associated with HCV genotypes, and it is known that the effect on HCV of genotype 1b is low and that the effect on HCV of genotype 2a is higher (Non Patent Literature 13). The causes why the therapeutic effect of interferon varies depending on HCV genotypes are still unknown, but a difference in replication mechanism or replication efficiency of HCV is thought to be one of the causes.

CITATION LIST

Patent Literature

Patent Literature 1:JP Patent Publication (Kokai) No. 2001-17187 A

Non Patent Literature

Non Patent Literature 1:Simmonds et. al., Hepatology, 1994, vol. 10, pp. 1321-1324
Non Patent Literature 2:Choo et al., Science, 1989, vol, 244, pp. 359-362
Non Patent Literature 3:Kato et al., J. Med. Virol., 1992, vol, 64. pp. 334-339
Non Patent Literature 4:Okamoto et al., J. Gen. Virol., 1992, vol. 73, pp. 673-679
Non Patent Literature 5; Yoshioka et al., Hepatology, 1992, vol. 16, pp. 293-299
Non Patent Literature 6:Lomann et al., Science. 1999, vol. 285, pp. 110-113
Non Patent Literature 7:Blight et al., Science, 2000, vol. 290, pp. 1972-1974
Non Patent Literature 8:Friebe et al., J. Virol, 2001, vol. 75. pp. 12047-12057
Non Patent Literature 9:Ikeda et al., J. Virol., 2002, vol. 76, pp. 2997-3006
Non Patent Literature 10:Kato et al., Gastroenterology, 2003, vol. 125, pp. 1808-1817
Non Patent Literature 11:Wakita et al., Nature Medicine, 2005, vol. 11, pp. 791-796

Non Patent Literature 12:Pietschmann et al. PLoS Pathog., 2009, vol, 5:e1000475

Non Patent Literature 13:Mori et al., Biochem. Biophys. Res. Commun., 1992, vol 183, pp. 334-342

SUMMARY OF INVENTION

Problem to Be Solved by Invention

The subgenomic replicon RNAs of HCV are limited to several types derived bom HCV strains of genotypes 1a, 1b, and 2a. The fullgenomic replicon RNAs that can produce infectious HCV particles are only those derived from the JFH-1 strain genome of genotype 2a or derived from chimeric genomes each consisting of the structural gene derived from a strain other than the JFH-1 strain and the non-structural gene of the JFH-1 strain. It is therefore difficult to reveal a relationship between the HCV genotype and the replication mechanism or replication efficiency of HCV. In addition, the type of HCV particles that can be artificially prepared as an HCV vaccine raw material is currently limited to the genotype 2a.

In studies using subgenomic replicon RNAs or fullgenomic replicon RNAs derived from HCV of the same genotype, the replication mechanism or replication efficiency of HCV cannot be compared between different genotypes, and it is difficult to identify a factor necessary for replication, which can be a novel target candidate of an anti-HCV drag, or to screen for an anti-HCV drug capable of showing a medicinal effect independent of the replication mechanism or replication efficiency. Thus, the current situation is that any clue for developing an anti-HCV drug for HCV genotype 1b, on which the therapeutic effect of interferon is low, has not been found yet.

That is, it is thought that in the research field and the medical field of HCV, in order to investigate the mechanism of medicinal effect of interferon depending on the HCV genotype or develop an anti-HCV drug for HCV genotype 1b on which the therapeutic effect of interferon is low, acquisition of a genotype 1b HCV strain excellent in replication efficiency and production of a fullgenomic replicon RNA capable of producing infectious HCV particles are strongly demanded.

Accordingly, it is an object of the present invention to provide a subgenomic replicon RNA having excellent autonomous replication ability and a fullgenomic replicon RNA having excellent autonomous replication ability and infectious HCV particle-producing ability, derived from a novel HCV genotype 1b.

Means for Solving the Problem

The present inventors have diligently studied mutations in an HCV subgenomic replicon RNA autonomously replicated by transfecting cultured cells with an HCV subgenomic replicon RNA produced from an HCV genome of the NC1 strain, which is a novel HCV genotype 1b isolated from an acute severe hepatitis C patient, and, as a result, have revealed a mutation that significantly enhances autonomous replication ability. Subsequently, the inventors have produced HCV fullgenomic replicon RNAs having this mutation and have revealed mutations having HCV particle-producing ability by transfecting cultured cells with the HCV fullgenomic replicon RNAs. Furthermore, the inventors have found a combination of the mutations that significantly enhance the autonomous replication ability and have succeeded in production of HCV genotype 1b fullgenomic replicon RNAs highly pro- ducing infectious HCV particles (genotype 1b-derived infectious HCV particle-producing fullgenomic replicon RNAs) in cultured cells. Thus, the present invention has been accomplished.

That is, the present invention relates to:

[1] A nucleic acid comprising the nucleotide sequence shown in SEQ ID NO: 1 in the Sequence Listing, provided that when the nucleic acid is RNA, thymine (T) in the nucleotide sequence shown in SEQ ID NO: 1 shall be read as uracil (U);

[2] A nucleic acid having a mutation in the nucleotide sequence of the nucleic acid according to aspect [1], wherein the mutation causes substitution of the following (i) or (ii) as defined on the basis of the amino acid sequence shown in SEQ ID NO: 14 in the Sequence Listing (the amino acid sequence encoded by the sequence of nucleotide numbers from 342 to 9374 shown in SEQ ID NO: 1 in the Sequence Listing):

(i) substitution of serine at position 2197 with tyrosine (ii) substitution of serine at position 2204 with glycine;

[3] A nucleic acid having a mutation in the nucleotide sequence of the nucleic acid according to aspect [2], wherein the mutation causes substitution of the following (iii) as defined on the basis of the amino acid sequence shown in SEQ ID NO: 14 in the Sequence Listing (the amino acid sequence encoded by the sequence of nucleotide numbers from 342 to 9374 shown in SEQ ID NO: 1 in the Sequence Listing):

(iii) substitution of glutamic acid at position 1202 with glycine;

[4] A hepatitis C virus comprising the nucleic acid according to aspect [2] or [3] as a viral genome;

[5] A nucleic acid comprising nucleotide sequences that are derived from two or more hepatitis C virus genomes and encode a Core protein, an E1 protein, an E2 protein, a p7 protein, an NS2 protein, an NS3 protein, an NS4A protein, an NS4B protein, an NS5A protein, and an NS5B protein, in this order from the 5' side to the 3' side, wherein the nucleotide sequences encoding the NS3 protein, the NS4A protein, the NS4B protein, the NS5A protein, and the NS5B protein are derived from the nucleic acid according to aspect [2] or [3];

[6] The nucleic acid according to aspect [5], wherein at least a part of the nucleotide sequence encoding the NS2 protein is derived from the nucleic acid according to aspect [2] or [3];

[7] The nucleic acid according to aspect [5] or [6], comprising:

a 5' untranslated region of a hepatitis C virus genome on the 5' side of the nucleotide sequence encoding the Core protein; and a 3' untranslated region derived from the nucleic acid according to aspect [2] or [3] on the 3' side of the nucleotide sequence encoding the NS5B protein; and

[8] The nucleic acid according to any one of aspects [5] to [7], wherein the two or more hepatitis C virus genomes include the genome of a JFH-1 strain, a J6CF strain, or a TH strain.

In one embodiment, the nucleic acid according to aspect [5] may be a nucleic acid comprising a chimeric hepatitis C virus genome. The genome includes nucleotide sequences encoding:

a Core protein, an E1 protein, an E2 protein, and a p7 protein of a known hepatitis C virus strain;

an NS2 protein of the hepatitis C virus according to aspect [4], an NS2 protein of a known hepatitis C virus strain, or a chimeric NS2 protein consisting of a part of the NS2 protein of the hepatitis C virus according to aspect [4] and a part of the NS2 protein of a known hepatitis C virus strain which are ligated to each other; and an NS3 protein, an NS4A protein, an NS4B protein, an NS5A protein, and an NS5B protein of the hepatitis C virus according to aspect [4], wherein the nucleotide sequences encoding the Core protein, the E1 protein, the E2 protein, the p7 protein, the NS2 protein, the NS3 protein, the NS4A protein, the NS4B protein, the NS5A protein, and the NS5B protein are arranged in this order from the 5' side to the 3' side.

This nucleic acid preferably contains:

a 5' untranslated region of a viral genome of a known hepatitis C virus strain on the 5' side of the nucleotide sequence encoding the Core protein: and a 3' untranslated region of a vital genome of the hepatitis C virus according to aspect [4] on the 3' side of the nucleotide sequence encoding the NS5B protein. In such a nucleic acid, the known hepatitis C virus strain is preferably the JFH-1 strain, the J6CF strain, or the TH strain.

The present invention also relates to:

[9] A hepatitis C virus comprising a nucleic acid according to any one of aspects [5] to [8] as a viral genome.

A hepatitis C virus genome comprising the nucleic acid according to any one of aspects [1] to [3] and [5] to [8] is also preferred.

The present invention also relates to:

[10] A fullgenomic replicon RNA of hepatitis C virus comprising the nucleic acid according to any one of aspects [2], [3], and [5] to [8];

[11] An expression vector comprising the nucleic acid according to any one of aspects [2], [3], and [5] to [3];

[12] A cell transected with the nucleic acid according to any one of aspects [2], [3], and [5] to [8] or the fullgenomic replicon RNA according to aspect [10] or infected with the hepatitis C virus according to aspect [4] or [9] and producing hepatitis C virus particles;

[13] A hepatitis C virus vaccine comprising the hepatitis C virus according to aspect [4] or [9] or a part thereof;

[14] A neutralizing antibody against hepatitis C virus, which recognizes the hepatitis C virus according to aspect [4] or [9] as an antigen;

[15] A method of screening for an anti-hepatitis C virus substance, wherein the method including:

a step of culturing the cell according to aspect [12] or a mixture of the hepatitis C virus according to aspect [4] or [9] and a hepatitis C virus sensitive cell in the presence of a test substance and in the absence of the test substance;

a step of quantifying the amount of RNA or hepatitis C virus particles derived from the hepatitis C virus and generated in a culture in the culturing step; and a step of evaluating the result of the quantifying step, wherein the test substance is determined as a substance having an anti-hepatitis C virus activity if the amount of the RNA or the hepatitis C virus particles derived from the hepatitis C virus and detected in the culture obtained by the culturing in the presence of the test substance is smaller than the amount of RNA or hepatitis C virus particles derived from hepatitis C virus and detected in a culture obtained by culturing in the absence of the test substance;

[16] A nucleic acid comprising the 5' untranslated region consisting of the sequence of nucleotide numbers from 1 to 341, the NS3 protein-encoding nucleotide sequence consisting of the sequence of nucleotide numbers from 3420 to 5312, the NS4A protein-encoding nucleotide sequence consisting of the sequence of nucleotide numbers from 5313 to 5474. the NS4B protein-encoding nucleotide sequence consisting of the sequence of nucleotide numbers from 5475 to 6257, the NS5A protein-encoding nucleotide sequence consisting of the sequence of nucleotide numbers from 6258 to 7598, the NS5B protein-encoding nucleotide sequence consisting of the sequence of nucleotide numbers from 7599 to 9374. and the 3' untranslated region consisting of the sequence of nucleotide numbers from 9375 to 9607, of SEQ ID NO: 1 in the Sequence Listing;

[17] A nucleic acid having a mutation in the nucleotide sequence of the nucleic acid according to aspect [16], wherein the mutation causes any of the following substitution (a) to (e) as defined on the basis of the amino acid sequence shown in SEQ ID NO: 14 in the Sequence Listing (the amino acid sequence encoded by the sequence of nucleotide numbers from 342 to 9374 shown in SEQ ID NO: 1 in the Sequence Listing):

(a) substitution of serine at position 2197 with tyrosine (b) substitution of serine at position 2204 with glycine (c) substitution of serine at position 2197 with tyrosine and substitution of glutamic acid at position 1202 with glycine (d) substitution of serine at position 2204 with glycine and substitution of glutamic acid at position 1202 with glycine (e) substitution of proline at position 2161 with arginine;

[18] A subgenomic replicon RNA of hepatitis C virus, comprising the nucleic acid according to aspect [16] or [17];

[19] An expression vector comprising the nucleic acid according to aspect [16] or [17];

[20] A method of screening for an anti-hepatitis C virus substance, wherein the method including:

a step of culturing hepatitis C virus-sensitive cells transfected with the subgenomic replicon RNA according to aspect [18], both in the presence and in the absence of the test substance;

a step of quantifying the amount of a subgenomic replicon RNA obtained in a culture in the culturing step; and a step of evaluating the result of the quantifying step, wherein the test substance is determined as a substance having an anti-hepatitis C virus activity if the amount of the subgenomic replicon RNA detected in the culture obtained by culturing in the presence of the test substance is smaller than the amount of the subgenomic replicon RNA detected in the culture obtained by culturing in the absence of the test substance;

[21] The hepatitis C virus vaccine according to aspect [13], wherein the hepatitis C virus is inactivated or attenuated;

[22] A cell infected with the hepatitis C virus according to aspect [4] or [9];

[23] The nucleic acid according to aspect [2], wherein the nucleic acid consists of the nucleotide sequence shown in SEQ ID NO: 19 having a mutation causing substitution of serine at position 2197 with tyrosine or consists of the nucleotide sequence shown in SEQ ID NO: 20 having a mutation causing substitution of serine at position 2204 with glycine; and

[24] The nucleic acid according to aspect [3], wherein the nucleic acid consists of the nucleotide sequence shown in SEQ ID NO: 21 having a mutation causing substitution of serine at position 2197 with tyrosine and a mutation causing substitution of glutamic acid at position 1202 with glycine or consists of the nucleotide sequence shown in SEQ ID NO: 22 having a mutation causing substitution of serine at position 2204 with glycine and a mutation causing substitution of glutamic acid at position 1202 with glycine.

This description includes the contents as disclosed in the description and drawings of Japanese Patent Application No. 2011-080678, on which the priority of the present application is based.

Effects of Invention

The present invention can provide an HCV subgenomic replicon RNA of genotype 1b that can be amplified in cultured cells and an HCV fullgenomic replicon RNA that can produce infectious HCV particles, which can be used in screening for an anti-HCV drug that inhibits infection and replication of HCV of genotype 1b, research for revealing the replication mechanism of HCV, and also development of an HCV vaccine based on HCV particles.

BRIEF DESCRIPTION OF DRAWINGS

FIG. 7 shows changes over time in amount of the Core protein in a culture supernatant (HCV particle-producing ability) of Huh7 cells transfected with the HCV fullgenomic replicon RNA of the wild-type NC1 strain or its mutants (mutation of P2161R, R2192L, R2192Q, S2197Y, S2204G, and Y2871C).

EMBODIMENTS FOR CARRYING OUT THE INVENTION

Figure 1:
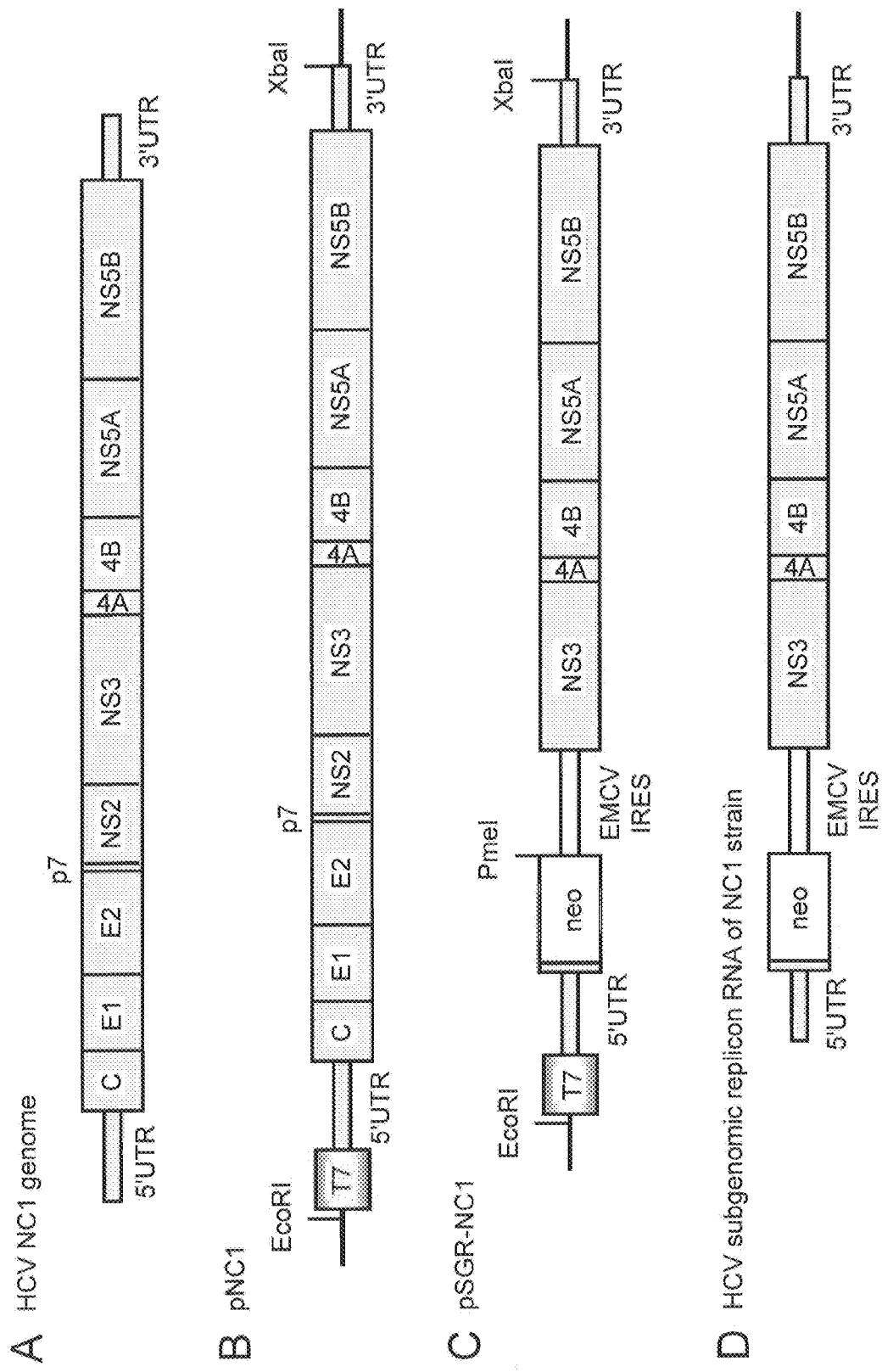
FIG. 1 is a diagram showing (A) the full-length genome of the HCV NC1 strain (wild-type); (B) the structure of an expression vector pNC1 for synthesizing an HCV fullgenomic replicon RNA of the NC1 strain; (C) the structure of an expression vector pSGR-NC1 for synthesizing an HCV subgenomic replicon RNA of the NC1 strain; and (D) the structure of an HCV subgenomic replicon RNA of the NC1 strain synthesized from the pSGR-Nc1 with T7 polymerase.

The scientific terms, technical terms, and nomenclature used throughout the description are intended to have the same meanings as those generally understood by those skilled in the art unless otherwise specifically defined. The general technology and technical terms in the fields of molecular biology and immunology are based on the procedures and definitions described in Sambrook et al., Molecular Cloning: A Laboratory Manual (Third Edition, 2001) and Ed Harlow et al., Antibodies; A Laboratory Manual (1988), Furthermore, all documents, patents, and patent applications cited in the description are incorporated by reference herein in their entirety.

(1) Nucleic Acid and HCV (Hepatitis C Virus) Replicon RNA According to the Present Invention The term "nucleic acid" includes RNA ami DNA. Throughout the description, the terms "protein coding region," "nucleotide sequence encoding protein," "sequence encoding protein." and "protein coding sequence" each refer to a nucleotide sequence encoding the amino acid sequence of a given protein, and the nucleotide sequence may or may not contain a start codon and a stop codon.

Throughout the description, in a case of a nucleic acid being RNA, when the nucleotide sequence or the nucleotide of the RNA is specified by referring to a SEQ ID NO in the Sequence Listing, thymine (T) in the nucleotide sequence shown in the SEQ IN NO shall be read as uracil (U).

HCV is a virus with a single-stranded (+) sense RNA as the genome, and the genome consists of a 5' untranslated region (hereinafter, also referred to as 5' UTR), structural genes, non-structural genes, and a 3' untranslated region (hereinafter, also referred to as 3' UTR). HCV is actually present as virus particles. The virus particles of HCV (HCV particles) contain HCV genomes inside the "structural proteins" forming the HCV particles.

The "structural gene" of HCV is a nucleic acid encoding a structural protein having a specific structural function and constituting HCV particles. The "structural protein" refers to a Core protein, an E1 protein, an E2 protein, and a p7 protein.

The "non-structural gene" of HCV is a nucleic acid encoding a non-structural protein having a function involved in, for example, replication of an HCV genome or processing of an HCV protein. The "non-structural protein" refers to an NS2 protein, an NS3 protein, an NS4.A. protein, an NS4B protein, an NS5A protein, and an NS5B protein.

The 5' UTR of HCV provides an internal ribosome entry site (hereinafter, referred to as IRES) for protein translation and an element necessary for replication. The 5' UTR of HCV is a region of about 340 nucleotides from the 5' end of a genome.

The 3' UTR of HCV aids replication of HCV. The 3' UTR of HCV contains a poly-U region and an additional region of about 100 nucleotides.

The term "replicon RNA" refers to an RNA that autonomously replicates in HCV-sensitive cells. The replicon RNA autonomously replicates when it is transacted into cells, and the copies of the replicated RNA can be stably present as RNA even when the cells are separated into daughter cells after cell division. The replicon RNA of HCV (HCV replicon RNA) means an autonomously-replicating RNA comprising a part or full-length of the HCV genome RNA, e.g., an HCV subgenomic replicon RNA or an HCV fullgenomic replicon RNA.

The "HCV full-length genome" is an RNA consisting of the sequence of full-length genome consisting of the 5' UTR, the structural genes, the non-structural genes, and the 3' UTR of HCV from the 5' side to the 3' side in this order. The "subgenome of HCV" is an RNA comprising a part of the HCV full-length genome. In particular, the "HCV subgenomic replicon RNA" is an RNA comprising the 5' UTR, a part of the non-structural genes, and the 3' UTR of HCV, wherein the RNA does not have an ability to produce infectious HCV particles, but can autonomously replicate the HCV genome-derived RNA when it is transfected into cells.

An HCV full-length genome having autonomous replication ability is a replicon RNA. A replicon RNA comprising the HCV full-length genome is also called HCV fullgenomic replicon RNA for distinguishing from subgenomic replicon RNAs. Accordingly, an RNA consisting of an HCV full-length genome sequence (HCV full-length genomic RNA) having autonomous replication ability is an HCV fullgenomic replicon RNA. That is, an "HCV fullgenomic replicon RNA" is an RNA comprising a 5' UTR, structural genes, non-structural genes, and a 3' UTR of HCV and preferably an RNA comprising a 5' UTR, sequences encoding a Core protein, an E1 protein, an E2 protein, a p7 protein, an NS2 protein, an NS3 protein, an NS4A protein, an NS4B protein, an NS5A protein, and an NS5B protein, and a 3' UTR of HCV. The HCV fullgenomic replicon RNA is more preferably an RNA comprising a 5' UTR, sequences encoding a Core protein, an E1 protein, an E2 protein, a p7 protein, an NS2 protein, an NS3 protein, an NS4A protein, an NS4B protein, an NS5A protein, and an NS5B protein, and a 3' UTR of HCV, in this order from the 5' side to the 3' side.

The HCV fullgenomic replicon RNA may further comprise a foreign gene such as a drug resistance gene and/or a reporter gene, and an IRES sequence. An HCV fullgenomic replicon RNA comprising a foreign gene and an IRES sequence is preferably an RNA comprising the 5' UTR of HCV, the foreign gene, the IRES sequence, sequences encoding the Core protein, the E1 protein, the E2 protein, the p7 protein, the NS2 protein, the NS3 protein, the NS4A protein, the NS4B protein, the NS5A protein, and the NS5B protein of HCV, and the 3' UTR of HCV, in this order from the 5' side to the 3' side.

The HCV subgenomic replicon RNA is preferably an RNA comprising the 5' UTR, sequences encoding the NS3 protein, the NS4A protein, the NS4B protein, the NS5A protein, and the NS5B protein, and the 3' UTR of HCV. The HCV subgenomic replicon RNA is more preferably an RNA comprising the 5' UTR, sequences encoding the NS3 protein, the NS4A protein, the NS4B protein, the NS5A protein, and the NS5B protein, and the 3' UTR of HCV, in this order from the 5' side to the 3' side.

The HCV subgenomic replicon RNA may further comprise a foreign gene such as a drug resistance gene and/or a reporter gene and an IRES sequence. In particular, in a case of using the HCV subgenomic replicon RNA in screening for an anti-HCV substance, in order to easily detect the replicon RNA, the HCV subgenomic replicon RNA preferably comprises a drug resistance gene and/or a reporter gene and an IRES sequence. An HCV subgenomic replicon RNA comprising a foreign gene and an IRES sequence is preferably an RNA comprising the 5' UTR of HCV, the foreign gene, the IRES sequence, sequences encoding the NS3 protein, the NS4A protein, the NS4B protein, the NS5A protein, and the NS5B protein of HCV, and the 3' UTR of HCV, in this order from the 5' side to the 3' side.

Examples of the drug resistance gene that can be contained in the HCV replicon RNA (HCV fullgenomic replicon RNA and HCV subgenomic replicon RNA) include neomycin resistance gene, hygromycin resistance gene, thymidine kinase gene, kanamycin resistance gene, pyrithiamine resistance gene, adenylyltransferase gene, zeocin resistance gene, and puromycin resistance gene. The neomycin resistance gene and the hygromycin resistance gene are preferred, and the neomycin resistance gene is more preferred.

Examples of the reporter gene that can be contained in the HCV replicon RNA include structural genes of enzymes that catalyze luminous reaction or color reaction. Preferred examples of the reporter gene include chloramphenicol acetyl transferase genes derived from transposon Tn9, β-glucuronidase or β-galactosidase genes derived from $E.\ coli$, luciferase genes, green fluorescent protein genes, acquorin genes derived from jellyfish, and secretory placental alkaline phosphatase (SEAP) genes.

The HCV replicon RNA may contain either one or both of the drug resistance gene and the reporter gene. The number of each of the drug resistance gene and reporter gene that may be contained in the HCV replicon RNA may be one, or two or more.

The IRES sequence that may be contained in the HCV replicon RNA means an internal ribosome entry site that can allow a ribosome to bind an internal region of RNA and start translation. Preferred examples of the IRES sequence include EMCV IRES (internal ribosome entry site of encephalomyocarditis virus), FMDV IRES, and HCV IRES. The EMCV IRES and the HCV IRES are more preferred, and the EMCV IRES is most preferred.

In the HCV replicon RNA, the drug resistance gene and/or the reporter gene is ligated so as to be translated in a proper reading frame (in-frame) from the HCV replicon RNA. The proteins encoded by the HCV replicon RNA are preferably connected to one another via, for example, a protease cleavage site therebetween such that the proteins are translated and expressed into a continuous polypeptide chain and are then cleaved into each protein by means of a protease and are released.

The HCV-sensitive cell refers to a cell that permits infection with HCV particles or replication of HCV replicon RNA in a cell culture system, and examples thereof include Huh7 cells. HepG2 cells, IMY-N9 cells, HeLa cells, 293 cells, and, Huh7.5 cells and Huh7.5.1 cells which are derivative strains of Huh7 cells. Other examples of the HCV-sensitive cell include Huh7 cells, HepG2 cells, IMY-N9 cells, HeLa cells, or 293 cells which are engineered to express a CD81 gene and/or a Claudin1 gene (Lmdenbach, B. D. et al., Science, 2005, vol, 309, pp. 623-626; Evans, M. J. et al., Nature, 2007, vol. 446, pp. 801-805; Akazawa, D. et al., J. Virol., 2007, vol. 81, pp. 5036-5045). In particular, Huh7 cells and derivative strains of Huh7 cells are most preferably used. In the present invention, the term "derivative strain" refers to a strain derived from the given cell.

A continuous polynucleotide chain comprising a Core protein, an E1 protein, an E2 protein, a p7 protein, an NS2 protein, an NS3 protein, an NS4A protein, an NS4B protein, an NS5A protein, and an NS5B protein produced by translation from an HCV full-length genome is called an HCV precursor protein. The Core protein, the E1 protein, the E2 protein, the p7 protein, the NS2 protein, the NS3 protein, the NS4A protein, the NS4B protein, the NS5A protein, and the NS5B protein of HCV are generated by cleavage of the HCV precursor protein by intracellular and viral proteases.

In the description, the position of an amino acid on an amino acid sequence shown by SEQ ID NO is expressed such that "(amino acid) at position 'X' as defined on the basis of the amino acid sequence shown in SEQ ID NO: 14". This expression means that the amino acid is the amino acid residue present at the "X"th position in the amino acid sequence shown in SEQ ID NO: 14 on the condition that the first amino acid (methionine) at the N-terminus in the amino acid sequences shown in SEQ ID NO: 14 is defined as the 1st position. When an amino acid in an amino acid sequence other than SEQ ID NO: 14 is designated using the expression of "(amino acid) at position 'X' as defined on the basis of the amino acid sequence shown in SEQ ID NO: 14", the actual position of the designated amino acid in the amino acid sequence other than SEQ ID NO: 14 may be the position "X" or may not be the position "X" as long as the amino acid is aligned with the amino acid at position "X" of SEQ ID NO: 14.

In the description, for example, amino acid mutation S2197Y means a mutation that the amino acid residue S (serine) at position 2197 is replaced by Y (tyrosine). Expressions representing other amino acid mutations are similarly comprehended. Here, each amino acid is expressed using a single character code that is generally used in the biology field (Sambrook et al., Molecular Cloning: A Laboratory Manual, Second Edition, 1989).

In the description, an amino acid or an amino acid residue is expressed using a single character code or a three character code that is generally used in the biology field, and an amino acid after post-translational modification such as hydration, glycosylation, and sulfation is also included therein.

In the description, the nucleotide number in the nucleotide sequence shown in SEQ ID NO is based on the nucleotide number on the condition that the first nucleotide at the 5' end of the nucleotide sequence shown by the SEQ ID NO is defined as the nucleotide 1.

In a preferred embodiment, the present invention provides a nucleic acid comprising the nucleotide sequence shown in SEO ID NO: 1 in the Sequence Listing, provided that when the nucleic acid is RNA, thymine (T) in the nucleotide sequence shown in SEQ ID NO: 1 shall be read as uracil (U). This nucleic acid contains the full genome (full-length genome) sequence of hepatitis C virus, i.e., the 5' untranslated region; nucleotide sequences encoding the Core protein, the E1 protein, the E2 protein, the p7 protein, the NS2 protein, the NS3 protein, the NS4A protein, the NS4B protein, the NS5A protein, and the NS5B protein, respectively; and the 3' untranslated region of the hepatitis C virus genome, in this order from the 5' side to the 3' side. The present invention also provides a mutant of this nucleic acid having a mutation that causes (i) substitution of serine at position 2197 with tyrosine or (ii) substitution of serine at position 2204 with glycine, as defined on the basis of the amino acid sequence shown in SEQ ID NO: 14 in the Sequence Listing (the amino acid sequence encoded by the sequence of nucleotide numbers from 342 to 9374 shown in SEQ ID NO: 1 in the Sequence Listing). The nucleic acid of SEQ ID NO: 1 and its mutant may further have a mutation that causes (iii) substitution of glutamic acid at position 1202 with glycine as defined on the basis of the amino acid sequence shown in SEQ ID NO: 14 in the Sequence Listing (the amino acid sequence encoded by the sequence of nucleotide numbers from 342 to 9374 shown in SEQ ID NO: 1 in the Sequence Listing). These nucleic acids are preferably isolated.

Preferred examples of such a nucleic acid include, but not limited to, a nucleic acid comprising the nucleotide sequence shown in SEQ ID NO: 19, SEQ ID NO: 20. SEQ ID NO: 21, or SEQ ID NO: 22.

These nucleic acids may be DNAs or RNAs, These nucleic acids may be fullgenomic replicon RNAs. When these nucleic acids are DNAs, they can also be used as templates for producing fullgenomic replicon RNAs.

In another preferred embodiment, the present invention provides a nucleic acid (chimeric nucleic acid) comprising nucleotide sequences encoding a Core protein, an E1 protein, an E2 protein, a p7 protein, an NS2 protein, an NS3 protein, an NS4A protein, an NS4B protein, an NS5A protein, and an NS5B protein derived from two or more hepatitis C virus genomes, in this order from the 5' side to the 3' side, wherein the nucleotide sequences encoding the NS3 protein, the NS4A protein, the NS4B protein, the NS5A protein, and the NS5B protein are derived from the nucleic acid of SEQ ID NO: 1 or its mutant. Furthermore, in such a nucleic acid, the nucleotide sequence encoding the NS2 protein is preferably at least partially derived from the nucleic acid of SEQ ID NO: 1 or its mutant. Such a nucleic acid preferably contains the 5' untranslated region of the viral genome of hepatitis C virus (preferably a known hepatitis C virus strain) at the 5' side of the nucleotide sequence encoding the Core protein and the 3' untranslated region derived from the nucleic acid of SEQ ID NO: 1 or its mutant (the genome of hepatitis C virus strain according to the present invention) at the 3' side of the nucleotide sequence encoding the NS5B protein. The two or more hepatitis C virus genomes include a genome of a known hepatitis C virus strain, for example, a hepatitis C virus genomic nucleic acid other than the nucleic acid of SEQ ID NO: 1 and its mutant, preferably the genome of a JFH-1 strain, a J6CF strain, or a TH strain.

One embodiment of the nucleic acid of this invention may be a nucleic acid comprising a chimeric hepatitis C virus genomic sequence comprising nucleotide sequences encoding:

a Core protein, an E1 protein, an E2 protein, and a p7 protein of a known hepatitis C virus strain;

an NS2 protein of the hepatitis C virus having the nucleic acid of SEQ ID NO: 1 or its mutant as a viral genome, an NS2 protein of a known hepatitis C virus strain, or a chimeric NS2 protein in which a part of the NS2 protein of the hepatitis C virus having the nucleic acid of SEQ ID NO: 1 or its mutant as a viral genome and a part of the NS2 protein of a known hepatitis C virus strain are ligated to each other; and an NS3 protein, an NS4A protein., an NS4B protein, an NS5A protein, and an NS5B protein of the hepatitis C virus having the nucleic acid of SEQ ID NO: 1 or its mutant as a viral genome, wherein the nucleotide sequences encoding the Core protein, the E1 protein, the E2 protein, the p7 protein, the NS2 protein, the NS3 protein, the NS4A protein, the NS4B protein, the NS5A protein, and the NS5B protein are arranged in this order from the 5' side to the 3' side.

These nucleic acids may be DNAs or RNAs. These nucleic acids may be fullgenomic replicon RNAs. When these nucleic acids are DNAs, they can also be used as templates for producing fullgenomic replicon RNAs.

In a preferred embodiment, the present invention also provides a nucleic acid comprising the 5' untranslated region consisting of the sequence of nucleotide numbers from 1 to 341, the NS3 protein-encoding nucleotide sequence consisting of the sequence of nucleotide numbers from 3420 to 3312, the NS4A protein-encoding nucleotide sequence consisting of the sequence of nucleotide numbers from 5313 to 5474, the NS4B protein-encoding nucleotide sequence consisting of the sequence of nucleotide numbers from 5475 to 6257, the NS5A protein-encoding nucleotide sequence consisting of the sequence of nucleotide numbers from 6258 to 7598. the NS5B protein-encoding nucleotide sequence consisting of the sequence of nucleotide numbers from 7599 to 9374. and the 3' untranslated region consisting of the sequence of nucleotide numbers from 9375 to 9607, of SEQ ID NO: 1 in the Sequence Listing. The present invention also provides a mutant of this nucleic acid, wherein the mutant has a mutation causing substitution selected from the group consisting of (a) substitution of serine at position 2197 with tyrosine, (b) substitution of serine at position 2204 with glycine, (e) substitution of serine at position 2197 with tyrosine and substitution of glutamic acid at position 1202 with glycine, (d) substitution of serine at position 2204 with glycine and substitution of glutamic acid at position 1202 with glycine, and (e) substitution of proline at position 2161 with arginine, as defined on the basis of the amino acid sequence shown in SEQ ID NO: 14 in the Sequence Listing (the amino acid sequence encoded by the sequence of nucleotide numbers from 342 to 9374 shown in SEQ ID NO: 1 in the Sequence Listing).

Preferred examples of such a nucleic acid include, but not limited to, a nucleic acid comprising the nucleotide sequence shown in SEQ ID NO: 16, SEQ ID NO: 17, SEQ ID NO: 18, or SEQ ID NO: 52.

These nucleic acids may be DNAs or RNAs. These nucleic acids may contain HCV subgenome sequences and may be, for example, subgenomic replicon RNAs. When these nucleic acids are DNAs, they can also be used as templates for producing subgenomic replicon RNAs.

(2) Obtainment of HCV Subgenomic Replicon RNA of Which Replication Has Been Improved in Cultured Cells The nucleic acid consisting of the nucleotide sequence of SEQ ID NO: 1 in the Sequence Listing is the full-length genome nucleic acid of the NC1 strain, which is a novel HCV of genotype 1b isolated from an acute severe hepatitis C patient. The sequence can be a cDNA sequence of the full-length genomic RNA of the wild-type NC1 strain, while in the RNA sequence, the thymine (T) in the nucleotide sequence shall be read as uracil (U). The method of isolating the HCV genome from a patient is described in Kato, T. et al., Gastroenterology, 2003, vol. 125, pp. 1808-1817.

In the full-length HCV genome of the NC1 strain (SEQ ID NO: 1), the 5' UTR consists of the sequence of nucleotide numbers from 1 to 341 of SEQ ID NO: 1, the Core protein coding sequence consists of the sequence of nucleotide numbers from 342 to 914 of SEQ ID NO: 1, the E1 protein coding sequence consists of the sequence of nucleotide numbers from 915 to 1490 of SEQ ID NO: 1, the E2 protein coding sequence consists of the sequence of nucleotide numbers from 1491 to 2579 of SEQ ID NO: 1, the p7 protein coding sequence consists of the sequence of nucleotide numbers from 2580 to 2768 of SEQ ID NO: 1, the NS2 protein coding sequence consists of the sequence of nucleotide numbers from 2769 to 3419 of SEQ ID NO: 1, the NS3 protein coding sequence consists of the sequence of nucleotide numbers from 3420 to 5312 of SEQ ID NO: 1, the NS4A protein coding sequence consists of the sequence of nucleotide numbers front 5313 to 5474 of SEQ ID NO: 1, the NS4B protein coding sequence consists of the sequence of nucleotide numbers from 5475 to 6257 of SEQ ID NO: 1, the NS5A protein coding sequence consists of the sequence of nucleotide numbers from 6258 to 7598 of SEQ ID NO: 1, the NS5B protein coding sequence consists of the sequence of nucleotide numbers from 7599 to 9374 of SEQ ID NO: 1, and the 3' UTR consists of the sequence of nucleotide numbers from 9375 to 9607 of SEQ ID NO: 1. The structure of the full-length HCV genome of this NC1 strain is shown in FIG. 1A.

Specifically, in the full-length HCV genome of the NC1 strain (SEQ ID NO: 1), the 5' UTR consists of the nucleotide sequence shown in SEQ ID NO: 2, the Core protein coding sequence consists of the nucleotide sequence shown in SEQ ID NO: 3, the E1 protein coding sequence consists of the nucleotide sequence shown in SEQ ID NO: 4, the E2 protein coding sequence consists of the nucleotide sequence shown in SEQ ID NO: 5. the p7 protein coding sequence consists of the nucleotide sequence shown in SEQ ID NO: 6, the NS2 protein coding sequence consists of the nucleotide sequence shown in SEQ ID NO: 7, the NS3 protein coding sequence consists of the nucleotide sequence shown in SEQ ID NO: 8, the NS4A protein coding sequence consists of the nucleotide sequence shown in SEQ ID NO: 9, the NS4B protein coding sequence consists of the nucleotide sequence shown in SEQ ID NO: 10, the NS5A protein coding sequence consists of the nucleotide sequence shown in SEQ ID NO: 11, the NS5B protein coding sequence consists of the nucleotide sequence shown in SEQ ID NO: 12, and the 3' UTR consists of the nucleotide sequence shown in SEQ ID NO: 13.

The HCV subgenomic replicon RNA can be obtained by transcription from an expression vector. Basic technique relating to construction of an expression vector for producing the HCV subgenomic replicon RNA is described in Lohmann V. et al., Science, 1999, vol. 285, pp. 110-113 and Kato, T. et al., Gastroenterology, 2003. vol. 125, pp. 1808-1817. Specifically, for example, an expression vector for producing an HCV subgenomic replicon RNA can be constructed by inserting a cDNa in which the 5' UTR, 36 nucleotides of the region encoding the Core protein, a foreign gene (drug resistance gene or reporter gene), an EMCV IRES sequence, nucleotide sequences encoding the NS3 protein, the NS4A protein, the NS4B protein, the NS5A protein, and the NS5B protein, and the 3' UTR are ligated in this order from 5' to 3', into downstream of the T7 promoter. In ligating of each nucleotide sequence, an additional sequence such as a restriction enzyme site may be inserted at the ligation site.

The HCV subgenomic replicon RNA can be synthesized from the constructed expression vector for producing an HCV subgenomic replicon RNA using a polymerase. Examples of, for example, the in vitro method of producing an RNA using a nucleic acid comprising a cloned HCV cDNA under control of the T7 promoter as a template include synthesis with, for example, MEGAscript T7 kit (Ambion. Inc.). The HCV subgenomic replicon RNA transcribed from this vector autonomously replicates when the RNA is transfected into cells. The present invention encompasses cells transfected with the HCV subgenomic replicon RNA.

As the promoter, in addition to the T7 promoter, an SP6 promoter, a T3 promoter or the like can be used, but preferred is the T7 promoter.

As the vector, pUC19 (TaKaRa Bio Inc.), pBR322 (TaKaRa Bio Inc.), pGEM-T, pGEM-T Easy, PGEM-3Z (each of Promega Corp.), pSP72 (Promega Corp.), pCRII (Invitrogen Corp.), pT7Blue (Novagen, Inc.) and the like can be used.

The cells that are to be transfected with the HCV subgenomic replicon RNA may be any cell that permits replication of the HCV subgenomic replicon RNA, such as the HCV-sensitive cells. In particular, Huh7 cells and derivative strains of Huh7 cells are preferably used.

The transfection of the HCV subgenomic replicon RNA into cells can be performed by any known methods. Examples of the method include calcium phosphate coprecipitation, a DEAE-dextran method, lipofection, microinjection, and electroporation. Preferred are lipofection and electroporation, and more preferred is electroporation.

The replication ability of the transfected HCV subgenomic replicon RNA can be evaluated by, for example, measuring the function of the foreign gene iigated into the HCV subgenomic replicon RNA, i.e., measuring the Inaction shown by expression of the gene. In a case where the foreign gene is a drug resistance gene, the replication ability of an HCV subgenomic replicon RNA can be evaluated by counting the number of cells or the number of colonies of cells propagating on a selective medium containing a corresponding drug. In such a case, a larger number of cells or colonies of cells means higher replication ability. In a case where the foreign gene is an enzyme gene, the replication ability of an HCV subgenomic replicon RNA can be evaluated by measuring the enzyme activity. In this case, a higher enzyme activity means higher replication ability. Alternatively, the replication ability of an HCV subgenomic replicon RNA can be directly evaluated by quantifying the amount of replicated RNA by quantitative RT-PCR.

It has been shown that efficient replication of an HCV genome needs a mutation in the nucleotide sequence of the genome (Lohmann, V. et al., J. Virol., 2001, vol. 75, pp. 1437-1449). Mutation that enhances the replication ability is called adaptive mutation. Subculture of the cells transfected with the HCV subgenomic replicon RNA produced above may provide a cell strain showing enhanced replication of the HCV subgenomic replicon RNA. Continuous cell culture may cause an adaptive mutation in the HCV genome to significantly enhance the replication.

Examples of the adaptive mutation include an adaptive mutation in the JFH-1 strain of genotype 2a and an adaptive mutation in chimeric HCV particles composed of the H77 strain of genotype 1a and the JFH-1 strain (Zhong, J. et al., J. Virol., 2006, vol. 80, pp. 11082-11093; Kaul, A. et al., J. Virol., 2007, vol 81, pp. 2313168-2313179; International Publication No. WO08/147735; International Publication No. WO09/001975:and MinKyung, Y. et al., J. Virol., 2007, vol. 81, pp. 629-638). It has, however, been shown that the efficiency of RNA replication can be increased by 200 times or more or conversely decreased to one-fifth or less depending on the combination of adaptive mutations, and, therefore, an increase in number of adaptive mutations is not enough (Lohmann, V. et al., J. Virol., 2003, vol. 77, pp. 3007-3019). The effect of an adaptive mutation varies depending on the HCV strain. Thus, the details how the adaptive mutation affects the replication efficiency of the HCV genome have not been revealed yet.

Accordingly, it is suggested that an acceptable mutation varies depending on the strain of virus, design (construction) of HCV genome, and experiment conditions, in order to determine an acceptable mutation, it is necessary to perform experiments for each intended construction to obtain an acceptable mutant. In addition, the replication ability and HCV particle-producing ability are extremely varied by a mutation of only one amino acid caused by a nucleotide mutation in a nucleic acid. Hybridisation technique cannot detect a mutation of nucleic acid corresponding to one amino acid mutation. Accordingly, detection of one amino acid mutation requires sequencing of the nucleotide sequence of the HCV genome. An HCV genome sequence having enhanced ability to replicate HCV subgenomic replicon RNA can be revealed by isolating an HCV genomic RNA from a cell strain showing enhanced ability to replicate HCV subgenomic replicon RNA and determining the nucleotide sequence thereof.

Whether the mutation in HCV genomic RNA contributes to the HCV replication ability or not can be examined by introducing the mutation into the wild-type HCV genome (HCV genome not having mutation) and examining whether the change in HCV replication ability reappears or not. In addition, whether the mutation in the HCV genomic RNA is specific to the HCV genome used or is effective in another HCV genome can be examined by introducing the mutation into the wild-type HCV genome.

Mutation can be introduced into the wild-type HCV genome using a PCR method or a commercially available mutagenesis kit (e.g., KOD-Plus-Mutagenesis Kit manufactured by Toyobo Co., Ltd.). In the PCR method, for example, a target sequence portion can be amplified by PCR using a vector comprising a cloned cDNA of the wild-type HCV genome RNA as a template and using forward and reverse primers designed from the cDNA sequence. Specifically, the target nucleic acid can be amplified by synthesizing a plurality of different PCR products having sequences overlapping each other, mixing the PCR products to be used as templates, and performing PCR using a forward primer comprising the 5' end of the target nucleic acid and a reverse primer comprising the 5' end of the complementary strand of the nucleic acid. Each end of synthesized nucleic acid is cleaved with a restriction enzyme, and is ligated to a vector comprising a cloned cDNA of the wild-type HCV genome RNA cleaved with the same enzyme. Basic technique of such a procedure is also described in, for example. International Publication Nos. WO04/104198 and WO06/022422, Wakita. T. et al., 2005, Nat. Med., No. 11, pp. 791-796, and Lindenbach, B. D. et al., 2005, Science. No. 309, pp. 623-626.

HCV is translated as a single precursor protein in which ten viral proteins (Core protein, E1 protein, E2 protein, p7 protein, NS2 protein, NS3 protein. NS4A protein. NS4B protein, NS5A protein, and NS5B protein) are connected in this order, and then, by means of intracellular and viral proteases, the precursor protein is cleaved into ten viral proteins (Core protein, E1 protein, E2 protein. p7 protein, NS2 protein. NS3 protein, NS4A protein, NS4B protein, NS5A protein, and NS5B protein). The amino acid sequence of the precursor protein of the NC1 strain is shown in SEQ ID NO: 14. The amino acid sequence of the precursor protein of the NC1 strain shown in SEQ ID NO: 14 is encoded by the sequence of nucleotide numbers from 342 to 9374 (including the stop eodon) of the cDNA sequence of the full-length genomic RNA of the wild-type NC1 strain shown in SEQ ID NO: 1. In the present invention, the position of a mutation of an amino acid in the HCV protein is based on amino acid numbers on the condition that the methionine (M) being the translation start site of the precursor protein is counted as the 1st position. That is, the amino acid number showing a mutation is determined from the position of the mutation in the amino acid sequence as defined on the basis the amino acid sequence of the precursor protein shown in SEQ ID NO: 14. For example, the precursor protein of the NC1 strain consists of 3010 amino acid residues (SEQ ID NO: 14) starting from the methionine at the translation start site to the arginine (R) at position 3010, The amino acid at position 2197 of the NC1 strain is serine (S) in the NS5A protein, and mutation of the serine (S) to tyrosine (Y) is denoted as S2197Y, 2197SY, or 2197S→Y, The notation, such as S2197Y, generally indicates the mutation of an amino acid at a specific position, but in the description, the notation also indicates a nucleic acid mutation encoding the mutated amino acid. For example, in a case where serine (S) at position 2197 in the amino acid sequence encoded by the original nucleic acid is substituted with tyrosine (Y) due to mutation of a nucleotide in the nucleic acid, the nucleic acid encoding the amino acid sequence having such mutation can be called a nucleic acid containing S2197Y mutation or a nucleic acid into which S2197Y mutation has been introduced. Such a nucleic acid mutation may be also called nucleic acid mutation causing S2197Y mutation in the amino acid sequence. Furthermore, for example, an HCV replicon RNA having an S2197Y mutation introduced may be called S2197Y mutant HCV replicon RNA. In a case simultaneously having two mutations, for example, a nucleic acid having E1202G mutation and S2197Y mutation is denoted as a nucleic acid having E1202G/S2197Y mutations. The mutation of a nucleotide that causes a specific amino acid mutation can be determined based on genetic codes.

Adaptive mutations that enhance the replication ability of the HCV subgenomic replicon RNA of the NC1 strain are P2161R (mutation of the proline (P) at position 2161 to arginine (R)), R2192L (mutation of the arginine (R) at position 2192 to leucine (L)), R2192Q (mutation of the arginine (R) at position 2192 to glutamine (Q)), S2197Y (mutation of the serine (S) at position 2197 to tyrosine (Y)), S2204G (mutation of the serine (S) at position 2204 to glycine (G)), and Y2871C (mutation of the tyrosine (Y) at position 2871 to cysteine (C)). An HCV subgenomic replicon RNA having enhanced replication ability can be obtained by introducing these adaptive mutations alone or in combination into an HCV genome. In addition, these adaptive mutations may be introduced in combination with a mutation disclosed in a publication (Krieger et al., J. Virol., 2001, vol. 75, pp. 4614-4624). Any mutation disclosed in a publication that enhances the replication ability of the HCV subgenomic replicon RNA in combination with the mutation found in the present invention can be used. Examples of such a mutation include E1202G (mutation of the glutamic acid (E) at position 1202 to glycine (G)) (Krieger et al., J. Virol., 2001, vol. 75. pp. 4614-4624). In the present invention, a preferred mutation is S2197Y or S2204G, and more preferred mutations are a combination of E1202G and S2197Y (hereinafter, referred to as B1202G/S2197Y) and a combination of E1202G and S2204G (hereinafter, referred to as E1202G/S2204G). The E1202G is a mutation in the NS3 protein of the HCV genome. The S2197Y and the S2204G are mutations in the NS5A protein (see FIGS. 8 and 9).

One embodiment of the HCV subgenomic replicon RNA mentioned above is a nucleic acid comprising the 5' UTR of the NC1 strain, a nucleotide sequence encoding the proteins from the NS3 protein to the NS5B protein in the precursor protein, and the 3' UTR. or a nucleic acid comprising the same nucleotide sequences and also having a mutation of S2197Y, S2204G, E1202G/S2197Y, or E1202G/S2204G.

A preferred embodiment of the HCV subgenomic replicon RNA mentioned above is, for example, a nucleic acid comprising the 5' UTR (SEQ ID NO: 2), the NS3 protein coding sequence (SEQ ID NO: 8), the NS4A protein coding sequence (SEQ ID NO: 9), the NS4B protein coding sequence (SEQ ID NO: 10), the NS5A protein coding sequence (SEQ ID NO: 11), the NS5B protein coding sequence (SEQ ID NO: 12), and the 3' UTR (SEQ ID NO: 13), of the full-length HCV genome (SEQ ID NO: 1) of the NC1 strain, and preferably a nucleic acid comprising the 5' UTR, the NS3 protein coding sequence, the NS4A protein coding sequence, the NS4B protein coding sequence, the NS5A protein coding sequence, the NS5JB protein coding sequence, and the 3' UTR, of the full-length HCV genome of the NC1 strain and having a mutation of S2197Y or S2204G or a nucleic acid comprising the 5' UTR, the NS3 protein coding sequence, the NS4A protein coding sequence, the NS4B protein coding sequence, the NS5A protein coding sequence, the NS5B protein coding sequence, and the 3' UTR, of the full-length HCV genome of the NC1 strain and having a mutation of E1202G/S2197Y or E1202G/S2204G.

Another preferred embodiment of the HCV subgenomic replicon RNA mentioned above is, for example, a nucleic acid comprising the 5' UTR, the NS3 protein coding sequence, the NS4A protein coding sequence, the NS4B protein coding sequence, the NS5A protein coding sequence, the NS5B protein coding sequence, and the 3' UTR, of the full-length HCV genome of the NC1 strain and having a mutation of F2161R, R2192L, R2192Q, or Y2871C, and preferably a nucleic acid comprising the 5' UTR, the NS3 protein coding sequence, the NS4A protein coding sequence, the NS4B protein coding sequence, the NS5A protein coding sequence, the NS5B protein coding sequence, and the 3' UTR, of the full-length HCV genome of the NC1 strain and having a mutation of P2161R.

These HCV subgenomic replicon RNAs more preferably each contain the 5' UTR, the NS3 protein coding sequence, the NS4A protein coding sequence, the NS4B protein coding sequence, the NS5A protein coding sequence, the NS5B protein coding sequence, and the 3' UTR arranged in this order from 5' to 3'.

The HCV subgenomic replicon RNA may further contain a drug resistance gene and/or a reporter gene and an IRES sequence. On this occasion, it is preferable to insert the drug resistance gene and/or the reporter gene downstream of the 5' UTR and the IRES sequence further downstream of the gene.

A more preferred embodiment of the HCV subgenomic replicon RNA mentioned above is, for example, a nucleic acid consisting of the nucleotide sequence shown in SEQ ID NO: 16 (the HCV subgenomic replicon RNA of the wild-type NC1 strain) or an RNA which is a nucleic acid comprising the same nucleotide sequence and has a mutation of S2197Y, S2204G,. E1202G/S2197Y, E1202G/S2204G, or P2161R, and more preferably, a nucleic acid consisting of the nucleotide sequence shown in SEQ SO NO: 17 (a sequence having a mutation of S2197Y in the HCV subgenomic replicon RNA of the wild-type NC1 strain). SEQ ID NO: 18 (a sequence having a mutation of S2204G in the HCV subgenomic replicon RNA of the wild-type NC1 strain), or SEQ ID NO: 52 (a sequence having a mutation of P2161R in the HCV subgenomic replicon RNA of the wild-type NC1 strain).

The nucleic acid constituting the HCV subgenomic replicon RNA also includes a nucleic acid which further has another mutation of a nucleotide other than the nucleotide that causes the above-mentioned mutation, which provides replication ability and infectivity equivalent to those of the nucleic acid comprising the mutation mentioned above. Examples of such additional mutation may be substitutions of one or more nucleotides, and the nucleic acid having the additional mutation has a nucleotide sequence homology of 90% or more, preferably 95% or more, and more preferably 97% or more to the original nucleic acid.

(3) Production of HCV Fullgenomic Replicon RNA

The HCV fullgenomic replicon RNA includes the HCV full-length genomic RNA itself. The HCV fullgenomic replicon RNA can be produced by introducing an adaptive mutation that enhances the replication ability of the HCV subgenomic replicon RNA into the HCV full-length genomic RNA derived from the wild-type NC1 strain. Here, the HCV genome in which the above-mentioned adaptive mutation has been introduced into the HCV full-length genomic RNA of the wild-type NC1 strain is called NC1 strain mutant or mutant of NC1 strain.

A mutation may be introduced into the HCV full-length genome of the wild-type NC1 strain by the above-mentioned method or may be introduced by ligating a structural gene portion of the wild-type HCV genome to the subgenomic replicon mutant.

The expression vector used in production of the HCV fullgenomic replicon RNA can be produced by using the technique described in International Publication No. WO05/080575. Specifically, a DNA clone is produced by reconstructing a cDNA corresponding to the full-length genomic RNA of HCV and inserting it downstream of a promoter by a common method. The promoter is preferably contained in a plasmid clone. The promoter such as T7 promoter. SP6 promoter, and T3 promoter can be used, and T7 promoter is preferred. The vector such as pUC19 (TaKaRa Bio Inc.), pBR322 (TaKaRa Bio Inc.), pGEM-T, pGEM-T Easy, pGEM-3Z (each of Promega Corp.), pSP72 (Promega Corp,), pCRII (Invitrogen Corp.), and pT7Blue (Novagen, Inc.) can be used.

The HCV fullgenomic replicon RNA can be produced from an expression vector by synthesizing RNA by means of a polymerase using the produced DNA clone above as a template. In a case of producing the RNA in vitro using a nucleic acid in which HCV cDNA is cloned under control of the T7 promoter as a template, synthesis with, for example. MEGAscript T7 kit (Ambion, Inc.) can be employed. The RNA synthesis can be started from the 5' UTR by a common method. When the DNA clone is a plasmid clone, RNA can also be synthesized using a DNA fragment cleaved out from the plasmid clone with a restriction enzyme as a template. It is preferable that the 3' end of the synthesized RNA coincide with the end of the 3' UTR of the HCV genome RNA and that any other sequence be not added and deleted.

The thus-synthesized RNA is a HCV fullgenomic replicon RNA. Specifically, the HCV fullgenomic replicon RNA is an RNA consisting of the 5' UTR, nucleotide sequences encoding a Core protein, an E1 protein, an E2 protein, a p7 protein, an NS2 protein, an NS3 protein, an NS4A protein, an NS4B protein, an NS5A protein, and an NS5B protein, and the 3' UTR of HCV that are connected in this order from 5' to 3'.

One embodiment of the HCV fullgenomic replicon RNA is a nucleic acid in which an adaptive mutation mentioned above has been introduced into the full-length genomic RNA of the NC1 strain. A preferred embodiment of this HCV fullgenomic replicon RNA is, for example, a nucleic acid comprising the full-length genomic RNA of the NC1 strain (SEQ ID NO: 1), i.e., the 5' UTR (SEQ ID NO: 2), the Core protein coding sequence (SEQ ID NO: 3), the E1 protein coding sequence (SEQ ID NO: 4), the E2 protein coding sequence (SEQ ID NO: 5), the p7 protein coding sequence (SEQ ID NO: 6). the NS2 proiein coding sequence (SEQ ID NO: 7), the NS3 protein coding sequence (SEQ ID NO: 8). the NS4A protein coding sequence (SEQ ID NO: 9), the NS4B protein coding sequence (SEQ ID NO: 10). the NS5A protein coding sequence (SEQ ID NO: 11), the NS5B protein coding sequence (SEQ ID NO: 12), and the 3' UTR (SEQ ID NO: 13), and having a mutation of S2197Y or S2204G, and preferably a nucleic acid comprising the full-length genomic RNA (SEQ ID NO: 1) of the NC1 strain, i.e., the 5' UTR, the Core protein coding sequence, the E1 protein coding sequence, the E2 protein coding sequence, the p7 protein coding sequence, the NS2 protein coding sequence, the NS3 protein coding sequence, the NS4A protein coding sequence, the NS4B protein coding sequence, the NS5A protein coding sequence, the NS5B protein coding sequence, and the 3' UTR, and having a mutation of E1202G/S2197Y or E1202G/S2204G, and more preferably a nucleic acid in which the 5' UTR, the Core protein coding sequence, the E1 protein coding sequence, the E2 protein coding sequence, the p7 protein coding sequence, the NS2 protein coding sequence, the NS3 protein coding sequence, the NS4.A protein coding sequence, the NS4B protein coding sequence, the NS5A protein coding sequence, the NS5B protein coding sequence, and the 3' UTR are arranged in this order from 5' to 3'.

The HCV fuHgenomic replicon RNA may further contain a drug resistance gene and/or a reporter gene and an IRES sequence. On this occasion, it is preferable to insert the drug resistance gene and/or the reporter gene downstream of the 5' UTR and the IRES sequence further downstream of the gene.

A more preferred embodiment of the HCV fullgenomic replicon RNA mentioned above is, for example, an RNA comprising the nucleotide sequence shown in SEQ ID NO: 19 (fullgenomic nucleotide sequence containing a mutation of S2197Y), S.EQ ID NO: 20 (fullgenomic nucleotide sequence containing a mutation of S2204G), SEQ ID NO: 21 (fullgenomic nucleotide sequence containing a mutation of E1202G/S2197Y), or SEQ ID NO: 22 (fullgenomic nucleotide sequence containing a mutation of E1202G/S2204G). Particularly preferred is an RNA comprising the nucleotide sequence shown in SEQ ID NO: 21 (fullgenomic nucleotide sequence containing a mutation of R1202G/S2197Y) or SEQ ID NO: 22 (fullgenomic nucleotide sequence containing a mutation of E1202G/S2204G). Specific examples of the nucleic acid include a nucleic acid consisting of the nucleotide sequence shown in SEQ ID NO: 19 containing a mutation causing substitution of serine at position 2197 with tyrosine; a nucleic acid consisting of the nucleotide sequence shown in SEQ ID NO: 20 containing a mutation causing substitution of serine at position 2204 with glycine; a nucleic acid consisting of the nucleotide sequence shown in SEQ ID NO: 21 containing a mutation causing substitution of serine at position 2197 with tyrosine and a mutation causing substitution of glutamic acid at position 1202 with glycine; and a nucleic acid consisting of the nucleotide sequence shown in SEQ ID NO: 22 containing a mutation causing substitution of serine at position 2204 with glycine and a mutation causing substitution of glutamic acid at position 1202 with glycine.

The transfection of the HCV fullgenomic replicon RNA or the nucleic acid above into HCV-sensitive cells results in autonomous replication of the RNA or the nucleic acid and production of HCV particles. The infection of HCV-sensitive cells with the hepatitis C virus comprising the nucleic acid above as a viral genome results its production of HCV particles. That is, cells transfected with the HCV fullgenomic replicon RNA or the nucleic acid above or cells infected with the hepatitis C virus comprising the nucleic acid above as a viral genome can be used for mass production of HCV particles.

More specifically, HCV particles produced by the HCV-sensitive cells transfected with the HCV fullgenomic replicon RNA or the nucleic acid above or the HCV-sensitive cells infected with the hepatitis C virus comprising the nucleic acid above as the viral genome further infect another HCV-sensitive cell, which enables the replication and packaging of the HCV genomic RNA in the cell, and repeated production of HCV particles. The infection of cells with the HCV particles can be carried out by, for example, adding a culture supernatant of the cells transfected with the HCV fullgenomic replicon RNA or the nucleic acid above to HCV-sensitive cells (e.g., Huh7 cells).

Cells to be transfected with the HCV fullgenomic replicon RNA or the nucleic acid above or cells to be infected with the hepatitis C virus above are preferably cultured cells, which permit replication of HCV replicon RNA or formation of HCV particles. Examples of such cells include the above-mentioned HCV-sensitive cells, and particularly preferred are Huh7 cells and derivative strains of Huh7 cells.

The transfection of cells with the HCV fullgenomic replicon RNA can be performed by any brown methods. Examples of the method include calcium phosphate coprecipitation, a DEAE-dextran method, lipofection, microinjection, and electroporation. Preferred are lipfectlon and electroporation, and more preferred is electroporation.

The replication ability of the transfected HCV fullgenomic replicon RNA can be evaluated by, for example, measuring the function of the foreign gene ligated into the HCV fullgenomic replicon RNA, i.e., measuring the function shown by expression of the gene. In a case where the foreign gene is a drug resistance gene, the replication ability of an HCV fullgenomic replicon RNA can be evaluated by counting the number of cells or the number of colonies of cells propagating on a selective medium containing a corresponding drug. In such a case, a larger number of cells or colonies of cells means higher replication ability. In a case where the foreign gene is an enzyme gene, the replication ability of an HCV fullgenomic replicon RNA can be evaluated by measuring the enzyme activity. In this case, a higher enzyme activity means higher replication ability. Alternatively, the replication ability of an HCV fullgenomic replicon RNA can be directly evaluated by quantifying the amount of replicated RNA by quantitative RT-PCR.

The present invention encompasses the viral genome comprising the nucleic acid and the hepatitis C virus comprising the nucleic acid above as the viral genome.

(4) Production of Infectious HCV Particles

The HCV fullgenomic replicon RNA has HCV particle-producing ability in cultured cells. Whether HCV fullgenomic replicon RNA has HCV particle-producing ability or not can be evaluated by transfecting the RNA into cells and measuring the presence of HCV particles in the culture supernatant of the cells.

The HCV particle-producing ability of cells can be detected by using an antibody against a protein constituting the HCV particles released into the culture supernatant, e.g., the Core protein, the E1 protein, or the E2 protein. The presence of HCV particles can also be indirectly detected by amplifying the HCV fullgenomic replicon RNA in HCV particles in the culture supernatant through RT-PCR using a specific primer.

Whether the produced HCV particles have infectious ability or not can be evaluated by treating HCV-sensitive cells (e.g., Huh7 cells) with the culture supernatant of cells transfected with the HCV fullgenomic replicon RNA, and, e.g., after 48 hours, immunostaining the cells with an anti-Core antibody and counting the number of infected cells, or can be evaluated by subjecting the extract of cells to SDS-polyacrylamide gel electrophoresis and then detecting the Core protein by Western blotting.

It has been reported that when the infectious ability of HCV particles is low, the infectious ability can be detected through evaluation in the presence of a casein kinase I inhibitor. This method can detect infectious ability, but is not practical (Neddermann, P. et al., J. Virol, 2004 vol. 78, pp. 13306-13314).

(5) Production of Chimeric HCV Particles

Chimeric form of HCV particles (chimeric HCV particles) are HCV particles produced by a chimeric form of HCV genome (chimeric HCV genome) or a chimeric form of HCV fullgenomic replicon RNA (chimeric HCV fullgenomic replicon RNA) comprising HCV genomic sequences derived from two or more different strains.

The chimeric HCV genome is characterized by a chimeric gene of HCV comprising non-structural genes of a mutant of NC1 strain (NC1 strain having an adaptive mutation introduced) and structural genes of another HCV strain (an HCV strain different from the NC1 strain and the mutants of NC1 strain). Specifically, the mutant of NC1 strain to be used in the preparation of the chimeric HCV genome above contains a mutation of S2197Y, S2204G, E1202G/S2197Y, or E1202G/S2204G in the NC1 strain. More specifically, the mutant of NC1 strain is an RNA comprising the nucleotide sequence shown in SEQ ID NO: 19 (fullgenomic nucleotide sequence containing a mutation of S2197Y), SEQ ID NO: 20 (fullgenomic nucleotide sequence containing a mutation of S2204G), SEQ ID NO: 21 (fullgenomic nucleotide sequence containing a mutation of E1202G/S2197Y), or SEQ ID NO: 22 (fullgenomic nucleotide sequence containing a mutation of E1202G/S2204G).

The chimeric HCV genome can be produced by, for example, recombining structural genes in the genome of a mutant of NC1 strain, i.e., sequences encoding the Core protein, the E1 protein, the E2 protein, and the p7 protein with the structural genes of another HCV strain. This basic technique is described in, for example, Wakita, T. et al., Nat. Med., 2005, vol, 11, pp. 791-796; Lindenbach, B. D. et al., Science, 2005, vol. 309, pp. 623-626:Pietschmann, T. et al., Proc. Natl. Acad. Sci. U.S.A., 2007, vol, 103, pp. 7408-7413.

According to the phylogenetic analysis using nucleotide sequences of HCV strains, HCV is classified into six types including genotypes 1 to 6, each of which is further classified into several subtypes. Furthermore, the nucleotide sequences of the full-length genomes of some genotypes of HCV have been determined (Simmonds, P. et al., Hepatology, 1994, vol. 10, pp, 1321-1324; Choo, Q. L. et al., Science, 1989, vol. 244, pp. 359-362:Okamoto, H. et al., J. Gen. Virol., 1992, vol. 73. pp. 73-679; Mori, S. et al., Biochem. Biophys. Res. Commun., 1992, vol. 183. pp. 334-342). With respect to examples of known HCV strains of which genome sequences are revealed, specific examples of HCV strain of genotype 1a include H77 strain (GenBank Accession No. AF011751); specific examples of HCV strain of genotype 1b include J1 strain (GenBank Accession No. D89815), Con1 strain (GenBank Accession No. AJ238799, also referred to as Con-1 strain or con1 strain), and TH strain (Wakita, T. et al., J. Biol. Chem., 1994, vol. 269. pp. 14205-14210:JP Patent Publication (Kokai) No. 2004-179 A); specific examples of HCV strain of genotype 2a include JFH-1 strain (GenBank Accession No. AB047639, also referred io as JFH1 strain), J6CF strain (GenBank Accession No, AP177036), JCH-1 (GenBank Accession No. AB047640), JCH-2 (GenBank Accession No, AB04764), JCH-3 (GenBank Accession No. AB047632), JCH-4 (GenBank Accession No, AB047643), JCH-5 (GenBank Accession No. AB047644), and JCH-6 (GenBank Accession No. AB047645); specific examples of HCV strain of genotype 2b include HC-J8 strain (GenBank Accession No. D01221); specific examples of HCV strain of genotype 3a include NZL1 strain (GenBank Accession No. D17763) and S52 (GenBank Accession No. GU814263); specific examples of HCV strain of genotype 3b include Tr-Kj (GenBank Accession No, D49374); and specific examples of HCV strain of genotype 4a include ED43 (GenBank Accession No, Y11604). A list of GenBank Accession numbers of other strains has also been reported (Tokita. T. et al., J. Gen. Virol., 1998, vol. 79. pp. 1847-1857; Cristina, J. & Colina, R., Virol. J., 2006. vol. 3. pp. 1-8).

The chimeric HCV genome is a nucleic acid comprising a HCV-derived chimeric gene in which nucleotide sequences encoding a Core protein, an E1 protein, an E2 protein, and a p7 protein derived from an HCV strain other than the NC1 strain and mutants of NC1 strain; an NS2 protein derived from a mutant of NC1 strain or an HCV strain other than the NC1 strain and the mutants of NC1 strain; and an NS3 protein, an NS4A protein, an NS4B protein, an NS5A protein, and an NS5B protein derived from a mutant of NC1 strain, are arranged from the 5' side to the 3' side in an order of the nucleotide sequences encoding the Core protein, the E1 protein, the E2 protein, the p7 protein, the NS2 protein, the NS3 protein, the NS4A protein, the NS4B protein, the NS5A protein, and the NS5B protein. The NS2 protein may be a chimeric from of NS2 protein (chimeric NS2 protein) of the NS2 protein of a mutant of NC1 strain and an NS2 protein derived from an HCV strain other than the NC1 strain and mutants of NC1 strain. Here, the HCV strain other than the NC1 strain of HCV and mutants of NC1 strain is preferably one mentioned above as known strains of HCV.

Here, the chimeric NS2 protein is a NS2 protein in which a past of the amino acid sequence of the NS2 protein of a mutant of NC1 strain and a part of the amino acid sequence of an NS2 protein derived from an HCV strain other than the NC1 strain and mutants of NC1 strain are connected to each other to form a full-length amino acid sequence of NS2 as a whole. In the nucleic acid of the chimeric HCV genome above, the NS2 protein may be derived from a mutant of NC1 strain or may be a chimeric NS2 protein consisting of a pari of the NS2 protein derived from an HCV strain other than the NC1 strain and mutants of NC1 strain, and the remaining portion of the NS2 protein derived from a mutant of NC1 strain. In this case, the chimeric NS2 protein has the same function as that of the NS2 protein that is not a chimera. For example, if the part of the NS2 protein derived from an HCV strain other than the NC1 strain and mutants of NC1 strain consists of a nucleotide sequence encoding the N-terminal amino acid residue to the amino acid residue at position 16 of the NS2 protein, the remaining portion of the NS2 protein derived from the mutant of NC1 strain consists of a nucleotide sequence encoding the amino acid residue at position 17 from the N-terminus to the amino acid at the C-terminus.

The nucleic acid of the chimeric HCV genome preferably further comprises a 5' UTR on the 5' side of the nucleotide sequence encoding the Core protein and a 3' UTR on the 3' side of the region encoding the NS5B protein. The 5' UTR and/or the 3' UTR may be a sequence derived from any HCV strain and are preferably a 5' UTR derived from an HCV strain other than the NC1 strain and mutants of NC1 strain and a 3' UTR derived from a mutant of NC1 strain.

In the chimeric HCV genome, the HCV strain other than the NC1 strain and mutants of NC1 strain, i.e., a known HCV strain is a strain belonging to genotype 1a, 1b, or 2a. Examples of the strain belonging to genotype 1a include the H77 strain. Examples of the strain belonging to genotype 1b include the TH strain, the Con1 strain, the J1 strain, and derivative strains thereof. Examples of the strain belonging to genotype 2a include the JFH-1 strain and the J6CF strain. Preferred strains are the JFH-1 strain, the J6CF strain, and the TH strain. Particularly preferred is the JFH-1 strain. The genomic nucleotide sequence information of HCV strains other than the NC1 strain and mutants of NC1 strain is available from the documents mentioned above or GenBank.

Figure 12:
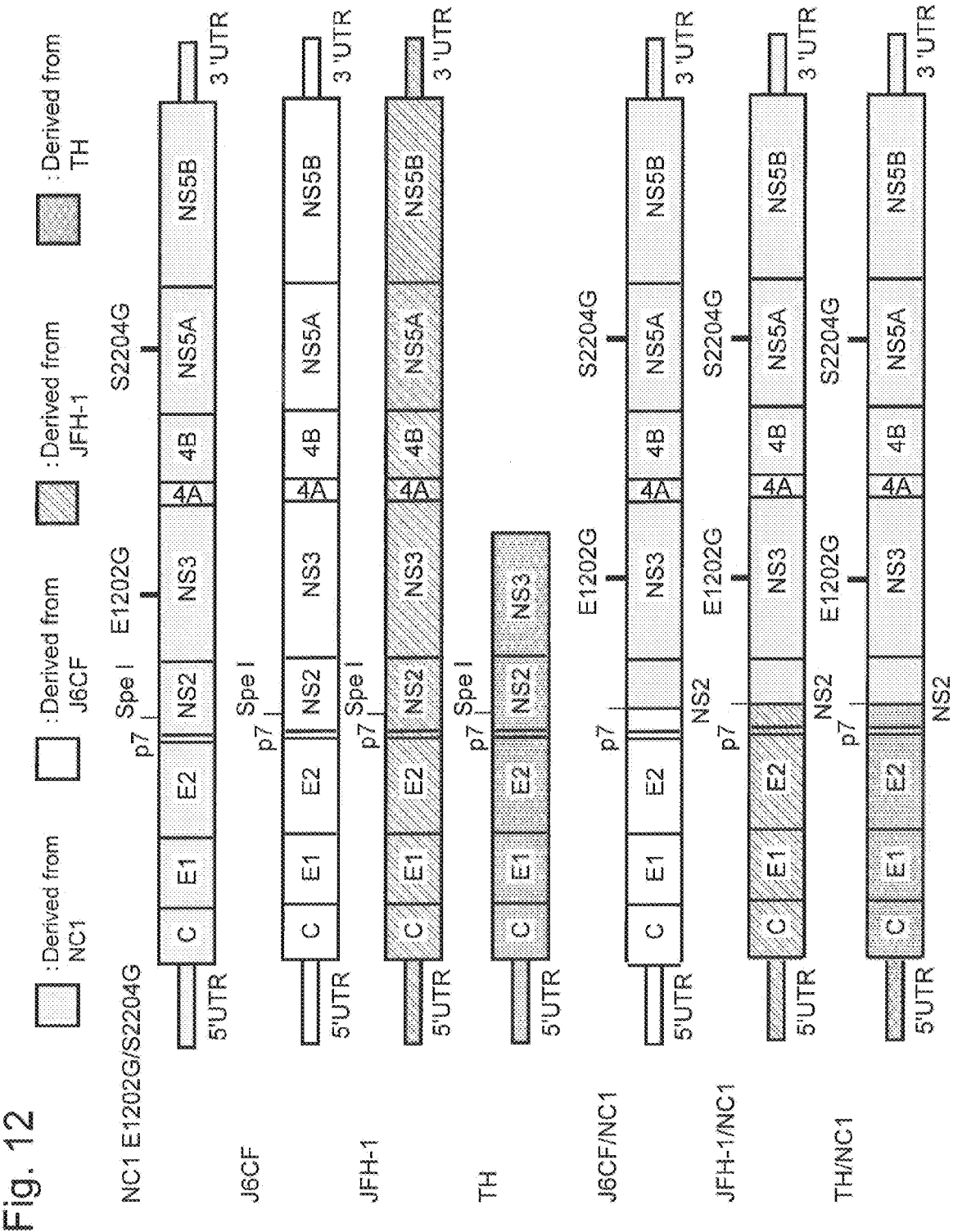
FIG. 12 is a diagram showing the structures of the HCV genomes of a mutant of the NC1 strain (NC1 strain having adaptive mutations), a J6CF strain, a JFH-1 strain, and a TH strain and the structures of chimeric HCV genomes each comprising non-structural genes of the mutant of NC1 strain (NC1 strain having adaptive mutations) and structural genes of the J6CF strain, the JFH-1 strain, or the TH strain.

The nucleic acid of the chimeric HCV genome may be a chimeric nucleic acid derived from the J6CF strain and the NC1 strain and has a mutation of S2197Y, S2204G, E1202G/ S2197Y, or E1202G/S2204G. The nucleic acid of the chimeric HCV genome may be a chimeric nucleic acid derived from the JFH-1 strain and the NC1 strain and has a mutation of S2197Y, S2204G, E1202G/S2197Y, or E1202G/S2204G. The nucleic acid of the chimeric HCV genome may be a chimeric nucleic acid derived from the TH strain and the NC1 strain and has a mutation of S2197Y. S2204G, E1202G/ S2197Y, or E1202G/S2204G, FIG. 12 shows the siructiues of the HCV genomes of the mutant of NC1 strain (NC1 strain having an adaptive mutation of E1202G/S2204G introduced), the J6CF strain, the JFH-1 strain, and the TH strain, and the structures of chimeric HCV genomes comprising the non-structural genes of the mutant of NC1 strain (NC1 strain having an adaptive mutation of E1202G/S2204G introduced) and the structural genes of the J6CF strain, the JFH-1 strain, or the TH strain.

The present invention provides an HCV viral genome comprising the nucleic acid (chimeric gene), a hepatitis C virus containing the nucleic acid as the viral genome, an HCV fullgenomic replicon RNA, an expression vector, and chimeric HCV particles. The chimeric HCV particles have characteristics that they can be highly efficiently produced in a cell culture system and that they have high infectivity.

The chimeric HCV gene can be produced by performing PCR to amplify the target regions of HCV genes using vectors comprising cloned cDNAs of the respective HCV genomic RNAs as templates and synthetic DNAs as primers and ligating the regions.

Furthermore, an expression vector for synthesizing an HCV genomic RNA can he produced by ligating the chimeric HCV gene cDNA into an appropriate restriction enzyme site downstream of a promoter such as a T7 promoter. Viral replication and packaging occur by transfecting the RNA transcribed from this expression vector into HCV-sensifive cells (e.g. Huh7 cells) to produce infectious HCV particles.

The replication ability in cells and the HCV particle-producing ability of the HCV fullgenomic replicon RNA comprising the chimeric HCV gene and the infectivity of the produced HCV particles can be confirmed by the methods described in the previous sections (3) and (4).

(6) Use of HCV subgenomic replicon RNA

The cells transfected with the HCV subgenomic replicon RNA can be used in screening for a compound that inhibits replication of the HCV subgenomic replicon RNA. That is, it is possible to screen for an anti-HCV substance by culturing the cells transfected with the HCV subgenomic replicon RNA in the presence of a test substance and detecting produced replicon RNA in the culture. Here, the culture includes culture supernatant and cell lysate. When the replicon RNA is not present in the culture or the amount of which is less than that in the absence of the test substance, the test substance is determined to be capable of inhibiting the replication of the HCV subgenomic replicon RNA.

For example, an HCV subgenomic replicon RNA, which is an RNA consisting of the 5' UTR (SEQ ID NO: 2), 36 nucleotides of the Core protein coding sequence (SEQ ID NO: 3), a luciferase gene, an EMCV IRES sequence, an NS3 protein coding sequence (SEQ ID NO: 8), an NS4A protein coding sequence (SEQ ID NO: 9), an NS4B protein coding sequence (SEQ ID NO: 10), an NS5A protein coding sequence (SEQ ID NO: 11), an NS5B protein coding sequence (SEQ ID NO: 12), and a 3' UTR (SEQ ID NO: 13), of the NC1 strain or its mutant, that are connected in this order from 5' to 3', is transfected into Huh7 cells, followed by addition of a test substance thereto. After 48 to 72 hours, the activity of luciferase is measured. If a test substance can inhibit the luciferase activity compared to the activity in the absence of the test substance, the test substance is determined to have an activity to inhibit replication of the HCV subgenomic replicon RNA.

(7) Use of HCV Particles

HCV particles (including chimeric HCV particles) obtained by transfection of the nucleic acid above or the HCV fullgenomic replicon RNA above into HCV-sensitive cells and the like can be used in screening for a neutralizing antibody or a compound that inhibits infection with HCV and screening for a compound that inhibits replication of HCV and also can be suitably used as a vaccine or as an antigen for producing an anti-HCV antibody.

The HCV particles can be used in screening for a substance that inhibits the infection or replication of HCV by, for example, culturing the cells producing the HCV particles or culturing the HCV particles with HCV-sensitive cells, i.e., culturing a mixture of the HCV particles and HCV-sensitive cells, or culturing HCV-infected cells that are infected with the HCV particles, in the presence or absence of a test substance, and detecting the HCV replicon RNA or HCV particles in the resulting culture. Here, the detection means quantitative measurement of the amount of the HCV replicon RNA or the HCV particles in Use culture. When the HCV replicon RNA or the HCV particles are not present in the culture or the amount of which is less than that in the absence of the test substance, the test substance is determined to be capable of inhibiting the infection or replication of HCV.

Specifically, for example, it is possible to screen for an anti-HCV substance by culturing HCV-sensitive. cells together with the HCV particles above in the presence or absence of a test substance, detecting the HCV replicon RNA or HCV particles in the resulting culture, and determining whether the test substance inhibits the replication of the HCV replicon RNA or the formation of the HCV particles.

The HCV replicon RNA in the culture can be detected by, for example, measuring the function of a foreign gene ligated into the HCV replicon RNA, i.e., the function shown by expression of the gene. In a case where the foreign gene is an enzyme gene, the HCV replicon RNA can be detected by measuring the enzyme activity. In another method, the HCV replicon RNA can be detected by quantifying the amount of replicated RNA by quantitative RT-PCR.

The presence of the HCV particles in the culture can also be indirectly detected by detecting a protein (e.g., the Core protein, the E1 protein, or the E2 protein) constituting the HCV particles released in the culture solution with an antibody against the protein; detecting the presence of a non-structural protein in the infected cells via immunostaining with an antibody against the non-structural protein; or amplifying the HCV genomic RNA in the HCV particles in the culture supernatant by RT-PCR using a specific primer and detecting it.

A specific example of the HCV fullgenomic replicon RNA comprising a foreign gene to be used in the screening is an HCV fullgenomic replicon RNA consisting of the 5' UTR of a mutant of NC1 strain, 36 nucleotides of the Core protein coding sequence, a luciferase gene, an EMCV IRES sequence, a Core protein coding sequence, an E1 protein coding sequence, an E2 protein coding sequence, a p7 protein coding sequence, an NS2 protein coding sequence, an NS3 protein coding sequence, an NS4A protein coding sequence, an NS4B protein coding sequence, an NS5A protein coding sequence, an NS5B protein coding sequence, and a 3' UTR that are connected in this order from 5' to 3'. In the connection of each nucleotide sequence, the connection site may contain an additional sequence such as a restriction enzyme site. The HCV fullgenomic replicon RNA is transfected into Huh7 cells to generate HCV particles, HCV-sensitive cells are infected with the HCV particles simultaneously with addition of a test substance, and the activity of luciferase is measured after 48 to 72 hours. A substance that inhibits the luciferase activity compared to that in the absence of the test substance is determined to have an activity to inhibit infection with HCV.

In the method described above, an anti-HCV substance is selected as one that can inhibit infection or replication of a virus.

In addition, in the method described above, a viral genome comprising the nucleic acid above and a hepatitis C virus comprising the nucleic acid as a viral genome can also be used.

Furthermore, the HCV particles can be used as a vaccine. In the use as a vaccine, specifically, the HCV particles or a part thereof may be directly used as a vaccine, but it is preferable to use them after attenuation or inactivation by a method known in the art. The virus can be inactivated by adding an inactivating agent such as formalin, β-propiolactone, or glutaraldehyde to, for example, a virus suspension and mixing them for reacting the agent with the virus (Appaiahgari, M. B. & Vrati S., Vaccine, 2004, vol. 22, pp. 3669-3675).

The HCV vaccine can be prepared as an administerable solution or suspension or can be prepared in a form of a solid (e.g., lyophilized preparation) suitable for dissolution or suspension in a liquid for being reconstituted immediately before the use. Such a solid or a preparation may be emulsified or capsulated in liposome.

The active immunogenic ingredient such as HCV particles can be often mixed with a pharmaceutically acceptable excipient that is compatible with the active ingredient. Suitable examples of the excipient include water, saline, dextrose, glycerol, ethanol, and mixtures thereof.

Furthermore, the HCV vaccine can optionally contain a small amount of an auxiliary agent (e.g., a humidifier or emulsifier), a pH adjuster, and/or an adjuvant for enhancing vaccine efficacy.

The adjuvant is a non-specific stimulant to the immune system. It enhances the immune response of a host against HCV vaccines. Accordingly, in a preferred embodiment the HCV vaccine contains an adjuvant. Efficacy of an adjuvant can be determined by measuring the amount of antibodies generated by administration of a vaccine based on HCV particles.

Examples of the effective adjuvant include, but not limited to, the followings: aluminum hydroxide, N-acetyl-muramyl-L-threonyl-D-isoglutamine (thr-MDP), N-acetyl-nor-muramyl-L-alanyl-D-isoglutamine (referred to as CGP11637 or nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (referred to as CGP19835A or MTP-PE), and RIBI. The RIBI contains three components extracted from bacteria, i.e., monophosphoryl lipid A, trehalose dimycolate, and cell wall skeleton (HPL+TDM+CWS), in 2% squalene/Tween® 80 emulsion.

The HCV vaccine can optionally contain one or more compounds having adjuvant activity. Specific examples of the adjuvants that are known in the art include Freund's complete adjuvants and Freund's incomplete adjuvants, vitamin E, nonionic block polymers, muramyl dipeptide, saponin, mineral oil, vegetable oil, and Carbopol. Examples of adjuvants that are particularly suitable for mucosal application include *Escherichia coli* (*E. coli*) thermolabile toxin (LT) and Cholera toxin (CT). Examples of other adequate adjuvants include aluminum hydroxide, aluminum phosphate, aluminum oxide, oil emulsion (e.g., Bayol® or Marcol 52®), saponin, and vitamin E solubilizates.

The HCV vaccine is generally administered parenterally, for example, by injection such as subcutaneous injection or intramuscular injection. Examples of other formulations that are suitable as other dosage forms for administration include suppositories and, optionally, oral preparations.

In injections for subcutaneous, intracutaneous, intramuscular, or intravenous administration, specific examples of the pharmaceutically acceptable carrier or diluent for the HCV vaccine include stabilizers, carbohydrates (e.g., sorbitol, mannitol, starch, sucrose, glucose, and dextran), proteins such as albumin and casein, protein-containing substances such as bovine serum and skimmed milk, and buffers (e.g., phosphate butter).

Examples of conventional binder and carrier that are contained in suppositories can include polyalkylene glycol and triglyceride. Such a suppository can be prepared from a mixture containing an active ingredient in a range of 0.5% to 50%, preferably in a range of 1% to 20%. The oral preparations contain common excipients. Examples of the excipients include pharmaceutical grade mannitol, lactose, starch, magnesium stearate, saccharine sodium, cellulose, and magnesium carbonate.

The HCV vaccine is in a form of solution, suspension, tablet, pill capsule, sustained-release dosage, or powder and contains 10% to 95%, preferably 25% to 70%, of an active ingredient (HCV particles or a part thereof). The HCV vaccine is administered by a method suitable for the dosage form and in an amount of showing a preventive and/or therapeutic effect. The amount of an antigen to be administered is usually in a range of 0.01 µg to 100,000 µg per one administration and depends on the patient to whom the vaccine is administered, the antibody-producing ability in the immune system of the patient, and the degree of protection intended. The amount also depends on the administration route such as oral, subcutaneous, intracutaneous, intramuscular, or intravenous administration.

The HCV vaccine may be administered in a single-administration schedule or a multiple-administration schedule, preferably in a multiple-administration schedule. In the multiple-administration schedule, one to ten separate administrations are performed at the time of initiation of inoculation, and another administration can be subsequently performed with the time interval that is necessary for maintaining and/or enhancing the immune response. For example, the second administration can be performed one to four months later. Administration may optionally also be subsequently performed several months later. The administration regimens are, at least partially, determined depending on the necessity of an individual, and the regimens depend on the judgment made by a doctor. The HCV vaccine may be administered to a healthy individual to induce an immune response to HCV in the healthy individual for preventing new HCV infection. Furthermore, the vaccine may be administered to a patient infected with HCV to induce a potent immune response to HCV in vivo, and thus the vaccine may be used as a therapeutic vaccine which eliminates HCV.

The HCV particles are also useful as an antigen for producing an anti-HCV antibody. The antibody can be produced by administering the HCV particles to a mammal or a bird. Examples of the mammal include mouse, rat, rabbit, goat, sheep, horse, cattle, guinea pig, dromedary, Bactrian camel, and lama. Dromedary, Bactrian camel, and lama are suitable for producing an antibody consisting of the H chain alone. Examples of the bird include chicken, geese, and ostrich. Serum is collected from the animal to which the HCV particles have been administered, and the antibody of interest can be obtained therefrom by a known method.

The present invention also provides such an anti-HCV antibody, which can be used as a neutralizing antibody that can inactivate HCV.

Animal cells immunized with the HCV particles can be used for producing hybridomas that produce monoclonal antibody-producing cells. The hybridomas can be produced by a well-known method such as the method described in Antibodies: A Laboratory Manual (Cold Spring Harbor Laboratory, 1988).

The monoclonal antibody-producing cells may be produced via cell fusion or another procedure such as immortalization of B lymphocytes by introduction of an oncogene DNA or infection with Epstein-Barr virus.

Monoclonal or polyclonal antibodies obtained by these methods are useful for diagnosis, therapy, and prevention of HCV.

The antibody produced by using the HCV particles as an antigen can be administered as a drug together with a pharmaceutically acceptable solubilizer. additive, stabilizer, buffer or the like. Any administration route may be used and preferably subcutaneous, intracutaneous, or intramuscular administration, and more preferably intravenous administration.

EXAMPLES

The present invention will now be described in more detail with reference to examples. It should be noted that these examples are provided for illustrative purposes and the technical scope of the present invention is not limited to these examples.

Example 1

Construction of HCV Subgenomic Replicon RNA Expression Vector of Wild-type NC1 Strain An HCV subgenomic replicon RNA expression vector, plasmid pSGR-NC1, was constructed using the non-structural region of a cloned DNA (full-length genomic clone DNA) corresponding to the full-length genomic RNA of the NC1 strain, which is a novel HCV of genotype 1b separated from an acute severe hepatitis C patient.

Specifically, RNA was extracted from patient's serum and purified with Isogen-LS (Nippon Gene Co., Ltd.), and cDNA was synthesized using a random hexamer primer. PCR primers were designed based on the conserved sequence (Con1 strain: GenBank Accession No. AJ238799) of a known HCV genome of genotype 1b. Five fragments of cDNA were amplified using the designed PCR primers and the synthesized cDNA as a template. The amplification product of the sequence at the 5' end, which is difficult to obtain, was obtained by a 5' RACE method. Each fragment was cloned into a cloning vector for sequencing, pGEM-T EASY (Promega Corp.). The nucleotide sequences of these clones were analyzed by a common method to determine the full-length genomic RNA sequence of the NC1 strain.

The nucleotide sequence of the full-length genomic clone DNA of the NC1 strain is shown in SEQ ID NO: 1. The 5' UTR of the NC1 strain is shown in SEQ ID NO: 2, the Core protein coding sequence is shown in SEQ ID NO: 3, the E1 protein coding sequence is shown in SEQ ID NO: 4, the E2 protein coding sequence is shown in SEQ ID NO: 5, the p7 protein coding sequence is shown in SEQ ID NO: 6, the NS2 protein coding sequence is shown in SEQ ID NO: 7, the NS3 protein coding sequence is shown in SEQ ID NO: 8, the NS4A protein coding sequence is shown in SEQ ID NO: 9, the NS4B protein coding sequence is shown in SEQ ID NO: 10, the NS5A protein coding sequence is shown in SEQ ID NO: 11, the NS5B protein coding sequence is shown in SEQ ID NO: 12. and the 3' UTR is shown in SEQ ID NO: 13.

The amino acid sequence of the HCV precursor protein (polypeptide) encoded by the nucleotide sequence of SEQ ID NO: 1 is shown in SEQ ID NO: 14. The amino acid sequence shown in SEQ ID NO: 14 is encoded by the sequence of nucleotide numbers from 342 to 9374 (including a stop codon) of the nucleotide sequence of SEQ ID NO: 1. The amino acid sequence of the region from the NS3 protein to the NS5B protein in the precursor protein of the NC1 strain is shown in SEQ ID NO: 15. This amino acid sequence (NS3 to NS5B region) of SEQ ID NO: 15 corresponds to the amino acids from position 1027 to 3010 of the amino acid sequence shown in SEQ ID NO: 14.

Plasmid pSGR-NC1 was constructed in accordance with the procedure described in the document by Kato et al. (Gastroenterology, 2003, vol 125, pp. 1808-1817) and International Publication No. WO05/028652.

Specifically, first, the cDNA of the full-length genomic RNA (FIG. 1A) of the NC1 strain was inserted into a plasmid vector pUC19 under control of the T7 promoter to produce a recombinant plasmid pNC1 (FIG. 1B). Subsequently, the structural region (Core protein, E1 protein, E2 protein, and p7 protein) and a part of the non-structural region of the recombinant plasmid pNC1 were substituted with a neomycin resistance gene (neo: also referred to as neomycin phosphotransferase gene) and an EMCV IRES (internal ribosome entry site of encephalomyocarditis virus) to construct a plasmid pSGR-NC1, which was used as expression vector pSGR-NC1.

FIG. 1C shows the structure of the expression vector pSGR-NC1. In the expression vector pSGR-NC1, the 5'UTR, the 36 nucleotides of the Core protein coding sequence (HCV-IRES), the NS3 to NS5B protein coding sequences, and the 3' UTR are sequences derived from the NC1 strain. In the Figure, "T7" denotes the T7 promoter. The T7 promoter is a sequence element necessary for transcribing the HCV subgenomic replicon RNAs from the respective expression vectors using the T7 RNA polymerase. The "neo" denotes a neomycin resistance gene, "EMCV IRES" denotes the internal ribosome entry site of encephalomyocarditis virus, "C" denotes a Core protein, "E1" denotes an E1 protein, "E2" denotes an E2 protein, "p7" denotes a p7 protein, "NS2" denotes an NS2 protein, "NS3" denotes an NS3 protein, "4A" denotes an NS4A protein, "4B" denotes an NS4B protein, "NS5A" denotes an NS5A protein, and "NS5B" denotes an NS5B protein. As shown in FIG. 1D, the HCV subgenomic replicon RNA (HCV subgenomic replicon RNA of the NC1 strain) produced from the expression vector pSGR-NC1 is the RNA produced by transcription of the region downstream of the T7 promoter. In the Figure, "XbaI" and "PmeI" indicate restriction enzyme sites. The same applies to FIGS. 3, 4. 6, 8, 9, and 13.

The cDNA of the NC1 subgenomic replicon RNA is ligated to downstream of the T7 promoter of the expression vector pSGR-NC1. The cDNA nucleotide sequence of the HCV subgenomic replicon RNA of the NC1 strain is shown in SEQ ID NO: 16. The amino acid sequence shown in SEQ ID NO: 15 is the region from the NS3 protein to the NS5B protein of the NC1 strain, which is encoded by the sequence of nucleotide numbers from 3420 to 9374 (including a stop codon) of the nucleotide sequence of SEQ ID NO: 1.

Example 2

Production of HCV Subgenomic Replicon RNA of Wild-type NC1 Strain

The expression vector pSGR-NC1 constructed in Example 1 was cleaved with restriction enzyme XbaI. Subsequently, 20 U of Mung Bean Nuclease was added to 10 to 20 μg of the XbaI cleaved fragment (the total amount of the reaction solution: 50 μL), followed by incubation at 30° C. for 30 minutes. Mung Bean Nuclease is an enzyme that catalyzes a reaction of smoothing through selective decomposition of the single-stranded portion of a double-stranded DNA. In general, RNA transcription by an RNA polymerase directly using the XbaI cleaved fragment as a template DNA synthesizes a replicon RNA having extra four nucleotides CUAG, a part of the XbaI recognition sequence, on the 3' end. In this Example, accordingly, the XbaI cleaved fragment was treated with Mung Bean Nuclease to remove the four nucleotides CTAG from the XbaI cleaved fragment.

Subsequently, proteins in the Mung Bean Nuclease treated solution containing the XbaI cleaved fragment was removed by a common method to obtain purified XbaI cleaved fragment not having four nucleotides CTAG, which was used as a template DNA in the subsequent reaction. RNA was synthesized in vitro from this template DNA through transcription reaction using the T7 promoter with MEGAscript® available from Ambion, Inc. Specifically, 20 μL of a reaction solution containing 0.5 to 1.0 μg of the template DNA was prepared in accordance with the instructions for use of the manufacturer, followed by reaction at 37° C. for 3 to 16 hours.

After completion of the RNA synthesis, the template DNA was removed by adding DNase (2 U) to the reaction solution and performing a reaction at 37° C. for 15 minutes, and then RNA extraction was performed with acidic phenol to obtain the HCV subgenomic replicon RNA of the NC1 strain (FIG. 1D) transcribed from the pSGR-NC1.

Example 3

Establishment of HCV Subgenomic Replicon-replicatiug Cell Clone of the NC1 Strain Total cellular RNA extracted from Huh7 cells by a common method was mixed with 1 μg of the HCV subgenomic replicon RNA of the wild-type NC1 strain produced in Example 2 and the total RNA amount was adjusted to 10 μg. Subsequently, the RNA mixture was transfected into Huh7 cells by electroporation. The electroporated Huh7 cells were seeded in a culture dish and were cultured for 16 to 24 hours, and G418 (neomycin) was then added to the culture dish. The culture was continued while replacing the culture solution twice a week.

Figure 2:
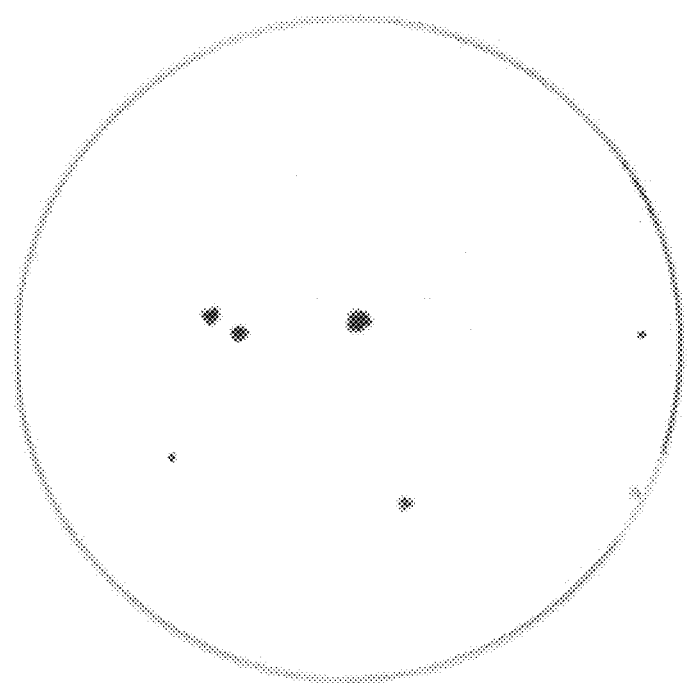
FIG. 2 shows the results of formation of colonies of cells transfected with the HCV subgenomic replicon RNA of the wild-type NC1 strain.

After the culture for 21 days after the seeding, viable cells were stained with crystal violet. As a result colony formation of the cells transfected with the HCV subgenomic replicon RNA of the NC1 strain was confirmed. The colony formation indicates that the HCV subgenomic replicon RNA was replicated in the cells (FIG. 2).

The colonies of viable cells were further cloned from the culture dish after 21 days of the culture, and the culture of the subgenomic replicon RNA-transfected cells forming colonies was continued. The cloning of the colonies established some strains of cell clones. These cell clones were designated as NC1 subgenomic replicon cells. It is thought that in the thus-established cell clones, the transfected HCV subgenomic replicon RNA of the NC1 strain autonomously replicates.

Example 4

Sequence Analysis of HCV Subgenomic Replicon RNA in NC1 Subgenomic Replicon Cell Sequence analysis of the HCV subgenomic replicon RNA present in the NC1 subgenomic replicon cell established in Example 3 was performed. First, total RNA was extracted from 32 clones of the NC1 subgenomic replicon cells, and the HCV subgenomic replicon RNA contained in the RNA was amplified by RT-PCR. The amplification was performed using 5'-TAATACGACTCACTATAG-3' (SEQ ID NO: 27) and 5'-GCGGCTCACGGACCTTTCAC-3' (SEQ ID NO: 28) as primers. The amplification product was cloned Into a cloning vector for sequencing and was subjected to common sequence analysis.

Figure 3:
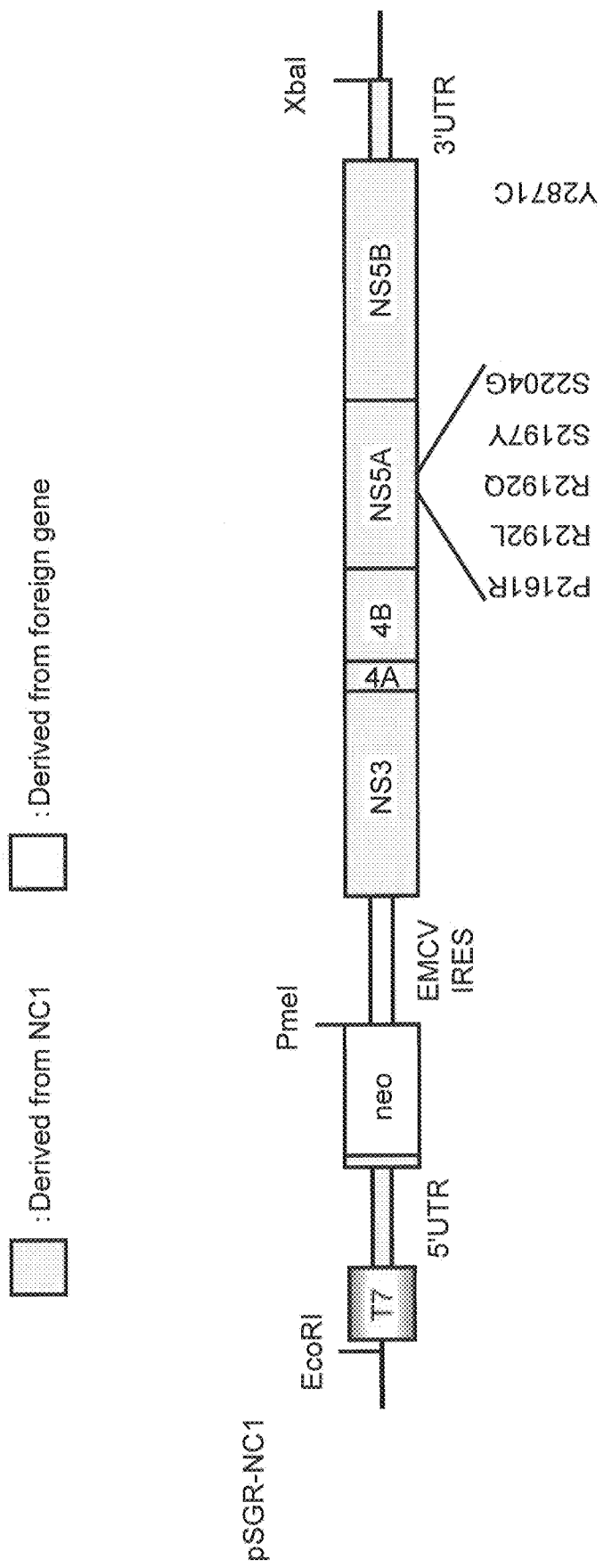
FIG. 3 is a diagram showing the positions of amino acid substitutions (mutations) identified in HCV subgenomic replicon-replicating cells of the wild-type NC1 strain, on the pSGR-NC1.

As a result, nucleotide substitutions that cause amino acid substitutions were found in HCV subgenomic replicon RNA obtained from the cells: five substitutions (P2161R, R2192L, R2192Q, S2197Y, and S2204G) in the NS5A protein region and one substitution (Y2871C) in the NS5B protein region that are non-structural regions. The positions of these amino acid substitutions on the expression vector pSGR-NC1 are shown in FIG. 3. These positions of the amino acid substitutions are shown based on the full-length amino acid sequence of the precursor protein of the NC1 strain (SEQ ID NO: 14).

Example 5

Mutation Induction into HCV Subgenomic Replicon RNA of Wild-type NC1 Strain and Analysis Thereof Influence of the nucleotide substitutions, i.e., nucleotide mutation found in Example 4, on the replication of the HCV subgenomic replicon RNA of the wild-type NC1 strain in cells was investigated.

The nucleotide substitutions that cause amino acid substitutions, i.e., five substitutions (P2161R, R2192L, R2192Q, S2197Y, and S2204G) in the NS5A protein region and one substitution (Y2871C) in the NS5B protein region, respectively, were each introduced into the HCV subgenomic replicon RNA expression vector pSGR-NC1 of the NC1 strain produced in Example 1.

Figure 4:
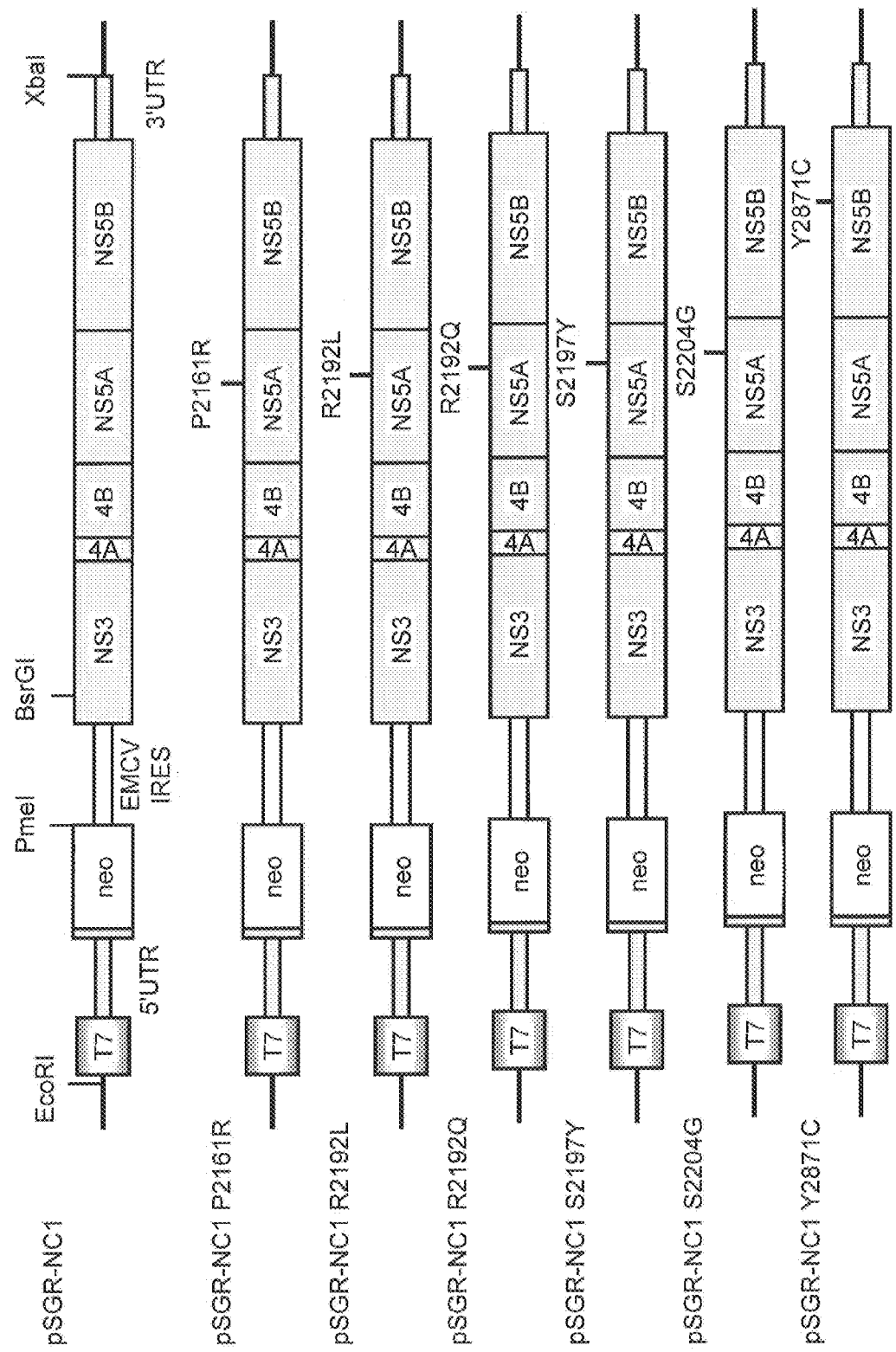
FIG. 4 is a diagram showing the structures of expression vectors for synthesizing HCV subgenomic replicon RNAs of mutants of NC1 strain.

FIG. 4 shows the structures of the HCV subgenomic replicon RNA expressing plasmid vectors having the amino acid substitutions introduced. The expression vector pSGR-NC1 having P2161R substitution introduced is called "pSGR-NC1 P2161R." Expression vectors having other amino acid substitutions introduced were called in the same way. In the Figure, "EcoRI," "PmeI," "BsrGI," and "XbaI" indicate restriction enzyme sites.

Specifically, nucleotide substitutions were introduced into pSGR-NC1 by repeating PCR using the pSGR-NC1 and its PCR product as template DNAs. The PCR conditions were as follows. First to the template DNAs for PCR were added 10 µL of 5× buffer and 4 µL of 2.5 mM dNTPs mixture attached to a Phusion® High-Fidelity DNA Polymerase kit (FINNZYMES), and 0.25 µL each of 100 µM primers (forward and reverse primers) then deionized water to adjust the final total amount to 49.5 µL. Subsequently, 0.5 µL of Phusion® DNA Polymerase (FINNZYMES) was added, and PCR was performed for 30 cycles where one cycle consists of 98° C. for 10 seconds, 55° C. for 15 seconds, and 72° C. for 50 seconds.

First, PCR using pSGR-NC1 as a template DNA and 6620S-Con.1 (5'-TACGCGGGTGGGGGATTTCCACTA-3' (SEQ ID NO: 29)) and 3197SY-R (5'-GCTGGCCAAAT-AGGGGGGGGGACCCTCGGGC-3' SEQ ID NO: 30)) as primers was performed under the above-mentioned PCR conditions. The resulting PCR product was designated as PCR product no. 1.

Subsequently. PCR using pSGR-NC1 as a template DNA and 3197SY-S (5'-TCCCCCCCCTATTTGGCCAGCTCCT-TCAGCT-3' (SEQ ID NO: 31)) and 6447R-1b-rep (5'-AC-GATAAGACGAGCTGGCTT-3' (SEQ ID NO: 32)) as primers was performed under the above-mentioned PCR conditions. The resulting PCR product was designated as PCR product no. 2.

Each PCR product was purified and dissolved in 15 µL of H₂O. The DNA (1 µL) of the PCR product no. 1 was mixed with the DNA (1 µL) of the PCR product no, 2. PCR using the resulting mixture as a template DNA and 6620S-Con.1 (5'-TACGCGGGTGGGGGATTTCCACTA-3' (SEQ ID NO: 29)) and 6447R-1b-rep (5'-ACGATAAGACGAGCTG-GCTT-3' (SEQ ID NO: 32)) as primers was performed under the above-mentioned PCR conditions. The resulting PCR product was designated as PCR product no. 3. The PCR product was purified and dissolved in 30 µL of H₂O.

The pSGR-NC1 and purified PCR product no. 3 were digested with restriction enzymes EcoRI and MunI, and each HCV cDNA fragment was separated by agarose gel electrophoresis, followed by purification. The two DNA fragments were mixed with Ligation Mix (TaKaRa Bio Inc.) to ligate the two DNA fragments. The resulting recombinant expression vector (having nucleotide substitution causing amino acid substitution S2197Y) was designated as pSGR-NC1 S2197Y. The sequence of the HCV subgenomic replicon RNA synthesized from pSGR-NC1 S2197Y is shown in SEQ ID NO: 17.

PCR using pSGR-NC1 as a template DNA and 6620S-Con.1 (5'-TACGCGGGTGGGGGATTTCCACTA-3' (SEQ ID NO: 29)) and 2204SG-R (5'-GACAACTGACCAGCT-GAAGAGCTGGCCAAA-3' (SEQ ID NO: 33) as primers was performed under the above-mentioned PCR conditions. The resulting PCR product was designated as PCR product no. 4.

Subsequently, PCR using pSGR-NCT as a template DNA and 2204SG-S (5'-CTCTTCAGCTGGTCAGTTGTCT-GCGGTCTC3' (SEQ Id NO: 34)) and 6447R-1b-rep (5'-ACGATAAGACGAGCTGGCTT-3' (SEQ ID NO: 32)) as primers was performed under the above-mentioned PCR conditions. The resulting PCR product was designated as PCR product no. 5.

Each PCR product was purified and dissolved in 15 µL of H₂O. The DNA (1 µL) of the PCR product no. 4 was mixed with the DNA (1 µL) of the PCR product no. 5. PCR using the resulting mixture as a template DNA and 6620S-Con.1 (5-TACGCGGGTGGGGGATTTCCACTA-3' (SEQ ID NO: 29)) and 6447R-1b-rep (5'-ACGATAAGACGAGCTG-GCTT-3' (SEQ ID NO: 32)) as primers was performed under the above-mentioned PCR conditions. The resulting PCR product was designated as PCR product no. 6. The PCR product was purified and dissolved in 30 µL of H₂O.

The pSGR-NC1 and purified PCR product no. 6 were digested with restriction enzymes EcoRI and MunI, and each HCV cDNA fragment was separated by agarose gel electrophoresis, followed by purification. The two DNA fragments were mixed with Ligation Mix (TsKaRa Bio Inc.) to ligate the two DNA fragments. The resulting recombinant expression vector (having nucleotide substitution causing amino acid substitution S2204G) was designated as pSGR-NC1 S2204G. The sequence of the HCV subgenomic replicon RNA synthesized from pSGR-NC1 S2204G is shown in SEQ ID NO: 18.

PCR using pSGR-NC1 as a template DNA and 6620S-Con.1 (5'-TACGCGGGTGGGGGATTTCCACTA-3' (SEQ ID NO: 29)) and 2161PR-R (5'-GGGTTCACATCGAAGCT-GTGACCCGACC-3' (SEQ ID NO: 35)) as primers was performed under the above-mentioned PCR conditions. The resulting PCR product was designated as PCR product no. 7.

Subsequently, PCR using pSGR-NC1 as a template DNA and 2161PR-S (5'-TCACAGCTTCGATGTGAAC- CCGAGCCGGAT-3' (SEQ ID NO: 36)) and 6447R-1b-rep (5'-ACGATAAGACGAGCTGGCTT-3' (SEQ ID NO: 32)) as printers was performed under the above-mentioned PCR conditions. The resulting PCR product was designated as PCR product no. 8.

Each PCR product was purified and dissolved in 15 µL of H₂O. The DNA (1 µL) of the PCR product no. 7 was mixed with the DNA (1 µL) of the PCR product no. 8. PCR using the resulting mixture as a template DNA and 6620S-Con.1 (5'-TACGCGGGTGGGGGATTTCCACTA-3' (SEQ ID NO: 29)) and 6447R-1b-rep (5'-ACGATAAGACGAGCTGGCTT-3' (SEQ ID NO: 32)) as primers was performed under the above-mentioned PCR conditions. The resulting PCR product was designated as PCR product no. 9. The PCR product was purified and dissolved in 30 µL of H₂O.

The pSGR-NC1 and purified PCR product no. 9 were digested with restriction enzymes EcoRI and MunI, and each HCV cDNA fragment was separated by agarose gel electrophoresis, followed by purification. The two DNA fragments were mixed with Ligation Mix (TaKaRa Bio Inc.) to ligate the two DNA fragments. The resulting recombinant expression vector (having nucleotide substitution causing amino acid substitution P2161R) was designated as pSGR-NC1 P2161R. The sequence of the HCV subgenomic replicon RNA synthesized from pSGR-NC1 P2161R is shown In SEQ ID NO: 52.

PCR using pSGR-NC1 as a template DNA and 6620S-Con.1 (5'-TACGCGGGTGGGGGATTTCCACTA-3' (SEQ ID NO: 29)) and 2192RL-R (5'-GGGGGACCCTAGGGC-CAGCCTGCGCTTAGC-3' (SEQ ID NO: 37)) as primers was performed under the above-mentioned PCR conditions. The resulting PCR product was designated as PCR product no. 10.

Subsequently, PCR using pSGR-NC1 as a template DNA and 2192RL-S (5'-AGGCTGGCCCTAGGGTC-CCCCCCCTCTTT-3' (SEQ ID NO: 38) and 6447R-1b-rep (5'-ACGATAAGACGAGCTGGCTT-3' (SEQ ID NO: 32)) as primers was performed under the above-mentioned PCR conditions. The resulting PCR product was designated as PCR product no. 11.

Each PCR product was purified and dissolved in 15 µL of H₂O. The DNA (1 µL) of the PCR product no. 10 was mixed with the DNA (1 µL) of the PCR product no. 11. PCR using the resulting mixture as a template DNA and 6620S-Con.1 (5'-TACGCGGGTGGGGGATTTCCACTA-3' (SEQ ID NO: 29)) and 6447R-1b-rep (5'-ACGATAAGACGAGCTGGCTT-3' (SEQ ID NO: 32) as primers was performed under the above-mentioned PCR conditions. The resulting PCR product was designated as PCR product no. 12, The PCR product was purified and dissolved in 30 µL of H₂O.

The pSGR-NC1 and purified PCR product no. 12 were digested with restriction enzymes EcoRI and MunI, and each HCV cDNA fragment was separated by agarose gel electrophoresis, followed by purification. The two DNA fragments were mixed with Eigation Mix (TaKaRa Bio Inc.) to ligate the two DNA fragments. The resulting recombinant expression vector (having nucleotide substitution causing amino acid substitution R2192L) was designated as pSGR-NC1 R2192L.

PCR using pSGR-NC1 as a template DNA and 6620S-Con.1 (5-TACGCGGGTGGGGGATTTCCACTA-3' (SEQ ID NO: 29)) and 2192RQ-R (5'-GGGGGACCCTTGGGC-CAGCCTGCGCTTAGC-3' (SEQ ID NO: 39)) as primers was performed under the above-mentioned PCR conditions. The resulting PCR product was designated as PCR product no. 13.

Subsequently, PCR using pSGR-NC1 as a template DNA and 2192RQ-S (5-AGGCTGGCCCAAGGGTC-CCCCCCCTCTTT-3' (SEQ ID NO: 40)) and 6447R-1b-rep (5'-ACGATAAGACGAGCTGGCTT-3' (SEQ ID NO: 32)) as printers was performed under the above-mentioned PCR conditions. The resulting PCR product was designated as PCR product no. 14.

Each PCR product was purified and dissolved in 15 µL of H₂O. The DNA (1 µL) of the PCR product no. 13 was mixed with the DNA (1 µL) of the PCR product no. 14. PCR using the resulting mixture as a template DNA and 6620S-Con.1 (5'-TACGCGGGTGGGGGATTTCCACTA-3' (SEQ ID NO: 29)) and 6447R-1-rep (5'-ACGATAAGACGAGCTGGCTT-3' (SEQ ID NO: 32)) as primers was performed under the above-mentioned PCR conditions. The resulting PCR product was designated as PCR product no. 15. The PCR product was purified and dissolved in 30 µL of H₂O.

The pSGR-NC1 and purified PCR product no. 15 were digested with restriction enzymes EcoRI and MunI, and each HCV cDNA fragment was separated by agarose gel electrophoresis, followed by purification. The two DNA fragments were mixed with Ligation Mix (TaKaRa Bio Inc.) to ligate the two DNA fragments. The resulting recombinant expression vector (having nucleotide substitution causing amino acid substitution R2192Q) was designated as pSGR-NC1 R2192Q.

PCR using pSGR-NC1 as a template DNA and 7094S-1b-rep (5'-GTCGGTCGCGCACGATGCAT-3' (SEQ ID NO: 41)) and 2871YC-R (5'-TTCAATGGAGCAAGTGGC-CCCGTAGATCT-3' (SEQ ID NO: 42)) us primers was performed under the above-mentioned PCR conditions. The resulting PCR product was designated as PCR product no. 16.

Subsequently, PCR using pSGR-NC1 as a template DNA and 22871YC-S (5'-GGGGCCACTTGCTCCATTGAAC-CACTTGAC-3' (SEQ ID NO: 43); and 6447R-1b-rep (5'-ACGATAAGACGAGCTGGCTT-3' (SEQ ID NO: 32)) was performed. The resulting PCR product was designated as PCR product no. 17.

Each PCR product was purified and dissolved in 15 µL of H₂. The DNA (1 µL) ) of the PCR product no. 16 was mixed with the DNA (1 µL) of the PCR product no. 17. PCR using the resulting mixture as a template DNA and 7094 S-1b-rep (5'-GTCGGTCGCGCACGATGCAT-3' (SEQ ID NO: 41)) and 6447-1b-rep (5'-ACGATAAGACGAGCTGGCTT-3' (SEQ ID NO: 32)) as primers was performed under the above-mentioned PCR conditions. The resulting PCR product was designated as PCR product no. 18. The PCR product was purified and dissolved in 30 µL of H₂O).

The pSGR-NC1 and purified PCR product no. 18 were digested with restriction enzymes EcoRI and MunI, and each HCV cDNA fragment was separated by agarose gel electrophoresis, followed by purification. The two DNA fragments were mixed with Ligation Mix (TaKaRa Bio Inc.) to ligate the two DNA fragments. The resulting recombinant expression vector (having nucleotide substitution causing amino acid substitution Y2871C) was designated as pSGR-NC1 Y2871C.

HCV subgenomic replicon RNAs were synthesized from expression vectors, pSGR-NC1, pSGR-NC1 S2197Y, pSGR-NC1 S2204G, pSGR-NC1 P2161R, pSGR-NC1 R2192L, pSGR-NC1 R2192Q, and pSGR-NC1 Y2871C, as described in Example 2. Each synthetic HCV subgenomic replicon RNA (1 µg) was transfected into Huh7 cells by electroporation. The electroporated Huh7 cells were seeded in a culture dish and were cultured for 16 to 24 hours, and G418 (neomycin) was then added to the culture dish. The culture was continued while replacing the culture solution twice a week. After the culture for 21 days after the seeding, viable cells were stained with crystal violet.

Figure 5:
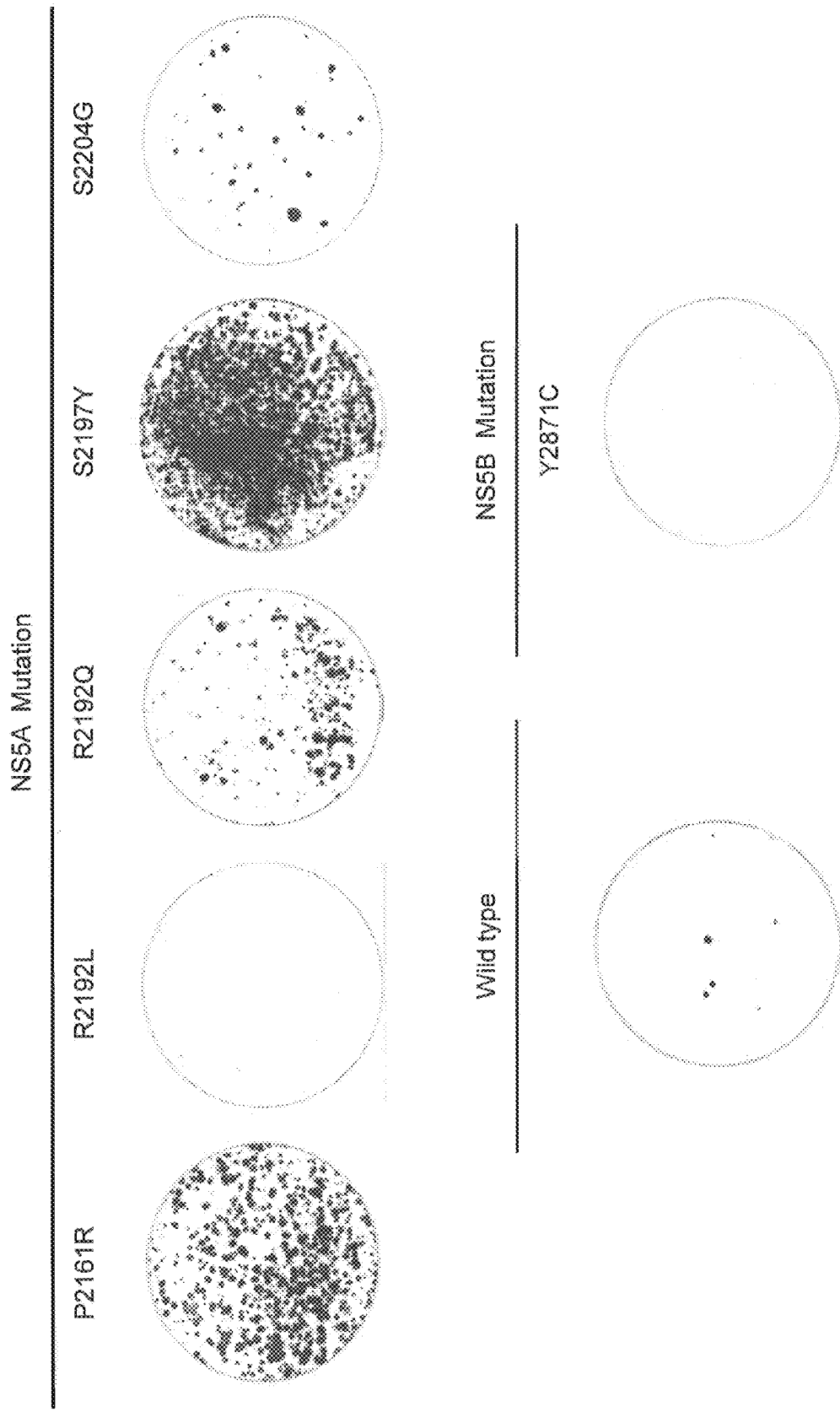
FIG. 5 shows the results of formation of colonies of cells transfected with the HCV subgenomic replicon RNAs of the wild-type NC1 strain or its mutants.

The results are shown in FIG. 5. In the Figure, "P2161R," "R2192L," "R2192Q," "S2197Y," "S2204G," "wild-type," and "Y2871C" respectively show the results of staining of the cells transfected with HCV subgenomic replicon RNAs produced from pSGR-NC1 P2161R, pSGR-NC1 R2192L, pSGR-NC1 R2192Q, pSGR-NC1 S2197Y, pSGR-NC1 S2204G. pSGR-NC1, and pSGR-NC1 Y2871C.

As a result, colony formation was confirmed in all cells transfected with any of the subgenomic replicon RNAs. The colony-forming ability was high in the cells transfected with the subgenomic replicon RNA of pSGR-NC1 P2161R, pSGR-NC1 R2192Q, pSGR-NC1 S2197Y, or pSGR-NC1 S2204G. In particular, pSGR-NC1 P2161R and pSGR-NC1 S2197Y showed high colony-forming ability (FIG. 5).

it was therefore demonstrated that the autonomous replication ability is maintained or enhanced even if the above-mentioned amino acid mutation is introduced into the HCV subgenomic replicon RNA of the NC1 strain, in particular, it was demonstrated that the autonomous replication ability of the HCV subgenomic replicon RNA of the NC1 strain is notably enhanced by introducing an amino acid mutation of P2161R or S2197Y.

Example 6

Construction of Expression Vector of HCV Fullgenomic Replicon RNA (Full-length Genomic RNA) of Mutant of NC1 Strain For the purpose of evaluating whether HCV particles can be produced in cultured cells by introducing the amino acid substitutions found in Example 4 into the HCV fullgenomie replicon RNA of the NC1 strain, a plasmid vector expressing the HCV fuUgenomic replicon RNA having a full-length HCV genome sequence was constructed.

Figure 6:
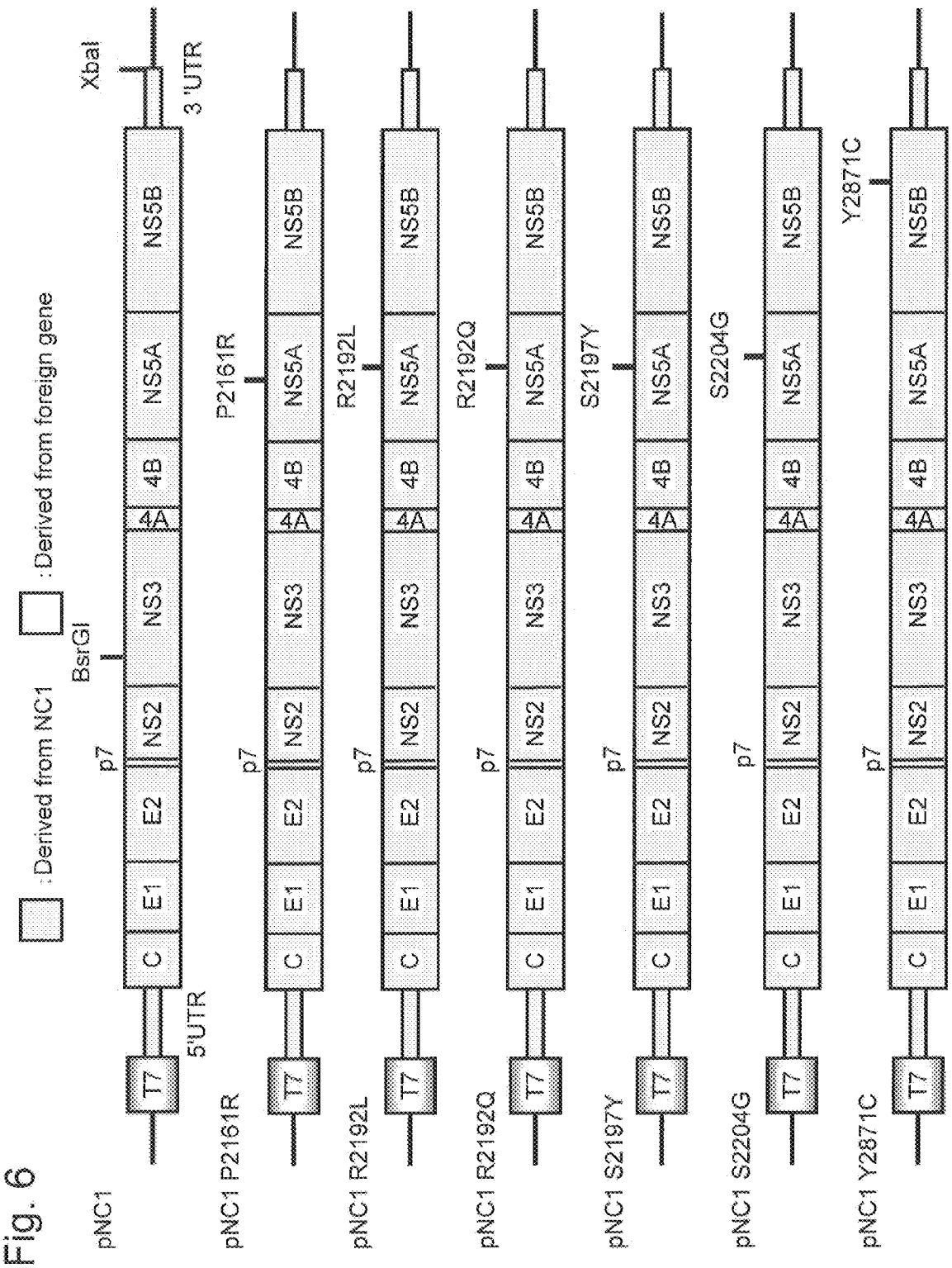
FIG. 6 is a diagram showing the structures of expression vectors for synthesizing HCV fullgenomic replicon RNAs of mutants of NC1 strain.

Specifically, the pNC1 produced in Example 1 and each pSGR-NC1 mutant (pSGR-NC1 S2197Y, pSGR-NC1 S2204G, pSGR-NC1 P2161R, pSGR-NC1 R2192L, pSGR-NC1 R2192Q, and pSGR-NC1 Y2871C) produced in Example 5 were digested with restriction enzymes BsrGI and XbaI, and each HCV cDNA fragment was separated by agarose gel electrophoresis, followed by purification. The DNA fragment of the pNC1 and the DNA fragment of each pSGR-NC1 mutant were mixed with Ligation Mix (TaKaRa Bio Inc.) to ligate the two DNA fragments. The resulting expression vectors of the HCV fullgenomic replicon RNAs having the amino acid substitutions were designated as pNC1 S2197Y, pNC1 S2204G, pNC1 P2161R pNC1 R2192L, pNC1 R2192Q, and pNC1 Y2871C, respectively (FIG. 6). In the Figure, "BsrGI" and "XbaI" indicate restriction enzyme sites.

Example 7

Evaluation of HCV Particle-producing Ability in Cells Transfected with HCV Fullgenomic Replicon RNA of Mutant of NC1 Strain Each expression vector obtained in Example 6 was cleaved with restriction enzyme XbaI, followed by phenol/chloroform extraction and ethanol precipitation. Subsequently, the extra four nucleotides CTAG, derived from the XbaI recognition sequence, on the 3' end were removed from the XbaI cleaved fragment by treating the XbaI cleaved fragment with Mung Bean Nuclease. Subsequently, the Mung Bean Nuclease treated solution containing the XbaI cleaved fragment was subjected to proteinase K treatment phenol/chloroform extraction, and ethanol precipitation to purify the DNA fragment. RNA was synthesized from this template DNA using MEGAscript® T7 kit (Ambion, Inc.).

After completion of the RNA synthesis, the template DNA was removed by adding DNase (2 U) to the reaction solution for a reaction at 37° C. for 15 minutes, followed by RNA extraction with acidic phenol to obtain the HCV fullgenomic replicon RNA of the mutant of NC1 strain.

The resulting HCV fullgenomic replicon RNA of the mutant of NC1 strain is also a mutant of the NC1 full-length genomic RNA. The HCV fullgenomic replicon RNAs of the NC1 strain having S2197Y, S2204G, P2161R, R2192L. R2192Q, and Y2871C mutations introduced, i.e., NC1 full-length genomic RNA mutants, are called "NC1 S2197Y," "NC1 S2204G," "NC1 P2161R," "NC1 R2192L," "NC1 R2192Q," and "NC1 Y2871C," respectively.

The resulting HCV fullgenomic replicon RNA of the mutant of NC1 strain (10 µg) was transfected into Huh7 cells by electroporation. The electroporated Huh7 cells were seeded in a culture dish and were cultured for 16 to 24 hours, and G418 (neomycin) was then added to the culture dish. The culture was continued while replacing the culture solution twice a week. The amount of the HCV Core protein contained in the culture supernatant was quantified over time using an HCV antigen ELISA test kit (Ortho-Clinical Diagnostics K.K.) to confirm the production of HCV particles.

Figure 7:
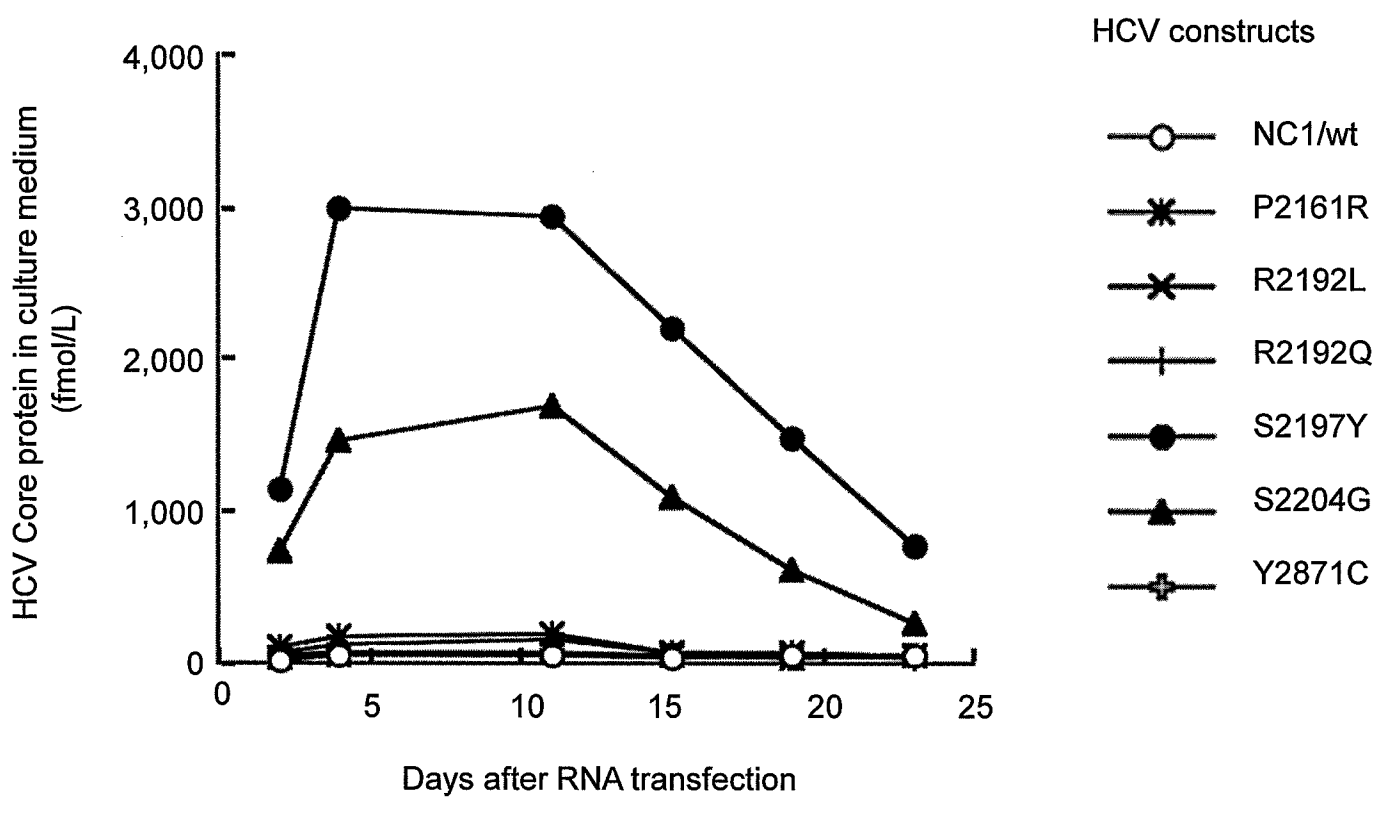

FIG. 7 shows the results. In the Figure, "NC1/wt" indicates cells transfected with the HCV fullgenomic replicon RNA of the wild-type NC1 strain not having mutation. "P2161R," "R2192L," "R2192Q," "S2197Y," "S2204G," and "Y2871C" indicate the cells transfected with the HCV fullgenomic replicon RNAs of mutants of NC1 strain having the respective mutations.

In the cells transfected with the HCV fullgenomic replicon RNA of the wild-type NC1 strain, the Core protein was very little detected in the culture supernatant. In contrast, in the cells transfected with the mutant HCV fullgenomic replicon RNAs having S2197Y and S2204G, respectively, the Core protein was detected in the culture supernatant after transfection with the RNA. In particular, the amount of the Core protein was high in the mutant S2197Y. This demonstrated that the mutant (NC1 S2197Y or NC1 S2204G), in which a S2197Y or S2204G mutation is introduced into the HCV fullgenomic replicon RNA of the wild-type NC1 strain, extracellularly produces HCV particles when being transfected into cultured cells. Interestingly, the mutation P2161R, showing high colony forming ability (autonomous replication ability) for subgenomic replicon resulted in very little production of the Core protein in the culture supernatant for the fullgenomic replicon.

SEQ ID NO: 23 shows the amino acid sequence of the precursor protein (from the Core protein to the NS5B protein) encoded by pNC1 S2197Y, and SEQ ID NO: 24 shows the amino acid sequence of the precursor protein encoded by pNC1 S2204G. SEQ ID NO: 19 shows the cDNA nucleotide sequence of the full-length genomic RNA of NC1 S2197Y (HCV fullgenomic replicon RNA of a mutant of NC1 strain synthesized from pNC1 S2197Y), and SEQ ID NO: 20 shows the cDNA nucleotide sequence of the full-length genomic RNA of NC1 S2204G (HCV fullgenomic replicon RNA of a mutant of NC1 strain synthesized from pNC1 S2204G).

Example 8

Evaluation of Infectivity of HCV Particles Derived From HCV Fullgenomic Replicon RNA (Full-length Genomic RNA) of NC1 S2197Y Infectivity of the HCV particles derived from the HCV fullgenomic replicon RNA (full-length genomic RNA) of NC1 S2197Y (hereinafter, referred to as NC1 S2197Y HCV particles), the production thereof was confirmed in Example 7. was investigated.

NC1 S2197Y HCV fullgenomic replicon RNA (full-length genomic RNA) was transfected into Huh7 cells by electroporation, as described in Example 7. The electroporated Huh7 cells were subcultured every 3 to 7 days. The culture supernatant was collected on the second or 15th days after the cell transfection, and the amount of the HCV Core protein contained in the culture supernatant was quantified using an HCV antigen ELISA test kit (Ortho-Clinical Diagnostics K.K.), The collected culture supernatant was added to other Huh7 cells, and the number of HCV-infected cells was counted after 72 hours by a focus assay to calculate the infectious titer. More specifically, Huh7 cells were seeded in a culture dish and were infected with the culture supernatant serially diluted with the culture medium on the following day, followed by culturing at 37° C. for 72 hours. The virus-infected cells were detected by immunostaining through an antigen-antibody reaction. The cells 72 hours after the infection were fixed in 10% formalin-PBS(−) solution at room temperature for 20 minutes and were then treated with 0.5% Triton X-PBS(−) at room temperature for 10 minutes. Subsequently, an anti-HCV Core (clone CP 14) monoclonal antibody diluted (300-fold dilution) with 5% skimmed milk-PBS(−) was added thereto as a primary antibody, followed by a reaction at room temperature for 1 hour. The cells were washed with PBS(−) three times, and an HRP-labeled goat anti-mouse antibody (300-fold dilution) was added thereto, followed by a reaction at room temperature for 1 hour. After washing with PBS(−) three times, Konica Immunostain HRP-1000 (Konica Minolta, Inc.) was added to the cells, and the number of virus antigen positive cell clusters (immune focus, also called focus) stained in blue was counted under a microscope.

The results are shown in Table 1. In the Table, "NC1 S2197Y(D2)" indicates the culture supernatant on the second day after transfection with NC1 S2197Y, and "NC1 S2197Y (D15)" indicates the culture supernatant on the 15th day after the transfection,

TABLE 1

| Culture supernatant (Days after transfection) | HCV Core (fmol/L) | Infectious titer (ffu/mL) | Infectious titer/HCV Core |
|---|---|---|---|
| NC1 S2197Y (D2) | 1,721 | 3 | 0.002 |
| NC1 S2197Y (D15) | 1,009 | 16 | 0.016 |

The infectious titer of the culture supernatant was 3 ffu/mL on the second day and 16 ffu/mL on the 15th day. These values were divided by the respective amounts of the HCV Core protein in the culture supernatant (i.e., 1,721 and 1,009 fmol/L, respectively). The resulting infectious titer per HCV protein unit was 0.002 (infectious titer/Core value,) in the culture supernatant on the second day and 0.016 (infectious titer/Core value) in the culture supernatant on the 15th day.

The results demonstrated that the HCV particles produced via transfection of cells with NC1 S2197Y HCV fullgenomic replicon RNA (full-length genomic RNA) have infectivity.

Example 9

Construction of Expression Vector of HCV Fullgenomic Replicon RNA (Full-length Genomic RNA) of the Mutant of NC1 Strain Having E1202G/K2040R/S2197Y Introduced In previous publications, it has been reported that the nucleotide substitution that causes amino acid substitution at position 1202 in the NS3 protein region being a non-structural region, i.e., E1202G (Krieger et al., J. Virol., 2001, vol. 75, pp. 4614-4624) and the nucleotide substitution that causes amino acid substitution at position 2040 in the NS5A protein region being a non-structural region, i.e., K2040R (Yi et al., J. Virol., 2004, vol, 78. pp. 7904-7915) are adaptive mutations for HCV replication. These adaptive mutations described in the publications were introduced together with the adaptive mutations obtained in Examples above that enhance the secretion of infectious HCV particles of the HCV fullgenomic replicon RNA (full-length genomic RNA) of the NC1 strain Specifically, introduction of the mutation was performed by PCR, as described in Example 5. The PCR conditions were as follows. First, to the template DNAs for PCR were added 10 μL of 5× buffer and 4 μL of 2.5 mM dNTPs mixture attached to a Phusion® High-Fidelity DNA Polymerase kit (FINNZYMES), and 0.25 μL each of 100 μM primers (forward and reverse primers) then deionized water to adjust the final total amount to 49.5 μL. Subsequently, 0.5 μL of Phusion® DNA Polymerase (FINNZYMES) was added, and PCR was performed for 25 cycles where one cycle consists of 98° C. for 10 seconds, 55° C. for 15 seconds, and 72° C. for 80 seconds.

First, PCR using pNC1 S2197Y as a template DNA and 3751S-NC1 (5'-TGTGTTGGACCGTCTACCAT-3' (SEQ ID NO: 44)) and 1b-1202EG-R (5-GCATGGTGGTTCCCATG-GACTCAACGGGTA-3' (SEQ ID NO: 45)) as primers was performed under the above-mentioned PCR conditions. The resulting PCR product was designated as PCR product no. 19.

Subsequently, PCR using pNC1 S2197Y as a template DNA and 1b-1202EG-S (5'-GTCCATGGGAACCACCAT-GCGGTCTCCGGT-3' (SEQ ID NO: 46)) and 4598R-NC1 (5'-CGGTAGTACGCTACAGCATT-3' (SEQ ID NO: 47)) as primers was performed under the above-mentioned PCR conditions. The resulting PCR product was designated as PCR product no. 20.

Each PCR product was purified and dissolved in 15 μL of H₂O. The DNA (μl) of the PCR product no. 19 was mixed with the DNA (1 μL) of the PCR product no. 20. PCR using the resulting mixture as a template DNA and 3751S-NC1 (5'-TGTGTTGGACCGTCTACCAT-3' (SEQ ID NO: 44)) and 4598R-NC1 (5'-CGGTAGTACGCTACAGCATT-3' (SEQ ID NO: 47)) as primers was performed under the above-mentioned PCR conditions. The resulting PCR product was designated as PCR product no. 21. The PCR product was purified and dissolved in 30 μL of H₂O.

The pNC1 S2197Y and purified PCR product no. 21 were digested with restriction enzymes BsrGI and XhoI, and each HCV cDNA fragment was separated by agarose gel electrophoresis, followed by purification. The two DNA fragments were mixed with Ligation Mix (TaKaRa Bio Inc.) to ligate the two DNA fragments. The resulting recombinant expression vector (having nucleotide substitutions causing amino acid substitutions S2197Y and E1202G) was designated as pNC1 E1202G/S2197Y. The sequence of HCV fullgenomic replicon RNA (full-length genomic RNA) synthesized from pNC1 E1202G/S2197Y is shown in SEQ ID NO: 21.

PCR using pNC1 S2197Y as a template DNA and 5292S-NC1 (5'-GCCGACCTGGAGGTCGTCAC-3' (SEQ ID NO: 48)) and 1b-2040KR-R (5'-GAACCGTTCCTGACATGTC-CACTGATCTGT-3' (SEQ ID NO: 49)) as primers was performed under the above-mentioned PCR conditions, The resulting PCR product was designated as PCR product no. 22.

Subsequently, PCR using pNC1 S2197Y as a template DNA and 1b-2040KR-S (5'-GGACATGTCAGGAACGGT-TCCATGAGGATC-3' (SEQ ID NO: 50)) and 6789R-NC1

(5'-GACCTGGAATGTGACCTCAT-3' (SEQ ID NO: 51)) as primers was performed under the above-mentioned PCR conditions. The resulting PCR product was designated as PCR product no. 23.

Each PCR product was purified and dissolved in 15 μL of H₂O. The DNA (1 μL) of the PCR product no. 22 was mixed with the DNA (1 μL) of the PCR product no. 23. PCR using the resulting mixture as a template DNA and 5292S-NC1 (5'-GCCGACCTGGAGGTCGTCAC-3' (SEQ ID NO: 48)) and 6789R-NC1 (5'-GACCTGGAATGTGACCTCAT-3' (SEQ ID NO: 51)) as primers was performed under the above-mentioned PCR conditions. The resulting PCR product was designated as PCR product no. 24, The PCR product was purified and dissolved in 30 μL of H₂O The pNC1 S2197Y and purified PCR product no. 24 were digested with restriction enzymes FseI and EcoRI, and each HCV cDNA fragment was separated by agarose gel electrophoresis, followed by purification. The two DNA fragments were mixed with Ligation Mix (TaKaRa Bio Inc.) to ligate the two DNA fragments. The resulting recombinant expression vector (having nucleotide substitutions causing amino acid substitutions S2197Y and K2040R) was designated as pNC1 K2040R/S2197Y.

Figure 8:
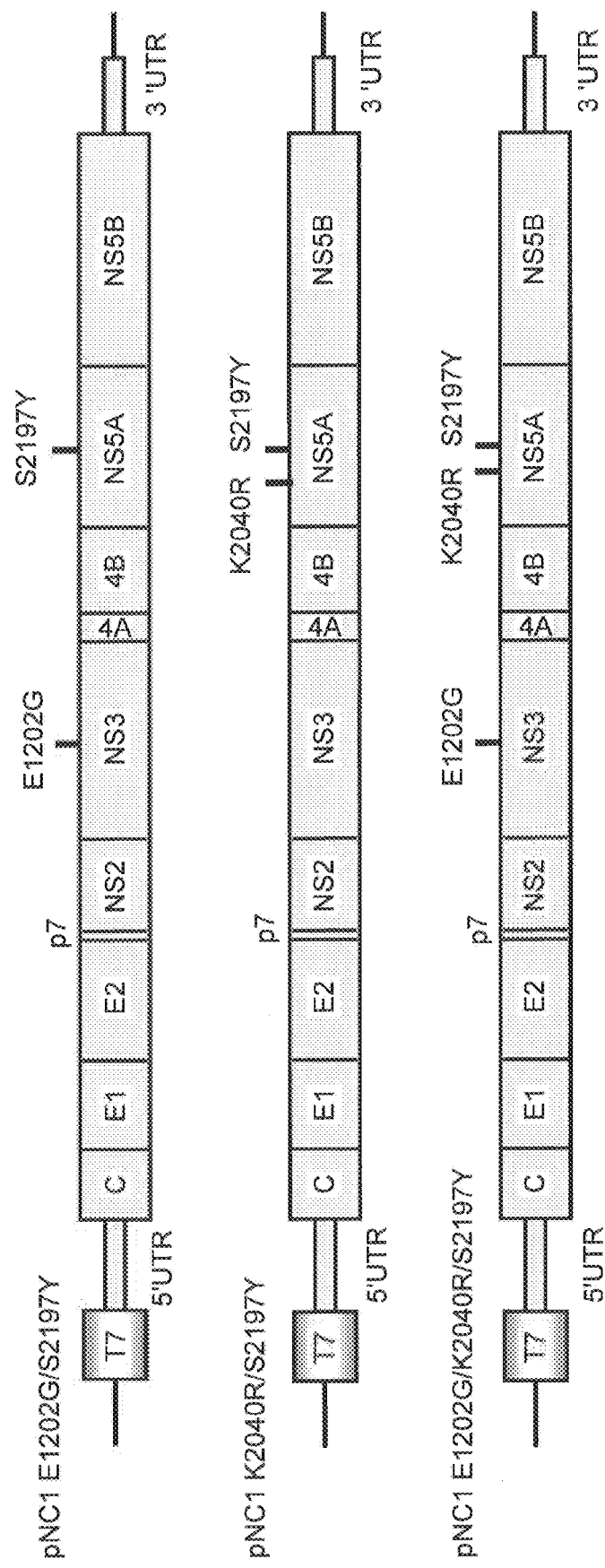
FIG. 8 is a diagram showing the structures of expression vectors of the HCV fullgenomic replicon RNAs of mutants of NC1 strain, pNC1 E1202G/S2197Y, pNC1 K2040R/S2197Y, and pNC1 E1202G/K2040R/S2197Y.

In accordance with a similar process, a recombinant expression vector pNC1 E1202G/K2040R/S2197Y having nucleotide substitutions that cause amino acid substitutions E1202G, K2040R, and S2197Y was produced. FIG. 8 shows the structures of these recombinant expression vectors.

Example 10

Construction of Expression Vector of HCV Fullgenomic Replicon RNA (Full-length Genomic RNA) of the mutant of NC1 strain having E1202G/K2040R/S2204G introduced Introduction of mutation was performed by PCR as described in Example 5. The PCR conditions were as follows. First, to the template DNAs for PCR were added 10 μL of 5× buffer and 4 μL of 2.5 mM dNTPs mixture attached to a Phusion® High-Fidelity DNA Polymerase kit (FINNZYMES), and 0.25 μL each of 100 μM primers (forward and reverse primers) then deionized water to adjust the final total amount to 49.5 μL. Subsequently, 0.5 μL of Phusion® DNA Polymerase (FINNZYMES) was added, and PCR was performed for 25 cycles where one cycle consists of 98° C. for 10 seconds, 55° C. for 15 seconds, and 72° C. for 80 seconds.

PCR using pNC1 S2204G as a template DNA and 3751S-NC1 (5'-TGTGTTGGACCGTCTACCAT-3(SEQ ID NO: 44)) and 1b-1202EG-R 5'-GCATGGTGGTTCCCATG-GACTCAACGGGTA-3' (SEQ ID NO: 45)) as primers was performed under the above-mentioned PCR conditions. The resulting PCR product was designated as PCR product no. 25.

Subsequently, PCR using pNC1 S2204G as a template DNA and 1b-1202EG-S (5'-GTCCATGGGAACCACCAT-GCGGTCTCCGGT-3' (SEQ ID NO: 46)) and 4598R-NC1 (5'-CGGTAGTACGCTACAGCATT3' (SEQ ID NO: 47)) as primers was performed under the above-mentioned PCR conditions. The resulting PCR product was designated as PCR product no. 26.

Each PCR product was purified and dissolved in 15 μL of H₂O. The DNA (1 μL) of the PCR product no. 25 was mixed with the DNA (1 μL) of the PCR product no. 26. PCR using the resulting mixture as a template DNA and 3751S-NC1 (5'-TGTGTTGGACCGTCTACCAT-3' (SEQ ID NO: 44)) and 4598R-NC1 (5'-CGGTAGTACGCTACAGCATT-3' (SEQ ID NO: 47)) as primers was performed under the above-mentioned PCR conditions. The resulting PCR product was designated as PCR product no. 27. The PCR product was purified and dissolved in 30 μL of H₂O.

The pNC1 S2204G and purified PCR product no. 27 were digested with restriction enzymes BsrGI and XhoI and each HCV cDNA fragment was separated by agarose gel electrophoresis, followed by purification. The two DNA fragments were mixed with Ligation Mix (TaKaRa Bio Inc.) to ligate the two DNA fragments. The resulting recombinant expression vector (having nucleotide substitutions causing amino acid substitutions S2204G and E1202G) was designated as pNC1 E1202G/S2204G. The sequence of the HCV fullgenomic replicon RNA (full-length genomic RNA) synthesized from pNC1 E1202G/S2204G is shown in SEQ ID NO: 22.

PCR using pNC1 S2204G as a template DNA and 5292S-NC1 (5'-GCCGACCTCGGAGGTCGTCAC-3' (SEQ Id NO: 48)) and 1b-2040KR-R (5'-GAACCGTTCCTGACATGTC-CACTGATCTGT-3' (SEQ ID NO: 49)) as primers was performed under the above-mentioned PCR conditions. The resulting PCR product was designated as PCR product no. 28.

Subsequently, PCR using pNC1 S2204G as a template DNA and 1b-2040KR-S (5'-GGACaTGTCAGGAACGGT-TCCATGAGGATC-3' (SEQ ID NO: 50); and 6789R-NC1 (5-GACCTGGAATGTGACCTCAT-3' (SEQ ID NO: 51)) as primers was performed under the above-mentioned PCR conditions. The resulting PCR product was designated as PCR product no. 29.

Each PCR product was purified and dissolved in 15 μL of H₂O. The DNA (1 μL) of the PCR product no. 28 was mixed with the DNA (1 μL) of the PCR product no. 29, PCR using the resulting mixture as a template DNA and 5292S-NC1 (5'-GCCGACCTGGAGGTCGTCAC-3' (SEQ ID NO: 48)) and 6789R-NC1 (5'-GACCTGGAATGTGACCTCAT-3' (SEQ ID NO: 51)) as primers was performed under the above-mentioned PCR conditions. The resulting PCR product was designated as PCR product no. 30. The PCR product was purified and dissolved in 30 μL of H₂O.

The pNC1 S2204G and purified PCR product no. 30 were digested with restriction enzymes FseI and EcoRI, and each HCV cDNA fragment was separated by agarose gel electrophoresis, followed by purification. The two DNA fragments were mixed with Ligation Mix (TaKaRa Bio Inc.) to ligate the two DNA fragments. The resulting recombinant expression vector (having nucleotide substitutions causing amino acid substitutions S2204G and K2040R) was designated as pNC1 K2040R/S2204G.

Figure 9:
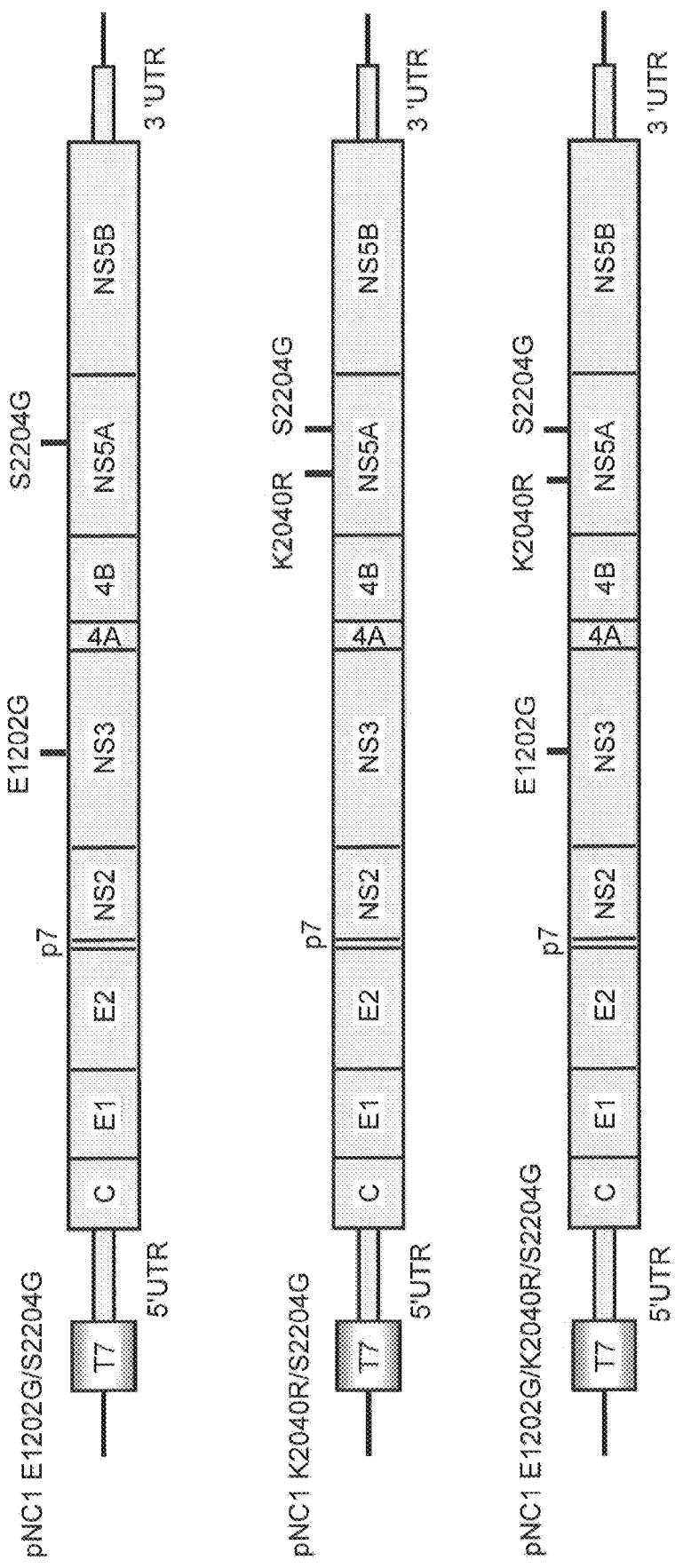
FIG. 9 is a diagram showing the structures of expression vectors of the HCV fullgenomic replicon RNAs of mutants of NC1 strain, pN1 E1202G/S2204G, pNC1 K2040R/S2204G, and pNC1 E1202G/K2040R/S2204G.

In accordance with a similar process, a recombinant expression vector pNC1 E1202G/K2040R/S2204G having nucleotide substitutions that cause amino acid substitutions E1202G, K2040R, and S2204G was produced. FIG. 9 shows the structures of these recombinant expression vectors.

Example 11

Evaluation of HCV Replication Ability in Cells Transfected with HCV Fullgenomic Replicon RNA of the Mutant of NC1 Strain Having a Combination of S2197Y, S2204G. E1202G. and K2040R Mutations HCV fullgenomic replicon RNAs (full-length genomic RNAs) were produced as described in Example 7 using expression vector pNC1 constructed in Example 1, expression vectors pNC1 S2197Y and pNC1 S2204G constructed in Example 6, expression vectors pNC1 E1202G/S2197Y, pNC1 K2040R/S2197Y, and PNC1 E1202G/K2040R/

S2197Y constructed in Example 9, and expression vectors pNC1 E1202G/S2204G, pNC1 K2040R/S2204G, and pNC1 E1202G/K2040R/S2204G constructed in Example 10.

The NC1 strain-derived HCV fullgenomic replicon RNAs (NC1 full-length genomic RNA mutants) having introduced mutations of E1202g/s2197Y, K2040R/S2197Y, E1202G/ K2040R/S2197Y, E1202G/S2294G, K2040R/S2204G, and E1202G/K2040R/S2204G are called "NC1 E1202G/ S2197Y," "NC1 K2040R/S2197Y," "NC1 E1202G/K2040R/ S2197Y," "NC1 E1202G/S2204G," "NC1 K2040R/ S2204G," and "NC1 E1202G/K2040R/S2204G," respectively.

The resulting HCV fullgenomic replicon RNAs (full-length genomic RNAs), i.e., NC1 (wild-type) (SEQ ID NO: 1). NC1 S2197Y (SEQ ID NO: 19), NC1 S2204G (SEQ ID NO: 20), NC1 E1202G/S2197Y (SEQ ID NO: 21), NC1 K2040R/S2197Y, NC1 E1202G/K2040R/S2197Y. NC1 E1202G/S2204G (SEQ ID NO: 22), NC1 K2040R/S2204G, and NC1 E1202G/K2040R/S2204G were each transfected to Huh7 cells by electroporation. The cells were collected at 4, 24, 48, 72, and 96 hours after the transtection. and the amount of the HCV Core protein contained in the cells was quantified using an HCV antigen ELISA test kit (Ortho-Clinical Diagnostics K.K.) to evaluate the intracellular HCV replication ability.

Figure 10:
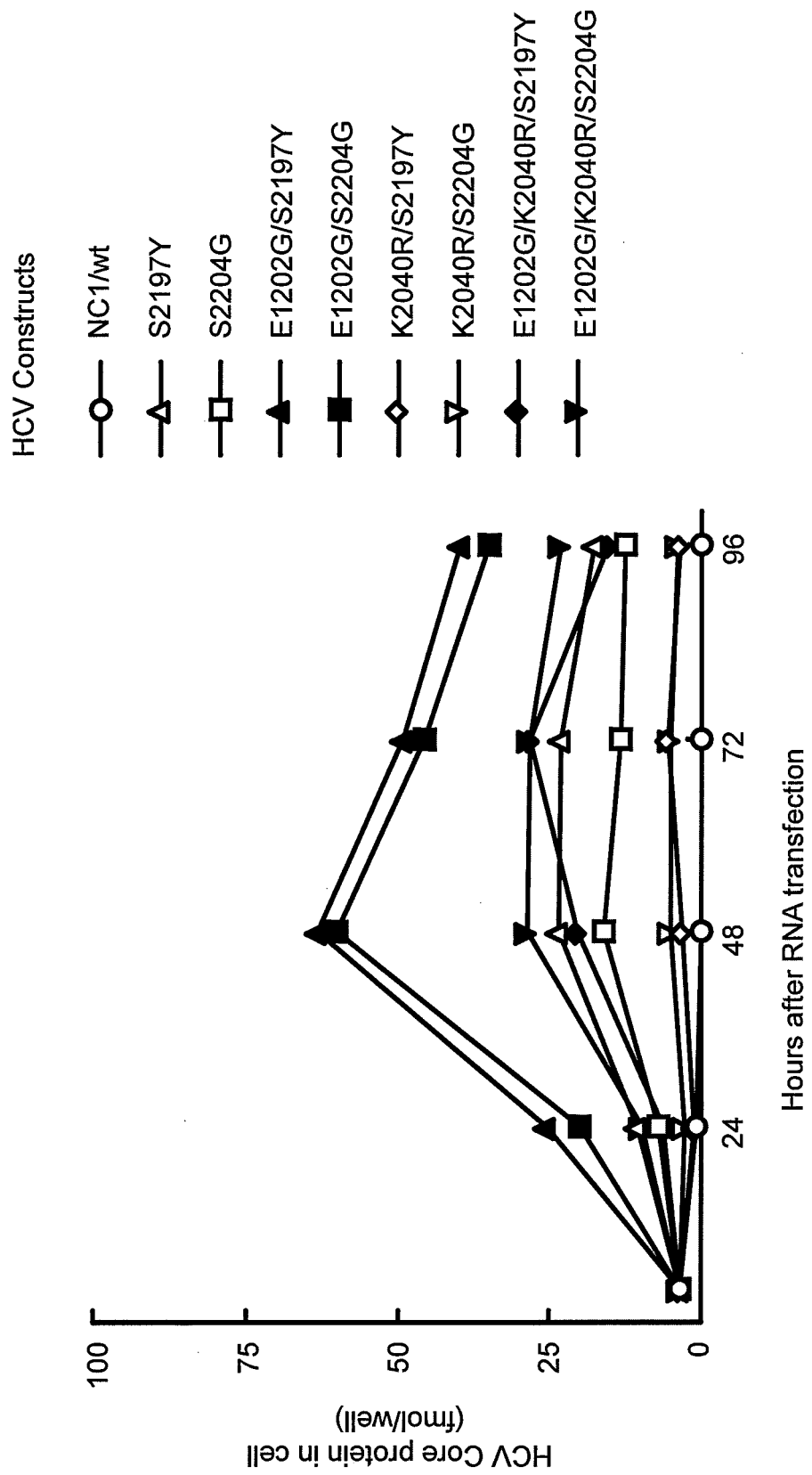
FIG. 10 shows changes over time in amount of the Core protein (HCV-replicating ability) in Huh7 cells transfected with the HCV fullgenomic replicon RNA of the wild-type NC1 strain or its mutants (mutations of E1202G, K2040R, S2197Y, and S2204G and combinations thereof).

The results are shown in FIG. 10. In the Figure, "NC1/wt" Indicates cells transfected with the HC fullgenomic replicon RNA of the wild-type NC1 strain not having mutation. "S2197Y," "S2204G," "E1202G/S2197Y," "E1202G/ S2204G," "K2040R/S2197Y," "K2040R/S2204G," "E1202G/K2040R/S2197Y" and "E1202G/K2040R/ S2204G" indicate cells transfected with the HCV replicon RNAs of the mutants of NC1 strain having the respective mutations.

In the cells transfected with the HCV fullgenomic replicon RNA of the wild-type NC1 strain, the intracellular expression of the Core protein was very little detected. In contrast, in the cells transfected with the HCV fullgenomic replicon RNAs of the mutants of NC1 strain, the amount of the Core protein in the cells increased after transfection with the RNA. In particular, the amount was high in mutants E1202G/S2197Y and E1202G/S2204G. In the case of introduction of K2040R mutation in addition to these mutations, i.e., E1202G/ K2040R/S2197Y and E1202G/K2040R/S2204G mutations, the amount of the Core protein in the cells decreased instead.

The results demonstrated that the mutants of the HCV fullgenomic replicon RNAs of the wild-type NC1 strain having E1202G/S2197Y or E1202G/S2204G mutations, NC1 E1202G/S2197Y (SEQ ID NO: 21) and NC1 E1202G/ S2204G (SEQ ID NO: 22), autonomously replicate efficiently in cells when they are transfected into the cells.

Example 12

Evaluation of HCV Particle-producing Ability in Cells Transfected with HCV Fullgenomic Replicon RNA of the Mutant of NC1 Strain Having a Combination of S2197Y, S2204G, E1202G, and K2040R Mutations The HCV particle-producing amount was evaluated by quantifying the amount of HCV Core protein in the culture supernatant of Huh7 cells transfected with the HCV fullgenomic replicon RNA. (full-length genomic RNA) in Example 11. The culture supernatant was collected at 4, 24, 48, 72, and 96 hours after the transfection with the HCV fullgenomic replicon RNA, and the amount of the HCV Core protein contained in the culture supernatant was quantified using an HCV antigen ELISA test kit (Ortho-Clinical Diagnostics K.K.).

Figure 11:
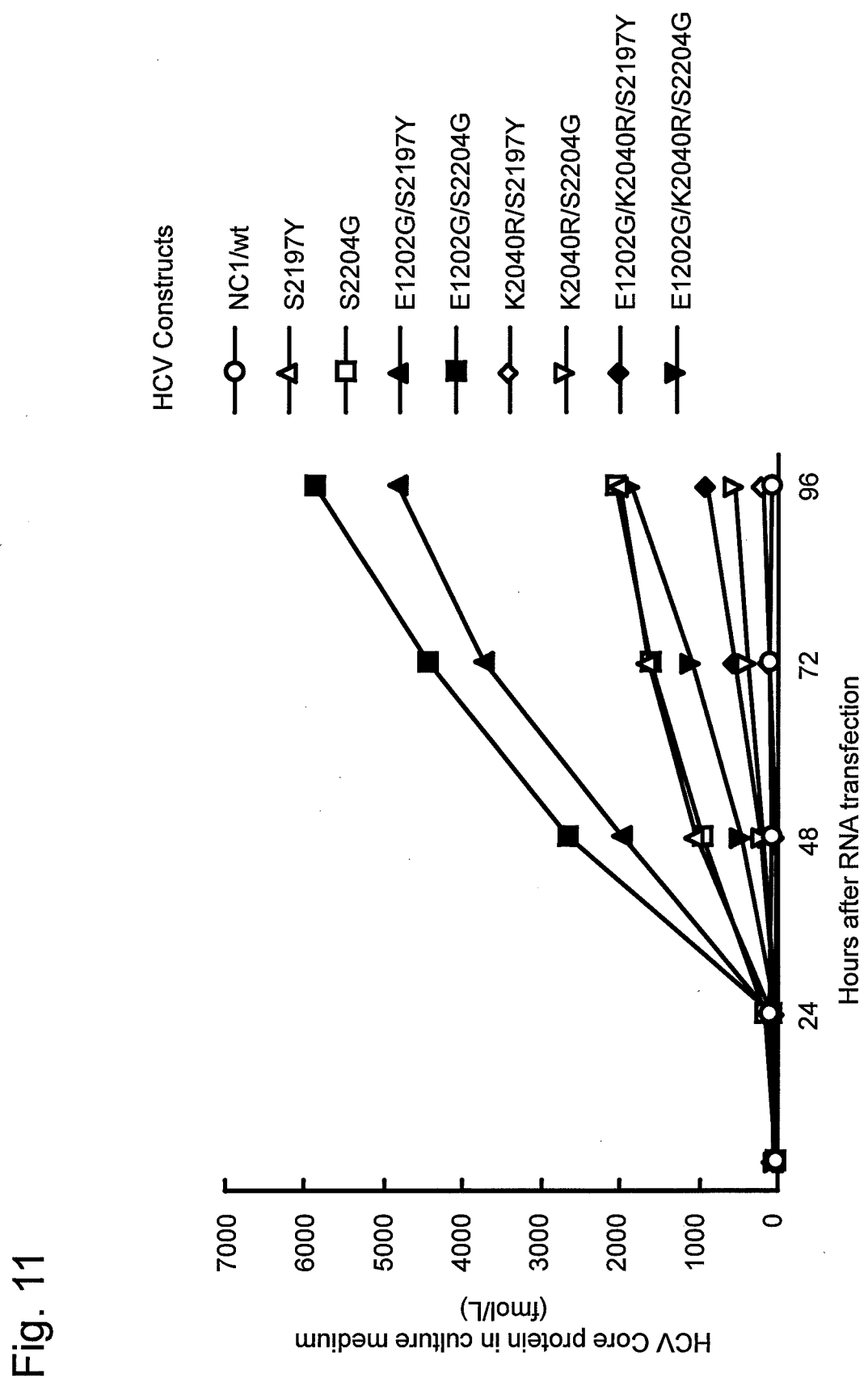
FIG. 11 shows changes over time in amount of the Core protein (HCV particle-producing ability) in culture supernatant of Huh7 cells transfected with the HCV fullgenomic replicon RNA of the wild-type NC1 strain or its mutants (mutation of E1202G, K2040R, S2197Y, and S2204G and combinations thereof).

The results are shown in FIG. 11. In the Figure, "NC1/wt" indicates the cells transfected with the HCV fullgenomic replicon RNA of the wild-type NC1 strain not having mutation. "S2197Y," "S2204G," "E1202G/S2197Y," "E1202G/ S2204G," "K2040R/S2197Y" "K2040R/S2204G," "E1202G/K2040R/S2197Y," and "E1202G/K2040R/ S2204G" indicate the cells transfected with the HCV fullgenomic replicon RNAs of the mutants of NC1 strain having the respective mutations.

In the cells transfected with the HCV fullgenomic replicon RNA of the wild-type NC1 strain, the Core protein was very little detected in the culture supernatant. In contrast, in the cells transfected with the HCV fullgenomic replicon RNAs of the mutants of NC1 strain, the amount of the Core protein in the culture supernatant increased after transfection with the RNA. In particular, the amount was high in mutants E1202G/ S2197Y and E1202G/S2204G. In the case of introduction of R2040R mutation in addition to these mutations, i.e., E1202G/K2040R/S2197Y and E1202G/K2040R/S2204G mutations, the amount of the Core protein in the culture supernatant decreased instead.

The results demonstrated that the mutants of the HCV fullgenomic replicon RNAs of the wild-type NC1 strain having E1202G/S2197Y or E1202G/S2204G mutations. NC1 E1202G/S2197Y (SEQ ID NO: 21) and NC1 E1202G/ S2204G (SEQ ID NO: 22), efficiently produce HCV particles into the culture supernatants when they are transfected into cells.

SEQ ID NO: 25 shows the amino acid sequence of the precursor protein (from the Core protein to the NS5B protein) encoded by pNC1 E1202G/S2197Y, and SEQ ID NO: 26 shows the amino acid sequence of the precursor protein encoded by pNC1 E1202G/S2204G. SEQ ID NO: 21 shows the cDNA nucleotide sequence of the full-length genomic RNA of the NC1 E1202G/S2197Y (HCV fullgenomic replicon RNA of a mutant of NO 1 strain synthesized from pNC1 E1202G/S2197Y), and SEQ ID NO: 22 shows the cDNA nucleotide sequence of the full-length genomic RNA of the NC1 E1202G/S2204G (HCV fullgenomic replicon RNA of a mutant of NC1 strain synthesized from pNC1 E1202G/ S2204G).

Example 13

Evaluation of Infectivity of HCV Particles Derived from HCV Fullgenomic Replicon RNA (Full-length Genomic RNA) of NC1 E1202G/S2197Y and NC1 E1202G/S2204G Infectivity of the HCV particles derived from each HCV fullgenomic replicon RNA (full-length genomic RNA) of NC1 S2197Y. NC1 E1202G/S2197Y. NC1 E1202G/ K2040R/S2197Y, NC1 S2204G, NC1 E1202G/S2204G, and NC1 E1202G/K2040R/S2204G, which was confirmed to produce HCV particles in Example 12, was investigated.

The infectious titer was calculated via counting the number of HCV-infected cells by a focus assay as described in Example 8 using the culture supernatant 72 hours after the transfection of Huh7 cells with the HCV fullgenomic replicon RNA (full-length genomic RNA) in Example 12. In addition, as described in Example 8, the amount of the HCV Core protein contained hi the culture supernatant was quantified with an HCV antigen ELISA test kit (Ortho-Clinical Diagnostics K.K.).

The results are shown in Table 2. The infectious titers in the culture supernatant of NC1 E1202G/S2197Y and NC1 E1202G/S2204G were high. 792.0 ffu/mL and 675.0 ffu/mL, respectively; whereas the infectious titer was 23.3 ffu/mL in the culture supernatant of NC1 S2197Y and 13.3 ffu/mL in the culture supernatant of NC1 S2204G, The value obtained by dividing the infectious titer by the amount of HCV Core protein in the culture supernatant was 0.097 in the culture supernatant of NC1 E1202G/S2197Y and was 0.097 in the culture supernatant of NC1 E1202G/S2204G, whereas the value was 0.009 in the culture supernatant of NC1 S2197Y and was 0.008 in the culture supernatant of NC1 S2204G.

TABLE 2

| Culture supernatant (3 days after transfection) | HCV Core (fmol/L) | Infectious titer (ffu/mL) | Infectious titer/HCV Core |
|---|---|---|---|
| NC1 S2197Y | 2467.5 | 23.3 | 0.009 |
| NC1 E1202G/S2197Y | 8193.3 | 792.0 | 0.097 |
| NC1 S2204G | 1643.6 | 13.3 | 0.008 |
| NC1 E1202G/S2204G | 6987.1 | 675.0 | 0.097 |

The results demonstrated that the HCV particles produced by cells transfected with the mutants of the HCV fullgenomic replicon RNA of the wild-type NC1 strain having E1202G/S2197Y or E1202G/S2204G mutations, NC1 E1202G/S2197Y (SEQ ID NO: 21) and NC1 E1202G/S2204G (SEQ ID NO: 22), have high infectivity.

The sequences shown in Sequence Listing are as follows.
SEQ ID NO:1: cDNA sequence of full-length genomic RNA of wild-type NC1 strain (FIG. 1A)
SEQ ID NO:2: cDNA nucleotide sequence of 5' UTR of wild-type NC1 strain genomic RNA
SEQ ID NO:3: cDNA nucleotide sequence of Core protein coding sequence of wild-type NC1 strain genomic RNA
SEQ ID NO:4: cDNA nucleotide sequence of E1 protein coding sequence of wild-type NC1 strain genomic RNA
SEQ ID NO:5: cDNA nucleotide sequence of E2 protein coding sequence of wild-type NC1 strain genomic RNA
SEQ ID NO:6: cDNA nucleotide sequence of p7 protein coding sequence of wild-type NC1 strain genomic RNA
SEQ ID NO:7: cDNA nucleotide sequence of NS2 protein coding sequence of wild-type NC1 strain genomic RNA
SEQ ID NO:8: cDNA nucleotide sequence of NS3 protein coding sequence of wild-type NC1 strain genomic RNA
SEQ ID NO: 9: cDNA nucleotide sequence of NS4A protein coding sequence of wild-type NC1 strain genomic RNA
SEQ ID NO:10: cDNA nucleotide sequence of NS4B protein coding sequence of wild-type NC1 strain genomic RNA
SEQ ID NO:11: cDNA nucleotide sequence of NS5A protein coding sequence of wild-type NC1 strain genomic RNA
SEQ ID NO:12: cDNA nucleotide sequence of NS5B protein coding sequence of wild-type NC1 strain genomic RNA
SEQ ID NO:13: cDNA nucleotide sequence of 3' UTR of wild-type NC1 strain genomic RNA
SEQ ID NO:14: amino acid sequence of precursor protein of wild-type NC1 strain
SEQ ID NO:15: amino acid sequence of ranging from NS3 protein region to NS5B protein region in precursor protein of wild-type NC1 strain
SEQ ID NO:16: cDNA nucleotide sequence of HCV subgenomic replicon RNA of wild-type NC1 strain (FIG. 1D)
SEQ ID NO:17: cDNA nucleotide sequence of HCV subgenomic replicon RNA of mutant NC1 S3197Y synthesized from pSGR-NC1 S2197Y
SEQ ID NO:18: cDNA nucleotide sequence of HCV subgenomic replicon RNA of mutant NC1 S2204G synthesized from pSGR-NC1 S2204G
SEQ ID NO:19: cDNA nucleotide sequence of full-length genomic RNA of mutant NC1 S2197Y (HCV fullgenomic replicon RNA of mutant of NC1 strain synthesized from pNC1 S2197Y)
SEQ ID NO:20: cDNA nucleotide sequence of full-length genomic RNA of mutant NC1 S2204G (HCV fullgenomic replicon RNA of mutant of NC1 strain synthesized from pNC1 S2204G)
SEQ ID NO:21 cDNA nucleotide sequence of full-length genomic RNA of mutant NC1 E1202G/S2197Y (HCV fullgenomic replicon RNA of mutant of NC1 strain synthesized from pNC1 E1202G/S2197Y)
SEQ ID NO:22: cDNA nucleotide sequence of full-length genomic RNA of mutant NC1 E1202G/S2204G (HCV fullgenomic replicon RNA of mutant of NC1 strain synthesized from pNC1 E1202G/S2204G)
SEQ ID NO:23: amino acid sequence of precursor protein encoded by pNC1 S2197Y
SEQ ID NO:24: amino acid sequence of precursor protein encoded by pNC1 S2204G
SEQ ID NO:25: amino acid sequence of precursor protein encoded by pNC1 E1202G/S2197Y
SEQ ID NO:26: amino acid sequence of precursor protein encoded by pNC1 E1202G/S2204G
SEQ ID NO:27: primer 5'-TAATACGACTCACTATAG-3'
SEQ ID NO:28: primer 5'-GCGGCTCACGGACCTTTCAC-3'
SEQ ID NO:29: primer 6620S-Con.1 5'-TACGCGGGTGGGGGATTTCCACTA-3'
SEQ ID NO:30: primer 3197SY-R 5'-GCTGGCCAAAT-AGGGGGGGGGACCCTCGGGC-3'
SEQ ID NO:31: primer 3197SY-S 5'-TC-CCCCCCCTATTTGGCCAGCTCTTCAGCT-3'
SEQ ID NO:32: primer 6447R-1b-rep 5'-ACGATAAGAC-GAGCTGGCTT-3'
SEQ ID NO:33: primer 2204SG-R 5'-GACAACTGAC-CAGCTGAAGAGCTGGCCAAA-3'
SEQ ID NO:34; primer 2204SG-S 5'-CTCTTCAGCTGGT-CAGTTGTCTGCGGTCTC-3'
SEQ ID NO:35: primer 2161PR-K 5'-GGGTTCACATC-GAAGCTGTGACCCGACC-3'
SEQ ID NO:36: primer 2161PR-S 5'-TCACAGCTTCGAT-GTGAACCCGAGCCGGAT-3'
SEQ ID NO:37: primer 2192RL-R 5'-GGGGGAC-CCTAGGGCCAGCCTGCGCTTAGC-3'
SEQ ID NO:38: primer 2192RL-S 5'-AGGCTGGC-CCTAGGGTCCCCCCCCTCTTT-3'
SEQ ID NO:39: primer 2192RQ-R 5'-GGGGGACCCT-TGGGCCAGCCTGCGCTTAGC-3'
SEQ ID NO:40; primer 2192RQ-S 5'-AGGCTGGC-CCAAGGGTCCCCCCCCTCTTT-3'
SEQ ID NO:41; primer 7094S-1b-rep 5'-GTCGGTCGCG-CACGATGCAT-3'
SEQ ID NO:42; primer 3871YC-R 5'-TTCAATGGAG-CAAGTGGCCCCGTAGATCT-3'
SEQ ID NO:43: primer 2871YC-S 5'-GGGGCCACT-TGCTCCATTGAACCACTTGAC-3'
SEQ ID NO:44: primer 3751S-NC1 5'-TGTGTTGGAC-CGTCTACCAT-3'
SEQ ID NO:45: primer 1b-1213EG-R 5'-GCATGGTGGT-TCCCATGGACTCAACGGGTA-3'
SEQ ID NO:46: primer 1b-1202EG-S 5'-GTCCATGG-GAACCACCATGCGGTCTCCGGT-3'

SEQ ID NO:47: primer 4598R-NC1 5'-CGGTAGTACGC-TACAGCATT-3'
SEQ ID NO:48: primer 5292S-NC1 5'-GCCGACCTGGAG-GTCGTCAC-3'
SEQ ID NO:49: primer 1b-2040KR-R 5'-GAACCGTTCCT-GACATGTCCACTGATCTGT-3'
SEQ ID NO:50: primer 1b-2040KR-S 5'-GGACATGTCAG-GAACGGTTCCATGAGGATC-3'
SEQ ID NO:51: primer 6789R-NC1 5'-GACCTGGAATGT-GACCTCAT-3'
SEQ ID NO:52: cDNA nucleotide sequence of HCV subgenomic replicon RNA of mutant NC1 P2161R synthesized from pSGR-NC1 P2161R Industrial Applicability A fullgenomic replicon RNA that can be amplified in cultured cells and produces infectious HCV particles of genotype 1 b is provided. The fullgenomic replicon RNA can be used in screening for an anti-HCV drug that inhibits infection and replication of HCV of genotype 1b, research for revealing the replication mechanism of HCV, development of an HCV vaccine, and other application. A subgenomic replicon RNA having high replication ability is also provided, which can be used in screening for an anti-HCV drug that inhibits replication of HCV of genotype 1b.

Sequence Listing Free Text
SEQ ID NOs: 27 to 51: primers

The invention claimed is:

1. A nucleic acid comprising the nucleotide sequence shown in SEQ ID NO: 1, provided that when the nucleic acid is RNA, thymine (T) in the nucleotide sequence shown in SEQ ID NO: 1 shall be read as uracil (U), and comprising mutation(s) in the nucleotide sequence shown in SEQ ID NO: 1, wherein the mutation(s) cause substitution(s) of any of the following (i) to (iv) as defined on the basis of the amino acid sequence shown in SEQ ID NO: 14 (the amino acid sequence encoded by the sequence of nucleotide numbers from 342 to 9374 shown in SEQ ID NO: 1):
   (i) substitution of serine at position 2197 with tyrosine,
   (ii) substitution of serine at position 2204 with glycine,
   (iii) substitution of serine at position 2197 with tyrosine and substitution of glutamic acid at position 1202 with glycine, and
   (iv) substitution of serine at position 2204 with glycine and substitution of glutamic acid at position 1202 with glycine.

2. A hepatitis C virus comprising the nucleic acid according to claim 1 as a viral genome.

3. A nucleic acid comprising nucleotide sequences that are derived from two or more hepatitis C virus genomes and encode a Core protein, an E1 protein, an E2 protein, a p7 protein, an NS2 protein, an NS3 protein, an NS4A protein, an NS4B protein, an NS5A protein, and an NS5B protein, in this order from the 5' side to the 3' side, wherein the nucleotide sequences encoding the NS3 protein, the NS4A protein, the NS4B protein, the NS5A protein, and the NS5B protein are derived from the nucleic acid according to claim 1.

4. The nucleic acid according to claim 3, wherein at least a part of the nucleotide sequence encoding the NS2 protein is from SEQ ID No: 1.

5. The nucleic acid according to claim 3, comprising:

a 5' untranslated region of a hepatitis C virus genome on the 5' side of the nucleotide sequence encoding the Core protein; and
a 3' untranslated region consisting of the sequence of nucleotide numbers from 9375 to 9607 shown in SEQ ID NO: 1 on the 3' side of the nucleotide sequence encoding the NS5B protein, provided that when the nucleic acid is RNA, thymine (T) in the nucleotide sequence shown in SEQ ID NO: 1 shall be read as uracil (U).

6. The nucleic acid according to claim 3, wherein the two or more hepatitis C virus genomes include the genome of a JFH-1 strain, a J6CF strain, or a TH strain.

7. A hepatitis C virus comprising the nucleic acid according to claim 5 as a viral genome.

8. A fullgenomic replicon RNA of hepatitis C virus comprising the nucleic acid according to claim 1.

9. A cell transfected with a fullgenomic replicon RNA comprising the nucleic acid according to claim 1 and producing hepatitis C virus particles.

10. An immunogenic composition comprising the hepatitis C virus according to claim 2 or a part thereof.

11. A nucleic acid comprising a nucleotide sequence consisting of the 5' untranslated region consisting of the sequence of nucleotide numbers from 1 to 341,
the NS3 protein-encoding nucleotide sequence consisting of the sequence of nucleotide numbers from 3420 to 5312,
the NS4A protein-encoding nucleotide sequence consisting of the sequence of nucleotide numbers from 5313 to 5474,
the NS4B protein-encoding nucleotide sequence consisting of the sequence of nucleotide numbers from 5475 to 6257, the NS5A protein-encoding nucleotide sequence consisting of the sequence of nucleotide numbers from 6258 to 7598, the NS5B protein-encoding nucleotide sequence consisting of the sequence of nucleotide numbers from 7599 to 9374, and the 3' untranslated region consisting of the sequence of nucleotide numbers from 9375 to 9607 of SEQ ID NO: 1, provided that when the nucleic acid is RNA, thymine (T) in the nucleotide sequence shown in SEQ ID NO: 1 shall be read as uracil (U), and comprising mutation(s) in said nucleotide sequence, wherein the mutation(s) cause substitution(s) of any of the following (a) to (f) as defined on the basis of the amino acid sequence shown in SEQ ID NO: 14 (the amino acid sequence encoded by the sequence of nucleotide numbers from 342 to 9374 shown in SEQ ID NO: 1):

(a) substitution of serine at position 2197 with tyrosine,
(b) substitution of serine at position 2204 with glycine,
(c) substitution of serine at position 2197 with tyrosine and substitution of glutamic acid at position 1202 with glycine,
(d) substitution of serine at position 2204 with glycine and substitution of glutamic acid at position 1202 with glycine,
(e) substitution of proline at position 2161 with arginine, and
(f) substitution of arginine at position 2192 with glutamine.

12. A subgenomic replicon RNA of hepatitis C virus, comprising the nucleic acid according to claim 11, wherein the nucleic acid comprises the 5' untranslated region consisting of the sequence of nucleotide numbers from 1 to 341, the NS3 protein-encoding nucleotide sequence consisting of the sequence of nucleotide numbers from 3420 to 5312, the NS4A protein-encoding nucleotide sequence consisting of the sequence of nucleotide numbers from 5313 to 5474, the NS4B protein-encoding nucleotide sequence consisting of the sequence of nucleotide numbers from 5475 to 6257, the NS5A protein-encoding nucleotide sequence consisting of the sequence of nucleotide numbers from 6258 to 7598, the NS5B protein-encoding nucleotide sequence consisting of the sequence of nucleotide numbers from 7599 to 9374, and the 3' untranslated region consisting of the sequence of nucleotide numbers from 9375 to 9607, of SEQ ID NO: 1, provided that thymine (T) in the nucleotide sequence shown in SEQ ID NO: 1 shall be read as uracil (U).

13. A hepatitis C virus-sensitive cell transfected with the subgenomic replicon RNA according to claim 12.

14. A fullgenomic replicon RNA of hepatitis C virus comprising the nucleic acid according to claim 3.

15. A fullgenomic replicon RNA of hepatitis C virus comprising the nucleic acid according to claim 5.

16. A cell infected with the hepatitis C virus according to claim 2 and producing hepatitis C virus particles.

17. The nucleic acid according to claim 1, comprising the nucleotide sequence shown in SEQ ID NO: 19, SEQ ID NO: 20, SEQ ID NO: 21, or SEQ ID NO: 22, provided that when the nucleic acid is RNA, thymine (T) in the nucleotide sequence shown in SEQ ID NO: 19, SEQ ID NO: 20, SEQ ID NO: 21, or SEQ ID NO: 22 shall be read as uracil (U), respectively.

18. The subgenomic replicon RNA according to claim 12, comprising the nucleotide sequence shown in SEQ ID NO: 16, provided that thymine (T) in the nucleotide sequence shown in SEQ ID NO: 16 shall be read as uracil (U).

19. The nucleic acid according to claim 11, comprising the nucleotide sequence shown in SEQ ID NO: 17, SEQ ID NO: 18, or SEQ ID NO: 52, provided that when the nucleic acid is RNA, thymine (T) in the nucleotide sequence shown in SEQ ID NO: 17, SEQ ID NO: 18, or SEQ ID NO: 52 shall be read as uracil (U), respectively.

* * * * *